United States Patent
Benders et al.

(10) Patent No.: US 9,267,132 B2
(45) Date of Patent: *Feb. 23, 2016

(54) METHODS FOR CLONING AND MANIPULATING GENOMES

(75) Inventors: Gwynedd A. Benders, San Diego, CA (US); John I. Glass, Germantown, MD (US); Clyde A. Hutchison, La Jolla, CA (US); Carole Lartigue, Gaithersburg, MD (US); Sanjay Vashee, Boyds, MD (US); Mikkel A. Algire, Jessup, MD (US); Hamilton O. Smith, San Diego, CA (US); Charles E. Merryman, Sykesville, MD (US); Vladimir N. Noskov, Montgomery Village, MD (US); Ray-Yuan Chuang, Rockville, MD (US); Daniel G. Gibson, Crofton, MD (US); J. Craig Venter, La Jolla, CA (US)

(73) Assignee: Synthetic Genomics, Inc., La Jolla, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/783,489

(22) Filed: May 19, 2010

(65) Prior Publication Data

US 2011/0053273 A1    Mar. 3, 2011

Related U.S. Application Data

(63) Continuation-in-part of application No. 12/718,911, filed on Mar. 5, 2010, and a continuation-in-part of application No. PCT/US2010/026434, filed on Mar. 5, 2010.

(60) Provisional application No. 61/158,320, filed on Mar. 6, 2009, provisional application No. 61/322,269, filed on Apr. 8, 2010.

(51) Int. Cl.
C12N 15/10    (2006.01)

(52) U.S. Cl.
CPC .......... *C12N 15/10* (2013.01); *C12N 15/1031* (2013.01); *C12N 15/1079* (2013.01); *C12N 15/1093* (2013.01)

(58) Field of Classification Search
CPC . C12N 15/09; C12N 15/1031; C12N 15/1093
USPC ........................................... 435/440
See application file for complete search history.

(56) References Cited

U.S. PATENT DOCUMENTS

2007/0264688 A1* 11/2007 Venter et al. ............ 435/69.1
2007/0269862 A1   11/2007 Glass et al.

FOREIGN PATENT DOCUMENTS

| AU | 2002325859 B2 | 5/2008 | |
|----|---------------|--------|--|
| JP | WO 03/048346 A | 6/2003 | |
| WO | WO 2006/110680 | * 10/2006 | ............. C12N 15/85 |
| WO | WO 2006/110680 A1 | 10/2006 | |
| WO | WO 2008/016380 A2 | 2/2008 | |
| WO | WO 2008/024129 A2 | 2/2008 | |
| WO | WO 2008/144192 A1 | 11/2008 | |
| WO | WO 2009/048885 A2 | 4/2009 | |
| WO | WO 2009/134814 A2 | 11/2009 | |
| WO | WO 2010/102257 A2 | 9/2010 | |

OTHER PUBLICATIONS

List of Organisms by Chromosome Count, Wikipedia; last visited Mar. 26, 2013.*
Wieloch, J. Microbiological Methods 67:1-8, 2006.*
Gordon et al, PLoS Genetics 7(7):1-13, 2011.*
Naylor, British Phycological Bulletin 1(6): 34-40, 1958.*
Bacterial Chromosomes, http://www.sci.sdsu.edu/~smaloy/MicrobialGenetics/topics/chroms-genes-prots/chromosomes.html; last visited Mar. 26, 2013.*
Lartigue et al, Science 317:632-638, 2007.*
Strathern et al, Methods in Enzymol. 194:319-329, 1991.*
Benders et al., "Cloning whole bacterial genomes in yeast", *Nucleic Acids Res.*, May 2010; 38(8):2558-2569. Epub. Mar. 7, 2010.
Gibson et al., "Complete chemical synthesis, assembly, and cloning of a Mycoplasma genitalium genome", *Science*, Feb. 29, 2008; 319(5867):1215-1220. Epub. Jan. 24, 2008.
Gibson et al., "One-step assembly in yeast of 25 overlapping DNA fragments to form a complete synthetic Mycoplasma genitalium genome", *Proc. Natl. Acad. Sci. U.S.A.*, Dec. 23, 2008;105(51):20404-20409. Epub. Dec. 10, 2008.
Kouprina et al., "Selective isolation of large chromosomal regions by transformation-associated recombination cloning for structural and functional analysis of mammalian genomes", *Methods Mol. Biol.*, 349:85-101 (2006).
Lartigue et al., "Creating bacterial strains from genomes that have been cloned and engineered in yeast", *Science.*, Sep. 25, 2009; 325(5948):1693-1696. Epub. Aug. 20, 2009.
Lartigue et al., "Genome transplantation in bacteria: changing one species to another", *Science*, Aug. 3, 2007; 317(5838):632-638. Epub. Jun. 28, 2007.
Noskov et al., "A general cloning system to selectively isolate any eukaryotic or prokaryotic genomic region in yeast", *BMC Genomics*, Apr. 29, 2003; 4(1):16. Epub. Apr. 29, 2003.
Pennisi E., "Genetics. Replacement genome gives microbe new identity", *Science*, 316(5833):1827 (2007).
Bheemanaik et al., "Structure, function and mechanism of exocyclic DNA methyltransferases", *Biochem. J.*, 399(2):177-190 (2006).

(Continued)

*Primary Examiner* — Kevin Hill
(74) *Attorney, Agent, or Firm* — DLA Piper LLP (US)

(57) ABSTRACT

Compositions and methods are disclosed herein for cloning a synthetic or a semi-synthetic donor genome in a heterologous host cell. In one embodiment, the donor genome can be further modified within a host cell. Modified or unmodified genomes can be further isolated from the host cell and transferred to a recipient cell. Methods disclosed herein can be used to alter donor genomes from intractable donor cells in more tractable host cells.

22 Claims, 25 Drawing Sheets

(56) References Cited

OTHER PUBLICATIONS

Carole Lartigue: "*Creating Bacterial Strains From Genomes That Have Been Cloned and Engineered in Yeast*", Science; Sep. 25, 2009, vol. 325, pp. 1693-1696.
Zhou, Fuchun et al.: "*A sequence-independent in vitro transposon-based strategy for efficient cloning of genomes of large DNA viruses as bacterial artificial chromosomes*"; Nucleic Acids Research, 37:1, Jan. 2009.
Kouprina, N. et al.: "*Rescue of targeted regions of mammalian chromosomes by in vivo recombination in yeast*"; Genome Research, 8:1, Jun. 1998, pp. 666-672.
Kouprina, N. et al.: "*Construction of Human Chromosome 16- and 5-Specific Circular YAC/BAC Libraries by in Vivo Recombination in Yeast (TAR Cloning)*"Genomics, 53:1, Oct. 1, 1998, pp. 21-28.

* cited by examiner

BssHII

230

1
89
309
IS1296
159
vector
777
*M. mycoides*
YCpMmyc1.1
1.1 Mb
884
392
708
BssHII
1020 608
2

| Fragment | Size (kb) |
|----------|-----------|
| 1 | 668 |
| 2 | 419 |

FIG. 7B (+ Mcap extracts)    (+ M. mycoides LC extracts)    (− extract)

FIG. 7C

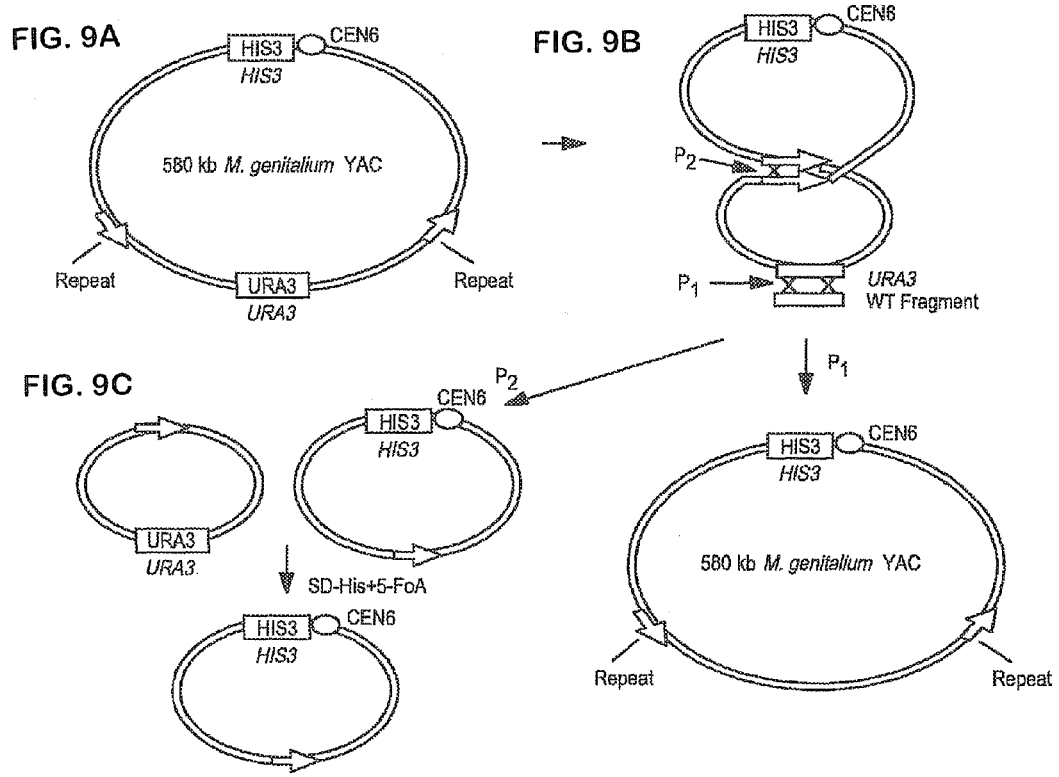

*AGGAAGGCTGTGTGAATTTCATTCGACAAGATAAAGGAAATTAGAACATTTACTTTAGTTACAAATAATGAAAA*
*TAATATAGGGATTGATGTTTGCTATGAACGCTTGTTTAGAATAAATAATGGTAAATCAACTGATAATAAAACAG*
*ATTTTAAATGAATAGAAAAAAACGAACCCTATCTGTCTAATTTAGATGTTTTTGATATTAAATACTATTCAACT*
*AAATTGTTTGAAGATAATAGTGCTAATGAAATAATCAAAAAACAATTCATAAAAATGTTAAATGATCTAAAAAT*
*AAATGCTGATGATATTTCTACAATTAAAACTTTAAGACAATTAACTGCACTAAAACCAATCTCAGGTGGACAAA*

*ACA*ATGAGATTAACTAATAAACAAGAATTTGTAGTGCAAGATATTGTTAAAGAAGATTATTAA*ATTGTTA*
*AAATAAAAAATTACTTATTTAAGCGGGACTATTTCTATTTTATTTAAAGAAGTCTTATGATTGAATGTAAAAGT*
*TCTAATGTATTAACCCCTGTTACATTAAATACAACCATATCTATTTTTAATTAATCTCCTGAAAGTACAAGTTC*
*TTAATTCCTAACCATGCCTATTAAATTTAAGATCAAGAGCAGTTTTTCTAACCCCCGAAAAAAAACTCACAACA*
*AAAA*
(SEQ ID NO: 195)

SEQUENCE LISTING

<160> NUMBER OF SEQ ID NOS: 195

<210> SEQ ID NO 1
<211> LENGTH: 59
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
gatttattct tcaagaaaat acatcaattt tgataagtag ttcaaatatg tatccgctc 59

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
gctgcgctcg gtcgttcggc 20

<210> SEQ ID NO 3
<211> LENGTH: 86
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 3
taccaacgat gttccctcca ccaaaggtgt tcttatgtag ttttacacag gagtctggac    60
ttgactgtgt aaaagtaaaa aggcca                                        86

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctacttatca aaattgatgt                                               20

<210> SEQ ID NO 5
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttcttaaaaa aacaaaaaaa gattttccaa ataaattgcg tcagatcttt atataacaac    60

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aattaaaagt tagtgaacaa                                               20

<210> SEQ ID NO 7
<211> LENGTH: 86
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agctgatacc gctcgccgca gccgaacgac cgagcgcagc gataaagtcc gtataattgt    60
gtaaaattat tattattttt gacacc                                        86

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgcaatttat ttggaaaatc                                               20

<210> SEQ ID NO 9
```

```
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gatacgaggc gcgtgtaagt tacaggcaag cgatcctagt acactctata ttttttatg     60

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctacataaga acacctttgg                                                20

<210> SEQ ID NO 11
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
actggtgctt cactgttttc ttgttcacta acttttaatt atcacgtgct ataaaataa     60

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggatcgcttg cctgtaactt                                                20

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cgatcttatt aatggcataa aag                                            23

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cattaattgt gtttaaatta atacttg                                        27

<210> SEQ ID NO 15
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atcgtgcgca taacgatg                                                   18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcttgatcta agaattgc                                                   18

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
atattaaagc taccttattt gatg                                            24

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aagagcgtaa atcagtggc                                                  19

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tttttgtttg gtgctaat                                                   18

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
caattttcta taagcgttgc                                                 20

<210> SEQ ID NO 21
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 21
tggggatact gaaaatatta c                                              21

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ctgaaatgat ccctttaa                                                  18

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aaaaacaagc tttacaagag                                                20

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
catcttgatc caacttattt a                                              21

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
agctattggt cctgaaacac                                                20

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26 acccctttt ttgctaaaag g                                               21

<210> SEQ ID NO 27
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 27
ttaacttcgt taaaagtgaa t                                                 21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aatggattac taatgagctt g                                                 21

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
atccagtaaa aaccttga                                                     18

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aaatgatttt attgctgtta c                                                 21

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tttgcgttcc ttagcacg                                                     18

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tataaaacaa caattactga ag                                                22

<210> SEQ ID NO 33
<211> LENGTH: 20
<212> TYPE: DNA
<213> ORGANISM: Artificial Sequence
<220> FEATURE:
```

<223> OTHER INFORMATION: Description of Artificial Sequence: Synthetic
       primer

<400> SEQUENCE: 33
caactgatac accaaccatc                                                    20

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 34
ttatggtagt ggttttcaca t                                                  21

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 35
gctttggtta tcatatgtga ac                                                 22

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 36
caaatccttg atctttaatt acttg                                              25

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 37
tattggtgaa ccagtggg                                                      18

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 38
ccttgttcaa cacgtaatac tg                                                 22

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
gtgagcaaca atgttttgag                                               20

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
caactccacc aagtactcc                                                19

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ctaaaccatc agaattaggt tc                                            22

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gcaaagtcac agatcaacaa                                               20

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
caactccaga aggtgctc                                                 18

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ctaaactaat tctaatagca ccc                                           23

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 45
tcgatcatta ttttatatgt tgtg                                          24

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tataattctt actccagcat ttc                                           23

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gctcatcagc ttgactaatt tg                                            22

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ctaatctcag atattcaagc ag                                            22

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ttaattttgg catcaagtgc tg                                            22

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
agaacaataa ctagtctata cac                                           23

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 51
tgaaaccaag attcagattg c                                              21

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ggtcgtctat gtgtaagtca cc                                             22

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
aatttgactc aacacggg                                                  18

<210> SEQ ID NO 54
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gacgggcggt gtgtac                                                    16

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
tatttaccga cgaaattaat acc                                            23

<210> SEQ ID NO 56
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
attttcctat ataccacttt ctttttc                                        27

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
```
cttagaactt tacagctcca aac         23

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ctggttattg gccaccaac         19

<210> SEQ ID NO 59
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
atggtgggat tgccc         15

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
atatttggac agttttttcgc c         21

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ccgaaagttg agaagttaaa gg         22

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
agaaatattt gaaattttta tctaaaaagc         30

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63

```
aatctcctct tgttttaatg gag                                                  23

<210> SEQ ID NO 64
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ttgcaagcga ttttgtg                                                         17

<210> SEQ ID NO 65
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
aaacctatgc aaatatttta acgat                                                25

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
acttgtaaaa gtaaagaacc actgc                                                25

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
catggtaatg gccaaagc                                                        18

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gttgatcggg ttgatgtttt at                                                   22

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
taaggctgat aaaagtggta attc                                                 24
```

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ctttagtatg ttctaagcga aagc                                          24

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gggtcaaacg tgaactttaa g                                             21

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
aacggaaggt aactatgaag ct                                            22

<210> SEQ ID NO 73
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
agtttggctc gtgcaaaaat ag                                            22

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ttttcggttt tatgaaccgt tc                                            22

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tatttaccga cgaaattaat acc                                           23

<210> SEQ ID NO 76
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
attttcctat ataccacttt cttttttc                                         27

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
agtagtcttt gataatggct aagg                                             24

<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
cctgtatgag ggctttcag                                                   19

<210> SEQ ID NO 79
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gtgcttgact gtgagacata ca                                               22

<210> SEQ ID NO 80
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
aatcggcgaa cagcc                                                       15

<210> SEQ ID NO 81
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
tgcaccaact ccagca                                                      16

```
<210> SEQ ID NO 82
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
atatccaata gttcattctt attgg                                          25

<210> SEQ ID NO 83
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gaagcggaaa aacggc                                                    16

<210> SEQ ID NO 84
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
caattaatgg aagaattttt attttcatt                                      29

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
acaaaacaaa caccaccacg                                                20

<210> SEQ ID NO 86
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
cggcgtgatg attcatc                                                   17

<210> SEQ ID NO 87
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
aatgctaccc caaacggt                                                  18

<210> SEQ ID NO 88
```

<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 88
tgagctttat tgccatcctt t            21

<210> SEQ ID NO 89
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 89
tagataatga agcgtcttca ttacc            25

<210> SEQ ID NO 90
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 90
acttctacta gcgtcaattt aactcaac            28

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 91
aacctctttc agaaaggagg            20

<210> SEQ ID NO 92
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 92
aactttaatt ggtttggaga ttattcttta g            31

<210> SEQ ID NO 93
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 93
acttttaaca ccatcactcg cta            23

<210> SEQ ID NO 94
<211> LENGTH: 30

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
caaacaacta gagggtaaat actttattgt                                        30

<210> SEQ ID NO 95
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
caaccttttg ttcgatacta aagag                                             25

<210> SEQ ID NO 96
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
aatttctttc tcattttgg tttagtcc                                           28

<210> SEQ ID NO 97
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
ttaataacaa aaaatctct attaaaaaaa ccaactttaa agttggtttg aaattctaaa        60
atcgatgtcg aaagctacat                                                   80

<210> SEQ ID NO 98
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
ggatagagtg tctggcttcg gaccagaagg ttatgggttc aagtcctatt gggcgcgcca      60
ctcgagccac tatttatacc                                                   80

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
tttctatgaa ctacatgatc tt                                                22
```

```
<210> SEQ ID NO 100
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
gttgtagaat tgccaggt                                                 18

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
aagggaagga tagtagtggg                                               20

<210> SEQ ID NO 102
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
aggtgttggt ggtttggt                                                 18

<210> SEQ ID NO 103
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
taagacttgg caaggtag                                                 18

<210> SEQ ID NO 104
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
tcttgatagg aaagtcct                                                 18

<210> SEQ ID NO 105
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
gaaccaccct tagaaagg                                                 18
```

<210> SEQ ID NO 106
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 106
gataattgtt aaattcttaa ttg                                              23

<210> SEQ ID NO 107
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 107
ggtcaaacta gaacttga                                                    18

<210> SEQ ID NO 108
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 108
agcattagct tcattactaa ag                                               22

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 109
taacatttat gaaaaacgaa                                                  20

<210> SEQ ID NO 110
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 110
accattttta ataatgtaca tag                                              23

<210> SEQ ID NO 111
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 111
ttgccattac tactactact act                                              23

<210> SEQ ID NO 112

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
tcttcatcaa cttcatca                                                        18

<210> SEQ ID NO 113
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
tatgttcatc ccttcagg                                                        18

<210> SEQ ID NO 114
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
ctctctaatg cagggaga                                                        18

<210> SEQ ID NO 115
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
tgaactcaca aaaacaac                                                        18

<210> SEQ ID NO 116
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
tgcagaagaa gttgttac                                                        18

<210> SEQ ID NO 117
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
acaaaatcac ctaaagaaac aat                                                  23

<210> SEQ ID NO 118
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
ggttaatttg agaagaacat attg                                          24

<210> SEQ ID NO 119
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
aaccaatcag tacccttgc                                                19

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
agcaaactta attagtggga c                                             21

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
caaacacttt cgtgaaacag g                                             21

<210> SEQ ID NO 122
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
gtttcaactc caataatagt aggg                                          24

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
caccgcttca gtcactacaa g                                             21

<210> SEQ ID NO 124
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 124
gctattgaat cacctgatcc tg                                           22

<210> SEQ ID NO 125
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
ggcacctaag ttttgaga                                                18

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
cttgaaatgc taatttggtg                                              20

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
tgaaaccaag attcagattg c                                            21

<210> SEQ ID NO 128
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
ggtcgtctat gtgtaagtca cc                                           22

<210> SEQ ID NO 129
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
aatttgactc aacacggg                                                18

<210> SEQ ID NO 130
<211> LENGTH: 16
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 130
gacgggcggt gtgtac                                                         16

<210> SEQ ID NO 131
<211> LENGTH: 76
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
tacgaggcgc gtgtaagtta caggcaagcg atcctagtac actctatatc agagcagatt         60
gtactgagag tgcacc                                                         76

<210> SEQ ID NO 132
<211> LENGTH: 76
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
ctacataaga acacctttgg tggagggaac atcgttggta ccattgggcg cgcatctgtg         60
cggtatttca caccgc                                                         76

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
attattccat cattaaaaga                                                     20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
agtcaagtcc agactcctgt                                                     20

<210> SEQ ID NO 135
<211> LENGTH: 90
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
cagatggtat tcctgaaagg atatcaataa taagtgaaag ttttttttctt atttttggtt        60 gcggccgctt gatttcggtt tctttgaaat                                          90
```

<210> SEQ ID NO 136
<211> LENGTH: 85
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 136

| | | |
|---|---|---|
| ttaattattg ctagttatat aggggttaga acttcatttt tccttgttta tcgatgcagc | 60 |
| ggccgcgggt cctttcatc acgtg | 85 |

<210> SEQ ID NO 137
<211> LENGTH: 1708
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 137

| | |
|---|---|
| ttgatttcgg tttctttgaa attttttga ttcggtaatc tccgaacaga aggaagaacg | 60 |
| aaggaaggag cacagactta gattggtata tatacgcata tgtagtgttg aagaaacatg | 120 |
| aaattgccca gtattcttaa cccaactgca cagaacaaaa acctgcagga acgaagata | 180 |
| aatcatgtcg aaagctacat ataaggaacg tgctgctact catcctagtc ctgttgctgc | 240 |
| caagctattt aatatcatgc acgaaaagca aacaaacttg tgtgcttcat tggatgttcg | 300 |
| taccaccaag gaattactgg agttagttga agcattaggt cccaaaattt gtttactaaa | 360 |
| aacacatgtg gatatcttga ctgatttttc catggagggc acagttaagc cgctaaaggc | 420 |
| attatccgcc aagtacaatt ttttactctt cgaagacaga aaatttgctg acattggtaa | 480 |
| tacagtcaaa ttgcagtact ctgcgggtgt atacagaata gcagaatggg cagacattac | 540 |
| gaatgcacac ggtgtggtgg gcccaggtat tgttagcggt ttgaagcagg cggcagaaga | 600 |
| agtaacaaag gaacctagag gcctttgat gttagcagaa ttgtcatgca agggctccct | 660 |
| atctactgga gaatatacta agggtactgt tgacattgcg aagagcgaca agatttttgt | 720 |
| tatcggcttt attgctcaaa gagacatggg tggaagagat gaaggttacg attggttgat | 780 |
| tatgacaccc ggtgtggggtt tagatgacaa gggagacgca ttgggtcaac agtatagaac | 840 |
| cgtggatgat gtggtctcta caggatctga cattattatt gttggaagag gactatttgc | 900 |
| aaagggaagg gatgctaagg tagagggtga acgttacaga aaagcaggct gggaagcata | 960 |
| tttgagaaga tgcggccagc aaaactaaaa aactgtatta aagtaaatg catgtatact | 1020 |
| aaactcacaa attagagctt caatttaatt atatcagtta ttacccacgg attagaagcc | 1080 |
| gccgagcggg tgacagccct ccgaaggaag actctcctcc gtgcgtcctc gtcctcaccg | 1140 |
| gtcgcgttcc tgaaacgcag atgtgcctcg cgccgcactg ctccgaacaa taaagattct | 1200 |
| acaatactag cttttatggt tatgaagagg aaaaattggc agtaacctgg ccccacaaac | 1260 |
| cttcaaatga acgaatcaaa ttaacaacca taggatgata atgcgattag ttttttagcc | 1320 |
| ttatttctgg ggtaattaat cagcgaagcg atgattttg atctattaac agatatataa | 1380 |
| atgcaaaaac tgcattaacc actttaacta atactttcaa cattttcggt ttgtattact | 1440 |
| tcttattcaa atgtaataaa agtatcaaca aaaaattgtt aatatacctc tatactttaa | 1500 |
| cgtcaaggag aaaaaaccgg cctgagcaga ggaagagcaa gataaaaggt agtatttgtt | 1560 |
| ggcgatcccc ctagagtctt ttacatcttc ggaaaacaaa aactattttt tctttaattt | 1620 |

```
cttttttttac tttctatttt taatttatat atttatatta aaaaatttaa attataatta    1680
tttttatagc acgtgatgaa aaggaccc                                        1708

<210> SEQ ID NO 138
<211> LENGTH: 302
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138
ttaaagtcag ttatttatct acagcaattg ctgtcattac tttaattatt tgttcttaaa      60
gcaacattcc cttaccaaaa tttaggtttc ttgcttgtgg agtttaccgc gtttcatacc    120
tggttttcac caagctcgtc tctgtggcac tttcaaaaca tcatcatagt attaaccta    180 gactagttat gtcgttatgg ctatcacatc ctaaatctta tcgctttgat ttacacaaac    240
actacttgca ttccagcaag tgcaagcatg gactttcctc tactttaaat atatctttaa    300
ag                                                                    302

<210> SEQ ID NO 139
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
ttaaagtcag ttatttatct acagc                                            25

<210> SEQ ID NO 140
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
ctttaaagat atatttaaag tagagg                                           26

<210> SEQ ID NO 141
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
cagatggtat tcctgaaagg atatcaataa taagtgaaag ttttttttctt attttggtt      60 cagagcagat tgtactgaga                                                  80

<210> SEQ ID NO 142
<211> LENGTH: 78
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
```

```
ttaattattg ctagttatat aggggttaga acttcatttt tccttgttta tcgatgcacg    60
catctgtgcg gtatttca                                                  78
```

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143

```
gccattgttt cactaattgc                                                20
```

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144

```
taatcctatc tttggagctt                                                20
```

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145

```
ctccatcatg cgcagtaata                                                20
```

<210> SEQ ID NO 146
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146

```
ctttaaagat atatttaaag tagagg                                         26
```

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147

```
ttgatttcgg tttctttgaa                                                20
```

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
caggcaggaa tttgattccc                                                    20

<210> SEQ ID NO 149
<211> LENGTH: 7451
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 149

```
gacgaaaggg cctcgtgata cgcctatttt tataggttaa tgtcatgata ataatggttt    60
cttagacgtc aggtggcact tttcggggaa atgtgcgcgg aacccctatt tgtttatttt   120
tctaaataca ttcaaatatg tatccgctca tgagacaata accctgataa atgcttcaat   180
aatattgaaa aaggaagagt atgagtattc aacatttccg tgtcgccctt attccctttt   240
ttgcggcatt ttgccttcct gttttttgctc acccagaaac gctggtgaaa gtaaaagatg   300
ctgaagatca gttgggtgca cgagtgggtt acatcgaact ggatctcaac agcggtaaga   360
tccttgagag ttttcgcccc gaagaacgtt ttccaatgat gagcactttt aaagttctgc   420
tatgtggcgc ggtattatcc cgtattgacg ccgggcaaga gcaactcggt cgccgcatac   480
actattctca gaatgacttg gttgagtact caccagtcac agaaaagcat cttacggatg   540
gcatgacagt aagagaatta tgcagtgctg ccataaccat gagtgataac actgcggcca   600
acttacttct gacaacgatc ggaggaccga aggagctaac cgcttttttg cacaacatgg   660
gggatcatgt aactcgcctt gatcgttggg aaccggagct gaatgaagcc ataccaaacg   720
acgagcgtga caccacgatg cctgtagcaa tggcaacaac gttgcgcaaa ctattaactg   780
gcgaactact tactctagct tcccggcaac aattaataga ctggatggag gcggataaag   840
ttgcaggacc acttctgcgc tcggcccttc cggctggctg gtttattgct gataaatctg   900
gagccggtga gcgtgggtct cgcggtatca ttgcagcact ggggccagat ggtaagccct   960
cccgtatcgt agttatctac acgacgggga gtcaggcaac tatggatgaa cgaaatagac  1020
agatcgctga gataggtgcc tcactgatta agcattggta actgtcagac caagtttact  1080
catatatact ttagattgat ttaaaacttc atttttaatt taaaaggatc taggtgaaga  1140
tcctttttga taatctcatg accaaaatcc cttaacgtga gttttcgttc cactgagcgt  1200
cagaccccgt agaaaagatc aaaggatctt cttgagatcc ttttttttctg cgcgtaatct  1260
gctgcttgca aacaaaaaaa ccaccgctac cagcggtggt ttgtttgccg gatcaagagc  1320
taccaactct ttttccgaag gtaactggct tcagcagagc gcagatacca aatactgtcc  1380
ttctagtgta gccgtagtta ggccaccact tcaagaactc tgtagcaccg cctacatacc  1440
tcgctctgct aatcctgtta ccagtggctg ctgccagtgg cgataagtcg tgtcttaccg  1500
ggttggactc aagacgatag ttaccggata aggcgcagcg gtcgggctga acggggggtt  1560
cgtgcacaca gcccagcttg gagcgaacga cctacaccga actgagatac ctacagcgtg  1620
agcattgaga aagcgccacg cttcccgaag ggagaaaggc ggacaggtat ccggtaagcg  1680
gcagggtcgg aacaggagag cgcacagggg agcttccagg gggaaacgcc tggtatcttt  1740
atagtcctgt cgggtttcgc cacctctgac ttgagcgtcg attttgtga tgctcgtcag  1800
gggggcggag cctatggaaa aacgccagca acgcggcctt tttacggttc ctggcctttt  1860
gctggccttt tgctcacatg ttctttcctg cgttatcccc tgattctgtg ataaccgta  1920
```

```
ttaccgcctt tgagtgagct gataccgctc gccgcagccg aacgaccgag cgcagcgagt    1980
cagtgagcga ggaagcggaa gagcgcccaa tacgcaaacc gcctctcccc gcgcgttggc    2040
cgattcatta atgcagctgg cacgacaggt ttcccgactg gaaagcgggc agtgagcgca    2100
acgcaattaa tgtgagttac ctcactcatt aggcacccca ggctttacac tttatgcttc    2160
cggctcgtat gttgtgtgga attgtgagcg gataacaatt tcacacagga acagctatg     2220 accatgatta cgccaagctc ggaattaacc ctcactaaag ggaacaaaag cttgcatgcc    2280
tgcagaatta aaagttagtg aacaagaaaa cagtgaagca ccagtttctg aaccaaaaga    2340
agacgaaaaa acaaaaaaag attaagcaat ttatttggaa atctttttt tgttttttta     2400 agaaatattt attgttttt ttaaaaaatt atgtacaatt gctactataa gggaagaaa      2460 aaaagaaaga tataaattgt ataaagtagg gttagaagca attaataatt attattaatg    2520
ttatttttct cttatatatt caatgtaatt ttaattacat ttgcttttaa taaaaacact    2580
acttaataga gaaaggaaat ataagatcct ttgaatggag gaaaatcaca tgaaaattat    2640
taatattgga gttttagctc atgttgatgc aggaaaaact accttaacag aaagcttatt    2700
atataacagt ggagcgatta cagaattagg aagcgtggac aaaggtacaa cgaggacgga    2760
taatacgctt ttagaacgtc agagaggaat tacaattcag acaggaataa cctcttttca    2820
gtgggaaaat acgaaggtga acatcataga cacgccagga catatggatt tcttagcaga    2880
agtatatcgt tcattatcag ttttagatgg ggcaattcta ctgatttctg caaaagatgg    2940
cgtacaagca caaactcgta tattatttca tgcacttagg aaaatgggga ttcccacaat    3000
cttttttatc aataagattg accaaaatgg aattgattta tcaacggttt atcaggatat    3060
taaagagaaa ctttctgccg aaattgtaat caaacagaag gtagaactgt atcctaatgt    3120
gtgtgtgacg aactttaccg aatctgaaca atgggatacg gtaatagagg gaacgatga    3180 ccttttagag aaatatatgt ccggtaaatc attagaagca ttggaactcg aacaagagga    3240
aagcataaga tttcagaatt gttctctgtt ccctctttat catggaagtg caaaaagtaa    3300
tatagggatt gataacctta tagaagttat tactaataaa ttttattcat caacacatcg    3360
aggtccgtct gaactttgcg gaaatgtttt caaaattgaa tatacaaaaa aaagacaacg    3420
tcttgcatat atacgccttt atagtggagt actacattta cgagattcgg ttagagtatc    3480
agaaaaggaa aaaataaaag ttacagaaat gtatacttca ataaatggtg aattatgtaa    3540
gattgataga gcttattctg gagaaattgt tattttgcaa aatgagtttt tgaagttaaa    3600
tagtgttctt ggagatacaa aactattgcc acagagaaaa aagattgaaa atccgcaccc    3660
tctactacaa acaactgttg aaccgagtaa acctgaacag agagaaatgt tgcttgatgc    3720
ccttttggaa atctcagata gtgatccgct tctacgatat tacgtggatt ctacgacaca    3780
tgaaattata ctttctttct tagggaaagt acaaatggaa gtgattagtg cactgttgca    3840
agaaaagtat catgtggaga tagaaataac agagcctaca gtcatttata tggagagacc    3900
gttaaaaaat gcagaatata ccattcacat cgaagtgccg ccaaatcctt tctgggcttc    3960
cattggtcta tctgtatcac cgcttccgtt gggaagtgga atgcagtatg agagctcggt    4020
ttctcttgga tacttaaatc aatcatttca aaatgcagtt atggaaggga tacgctatgg    4080
ttgtgaacaa ggattgtatg gttggaatgt gacggactgt aaaatctgtt ttaagtatgg    4140
cttatactat agccctgtta gtaccccagc agatttcggg atgcttgctc ctattgtatt    4200
ggaacaagtc ttaaaaaaag ctggaacaga attgttagag ccatatctta gttttaaaat    4260
ttatgcgcca caggaatatc tttcacgagc atacaacgat gctcctaaat attgtgcgaa    4320
```

```
catcgtagac actcaattga aaaataatga ggtcattctt agtggagaaa tccctgctcg    4380
gtgtattcaa gaatatcgta gtgatttaac tttctttaca aatggacgta gtgtttgttt    4440
aacagagtta aaagggtacc atgttactac cggtgaacct gtttgccagc cccgtcgtcc    4500
aaatagtcgg atagataaag tacgatatat gttcaataaa ataacttagt gtaatttaag    4560
ttgttatata aagatctgaa ctgcaggtcg actctagagg atcctcaatt actttagctg    4620
cttttgataa attatctaat aaaactattc tatttattga aaaattcata attactcctt    4680
ttttaaaaca aattgttttt actttatttt agaaaataat tgggtttgtt atatattact    4740
atttctaata cttatttcta aattattaat attatgaggt taatttgtgg ataactgtta    4800
ataagttagg tttaaatagc tatttttatt attttgttaa aattttgttc ttcaaaatat    4860
caacagtctt ttttaattgc ttatcttttt ttaacattgt ttctattttt ctttcagcat    4920
taataactgt tgtgtgatct ctaccaccaa attcttctcc aatttgagct aaagtgtgat    4980
ttaaaatctc ttttgttaaa aacattgcta tatgtcttgc tgttacaatt gacttacttc    5040
tagcctttcc atcaatagca ttaactgaaa taccatattt ttcactaaca acttctttaa    5100 ttttttttaac atttaaaata cctaattttg aagtaggtat atctctaaat agatcagaaa    5160
ttatttctat agtaataatt ttttcttctg gattttgttg agatcaaaag tttaatcttg    5220
aaacacttcc tttaattttt ctaacatcat ctgaataata attagaaata aaattaattg    5280
cttcactagt tacttctgat ttaatatttt gatttttaat ttctttttta atgatagctg    5340 ttgctgttttt attatctagt ttttgaatag caatacttaa tcccatatta aatctagtaa    5400
ttaatctatt atcaaaacca tttaataatt caggagattt atcacttgaa aaaaacaatt    5460
gtttatcatt ttctataaag ttattaaaaa tagtaaaaaa tatttcatta gttttttctt    5520
tataacttaa aaattgaaca tcatcaataa ttaatacatc attttgacat acttcatttt    5580
taaattgctc aatctctttta tgagtttttt gtaatatatc aactgctttt cttgcaaact    5640
catcaccact catataacta acttttagat cagaaaatt agattcaata tagttttttg    5700
cagcttttag taaatgagtt tttcccattc cagattcacc ataaataaac aatggattat    5760
aagaaattcc agggtttttg cttgctgttt gaactgctat aaaagcttgt tcattacttg    5820
caccaattac aaaattttca aatgtgtttt cattaatttt tttaacttttt ttagtaatga    5880 tatcagaatg atctttatta attagttcat cttttttctag ttgttttta tattcttgtt    5940 cgtatgtaaa actaatattt acaggttctt ttaaaatatt tttatctca ttttcaatag    6000 tttgacgaaa ctgtttttata gctaacaaac caaattgtga tttaacaaca acaatataat    6060
cagaaatccc ctttttatga atatttattg tctttatata gtcgttatac acggattcat    6120 caatatttttt attagccatt aaacttagtt taagttctttt taaaatatcg tttacgttca    6180
tatttgtctc caaaaatatt atagttaaac acttgttaaa aatgtggaaa acgtggaaaa    6240
aatccttata acatagatat attaacaaat taacaaattc taaaatctta tttttaatggt    6300 gttattttat agttatcaac ttatcaacaa ttaactaaca tttttgttag taatttgtag    6360
ttttatctac atttgattga gaagctaaaa tttaagttta taagtgtatt tttaaagcaa    6420
aatattatat aattaggtgt gaattattta ttttttttgta aaggaggtag tggtatgaaa    6480
agaacttgac aaccatcaaa actaaaacat gcaggtgttc atggatttag agcaagaatg    6540
gctaggatcc ccgggtaccg agctcgaatt cgccctatag tgagtcgtat tacaattcac    6600
tggccgtcgt tttacaacgt cgtgactggg aaaaccctgg cgttacccaa cttaatcgcc    6660
```

-continued

| | |
|---|---|
| ttgcagcaca tcccccttc gccagctggc gtaatagcga agaggcccgc accgatcgcc | 6720 |
| cttcccaaca gttgcgtagc ctgaatggcg aatggcgcga cgcgccctgt agcggcgcat | 6780 |
| taagcgcggc gggtgtggtg gttacgcgca gcgtgaccgc tacacttgcc agcgccctag | 6840 |
| cgcccgctcc tttcgctttc ttcccttcct ttctcgccac gttcgccggc tttccccgtc | 6900 |
| aagctctaaa tcggggctc cctttagggt tccgatttag tgctttacgg cacctcgacc | 6960 |
| ccaaaaaact tgattagggt gatggttcac gtagtgggcc atcgccctga tagacggttt | 7020 |
| ttcgcccttt gacgttggag tccacgttct ttaatagtgg actcttgttc caaactggaa | 7080 |
| caacactcaa ccctatctcg gtctattctt ttgatttata agggattttg ccgatttcgg | 7140 |
| cctattggtt aaaaaatgag ctgatttaac aaaaatttaa cgcgaatttt aacaaaatat | 7200 |
| taacgtttac aatttcctga tgcggtattt tctccttacg catctgtgcg gtatttcaca | 7260 |
| ccgcatatgg tgcactctca gtacaatctg ctctgatgcc gcatagttaa gccagccccg | 7320 |
| acacccgcca cacccgctg acgcgccctg acgggcttgt ctgctcccgg catccgctta | 7380 |
| cagacaagct gtgaccgtct ccgggagctg catgtgtcag aggttttcac cgtcatcacc | 7440 |
| gaaacgcgcg a | 7451 |

<210> SEQ ID NO 150
<211> LENGTH: 7473
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 150

| | |
|---|---|
| gacgaaaggg cctcgtgata cgcctatttt tataggttaa tgtcatgata ataatggttt | 60 |
| cttagacgtc aggtggcact tttcggggaa atgtgcgcgg aacccctatt tgtttatttt | 120 |
| tctaaataca ttcaaatatg tatccgctca tgagacaata accctgataa atgcttcaat | 180 |
| aatattgaaa aaggaagagt atgagtattc aacatttccg tgtcgccctt attccctttt | 240 |
| ttgcggcatt ttgccttcct gttttttgctc acccagaaac gctggtgaaa gtaaaagatg | 300 |
| ctgaagatca gttgggtgca cgagtgggtt acatcgaact ggatctcaac agcggtaaga | 360 |
| tccttgagag ttttcgcccc gaagaacgtt ttccaatgat gagcactttt aaagttctgc | 420 |
| tatgtggcgc ggtattatcc cgtattgacg ccgggcaaga gcaactcggt cgccgcatac | 480 |
| actattctca gaatgacttg gttgagtact caccagtcac agaaaagcat cttacggatg | 540 |
| gcatgacagt aagagaatta tgcagtgctg ccataaccat gagtgataac actgcggcca | 600 |
| acttacttct gacaacgatc ggaggaccga aggagctaac cgcttttttg cacaacatgg | 660 |
| gggatcatgt aactcgcctt gatcgttggg aaccggagct gaatgaagcc ataccaaacg | 720 |
| acgagcgtga ccaccgatg cctgtagcaa tggcaacaac gttgcgcaaa ctattaactg | 780 |
| gcgaactact tactctagct tcccggcaac aattaataga ctggatggag gcggataaag | 840 |
| ttgcaggacc acttctgcgc tcggcccttc cggctggctg gtttattgct gataaatctg | 900 |
| gagccggtga gcgtgggtct cgcggtatca ttgcagcact ggggccagat ggtaagccct | 960 |
| cccgtatcgt agttatctac acgacgggga gtcaggcaac tatggatgaa cgaaatagac | 1020 |
| agatcgctga gataggtgcc tcactgatta agcattggta actgtcagac caagtttact | 1080 |
| catatatact ttagattgat ttaaaacttc attttaatt taaaaggatc taggtgaaga | 1140 |
| tcctttttga taatctcatg accaaaatcc cttaacgtga gttttcgttc cactgagcgt | 1200 |

```
cagaccccgt agaaaagatc aaaggatctt cttgagatcc ttttttttctg cgcgtaatct    1260 gctgcttgca aacaaaaaaa ccaccgctac cagcggtggt ttgtttgccg gatcaagagc    1320
taccaactct ttttccgaag gtaactggct tcagcagagc gcagatacca aatactgtcc    1380
ttctagtgta gccgtagtta ggccaccact tcaagaactc tgtagcaccg cctacatacc    1440
tcgctctgct aatcctgtta ccagtggctg ctgccagtgg cgataagtcg tgtcttaccg    1500
ggttggactc aagacgatag ttaccggata aggcgcagcg gtcgggctga acggggggtt    1560
cgtgcacaca gcccagcttg gagcgaacga cctacaccga actgagatac ctacagcgtg    1620
agcattgaga aagcgccacg cttcccgaag ggagaaaggc ggacaggtat ccggtaagcg    1680
gcagggtcgg aacaggagag cgcacgaggg agcttccagg gggaaacgcc tggtatcttt    1740
atagtcctgt cgggtttcgc cacctctgac ttgagcgtcg attttgtga tgctcgtcag    1800 gggggcggag cctatggaaa aacgccagca acgcggcctt tttacggttc ctggccttt    1860 gctggccttt tgctcacatg ttctttcctg cgttatcccc tgattctgtg gataaccgta    1920
ttaccgcctt tgagtgagct gataccgctc gccgcagccg aacgaccgag cgcagcgagt    1980
cagtgagcga ggaagcggaa gagcgcccaa tacgcaaacc gcctctcccc gcgcgttggc    2040
cgattcatta atgcagctgg cacgacaggt ttcccgactg gaaagcgggc agtgagcgca    2100
acgcaattaa tgtgagttac ctcactcatt aggcacccca ggctttacac tttatgcttc    2160
cggctcgtat gttgtgtgga attgtgagcg gataacaatt tcacacagga aacagctatg    2220
accatgatta cgccaagctc ggaattaacc ctcactaaag ggaacaaaag cttgcatgcc    2280
tgcagttcag atctttatat aacaacttaa attcactaa gttatttat tgaacatata    2340 tcgtacttta tctatccgac tatttggacg acggggctgg caaacaggtt caccggtagt    2400
aacatggtac cctttaact ctgttaaaca aacactacgt ccatttgtaa agaaagttaa    2460
atcactacga tattcttgaa tacaccgagc agggatttct ccactaagaa tgacctcatt    2520 attttttcaat tgagtgtcta cgatgttcgc acaatattta ggagcatcgt tgtatgctcg    2580
tgaaagatat tcctgtggcg cataaatttt aaaactaaga tatggctcta acaattctgt    2640
tccagctttt tttaagactt gttccaatac aataggagca agcatccgaa aatctgctgg    2700
ggtactaaca gggctatagt ataagccata cttaaaacag attttacagt ccgtcacatt    2760
ccaaccatac aatccttgtt cacaaccata gcgtatccct tccataactg cattttgaaa    2820
tgattgattt aagtatccaa gagaaaccga gctctcatac tgcattccac ttcccaacgg    2880
aagcggtgat acagatagac caatggaagc ccagaaagga tttggcggca cttcgatgtg    2940
aatggtatat tctgcatttt ttaacggtct ctccatataa atgactgtag gctctgttat    3000
ttctatctcc acatgatact tttcttgcaa cagtgcacta atcacttcca tttgtacttt    3060
ccctaagaaa gaaagtataa tttcatgtgt cgtagaatcc acgtaatatc gtagaagcgg    3120
atcactatct gagatttcca aaagggcatc aagcaacatt tctctctgtt caggtttact    3180
cggttcaaca gttgttgta gtagagggtg cggattttca atcttttttc tctgtggcaa    3240
tagttttgta tctccaagaa cactatttaa cttcaaaaac tcattttgca aaataacaat    3300
ttctccagaa taagctctat caatcttaca taattcacca tttattgaag tatacatttc    3360
tgtaactttt attttttcct tttctgatac tctaaccgaa tctcgtaaat gtagtactcc    3420
actataaagg cgtatatatg caagacgttg tctttttttt gtatattcaa ttttgaaaac    3480
atttccgcaa agttcagacg gacctcgatg tgttgatgaa taaaatttat tagtaataac    3540
ttctataagg ttatcaatcc ctatattact ttttgcactt ccatgataaa gagggaacag    3600
```

```
agaacaattc tgaaatctta tgctttcctc ttgttcgagt tccaatgctt ctaatgattt   3660
accggacata tatttctcta aaaggtcatc gtttccctct attaccgtat cccattgttc   3720
agattcggta aagttcgtca cacacacatt aggatacagt tctaccttct gtttgattac   3780
aatttcggca gaaagtttct ctttaatatc ctgataaacc gttgataaat caattccatt   3840
ttggtcaatc ttattgataa aaagattgt gggaatcccc attttcctaa gtgcatgaaa    3900
taatatacga gtttgtgctt gtacgccatc ttttgcagaa atcagtagaa ttgccccatc   3960
taaaactgat aatgaacgat atacttctgc taagaaatcc atatgtcctg cgtgtctat   4020
gatgttcacc ttcgtatttt cccactgaaa agaggttatt cctgtctgaa ttgtaattcc   4080
tctctgacgt tctaaaagcg tattatccgt cctcgttgta cctttgtcca cgcttcctaa   4140
ttctgtaatc gctccactgt tatataataa gctttctgtt aaggtagttt ttcctgcatc   4200
aacatgagct aaaactccaa tattaataat tttcatgtga ttttcctcca ttcaaaggat   4260
cttatatttc ctttctctat taagtagtgt ttttattaaa agcaaatgta attaaaatta   4320
cattgaatat ataagagaaa aataacatta ataataatta ttaattgctt ctaaccctac   4380
tttatacaat ttatatcttt ctttttttct ttcccttata gtagcaattg tacataattt   4440
tttaaaaaaa acaataaata tttcttaaaa aaacaaaaaa agattttcca aataaattgc   4500
ttaatctttt tttgttttt cgtcttcttt tggttcagaa actggtgctt cactgttttc    4560
ttgttcacta acttttaatt ctgcaggtcg atattttaca aaaatttgct tattatgaaa   4620
ttttattact ttccacaata aaaaatgatt tacaccataa aatgttaata atgtggaaaa   4680
caataaaaat attcaataaa aacaatgctt ttaaagaaaa tataaaaaat atttaatgtg   4740
gaaaaatatt aatttttatt aattttactc attttttagt acttttccac atcttttatt   4800
tataattaat aacgataaaa actattggag atgaaattaa tgaacacaaa agaattatga   4860
attgaagtta aagaaatatt atctcgtgat gaatcagttt ccccagaaat ttataactac   4920
tatattagtg acacaaactt atatactgta tctgataata actgcttaat tacaacaaaa   4980
tcagaaattg caattggtgt ttttgaagca ggattaaatg aaaaaattaa aaatatctta   5040
aaaaaactaa ctggaatcca atataatatt tcatttgaat tagaaaaaaa tatcaataag   5100
caagcatctg taattagtaa aattgacaca ttaacagaaa acaataaccct tgcttactat   5160
gaaaattata cttttgaaaa ttttgttcgt ggtgattcta atcacgaagc aatgcaagca   5220
gctttagcag ttgctttaga tcttggaaaa aaatgaaatc cattattcat atatggagac   5280
tctggactag gaaaaacaca tctattacat gcaattgaaa ataaggtaaa tgaaatttat   5340
aaaacaaata accgagtaaa atatttaaaa gctgatgagt ttggaaaaat tgctatggat   5400
atttaaaacc aaggccatga aattattgaa gcttttaaaa catcttatga catttacgat   5460
tgtttattaa ttgatgatat acaattatta gcaaaacgaa ataaaacaaa tgaattattt   5520
tttcatattt ttaactcata tattgaaaaa aataaacaaa ttgtaattac ttctgataaa   5580
tatcctgatg atctaggcgg ttttgaagct agaattattt ctcgtttttc atatggttta   5640
agtattggct tagattcacc agattttgaa acagcactta aaatattaga acaaaaacta   5700
aaacatcaaa ataacttagg attattttca gaagaatcac tagaatttat tgctttaaat   5760
tttaacagtg atgttagaaa gttagaagga gcaattaaac gattattatt tttagctgtt   5820
atgaacaaaa aaccaaatga aattattaca ttagctgatg ttgaaaaggc atttaaaaat   5880
gccccccctgc aaaataatga aaaaattacc cctaaaaaaa ttaaacaaat tgttgctgac   5940
```

| | |
|---|---|
| agttacaata ttactatcaa agcaatgatg agtaaatcac gagttagtaa tgttatgcaa | 6000 |
| gcacgacaat tagcaatgta tttttgtaga acattactag atgaaccatt tacaaggatt | 6060 |
| ggaacagagt tcggtggcaa agaccacaca actgtgatga atagtgttaa aaaagttgaa | 6120 |
| gcacacatta gtacaaacaa agaatttaaa catttagtaa atgcaattcg tagaaaaatt | 6180 |
| gaaggaagat agcacattat tttccacgat tgttttttaa taaaaataa tattattcaa | 6240 |
| aactttatca agttttccac attttctaca atataatact aataaataaa aacaatatt | 6300 |
| ttaacaatgg tatataatta tttatatatt acagaatata ctaaagtaag gagtaaaaaa | 6360 |
| aatgattgta acattaaaa gagataagat attagatgaa ttattgaaag taagtcggat | 6420 |
| aatttctcaa aagactttaa ttccttcatt attgggaatt ttaattgaag ttaaaaaga | 6480 |
| caaaattact tttactactt ctgatggtga tacatcaatt aaatcagaaa ttatgggcaa | 6540 |
| tgatttaaac attactcgac tctagaggat ccccgggtac cgagctcgaa ttcgccctat | 6600 |
| agtgagtcgt attacaattc actggccgtc gttttacaac gtcgtgactg ggaaaaccct | 6660 |
| ggcgttaccc aacttaatcg ccttgcagca catcccccct cgccagctg gcgtaatagc | 6720 |
| gaagaggccc gcaccgatcg cccttcccaa cagttgcgta gcctgaatgg cgaatggcgc | 6780 |
| gacgcgccct gtagcggcgc attaagcgcg gcgggtgtgg tggttacgcg cagcgtgacc | 6840 |
| gctacacttg ccagcgccct agcgcccgct cctttcgctt tcttcccttc ctttctcgcc | 6900 |
| acgttcgccg gctttccccg tcaagctcta atcgggggc tcccttagg gttccgattt | 6960 |
| agtgctttac ggcacctcga ccccaaaaaa cttgattagg gtgatggttc acgtagtggg | 7020 |
| ccatcgccct gatagacggt ttttcgccct ttgacgttgg agtccacgtt ctttaatagt | 7080 |
| ggactcttgt tccaaactgg aacaacactc aaccctatct cggtctattc ttttgattta | 7140 |
| taagggattt tgccgatttc ggcctattgg ttaaaaaatg agctgattta acaaaaattt | 7200 |
| aacgcgaatt ttaacaaaat attaacgttt acaatttcct gatgcggtat tttctcctta | 7260 |
| cgcatctgtg cggtatttca caccgcatat ggtgcactct cagtacaatc tgctctgatg | 7320 |
| ccgcatagtt aagccagccc cgacacccgc caacacccgc tgacgcgccc tgacgggctt | 7380 |
| gtctgctccc ggcatccgct tacagacaag ctgtgaccgt ctccgggagc tgcatgtgtc | 7440 |
| agaggttttc accgtcatca ccgaaacgcg cga | 7473 |

<210> SEQ ID NO 151
<211> LENGTH: 9517
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 151

| | |
|---|---|
| gacgaaaggg cctcgtgata cgcctatttt tataggttaa tgtcatgata ataatggttt | 60 |
| cttagacgtc aggtggcact tttcggggaa atgtgcgcgg aacccctatt tgtttatttt | 120 |
| tctaaataca ttcaaatatg tatccgctca tgagacaata accctgataa atgcttcaat | 180 |
| aatattgaaa aaggaagagt atgagtattc aacatttccg tgtcgccctt attcccttt | 240 |
| ttgcggcatt ttgccttcct gttttgctc acccagaaac gctggtgaaa gtaaaagatg | 300 |
| ctgaagatca gttgggtgca cgagtgggtt acatcgaact ggatctcaac agcggtaaga | 360 |
| tccttgagag ttttcgcccc gaagaacgtt ttccaatgat gagcactttt aaagttctgc | 420 |
| tatgtggcgc ggtattatcc cgtattgacg ccgggcaaga gcaactcggt cgccgcatac | 480 |

```
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc atttttaatt taaaaggatc taggtgaaga   1140
tcctttttga taatctcatg accaaaatcc cttaacgtga gttttcgttc cactgagcgt   1200
cagaccccgt agaaaagatc aaaggatctt cttgagatcc ttttttttctg cgcgtaatct   1260 gctgcttgca acaaaaaaa ccaccgctac cagcggtggt ttgtttgccg gatcaagagc   1320
taccaactct tttttccgaag gtaactggct tcagcagagc gcagatacca aatactgtcc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga cggggggtt    1560 cgtgcacaca gcccagcttg gagcgaacga cctacaccga actgagatac ctacagcgtg   1620
agcattgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg attttttgtga tgctcgtcag   1800 gggggcggag cctatggaaa aacgccagca acgcggcctt tttacggttc ctggccttt    1860 gctggccttt tgctcacatg ttctttcctg cgttatcccc tgattctgtg ataaccgta    1920 ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttac ctcactcatt aggcacccca ggctttacac tttatgcttc   2160
cggctcgtat gttgtgtgga attgtgagcg gataacaatt tcacacagga aacagctatg   2220
accatgatta cgccaagctc ggaattaacc ctcactaaag ggaacaaaag cttgcatgcc   2280
tgcagcggcc gcattgcatc aacgcatata gcgctagatt attgaagcat ttatcagggt   2340
tattgtctca tgagcggata catatttgaa tgtatttaga aaataaaca aataggggtt   2400 ccgcgcacat ttccccgaaa agtgccacct gacggatcgc ttgcctgtaa cttcacgcg    2460 cctcgtatct tttaatgatg gaataatttg gaatttact ctgtgtttat ttatttttat    2520
gttttgtatt tggattttag aaagtaaata aagaaggtag aagagttacg gaatgaagaa   2580
aaaaaaataa acaaggtttt aaaaaatttc aacaaaaagc gtactttaca tatatattta   2640
ttagacaaga aaagcagatt aaatagatat acattcgatt aacgataagt aaaatgtaaa   2700
atcacaggat tttcgtgtgt ggtcttctac acagacaaga tgaaacaatt cggcattaat   2760
acctgagagc aggaagagca agataaaagg tagtattttat tggcgatccc cctagagtct   2820
tttacatctt cggaaaacaa aaactatttt ttctttaatt tctttttttta ctttctattt   2880
```

```
ttaatttatg tatttatatt aaaaaattta aattataatt attttttatag cacgtgatga   2940
aaaggaccct aagaaaccat tattatcatg acattaacct ataaaaatag gcgtatcacg   3000
aggcccttc gtctcgcgcg tttcggtgat gacggtgaaa acctctgaca catgcagctc    3060
ccggagacgg tcacagcttg tccgtaagcg gatgccggga gcagacaagc ccgtcagggc   3120
gcgtcagcgg gtgttggcgg gtgtcggggc tggcttaact atgcggcatc agagcagatt   3180
gtactgagag tgcaccataa attcccgttt taagagcttg gtgagcgcta ggagtcactg   3240
ccaggtatcg tttgaacacg gcattagtca gggaagtcat aacacagtcc tttcccgcaa   3300
tttcttttt ctattactct tggcctcctc tagtacactc tatattttt tatgcctcgg     3360
taatgatttt catttttttt tccacctagc ggatgactct tttttttct tagcgattgg    3420
cattatcaca taatgaatta tacattatat aaagtaatgt gatttcttcg aagaatatac   3480
taaaaaatga gcaggcaaga taaacgaagg caaagatgac agagcagaaa gccctagtaa   3540
agcgtattac gaatgaaacc aagattcaga ttgcgatctc tttaaagggt ggtcccctag   3600
cgatagagca ctcgatcttc ccagaaaaag aggcagaagc agtagcagaa caggccacac   3660
gatcgcaagt gattaacgtc cacacaggta tagggtttct ggaccatatg atacatgctc   3720
tggccaagca ttccggctgg tcgctaatcg ttaagtgcat tggtgactta cacatagacg   3780
accatcacac cactgaagac tgcgggattg ctctcggtca agcttttaaa gaggccctag   3840
gggccgtgcg tggagtaaaa aggtttggat caggatttgc gcctttggat gaggcacttt   3900
ccagagcggt ggtagatctt tcgaacaggc cgtacgcagt tgtcgaactt ggtttgcaaa   3960
gggagaaagt aggagatctc tcttgcgaga tgatcccgca ttttcttgaa agctttgcag   4020
aggctagcag aattaccctc cacgttgatt gtctgcgagg caagaatgat catcaccgta   4080
gtgagagtgc gttcaaggct cttgcggttg ccataagaga agccacctcg cccaatggta   4140
ccaacgatgt tccctccacc aaaggtgttc ttatgtagtg acaccgatta tttaaagctg   4200
cagcatacga tatatataca tgtgtatata tgtataccta tgaatgtcag taagtatgta   4260
tacgaacagt atgatactga agatgacaag gtaatgcatc attctatacg tgtcattctg   4320
aacgaggcgc gctttccttt tttcttttg cttttctttt tttttctct tgaactcgac    4380
ggatctatgc ggtgtgaaat accgcacaga tgcgtaagga gaaataccg catcaggaaa   4440
ttgtaagcgt taatctagca gcacgccata gtgactggcg atgctgtcgg aatggacgat   4500
atcccgcaag aggcccggca gtaccggcat aaccaagcct atgcctacgg catccagggt   4560
gacggtgccg aggatgacga tgagcgcatt gttagatttc atacacggtg cctgactgcg   4620
ttagcaattt atgcagaatt aaaagttagt gaacaagaaa acagtgaagc accagtttct   4680
gaaccaaaag aagacgaaaa aacaaaaaaa gattaagcaa tttatttgga aaatcttttt   4740
ttgttttttt aagaaatatt tattgttttt tttaaaaaat tatgtacaat tgctactata   4800
agggaaagaa aaaagaaag atataaattg tataagtag ggttagaagc aattaataat    4860
tattattaat gttatttttc tcttatatat tcaatgtaat tttaattaca tttgctttta   4920
ataaaaacac tacttaatag agaaaggaaa tataagatct atgactgaat ataaccctac   4980
tgttagatta gctactagag atgatgttcc tagagctgtt agaactttag ctgctgcttt   5040
tgctgattat cctgctacta gacatactgt tgatcctgat agacatattg aaagagttac   5100
tgaattacaa gaattatttt taactagagt tggtttagat attggtaaag tttgggttgc   5160
tgatgatggt gctgctgttg ctgtttggac tactcctgaa agtgttgaag ctggtgctgt   5220
```

```
ttttgctgaa attggtccta gaatggctga attaagtggt agtagattag ctgctcaaca    5280
acaaatggaa ggtttattag ctcctcatag acctaaagaa cctgcttggt ttttagctac    5340
tgttggtgtt agtcctgatc atcaaggtaa aggtttaggt agtgctgttg ttttacctgg    5400
tgttgaagct gctgaaagag ctggtgttcc tgctttttta gaaactagtg ctcctagaaa    5460 tttaccttt tatgaaagat taggttttac tgttactgct gatgttgaag ttcctgaagg    5520
tcctagaact tggtgtatga ctagaaaacc tggtgcttaa agatctaaat taaagttggt    5580
tcattcaaag ttacaattcg tttaaaaagt gaataattaa ttattaatta atttattaaa    5640
aaacaaccaa aaggttgttt tttattttt aaaggatctg aactgcatgc aggtcgatat    5700
tttacaaaaa tttgcttatt atgaaatttt attactttcc acaataaaaa atgatttaca    5760
ccataaaatg ttaataatgt ggaaaacaat aaaaatattc aataaaaaca atgcttttaa    5820
agaaaatata aaaaatattt aatgtggaaa atattaatt tttattaatt ttactcattt    5880
tttagtactt ttccacatct tttatttata attaataacg ataaaaacta ttggagatga    5940
aattaatgaa cacaaaagaa ttatgaattg aagttaaaga aatattatct cgtgatgaat    6000
cagtttcccc agaaatttat aactactata ttagtgacac aaacttatat actgtatctg    6060
ataataactg cttaattaca acaaaatcag aaattgcaat tggtgttttt gaagcaggat    6120
taaatgaaaa aattaaaaat atcttaaaaa aactaactgg aatccaatat aatatttcat    6180
ttgaattaga aaaaaatatc aataagcaag catctgtaat tagtaaaatt gacacattaa    6240
cagaaaacaa taaccttgct tactatgaaa attatacttt tgaaaatttt gttcgtggtg    6300
attctaatca cgaagcaatg caagcagctt tagcagttgc tttagatctt ggaaaaaaat    6360
gaaatccatt attcatatat ggagactctg gactaggaaa aacacatcta ttacatgcaa    6420
ttgaaaataa ggtaaatgaa atttataaaa caaataaccg agtaaaatat ttaaaagctg    6480
atgagtttgg aaaaattgct atggatattt taaccaagg ccatgaaatt attgaagctt    6540
ttaaaacatc ttatgacatt tacgattgtt tattaattga tgatatacaa ttattagcaa    6600
aacgaaataa aacaaatgaa ttatttttc atattttaa ctcatatatt gaaaaaaata    6660
aacaaattgt aattacttct gataaatatc ctgatgatct aggcggtttt gaagctagaa    6720
ttatttctcg ttttttcatat ggtttaagta ttggcttaga ttcaccagat tttgaaacag    6780
cacttaaaat attagaacaa aaactaaaac atcaaaataa cttaggatta ttttcagaag    6840
aatcactaga atttattgct ttaaatttta acagtgatgt tagaaagtta gaaggagcaa    6900
ttaaacgatt attattttta gctgttatga acaaaaaacc aaatgaaatt attacattag    6960
ctgatgttga aaaggcattt aaaaatgccc ccctgcaaaa taatgaaaaa attacccta    7020 aaaaaattaa acaaattgtt gctgacagtt acaatattac tatcaaagca atgatgagta    7080
aatcacgagt tagtaatgtt atgcaagcac gacaattagc aatgtatttt tgtagaacat    7140
tactagatga accatttaca aggattggaa cagagttcgg tggcaaagac cacacaactg    7200
tgatgaatag tgttaaaaaa gttgaagcac acattagtac aaacaaagaa tttaaacatt    7260
tagtaaatgc aattcgtaga aaaattgaag gaagatagca cattatttc cacgattgtt    7320 ttttaataaa aaataatatt attcaaaact ttatcaagtt ttccacattt tctacaatat    7380
aatactaata aataaaaaac aatatttaa caatggtata aattattta tatattacag    7440 aatatactaa agtaaggagt aaaaaaaatg attgtaaaca ttaaagaga taagatatta    7500 gatgaattat tgaaagtaag tcggataatt tctcaaaaga ctttaattcc ttcattattg    7560
ggaattttaa ttgaagttaa aaaagacaaa attacttta ctacttctga tggtgataca    7620
```

```
tcaattaaat cagaaattat gggcaatgat ttaaacatta ctcgactcta gactaatgtt    7680
caattggatg atatagtaaa taatagccca caaaatcata aagaagcagg atttacaaaa    7740
ggttggtcta gtagatttga tacttggtat aaactatgta aagaatttgg tttcatatat    7800
tatgatatga ataaaaaaat tgaagtatca tcaagtggtc atatgttatg tgatgcatat    7860
ttagcaaatt ccaaaaatga ggacttagat aattcgggta aaaggataca aaaaatattt    7920
ctcaatgcat tgatgaaata ccaaacaaat aatccattta gaagaaatct aaatcaaaat    7980
tcaccaatac ctctattatt aaacgtatta aatttattat ctttaaactc acgttctaca    8040
ggattacaca gaagagagat accttttta atgtgttgag aaaataatga ttataaacaa    8100
ttatatgaat ttatcattaa ttttagaaat aagtatggat ttaaagcaag tgatgaaatt    8160
atttatgaag aatgtttaaa attattaaaa agctctaata agaagcgatt caaaatgagt    8220
caaataatga agaaagtgt tgatgattt attagaaaac taagaataac tggaatattt     8280
tctttacgtg gtttaggaag atttgttgac ataaacaaat tagaaataga gtcagttgat    8340
tatataatta aaaattatac aaaatacaat attttagta atgaatatga tttttataaa     8400
tatatgtctg aaatagatac caagatttta gaatttcaag aaatagctaa cactgaaata    8460
aataatatta gaatgaagac tctaagagaa atttctcaaa agtattctgt tgaacaaata    8520
tataaggaat taagaaattt acagttaaac aaaaactcag aagatgaata ttttaaacta    8580
attgattctc ctacaagact tgagtctaga ggatcccgg gtaccgagct cgaattcgcc     8640
ctatagtgag tcgtattaca attcactggc cgtcgtttta caacgtcgtg actgggaaaa    8700 cccctggcgtt acccaactta atcgccttgc agcacatccc ccttcgcca gctggcgtaa    8760 tagcgaagag gcccgcaccg atcgcccttc ccaacagttg cgtagcctga atggcgaatg    8820
gcgcgacgcg ccctgtagcg gcgcattaag cgcggcgggt gtggtggtta cgcgcagcgt    8880
gaccgctaca cttgccagcg ccctagcgcc cgctcctttc gctttcttcc cttcctttct    8940
cgccacgttc gccggctttc cccgtcaagc tctaaatcgg gggctccctt tagggttccg    9000
atttagtgct ttacggcacc tcgaccccaa aaaacttgat tagggtgatg gttcacgtag    9060
tgggccatcg ccctgataga cggtttttcg ccctttgacg ttggagtcca cgttctttaa    9120
tagtggactc ttgttccaaa ctggaacaac actcaaccct atctcggtct attcttttga    9180
tttataaggg attttgccga tttcggccta ttggttaaaa aatgagctga tttaacaaaa    9240
atttaacgcg aatttaaca aaatattaac gtttacaatt tcctgatgcg gtattttctc     9300
cttacgcatc tgtgcggtat ttcacaccgc atatggtgca ctctcagtac aatctgctct    9360
gatgccgcat agttaagcca gccccgacac ccgccaacac ccgctgacgc gccctgacgg    9420
gcttgtctgc tcccggcatc cgcttacaga caagctgtga ccgtctccgg gagctgcatg    9480
tgtcagaggt tttcaccgtc atcaccgaaa cgcgcga                             9517
```

<210> SEQ ID NO 152
<211> LENGTH: 74
<212> TYPE: DNA
<213> ORGANISM: Artificial Sequence
<220> FEATURE:
<223> OTHER INFORMATION: Description of Artificial Sequence: Synthetic primer

<400> SEQUENCE: 152

```
caggtggaca aaacaatgag attaactaat aaacaagaat ttgtagtgca tagggataac    60
agggtaatac ggat                                                      74
```

<210> SEQ ID NO 153
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
atcttgtcta tttaattcta aaacagggta ataactgata taattaaatt gaag        54

<210> SEQ ID NO 154
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
aatttaatta tatcagttat taccctgttt tagaattaaa tagacaagat aatgg       55

<210> SEQ ID NO 155
<211> LENGTH: 78
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
ataagtaatt ttttatttta acaatttaat aatcttcttt aacaatatct tgcactacaa   60
attcttgttt attagtta                                                 78

<210> SEQ ID NO 156
<211> LENGTH: 7477
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 156
aactacgtca ggtggcactt ttcggggaaa tgtgcgcgga acccctattt gtttattttt   60
ctaaatacat tcaaatatgt atccgctcat gagacaataa ccctgataaa tgcttcaata  120
atattgaaaa aggaagagta tgagtattca acatttccgt gtcgccctta ttcccttttt  180
tgcggcattt tgccttcctg ttttgctca cccagaaacg ctggtgaaag taaaagatgc  240
tgaagatcag ttgggtgcac gagtgggtta catcgaactg gatctcaaca gcggtaagat  300
ccttgagagt tttcgccccg aagaacgttt tccaatgatg agcactttta aagttctgct  360
atgtggcgcg gtattatccc gtgttgacgc cgggcaagag caactcggtc gccgcataca  420
ctattctcag aatgacttgg ttgagtactc accagtcaca gaaaagcatc ttacggatgg  480
catgacagta agagaattat gcagtgctgc cataaccatg agtgataaca ctgcggccaa  540
cttacttctg acaacgatcg gaggaccgaa ggagctaacc gcttttttgc acaacatggg  600
ggatcatgta actcgccttg atcgttggga accggagctg aatgaagcca taccaaacga  660
cgagcgtgac accacgatgc ctgtagcaat ggcaacaacg ttgcgcaaac tattaactgg  720
cgaactactt actctagctt cccggcaaca attaatagac tggatggagg cggataaagt  780

```
tgcaggacca cttctgcgct cggcccttcc ggctggctgg tttattgctg ataaatctgg    840
agccggtgag cgtgggtctc gcggtatcat tgcagcactg gggccagatg gtaagccctc    900
ccgtatcgta gttatctaca cgacggggag tcaggcaact atggatgaac gaaatagaca    960
gatcgctgag ataggtgcct cactgattaa gcattggtaa ctgtcagacc aagtttactc   1020
atatatactt tagattgatt taccccggtt gataatcaga aaagcccaa aaacaggaag    1080 attgtataag caaatattta aattgtaaac gttaatattt tgttaaaatt cgcgttaaat   1140
ttttgttaaa tcagctcatt ttttaaccaa taggccgaaa tcggcaaaat cccttataaa   1200
tcaaaagaat agcccgagat agggttgagt gttgttccag tttggaacaa gagtccacta   1260
ttaaagaacg tggactccaa cgtcaaaggg cgaaaaaccg tctatcaggg cgatggccca   1320
ctacgtgaac catcacccaa atcaagtttt tggggtcga ggtgccgtaa agcactaaat    1380
cggaacccta aagggagccc ccgatttaga gcttgacggg gaaagccggc gaacgtggcg   1440
agaaaggaag gaagaaagc gaaggagcg ggcgctaggg cgctggcaag tgtagcggtc     1500
acgctgcgcg taaccaccac acccgccgcg cttaatgcgc cgctacaggg cgcgtaaaag   1560
gatctaggtg aagatccttt ttgataatct catgaccaaa atcccttaac gtgagttttc   1620
gttccactga gcgtcagacc ccgtagaaaa gatcaaagga tcttcttgag atccttttt    1680 tctgcgcgta atctgctgct tgcaaacaaa aaaaccaccg ctaccagcgg tggtttgttt   1740
gccggatcaa gagctaccaa ctcttttttcc gaaggtaact ggcttcagca gagcgcagat   1800
accaaatact gtccttctag tgtagccgta gttaggccac cacttcaaga actctgtagc   1860
accgcctaca tacctcgctc tgctaatcct gttaccagtg gctgctgcca gtggcgataa   1920
gtcgtgtctt accgggttgg actcaagacg atagttaccg gataaggcgc agcggtcggg   1980
ctgaacgggg ggttcgtgca cacagcccag cttggagcga acgacctaca ccgaactgag   2040
atacctacag cgtgagctat gagaaagcgc cacgcttccc gaagggagaa aggcggacag   2100
gtatccggta gcggcagggt cggaacagga gagcgcacg agggagcttc caggggggaa    2160
cgcctggtat cttataagtc ctgtcgggtt tcgccacctc tgacttgagc gtcgattttt    2220
gtgatgctcg tcagggggc ggagcctatg gaaaaacgcc agcaacgcgg ccttttttacg   2280 gttcctggcc ttttgctggc cttttgctca catgttcttt cctgcgttat cccctgattc   2340
tgtggataac cgtattaccg cctttgagtg agctgatacc gctcgccgca gccgaacgac   2400
cgagcgcagc gagtcagtga gcgaggaagc tatggtgcac tctcagtaca atctgctctg   2460
atgccgcata gttaagccag tatacactcc gctatcgcta cgtgactggg tcatggctgc   2520
gccccgacac ccgccaacac ccgctgacgc gccctgacgg gcttgtctgc tcccggcatc   2580
cgcttacaga caagctgtga ccgtctccgg gagctgcatg tgtcagaggt tttcaccgtc   2640
atcaccgaaa cgcgcgaggc agctgcggta aagctcatca gcgtggtcgt gcagcgattc   2700
acagatgtct gcctgttcat ccgcgtccag ctcgttgagt ttctccagaa gcgttaatgt   2760
ctggcttctg ataaagcggg ccatgttaag gcggttttt tcctgtttgg tcactgatgc    2820
ctccgtgtaa gggggatttc tgttcatggg ggtaatgata ccgatgaaac gagagaggat   2880
gctcacgata cgggttactg atgatgaaca tgcccggtta ctggaacgtt gtgagggtaa   2940
acaactggcg gtatggatgc ggcgggacca gagaaaaatc actcagggtc aatgccagcc   3000
gaacgccagc aagacgtagc ccagcgcgtc ggccgccatg ccggcgataa tggcctgctt   3060
ctcgccgaaa cgtttggtgg cgggaccagt gacgaaggct tgagcgaggg cgtgcaagat   3120
tccgaatacc gcaagcgaca ggccgatcat cgtcgcgctc cagcgaaagc ggtcctcgcc   3180
```

```
gaaaatgacc cagagcgctg ccggcacctg tcctacgagt tgcatgataa agaagacagt    3240
cataagtgcg gcgacgatag tcatgccccg cgcccaccgg aaggagctga ctgggttgaa    3300
ggctctcaag ggcatcggtc gagatcccgg tgcctaatga gtgagctaac ttacattaat    3360
tgcgttgcgc tcactgcccg ctttccagtc gggaaacctg tcgtgccagc tgcattaatg    3420
aatcggccaa cgcgcgggga gaggcggttt gcgtattggg cgccagggtg gtttttcttt    3480
tcaccagtga cgggcaac agctgattgc ccttcaccgc ctggccctga gagagttgca    3540
gcaagcggtc cacgctggtt tgccccagca ggcgaaaatc ctgtttgatg gtggttaacg    3600
gcgggatata acatgagctg tcttcggtat cgtcgtatcc cactaccgag atatccgcac    3660
caacgcgcag cccggactcg gtaatggcgc gcattgcgcc cagcgccatc tgatcgttgg    3720
caaccagcat cgcagtggga acgatgccct cattcagcat ttgcatggtt tgttgaaaac    3780
cggacatggc actccagtcg ccttcccgtt ccgctatcgg ctgaatttga ttgcgagtga    3840
gatatttatg ccagccagcc agacgcagac gcgccgagac agaacttaat gggcccgcta    3900
acagcgcgat ttgctggtga cccaatgcga ccagatgctc cacgcccagt cgcgtaccgt    3960
cttcatggga gaaaataata ctgttgatgg gtgtctggtc agagacatca agaaataacg    4020
ccggaacatt agtgcaggca gcttccacag caatggcatc ctggtcatcc agcggatagt    4080
taatgatcag cccactgacg cgttgcgcga agagattgtg caccgccgct ttacaggctt    4140
cgacgccgct tcgttctacc atcgacacca ccacgctggc acccagttga tcggcgcgag    4200
atttaatcgc cgcgacaatt tgcgacgcg cgtgcagggc cagactggag gtggcaacgc    4260
caatcagcaa cgactgtttg cccgccagtt gttgtgccac gcggttggga atgtaattca    4320
gctccgccat cgccgcttcc acttttccc gcgttttcgc agaaacgtgg ctggcctggt    4380
tcaccacgcg ggaaacggtc tgataagaga caccggcata ctctgcgaca tcgtataacg    4440
ttactggttt cacattcacc accctgaatt gactctcttc cgggcgctat catgccatac    4500
cgcgaaaggt tttgcgccat tcgatggtgt ccggatctc gacgctctcc cttatgcgac    4560
tcctgcatta ggaagcagcc cagtagtagg ttgaggccgt tgagcaccgc cgccgcaagg    4620
aatggtgcat gccggcatgc cgcccttcg tcttcaagaa ttaattccca attccccagg    4680
catcaaataa aacgaaaggc tcagtcgaaa gactgggcct ttcgttttat ctgttgtttg    4740
tcggtgaacg ctctcctgag taggacaaat ccgccgggag cggatttgaa cgttgcgaag    4800
caacggcccg gagggtggcg ggcaggacgc ccgccataaa ctgccaggaa ttaattcccc    4860
aggcatcaaa taaaacgaaa ggctcagtcg aaagactggg cctttcgttt tatctgttgt    4920
ttgtcggtga acgctctcct gagtaggaca atccgccgg gagcggattt gaacgttgcg    4980
aagcaacggc ccgagggtg gcgggcagga cgcccgccat aaactgccag gaattaattc    5040
cccaggcatc aaataaaacg aaaggctcag tcgaaagact gggcctttcg ttttatctgt    5100
tgtttgtcgg tgaacgctct cctgagtagg acaaatccgc cggagcgga tttgaacgtt    5160
gcgaagcaac ggcccggagg gtggcgggca ggacgcccgc cataaactgc caggaattaa    5220
ttccccaggc atcaaataaa acgaaaggct cagtcgaaag actgggcctt tcgttttatc    5280
tgttgtttgt cggtgaacgc tctcctgagt aggacaaatc cgcgggagc ggatttgaac    5340
gttgcgaagc aacggcccgg agggtggcgg gcaggacgcc cgccataaac tgccaggaat    5400
taattcccca ggcatcaaat aaaacgaaag gctcagtcga aagactgggc ctttcgtttt    5460
atctgttgtt tgtcggtgaa cgctctcctg agtaggacaa atccgccggg agcggatttg    5520
```

```
aacgttgcga agcaacggcc cggagggtgg cgggcaggac gcccgccata aactgccagg    5580
aattggggat cggaattaat tcccggttta aaccggggat ctcgatcccg cgaaattaat    5640
acgactcact ataggggaat tgtgagcgga taacaattcc cctctagaaa taattttgtt    5700
taactttaag aaggagatat acatatggct agctcgcgag tcgacggcgg ccgcgaattc    5760
ctcgagggct cttcctgctt tgccaagggt accaatgttt taatggcgga tgggtctatt    5820
gaatgtattg aaaacattga ggttggtaat aaggtcatgg gtaaagatgg cagacctcgt    5880
gaggtaatta aattgcccag aggaagagaa actatgtaca gcgtcgtgca gaaaagtcag    5940
cacagagccc acaaaagtga ctcaagtcgt gaagtgccag aattactcaa gtttacgtgt    6000
aatgcgaccc atgagttggt tgttagaaca cctcgtagtg tccgccgttt gtctcgtacc    6060
attaagggtg tcgaatattt tgaagttatt acttttgaga tgggccaaaa gaaagccccc    6120
gacggtagaa ttgttgagct tgtcaaggaa gtttcaaaga gctacccaat atctgagggg    6180
cctgagagag ccaacgaatt agtagaatcc tatagaaagg cttcaaataa agcttatttt    6240
gagtggacta ttgaggccag agatctttct ctgttgggtt cccatgttcg taaagctacc    6300
taccagactt acgctccaat tctttatgag aatgaccact ttttcgacta catgcaaaaa    6360
agtaagtttc atctcaccat tgaaggtcca aaagtacttg cttatttact tggtttatgg    6420
attggtgatg gattgtctga cagggcaact ttttcggttg attccagaga tacttctttg    6480
atggaacgtg ttactgaata tgctgaaaag ttgaatttgt gcgccgagta taaggacaga    6540
aaagaaccac aagttgccaa aactgttaat ttgtactcta aagttgtcag aggtaatggt    6600
attcgcaata atcttaatac tgagaatcca ttatgggacg ctattgttgg cttaggattc    6660
ttgaaggacg gtgtcaaaaa tattccttct ttcttgtcta cggacaatat cggtactcgt    6720
gaaacatttc ttgctggtct aattgattct gatggctatg ttactgatga gcatggtatt    6780
aaagcaacaa taaagacaat tcatacttct gtcagagatg gtttggtttc ccttgctcgt    6840
tctttaggct tagtagtctc ggttaacgca gaacctgcta aggttgacat gaatgtcacc    6900
aaacataaaa ttagttatgc tatttatatg tctggtggag atgttttgct taacgttctt    6960
tcgaagtgtg ccggctctaa aaaattcagg cctgctcccg ccgctgcttt tgcacgtgag    7020
tgccgcggat tttatttcga gttacaagaa ttgaaggaag acgattatta tgggattact    7080
ttatctgatg attctgatca tcagttttg cttggatccc aggttgtcgt ccatgcatgc    7140
ggtggcctga ccggtctgaa ctcaggcctc acgacaaatc ctggtgtatc cgcttggcag    7200
gtcaacacag cttatactgc gggacaattg gtcacatata acggcaagac gtataaatgt    7260
ttgcagcccc acacctcctt ggcaggatgg gaaccatcca acgttcctgc cttgtggcag    7320
cttcaatgac tgcaggaagg ggatccggct gctaacaaag cccgaaagga agctgagttg    7380
gctgctgcca ccgctgagca ataactagca taaccccttg gggcctctaa acgggtcttg    7440
aggggttttt tgctgaaagg aggaactata tccggat                            7477
```

<210> SEQ ID NO 157
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157

```
gatctctaga ctaatgttca attggatgat atag                               34
```

<210> SEQ ID NO 158
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 158

```
gatctctaga ctcaagtctt gtaggagaat c                                    31
```

<210> SEQ ID NO 159
<211> LENGTH: 8411
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 159

```
gacgaaaggg cctcgtgata cgcctatttt tataggttaa tgtcatgata ataatggttt      60
cttagacgtc aggtggcact tttcggggaa atgtgcgcgg aacccctatt tgtttatttt     120
tctaaataca ttcaaatatg tatccgctca tgagacaata accctgataa atgcttcaat     180
aatattgaaa aaggaagagt atgagtattc aacatttccg tgtcgccctt attcccttt      240
ttgcggcatt ttgccttcct gttttgctc acccagaaac gctggtgaaa gtaaaagatg      300
ctgaagatca gttgggtgca cgagtgggtt acatcgaact ggatctcaac agcggtaaga     360
tccttgagag ttttcgcccc gaagaacgtt ttccaatgat gagcactttt aaagttctgc     420
tatgtggcgc ggtattatcc cgtattgacg ccgggcaaga gcaactcggt cgccgcatac     480
actattctca gaatgacttg gttgagtact caccagtcac agaaaagcat cttacggatg     540
gcatgacagt aagagaatta tgcagtgctg ccataaccat gagtgataac actgcggcca     600
acttacttct gacaacgatc ggaggaccga aggagctaac cgcttttttg cacaacatgg     660
gggatcatgt aactcgcctt gatcgttggg aaccggagct gaatgaagcc ataccaaacg     720
acgagcgtga caccacgatg cctgtagcaa tggcaacaac gttgcgcaaa ctattaactg     780
gcgaactact tactctagct tcccggcaac aattaataga ctggatggag gcggataaag     840
ttgcaggacc acttctgcgc tcggcccttc cggctggctg gtttattgct gataaatctg     900
gagccggtga gcgtgggtct cgcggtatca ttgcagcact ggggccagat ggtaagccct     960
cccgtatcgt agttatctac acgacgggga gtcaggcaac tatggatgaa cgaaatagac    1020
agatcgctga gataggtgcc tcactgatta agcattggta actgtcagac caagtttact    1080
catatatact ttagattgat ttaaaacttc atttttaatt taaaaggatc taggtgaaga    1140
tcctttttga atctcatg accaaaatcc cttaacgtga gttttcgttc cactgagcgt     1200
cagaccccgt agaaaagatc aaaggatctt cttgagatcc tttttttctg cgcgtaatct    1260
gctgcttgca acaaaaaaa ccaccgctac cagcggtggt ttgtttgccg gatcaagagc    1320
taccaactct ttttccgaag gtaactggct tcagcagagc gcagatacca atactgtcc     1380
ttctagtgta gccgtagtta ggccaccact tcaagaactc tgtagcaccg cctacatacc    1440
tcgctctgct aatcctgtta ccagtggctg ctgccagtgg cgataagtcg tgtcttaccg    1500
ggttggactc aagacgatag ttaccggata aggcgcagcg gtcgggctga cgggggggtt    1560
cgtgcacaca gcccagcttg gagcgaacga cctacaccga actgagatac ctacagcgtg    1620
agcattgaga aagcgccacg cttcccgaag ggagaaaggc ggacaggtat ccggtaagcg    1680
```

```
gcagggtcgg aacaggagag cgcacgaggg agcttccagg gggaaacgcc tggtatcttt       1740
atagtcctgt cgggtttcgc cacctctgac ttgagcgtcg attttgtga tgctcgtcag       1800 gggggcggag cctatggaaa aacgccagca acgcggcctt tttacggttc ctggccttt       1860 gctggccttt tgctcacatg ttctttcctg cgttatcccc tgattctgtg ataaccgta       1920 ttaccgcctt tgagtgagct gataccgctc gccgcagccg aacgaccgag cgcagcgagt       1980
cagtgagcga ggaagcggaa gagcgcccaa tacgcaaacc gcctctcccc gcgcgttggc       2040
cgattcatta atgcagctgg cacgacaggt ttcccgactg gaaagcgggc agtgagcgca       2100
acgcaattaa tgtgagttac ctcactcatt aggcacccca ggctttacac tttatgcttc       2160
cggctcgtat gttgtgtgga attgtgagcg ataacaatt tcacacagga aacagctatg       2220
accatgatta cgccaagctc ggaattaacc ctcactaaag gaacaaaag cttgcatgcc       2280 tgcagttcag atctttatat aacaacttaa attacactaa gttatttat tgaacatata       2340 tcgtacttta tctatccgac tatttggacg acggggctgg caaacaggtt caccggtagt       2400
aacatggtac ccttttaact ctgttaaaca aacactacgt ccatttgtaa agaaagttaa       2460
atcactacga tattcttgaa tacaccgagc agggatttct ccactaagaa tgacctcatt       2520 attttttcaat tgagtgtcta cgatgttcgc acaatattta ggagcatcgt tgtatgctcg       2580
tgaaagatat tcctgtggcg cataaatttt aaaactaaga tatggctcta acaattctgt       2640
tccagctttt tttaagactt gttccaatac aataggagca agcatccgaa atctgctgg       2700 ggtactaaca gggctatagt ataagccata cttaaaacag attttacagt ccgtcacatt       2760
ccaaccatac aatccttgtt cacaaccata gcgtatccct tccataactg cattttgaaa       2820
tgattgattt aagtatccaa gagaaaccga gctctcatac tgcattccac ttcccaacgg       2880
aagcggtgat acagatagac caatggaagc ccagaaagga tttggcggca cttcgatgtg       2940
aatggtatat tctgcatttt ttaacggtct ctccatataa atgactgtag gctctgttat       3000
ttctatctcc acatgatact tttcttgcaa cagtgcacta atcacttcca tttgtacttt       3060
ccctaagaaa gaaagtataa tttcatgtgt cgtagaatcc acgtaatatc gtagaagcgg       3120
atcactatct gagatttcca aaagggcatc aagcaacatt tctctctgtt caggtttact       3180
cggttcaaca gttgtttgta gtagagggtg cggattttca atcttttttc tctgtggcaa       3240
tagttttgta tctccaagaa cactatttaa cttcaaaaac tcattttgca aaataacaat       3300
ttctccagaa taagctctat caatcttaca taattcacca tttattgaag tatacatttc       3360
tgtaactttt attttttcct tttctgatac tctaaccgaa tctcgtaaat gtagtactcc       3420
actataaagg cgtatatatg caagacgttg tcttttttt gtatattcaa ttttgaaaac       3480
atttccgcaa agttcagacg gacctcgatg tgttgatgaa taaaatttat tagtaataac       3540
ttctataagg ttatcaatcc ctatattact ttttgcactt ccatgataaa gagggaacag       3600
agaacaattc tgaaatctta tgctttcctc ttgttcgagt tccaatgctt ctaatgattt       3660
accggacata tatttctcta aaaggtcatc gtttccctct attaccgtat cccattgttc       3720
agattcggta aagttcgtca cacacacatt aggatacagt tctaccttct gtttgattac       3780
aatttcggca gaaagtttct ctttaatatc ctgataaacc gttgataaat caattccatt       3840
ttggtcaatc ttattgataa aaaagattgt gggaatcccc attttcctaa gtgcatgaaa       3900
taatatacga gtttgtgctt gtacgccatc ttttgcagaa atcagtagaa ttgccccatc       3960
taaaactgat aatgaacgat atacttctgc taagaaatcc atatgtcctg gcgtgtctat       4020
```

```
gatgttcacc ttcgtatttt cccactgaaa agaggttatt cctgtctgaa ttgtaattcc    4080
tctctgacgt tctaaaagcg tattatccgt cctcgttgta cctttgtcca cgcttcctaa    4140
ttctgtaatc gctccactgt tatataataa gctttctgtt aaggtagttt ttcctgcatc    4200
aacatgagct aaaactccaa tattaataat tttcatgtga ttttcctcca ttcaaaggat    4260
cttatatttc ctttctctat taagtagtgt ttttattaaa agcaaatgta attaaaatta    4320
cattgaatat ataagagaaa aataacatta ataataatta ttaattgctt ctaaccctac    4380
tttatacaat ttatatcttt cttttttcct ttcccttata gtagcaattg tacataattt    4440
tttaaaaaaa acaataaata tttcttaaaa aaacaaaaaa agattttcca aataaattgc    4500
ttaatctttt tttgtttttt cgtcttcttt tggttcagaa actggtgctt cactgttttc    4560
ttgttcacta acttttaatt ctgcaggtcg atattttaca aaaatttgct tattatgaaa    4620
ttttattact ttccacaata aaaaatgatt tacaccataa aatgttaata atgtggaaaa    4680
caataaaaat attcaataaa aacaatgctt taaagaaaaa tataaaaaat atttaatgtg    4740
gaaaaatatt aattttttatt aatttttactc attttttagt acttttccac atcttttatt    4800
tataattaat aacgataaaa actattggag atgaaattaa tgaacacaaa agaattatga    4860
attgaagtta aagaaatatt atctcgtgat gaatcagttt ccccagaaat ttataactac    4920
tatattagtg acacaaactt atatactgta tctgataata actgcttaat tacaacaaaa    4980
tcagaaattg caattggtgt ttttgaagca ggattaaatg aaaaaattaa aaatatctta    5040
aaaaaactaa ctggaatcca atataatatt tcatttgaat tagaaaaaaa tatcaataag    5100
caagcatctg taattagtaa aattgacaca ttaacagaaa acaataaccct tgcttactat    5160 gaaaattata cttttgaaaa ttttgttcgt ggtgattcta atcacgaagc aatgcaagca    5220
gctttagcag ttgctttaga tcttggaaaa aaatgaaatc cattattcat atatggagac    5280
tctggactag gaaaaacaca tctattacat gcaattgaaa ataaggtaaa tgaaatttat    5340
aaaacaaata accgagtaaa atatttaaaa gctgatgagt ttggaaaaat tgctatggat    5400
attttaaacc aaggccatga aattattgaa gcttttaaaa catcttatga catttacgat    5460
tgtttattaa ttgatgatat acaattatta gcaaaacgaa ataaaacaaa tgaattattt    5520 tttcatatttt ttaactcata tattgaaaaa aataaacaaa ttgtaattac ttctgataaa    5580
tatcctgatg atctaggcgg ttttgaagct agaattattt ctcgttttc atatggttta    5640 agtattggct tagattcacc agattttgaa acagcactta aaatattaga acaaaaacta    5700
aaacatcaaa ataacttagg attattttca gaagaatcac tagaatttat tgctttaaat    5760
tttaacagtg atgttagaaa gttagaagga gcaattaaac gattattatt tttagctgtt    5820
atgaacaaaa aaccaaatga aattattaca ttagctgatg ttgaaaaggc atttaaaaat    5880 gccccctgc aaaataatga aaaaattacc cctaaaaaaa ttaaacaaat tgttgctgac    5940
agttacaata ttactatcaa agcaatgatg agtaaatcac gagttagtaa tgttatgcaa    6000
gcacgacaat tagcaatgta ttttttgtaga acattactag atgaaccatt tacaaggatt    6060
ggaacagagt tcggtggcaa agaccacaca actgtgatga atagtgttaa aaaagttgaa    6120
gcacacatta gtacaaacaa agaatttaaa catttagtaa atgcaattcg tagaaaaatt    6180
gaaggaagat agcacattat tttccacgat tgttttttaa taaaaaataa tattattcaa    6240
aactttatca agttttccac attttctaca atataatact aataaataaa aaacaatatt    6300
ttaacaatgg tatataatta tttatatatt acagaatata ctaaagtaag gagtaaaaaa    6360
aatgattgta aacattaaaa gagataagat attagatgaa ttattgaaag taagtcggat    6420
```

```
aatttctcaa aagactttaa ttccttcatt attgggaatt ttaattgaag ttaaaaaga    6480
caaaattact tttactactt ctgatggtga tacatcaatt aaatcagaaa ttatgggcaa    6540
tgatttaaac attactcgac tctagactaa tgttcaattg gatgatatag taaataatag    6600
cccacaaaat cataaagaag caggatttac aaaaggttgg tctagtagat ttgatacttg    6660
gtataaacta tgtaaagaat ttggtttcat atattatgat atgaataaaa aaattgaagt    6720
atcatcaagt ggtcatatgt tatgtgatgc atatttagca aattccaaaa atgaggactt    6780
agataattcg ggtaaaagga tacaaaaaat atttctcaat gcattgatga ataccaaac     6840
aaataatcca tttagaagaa atctaaatca aaattcacca atacctctat tattaaacgt    6900
attaaattta ttatctttaa actcacgttc tacaggatta cacagaagag agatacctttt   6960
tttaatgtgt tgagaaaata atgattataa acaattatat gaatttatca ttaattttag    7020
aaataagtat ggatttaaag caagtgatga aattatttat gaagaatgtt taaaattatt    7080
aaaaagctct aataagaagc gattcaaaat gagtcaaata atgaaagaaa gtgttgatga    7140
ttttattaga aaactaagaa taactggaat attttcttta cgtggtttag gaagatttgt     7200
tgacataaac aaattagaaa tagagtcagt tgattatata attaaaaatt atacaaaata     7260
caatattttt agtaatgaat atgattttta taaatatatg tctgaaatag ataccaagat     7320
tttagaattt caagaaatag ctaacactga aataaataat attagaatga agactctaag    7380
agaaatttct caaagtatt ctgttgaaca aatatataag gaattaagaa atttacagtt      7440
aaacaaaaac tcagaagatg aatatttaa actaattgat tctcctacaa gacttgagtc      7500
tagaggatcc ccgggtaccg agctcgaatt cgccctatag tgagtcgtat tacaattcac    7560
tggccgtcgt tttacaacgt cgtgactggg aaaaccctgg cgttacccaa cttaatcgcc   7620
ttgcagcaca tccccccttc gccagctggc gtaatagcga agaggcccgc accgatcgcc   7680
cttcccaaca gttgcgtagc ctgaatggcg aatggcgcga cgcgccctgt agcggcgcat   7740
taagcgcggc gggtgtggtg gttacgcgca gcgtgaccgc tacacttgcc agcgccctag   7800
cgcccgctcc tttcgctttc ttcccttcct ttctcgccac gttcgccggc tttccccgtc    7860
aagctctaaa tcggggctc cctttagggt tccgatttag tgctttacgg cacctcgacc     7920
ccaaaaaact tgattagggt gatggttcac gtagtgggcc atcgccctga tagacggttt   7980
ttcgcccttt gacgttggag tccacgttct ttaatagtgg actcttgttc caaactggaa    8040
caacactcaa ccctatctcg gtctattctt ttgatttata agggattttg ccgatttcgg    8100
cctattggtt aaaaaatgag ctgatttaac aaaaatttaa cgcgaatttt aacaaaatat   8160
taacgtttac aatttcctga tgcggtattt tctccttacg catctgtgcg gtatttcaca    8220
ccgcatatgg tgcactctca gtacaatctg ctctgatgcc gcatagttaa gccagccccg   8280
acacccgcca cacccgctg acgcgccctg acgggcttgt ctgctcccgg catccgctta     8340
cagacaagct gtgaccgtct ccgggagctg catgtgtcag aggttttcac cgtcatcacc   8400
gaaacgcgcg a                                                          8411
```

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
ttgatttcgg tttctttgaa                                          20

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
gggtaataac tgatataatt                                          20

<210> SEQ ID NO 162
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
gcttctaatt actagtgagt taactgataa aatcaaacaa caattaaagt ttgatttcgg    60
tttctttgaa                                                     70

<210> SEQ ID NO 163
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
ttaaagcaat ggctaaagta cctgaaccac aacaaaggtc aagtgcagtt gggtaataac    60
tgata                                                          65

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
caatattgga acactatggt                                          20

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
acatcaagtg tatcacactt                                          20

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 166
gttagtttac caatccagtc                                              20

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
aatgcttgga tatcaatatc                                              20

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
acggattaga agccgccgag                                              20

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
gatctgactt attatttcag                                              20

<210> SEQ ID NO 170
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
ttaaagaaac cgaaatcaag atctgactta ttatttca                          38

<210> SEQ ID NO 171
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
ctgaaataat aagtcagatc ttgatttcgg tttctttgaa                        40

<210> SEQ ID NO 172
<211> LENGTH: 88
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
aagtgtgata cacttgatgt ttatggtagt gatattgata tccaagcatt tagggataac    60
agggtaatac ggattagaag ccgccgag    88

<210> SEQ ID NO 173
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
aagactagac tctgaataac taattaatcc catttgtgta tcagtattta gggtaataac    60
tgatataatt    70

<210> SEQ ID NO 174
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
aattatatca gttattaccc caatattgga acactatggt    40

<210> SEQ ID NO 175
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
accatagtgt tccaatattg gggtaataac tgatataatt    40

<210> SEQ ID NO 176
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
aagtgtgata cacttgatgt ttatggtagt gatattgata tccaagcatt ttgatttcgg    60
tttctttgaa    70

<210> SEQ ID NO 177
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
aagactagac tctgaataac taattaatcc catttgtgta tcagtattta aatgcttgga    60
tatcaatatc    70

```
<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
aagtaactag caatttgttg                                                20

<210> SEQ ID NO 179
<211> LENGTH: 88
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
aagtgtgata cacttgatgt ttatggtagt gatattgata tccaagcatt tagggataac     60
agggtaatac ggattagaag ccgccgag                                       88

<210> SEQ ID NO 180
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
aagactagac tctgaataac taattaatcc catttgtgta tcagtattta aatgcttgga     60
tatcaatatc                                                           70

<210> SEQ ID NO 181
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
ggttttttct ccttgacgtt aa                                             22

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
atgtccaatt tactgaccgt                                                20

<210> SEQ ID NO 183
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
```
ctaatcgcca tcttccagca                                              20

<210> SEQ ID NO 184
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
aacgtcaagg agaaaaaacc atgtccaatt tactgaccgt                        40

<210> SEQ ID NO 185
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
acggtcagta aattggacat ggttttttct ccttgacgtt                        40

<210> SEQ ID NO 186
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
tgctggaaga tggcgattag ttgatttcgg tttctttgaa                        40

<210> SEQ ID NO 187
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
ttcaaagaaa ccgaaatcaa ctaatcgcca tcttccagca                        40

<210> SEQ ID NO 188
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
taccgttcgt ataatgtatg ctatacgaag ttatacggat tagaagccgc cgag        54

<210> SEQ ID NO 189
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
taccgttcgt atagcataca ttatacgaag ttatgggtaa taactgatat aatt        54

<210> SEQ ID NO 190
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
aagtgtgata cacttgatgt ttatggtagt gatattgata tccaagcatt taccgttcgt    60
ataatgtatg                                                            70

<210> SEQ ID NO 191
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
aagactagac tctgaataac taattaatcc catttgtgta tcagtatttt accgttcgta    60
tagcataca                                                             69

<210> SEQ ID NO 192
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
gatttttatg ctggatctgg aaca                                            24

<210> SEQ ID NO 193
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
tccgtattac cctgttatcc cta                                             23

<210> SEQ ID NO 194
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
ctacttcaaa tagtattctt ttaagcg                                         27

<210> SEQ ID NO 195
<211> LENGTH: 666
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 195
aggaaggctg tgtgaatttc attcgacaag ataaaggaaa ttagaacatt tactttagtt      60
acaaataatg aaaataatat agggattgat gtttgctatg aacgcttgtt tagaataaat     120
aatggtaaat caactgataa taaaacagat tttaaatgaa tagaaaaaaa cgaaccctat     180
ctgtctaatt tagatgtttt tgatattaaa tactattcaa ctaaattgtt tgaagataat     240
agtgctaatg aaataatcaa aaaacaattc ataaaaatgt taaatgatct aaaaataaat     300
gctgatgata tttctacaat taaaacttta agacaattaa ctgcactaaa accaatctca     360
ggtggacaaa acaatgagat taactaataa acaagaattt gtagtgcaag atattgttaa     420
agaagattat taaattgtta aaataaaaaa ttacttattt aagcgggact atttctattt     480
tatttaaaga agtcttatga ttgaatgtaa aagttctaat gtattaaccc ctgttacatt     540
aaatacaacc atatctattt ttaattaatc tcctgaaagt acaagttctt aattcctaac     600
catgcctatt aaatttaaga tcaagagcag tttttctaac ccccgaaaaa aaactcacaa     660
caaaaa                                                                666
```

METHODS FOR CLONING AND MANIPULATING GENOMES

CROSS-REFERENCE TO RELATED APPLICATIONS

This application is a continuation-in-part of U.S. application Ser. No. 12/718,911, filed Mar. 5, 2010, and a continuation-in-part of International Application No. PCT/US10/026,434, filed Mar. 5, 2010 which applications claim the benefit of U.S. Provisional Application No. 61/158,320, filed on Mar. 6, 2009, each of which is incorporated herein by reference in its entirety. This application also claims the benefit of U.S. Provisional Application No. 61/322,269, filed on Apr. 8, 2010, which is incorporated herein by reference in its entirety.

This application is related to U.S. application Ser. No. 12/247,126, filed Oct. 7, 2008 by Gibson et al., which claims the benefit of U.S. provisional application 60/978,388, filed Oct. 8, 2007; U.S. provisional application 60/983,549 filed Oct. 29, 2007; U.S. provisional application 61/062,214 filed Jan. 23, 2008; U.S. provisional application 61/023,392 filed Jan. 24, 2008, and U.S. provisional application 61/096,270 filed Sep. 11, 2008, each of which is incorporated by reference herein in its entirety.

INCORPORATION OF THE SEQUENCE LISTING

This application contains references to amino acid sequences and/or nucleic acid sequences which have been submitted concurrently herewith via EFS-Web as the sequence listing text file "JCVI07US.txt", file size 102,141 bytes, created on Mar. 3, 2010. The aforementioned sequence listing is hereby incorporated by reference in its entirety pursuant to 37 C.F.R. §1.52(e)(5).

BACKGROUND

The use of organisms that have advanced genetic systems as hosts for nucleic acid molecules isolated from a variety of species allows for the manipulation of the isolated nucleic acid sequences in the host. The ability to engineer organisms by cloning and modifying chromosomes and genomes in exogenous hosts is limited, however, by the size limitation on nucleic acid molecules that can be transferred to species such as yeast that have tractable genetics.

Nucleic acids cloned by conventional methods generally contain no more than a few genes, although larger nucleic acids (e.g., DNA) have been transferred into host cells. For example, the 16 kb mouse mitochondrial genome has been cloned in *E. coli* (Itaya et al., *Nat Methods* 5, 41 (2008); Yoon and Koob, *Nucleic Acids Res* 31, 1407 (2003)), *Bacillus subtilis* (Itaya et al., *Nat Methods* 5, 41 (2008); Yoon and Koob, *Nucleic Acids Res* 31, 1407 (2003)), and yeast (Wheeler et al., *Gene* 198, 203 (1997)). The 139 kb maize chloroplast genome has been cloned in yeast (Gupta and Hoo, *Plant Mol Biol* 17, 361 (1991), and the 135 kb rice chloroplast genome has been cloned in *B. subtilis* (Itaya et al., *Nat Methods* 5, 41 (2008)). About 10% of the 1.8 Mb *Haemophilus influenzae* genome has been cloned as episomal elements in *E. coli* (Smailus et al., *Syst Synth Biol;* 1, 139 (2007)). The 3.5 Mb *Synechocystis* PCC6803 genome was inserted in three noncontiguous regions into the *B. subtilis* genome, with the exception of the two ribosomal RNA operons (Itaya et al., *PNAS USA* 102, 15971 (2005)). A complete synthetic 0.6 Mb *Mycoplasma genitalium* genome has been assembled in yeast as a circular yeast centromeric plasmid (YCp) (Gibson et al., *Science* 319, 1215 (2008); Gibson et al., *PNAS USA*, 105(51):20404-9 (2008)).

U.S. Pat. No. 6,670,154 describes methods for converting modified bacterial genomes into artificial yeast chromosomes by fusing the bacteria with yeast that linearize the modified genomes. U.S. Patent Application Publication No. 2005/0019924 describes nucleic acids and methods for introducing prokaryotic genomes into eukaryotic cells as circular molecules and conversion into artificial chromosomes. WO 02/057437 describes YAC vectors containing cytomegalovirus (CMV) genomes. U.S. Pat. No. 7,083,971 describes a recombinatorial approach and system for cloning, manipulating, and delivering large nucleic acid segments. U.S. Patent Application Publication No. 2005/0003511 and Bradshaw et al., *Nucleic Acids Research*, 23, 4850-56 (1995) describe yeast-bacterial shuttle vectors for cloning large regions of DNA by homologous recombination.

The disclosed cloning and manipulation methods, however, are limited by the size of donor nucleic acids that can be transferred into a host cell, and do not provide for manipulating and/or transferring a nucleic acid molecule propagated in a host cell back into a recipient cell that is related to the donor, nor do they address incompatibility issues among different cell types used in cloning with regard to foreign nucleic acids. Additional methods are needed for cloning large nucleic acids, such as chromosomes or genomes, into alternate heterologous hosts, for manipulating the sequences of large nucleic acids in alternate hosts, and for transferring manipulated genomes back into recipient organisms that are similar to the donor organism, for example, organisms of the same genus (for example, from prokaryotic to eukaryotic cells and back).

To date, the barriers to transferring large nucleic acids, such as chromosomes and genomes, between organisms of different species or different genuses have not been overcome. For example transfer of the nucleic acids between species can be toxic to host, donor, and/or recipient cells. Manipulation and propagation of nucleic acids in organisms of different species, genuses, or groups and from prokaryotic to eukaryotic cells and back can also cause instability of the nucleic acids and inhibit their activation, such as expression of genes from the nucleic acids.

SUMMARY

Provided herein are methods, nucleic acids, and systems for transfer (cloning) of donor nucleic acids into host cells, for manipulation (e.g., modification) of donor nucleic acids, e.g., within host cells, and for transplantation of modified donor nucleic acids into recipient cells. The provided methods and other compositions are useful in transfer and manipulation of nucleic acids across branches of life, such as for manipulation of prokaryotic nucleic acids in eukaryotic host cells and transplant of the nucleic acids back into prokaryotic recipients.

The methods are useful for manipulation of donor nucleic acids of organisms having poor genetic systems by transfer into hosts having strong, well-characterized genetic systems, such as yeast. Thus, the methods, nucleic acids, and systems can be used for modifying nucleic acids of intractable organisms and to manipulate and engineer large nucleic acids, including genomes, for example, to produce synthetic genomes and cells, such as cells and genomes not previously in existence in the laboratory or in nature. The provided methods are useful for cloning, modifying, and transplanting nucleic acids and genomes that are larger than 300 kilobases (kb), such as genomes, including whole genomes and at least minimal genomes, and cellular, viral, and organelle genomes. Donor genomes can thereby be modified in host cells to produce modified donor genomes conferring one or more phenotypes not otherwise exhibited by the native donor genome. Methods are particularly advantageous when such modified donor genomes are difficult to produce in the original cell type harboring the donor genome, or when synthetic genomes can be quickly assembled and modified in the host cell prior to transplanting the modified genome back into the original desired cell type for production of a phenotype or product of interest.

The compositions and methods identified and described in the present application allow for new methods of transferring nucleic acid molecules and genomes from intractable donor cells into host cells where they can be modified to alter the genotype, and thereby the phenotype, to alter the nucleic acid molecule or genome. The modified genomes can be modified in one or more ways using the host cell's genetic machinery. The provided methods also provide for isolating a modified nucleic acid molecule or genome from a host cell. The isolated modified nucleic acid molecule or genome can be methylated ex vivo. A recipient cell can be treated with the methods described herein to allow for transfer of a modified nucleic acid molecule or genome into the cell. A modified nucleic acid molecule or genome can then be further transferred into recipient cell, thereby altering the phenotype of the recipient cell to that of the modified nucleic acid molecule or genome.

Provided herein is a method for cloning a donor genome, comprising: obtaining a donor genome from a donor cell or synthesizing a donor genome as one or more fragments; and introducing the donor genome and a host vector into a heterologous host cell, wherein the donor genome and the host vector are optionally joined prior to introduction into the host cell, thereby generating a host cell comprising the donor genome comprising the host vector, and further wherein the donor genome is an essentially intact cellular, viral, or organelle genome that is at least a minimal genome, and is greater than about 300 kb in length. In one embodiment, the donor genome is an essentially whole cellular, viral or organelle genome.

In the methods described herein, a donor genome and a host vector can be introduced into the host cell simultaneously or sequentially. If the donor genome and host vector are introduced into the host cell sequentially, the introduction can be in either order. Thus, in one embodiment, a donor genome can be introduced into the host cell followed by introduction of a host vector. Alternately, a host vector can be introduced into the host cell followed by introduction of a donor genome. In another embodiment, a host vector is joined with the donor genome prior to introduction into the host cell by transforming the host vector into a donor cell containing the donor genome.

The donor genome can be a single molecule. In one embodiment, a nucleic acid molecule containing a donor genome and a host vector can exist as a circular centromeric plasmid. Alternatively, the donor genome can exist as overlapping DNA fragments. A donor genome can be linearized or fragmented prior to introduction into the host cell.

Certain embodiments of the provided methods include further recovering the donor genome and host vector from the host cell.

In other embodiments, the methods further include introducing the donor genome into a recipient cell.

In yet other embodiments, the provided methods further include degrading or removing the genome of the recipient cell.

Donor genomes contemplated herein include, but are not limited to, a fungal genome, an archea genome, a cyanobacterial genome, an algal genome, a viral genome, a bacteriophage genome, an organelle genome, a mitochondrial genome, a chloroplast genome (e.g., a maize chloroplast genome, or a rice chloroplast genome), an organelle genome or a synthetic genome.

Host cells contemplated herein a eukaryotic cell or a prokaryotic cell. Host cells include, but are not limited to, a bacterial cell, a fungal cell, an insect cell, a plant cell or an algal cell. Host cells also include yeast cells.

A host vector described herein can be a centromeric plasmid. In one preferred embodiment, the host vector is a yeast centromeric plasmid and the host cell is a yeast cell.

A host vector described herein is a vector useful for homologous recombination.

Any of the methods described herein can further comprise modifying the donor genome within the host cell.

Furthermore, any of the methods described herein can further include recovering the donor genome comprising the host vector from the host cell. Optionally, the host vector can be removed from the donor genome. In one aspect, the methods further include introducing the recovered donor genome into a recipient cell.

The methods described herein can further include degrading or removing the endogenous genome of the recipient cell. When the method comprises the first instance of introduction of the donor genome into a recipient cell, the endogenous genome of the recipient cell is the native genome. Where multiple rounds of modifications occur (see, for example, FIGS. 1 and 16), the endogenous genome of the recipient cell may be a previously modified genome or a synthetic genome. Thus, in one embodiment, the provided methods further comprise modifying the donor genome in an iterative fashion.

A recovered donor genome may be methylated prior to introduction into a recipient cell by methylating one or more nucleotides in the donor genome.

A recipient cell can be, for example, a bacterial cell, a yeast cell, a fungal cell, an insect cell, a plant cell or an algal cell. In one aspect, a restriction endonuclease function of a recipient cell is absent, removed, or inactivated prior to introduction of the donor genome. For example, a restriction modification enzyme can be mutated in the recipient cell to render it inactive.

In a preferred embodiment the donor genome is derived from a prokaryotic cell (either natural or synthetic) and cloned in a eukaryotic cell where it may be optionally modified, and then recovered and introduced back into a prokaryotic cell. In certain preferred embodiments, the donor genome is derived from a bacterial cell (either natural or synthetic) and cloned in a yeast cell where it may be optionally modified, and then recovered and introduced back into a bacterial cell.

The methods provided herein further include introducing a second donor genome into the host cell where the second donor genome is different from the first donor genome, thereby producing a host cell containing two different donor genomes. Introducing the second donor genome can occur via mating the host cell containing the first donor genome with a second host cell containing the second donor genome. Introduction of the recovered donor genome into the recipient cell can phenotypically transform the recipient cell to a phenotype corresponding to the donor genome, incorporating any modifications thereto.

Provided herein is a process for making a cell which exhibits a phenotype encoded by a donor genome, said process comprising: (a) introducing into a host cell, the donor genome and a host vector suitable for cloning the donor genome in the host cell such that a product comprising the donor genome comprising the host vector is obtained; (b) recovering the product comprising the donor genome comprising the host vector obtained in step (a) from the host cell; (c) introducing the product of (b) into a recipient cell under conditions such that the recipient cell exhibits a phenotype encoded by the product; and (d) recovering the cell resulting from step (c); wherein the donor genome is an essentially intact cellular, viral, or organelle genome that is at least a minimal genome, and is greater than about 300 kb in length and comprises the minimal components of nucleic acid material necessary for the recipient cell to exhibit the phenotype encoded by the donor genome. In one aspect, the method further comprises modifying the donor genome of (a) within the host cell. In another aspect, the method further comprises degrading or removing an endogenous genome of the recipient cell. In yet another aspect, the method further comprises modifying the donor genome of (a) within the host cell and degrading or removing an endogenous genome of the recipient cell. In certain embodiments, such processes may be automated.

Provided herein is a cell which exhibits a desired phenotype encoded by a donor genome and not otherwise exhibited by the cell, wherein the cell is produced by the processes described herein.

Also provided herein is a cell which comprises a donor genome and exhibits a desired phenotype encoded by the donor genome and not otherwise exhibited by the cell, wherein the donor genome comprises greater than 300 kb of foreign genomic nucleic acid material and the minimal components of a genome necessary for the cell to exhibit the desired phenotype. Desired phenotypes may include the production of a expression product not native to the original cell, or modified (e.g., selective or regulated expression) or up-regulation of an existing expression product.

The provided methods also include cloning a plurality of genomes in a plurality of host cells. The plurality of genomes can be genomic variants. In one embodiment, introducing the plurality of genomes into host cells comprises introducing host vectors and a plurality of variant overlapping fragments into the host cells, thereby generating a combinatorial library of variant genomes.

In one aspect, following recovery of a donor genome from a host cell, the provided methods comprise introducing the donor genome into a recipient cell and the recipient cell supports gene expression from the donor genome to a greater extent than the host cell.

In one aspect, the provided methods comprise modifying the donor genome in a host cell; and modifying the donor genome comprises inducing one or more substitutions, one or more deletions, one or more insertions, one or more rearrangements, one or more recombinations, one or more homologous recombinations, or a combination thereof, into the donor genome.

In another aspect, the method comprises modifying the donor genome; and modification of the donor genome effects or improves a property of the donor genome compared to the donor genome prior to modification.

The provided methods also include transplantation into a recipient cell where transplantation can be carried out in the presence of polyethylene glycol (PEG). Various sizes of PEG that can be used in the present methods include, but are not limited to, sizes ranging from PEG 4,000 to PEG 20,000. In one embodiment, the size is PEG 8,000. Various concentrations of PEG can be used in the disclosed methods such as, for example, from about 1% to about 20%. In one embodiment, PEG is used in a concentration of about 5%.

Provided herein is a vector for whole genome modification, comprising a prokaryotic genome that is at least a minimal genome; a prokaryotic replication origin; a prokaryotic selection marker; a transposase and inverted repeats; one or more nucleic acid sequences capable of supporting segregation and replication in a eukaryotic cell; and a eukaryotic selection marker. In one aspect of the provided methods, the eukaryotic cell is a yeast cell. The prokaryotic genome, prokaryotic replication origin and selection marker can be bacterial. In one embodiment, the nucleic acid supporting segregation and replication in a eukaryotic cell comprises one or more of a CEN nucleic acid and an ARS nucleic acid. In another embodiment, the prokaryotic genome comprises at least at or about 300 kb in length. In another embodiment, the vector is stable in a eukaryotic and in a prokaryotic cell. Provided herein is a combinatorial library containing a plurality of vectors, wherein the prokaryotic genomes can be genome variants.

Provided herein is an isolated cell, a synthetic cell or a recombinant cell, comprising a foreign donor genome prepared by any of the methods described herein.

Provided herein is a yeast nucleic acid construct for seamless modification of target region within a target nucleic acid, comprising: a first portion of homology, containing homology to a portion of the target nucleic acid that is upstream or downstream of the target region along the length of the target nucleic acid; a nucleic acid encoding an endonuclease under the control of an inducible promoter; a nucleotide sequence recognized by the endonuclease; a yeast selectable marker; a second portion of homology, containing homology to a 5' portion of the target region; and a third portion of homology, containing homology to a 3' portion of the target region. In one embodiment, the second and third portions of homology flank the first portion of homology, the nucleic acid encoding the endonuclease, and the yeast selectable marker. The endonuclease recognition site can be adjacent to the second or the third homologous portion and can be on the opposite terminus of the construct relative to the first portion of homology. One or both of the second and third regions of homology comprises one or more substitutions, one or more deletions, one or more insertions, one or more rearrangements, one or more recombinations, one or more homologous recombinations, or one or more combinations thereof, compared to the homologous portion in the target nucleic acid.

Provided herein is a method for seamlessly introducing a modification in a target nucleic acid molecule, comprising: introducing a mutagenesis construct and a host vector into a host cell whereby the host vector recombines with the mutagenesis construct in the host cell, wherein the mutagenesis construct contains a first portion of homology to a 5' portion of the target nucleic acid molecule upstream of the modification; an endonuclease recognition site, a promoter, a gene encoding the endonuclease, and a selectable marker; a second repeat portion of homology that is homologous to the sequence of the genome upstream of a target locus; and a third portion of homology that is homologous to a 3' portion of the target region downstream of the modification; and incubating the cells under conditions whereby recombination occurs between the first portion of homology and the upstream or downstream portion, thereby seamlessly removing a portion of the construct, that promote one or more double-strand break cleavages in the nucleic acid molecule near the target site containing the construct, whereby a modification is seamlessly introduced into the target nucleic acid molecule.

Treatment to promote double-strand break cleavage can include expression of an endonuclease that cleaves the target nucleic acid molecule containing the construct at a recognition site, producing a double-strand break. In one aspect, the provided methods further comprise performing a selection step, thereby selecting cells in which the yeast selectable marker has been removed from the target nucleic acid.

The provided methods comprise transplantation into a recipient cell where transplantation is carried out by isolating the donor genome in the presence of agarose; incubating the donor genome in the presence of a methyltransferase, whereby the donor genome is methylated; melting the agarose; and incubating the donor genome with the recipient cell. Incubation with a methyltransferase can be incubation with a crude cell extract.

The provided methods can further include incubating the donor genome in the presence of a proteinase after incubation with the methyltransferase, thereby removing proteins.

Typically, the donor genomes and the modified genomes contemplated herein are large nucleic acids. In one embodiment the donor genome is at least at or about or greater than about 100 kb, about 150 kb, about 200 kb, about 250 kb, about 300 kb, about 350 kb, about 400 kb, about 450 kb, about 500 kb, about 550 kb, about 600 kb about 600 kb, about 650 kb, about 700 kb, about 750 kb, about 800 kb, about 850 kb, about 900 kb, about 1 megabase (MB), about 1.1 MB, about 1.2 MB, about 1.3 MB, about 1.4 MB, about 1.5 MB, about 1.6 MB, about 1.7 MB, about 1.8 MB, about 1.9 MB, about 2 MB, about 2.5 MB, about 3 MB, about 3.5 MB, about 4 MB, 4 about 5 MB, or greater in length, or any number therebetween.

BRIEF DESCRIPTION OF THE DRAWINGS

FIG. 18C provides a schematic of the *M. mycoides* YCpMmyc1.1 genome; the position of the integ minimal viral genome), or organelle function within a host cell (minimal organelle genome), under at least one set of environmental conditions. Thus, the term genome refers to whole genomes and portions thereof that are at least minimal genomes. The particular environmental conditions and property that is caused or sustained by the genome can be specified. In the case of an organelle or viral genome, or other genome that depends on a host cell for propagation and viability, the environmental conditions can include the environment of a suitable and functional host cell. Thus, the term genome encompasses minimal genomes and minimal replicative genomes, and genomes containing additional nucleic acid sequences beyond those found in such minimal genomes but not containing all the nucleic acid sequences present in a whole genome. The term "genome" encompasses naturally-occurring genomes and synthetic genomes, and includes genetically engineered genomes, such as genomes not previously existing in nature or in a laboratory, including modified genomes and hybrid genomes that contain nucleic acids and/or portions of genomes from more than one species. The term "genome" encompasses organelle genomes (e.g., mitochondrial and chloroplast genomes), genomes of self-replicating organisms (cellular genomes), including prokaryotic and eukaryotic organisms, fungi, yeast, bacteria (e.g., *Mycoplasma*), archeabacteria, vertebrates, mammals, and other organisms, and viral genomes and other genomes that depend on a host for propagation. Genomes further include those of organisms not falling into any known Linnean category and synthetic organisms. Exemplary genomes can be microorganism genomes, such as genomes of unicellular organisms including bacteria and yeast.

Figure 1:
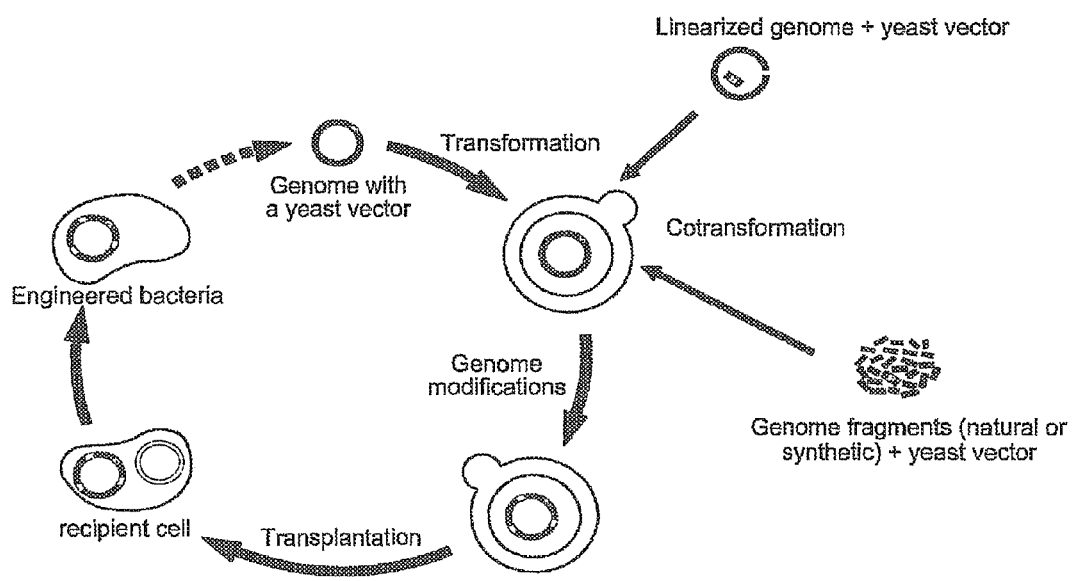
FIG. 1. illustrates various embodiments by which a donor genome and host vectors can be introduced (by transformation or cotransformation) into a host cell. One or more genome modifications can be made in the host cell. The modified genome can then be isolated and transplanted into a recipient cell.

As used herein, "cellular genome" refers to genomes containing nucleic acid sequences sufficient to cause and/or sustain viability of a cell. Such nucleic acid sequences include those encoding molecules required for replication, transcription, translation, energy production, transport, production of membranes and cytoplasmic components, and cell division. Cellular genomes include minimal cellular genomes, whole cellular genomes, and genomes having nucleic acids additional to minimal cellular genomes but not all the nucleic acids of whole cellular genomes. Cellular genomes differ from "viral genomes" and "organelle genomes" at least in that a cellular genome contains the nucleic acids sufficient for replication and/or viability of a cell whereas viral and organelle genomes contain the nucleic acids necessary to sustain or replicate the virus or organelle, e.g., within a host cell, but not to sustain the viability or replication of the host cell.

As used herein, "minimal genome" refers to a genome consisting of or consisting essentially of a minimal set of nucleic acids sufficient to effect and/or sustain viability of a cell (minimal cellular genome), viability, within a host cell, of an organism that depends on a host cell for viability (e.g., minimal viral genome), or organelle function within a host cell (minimal organelle genome), under at least one set of environmental conditions. It is understood that even whole organelle genomes do not necessarily encode all the proteins needed to perpetuate the organelle, and that some of the proteins are encoded by genes within the nucleus of the cell containing the organelle. Thus, minimal organelle genomes need only contain those genes necessary for organelle function within the environment of the cell. Similarly, it is understood that viruses depend on host cells for viability and thus minimal viral genomes need only support viability of the virus within a host cell. "Minimal replicating genomes" are minimal genomes that, in addition to the minimal nucleic acid sequences sufficient for survival, further contain nucleic acid sequences sufficient for self replication of a cell or organism.

As used herein, synthetic nucleic acid sequences, including synthetic genomes, all or part of which have been constructed from genetic components that have been chemically synthesized in vitro or copies of such components. The copies may have been produced by any of a number of methods as are known in the art, including cloning and amplification by in vivo or in vitro methods. A completely synthetic nucleic acid sequence or genome is one in which the entire nucleic acid or genome has been chemically synthesized in vitro or has been produced or assembled from copies of such in vitro chemically synthesized nucleic acids. By contrast, a "semi-synthetic" genome refers to a partially synthetic nucleic acid sequence or genome is a synthetic genome in which some of the genetic components are naturally-occurring, including nucleic acids cloned from naturally-occurring nucleic acids.

As used herein, a foreign or heterologous genome or nucleic acid sequence is a genome or nucleic acid sequence that is present in a host cell but is derived from a donor organism that is of a different species than the host cell. The donor organism can be of a different genus, order, kingdom, or other genetic classification, or can simply be of a different species in the same genus.

As used herein, a "target nucleic acid sequence" refers to a nucleic acid sequence that is targeted for modification, for example, by the modification methods described herein and known in the art. One or more modifications of a target nucleic acid sequence includes introduction of one or more mutations, one or more deletions, one or more substitutions and/or one or more insertions into the target nucleic acid sequence. Target regions are particular regions of the target nucleic acid sequences, such as a single gene locus, multiple gene loci, or portions thereof that are the subject of modification. In one example, the target region includes the region of the target nucleic acid sequence that is replaced with another nucleic acid sequence such as, for example, by homologous recombination. After modification of the target nucleic acid sequence, it is not necessary that the entire target region in the modified nucleic acid sequence be modified compared to the original target region. For example, modification of the target region can encompass a single insertion, deletion or substitution at a target position/residue within the target region, or can encompass modification of a number of positions/residues within one or more target portions of the target region.

B. Methods for Cloning and Manipulating Genomes and Large Nucleic Acids

Figure 16:
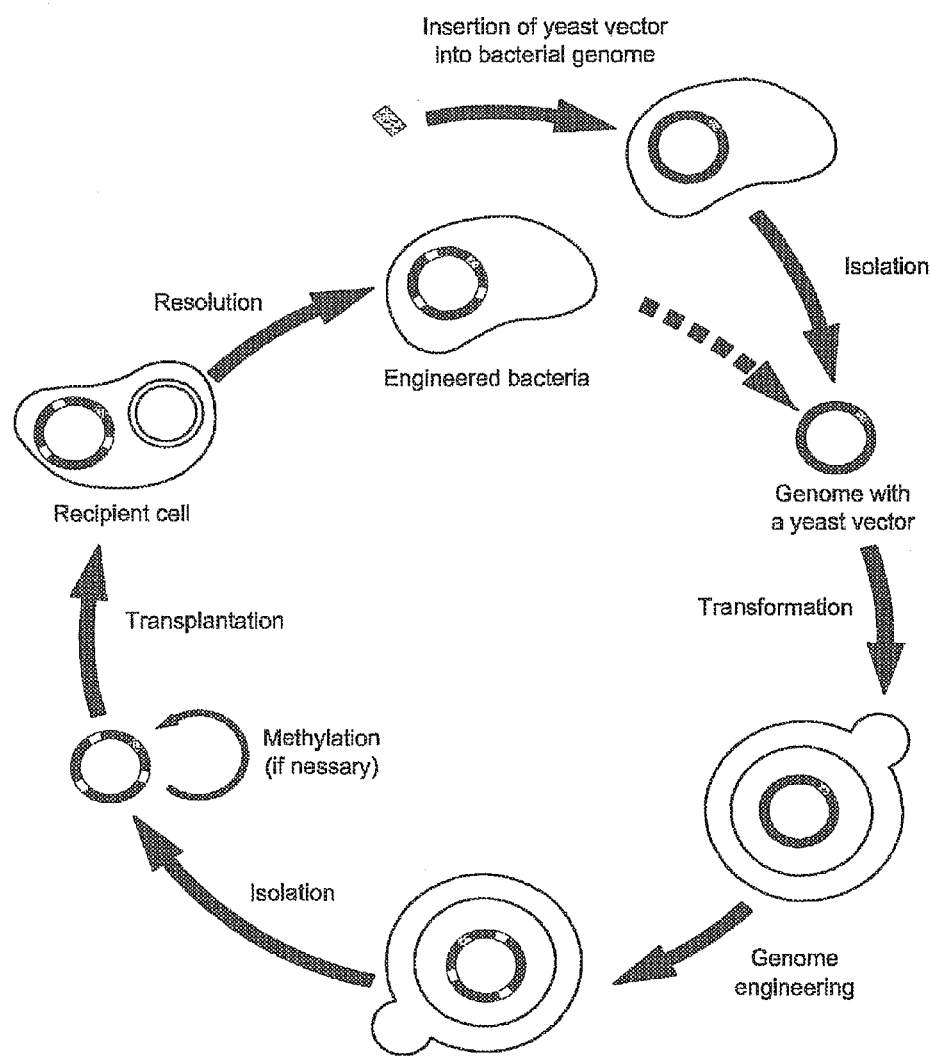

Provided herein are nucleic acids, methods and systems for introducing donor genomes and other donor nucleic acid sequences into heterologous host cells, for modifying the donor genomes and nucleic acid sequences within host cells, recovering donor genomes and nucleic acid sequences from the host cells, and introducing the recovered donor genomes and nucleic acid sequences into recipient cells. Included within the scope of the provided nucleic acid sequences, methods and systems, are aspects that minimize incompatibility, e.g. and/or toxicity between nucleic acid sequences, cells, and genetic systems of donors, hosts, and recipients. An exemplary embodiment of the provided methods is illustrated in FIG. 1, in which the methods are used to transform a bacterial donor genome into a yeast host cell, by joining it with a yeast host vector, modifying the donor genome within the yeast host cell, and transplanting the modified donor genome into a bacterial recipient cell, thereby generating an engineered bacterium. As indicated in FIG. 1, the modified genome present in that engineered bacterium can be isolated and serve as a donor genome in a subsequent round of the methods in an iterative fashion. A number of variations of this embodiment are contemplated and within the scope of this application, as described herein. Another exemplary method of the provided methods is illustrated in FIG. 16 in which the methods are used to insert a host yeast vector into a bacterial genome, isolate the genome with the integrated yeast vector, transform a yeast host cell with the bacterial genome/yeast vector, modify the bacterial genome, isolate the modified genome, optionally methylate the genome, and transplant the donor genome into a recipient cell.

Example 5 describes the successful combination of the provided methods to generate a new bacterial organism by transforming a donor bacterial genome into yeast host cells, modifying the donor genome within the yeast cells, and then transplanting the resulting modified donor genomes into recipient cells, whereupon gene expression from the modified donor genomes was induced. The results were verified by negative controls and sequencing of genomes in the recipient cells. This study demonstrated successful generation of a *M. mycoides* LC genome, containing a seamless deletion of the Type III restriction enzyme gene, which could not have been generated within the *Mycoplasma* using current state of the art method using its available native genetic systems. Transplantation produced a *M. mycoides* LC strain that had not previously existed in the laboratory or in nature. Thus, the provided methods can be used for successful genetic engineering outside of the cell encoding the genome being engineered.

Methods and tools, and resulting cells, for manipulating genomes and large nucleic acids are provided, for example, to engineer and alter organisms that can produce useful compounds, such as vaccines, drugs, biologically produced proteins or chemicals, and biofuels. In particular, methods are needed for manipulation of genomes and chromosomes of organisms having poor genetic systems, such as intractable organisms, to generate modified genes, genomes, and organisms that produce new gene products such as those useful in energy production and medicine.

Prior to the present application, available methods for manipulating genomes and other large nucleic acids were limited. Many organisms, including unicellular organisms such as prokaryotes, with desirable properties/characteristics/phenotypes, such as the ability to produce useful compounds and the capacity to function in extreme environments, have very poor or non-existent genetic systems (systems allowing modification of the organisms' nucleic acids in the laboratory). Accordingly, the present disclosure provides methods and tools needed to transfer these genomes and nucleic acids into other cells (host cells) that have more desirable genetic systems and to modify the genomes and nucleic acids within these other cells using the desirable systems.

In order to produce new gene products from the modified nucleic acids, the present invention also provides methods to transplant them from the host cells into an environment in which gene products can be expressed, such as an appropriate recipient cell. Although expression may be sufficient in host cells, for example, it may be desirable to transplant the donor genomes from the host cells into recipient cells that have cellular environments that more closely replicate that of the original donor cell or organism from which the natural or synthetic donor genome was derived. Generally, improved transfer, cloning, modification, and transplantation methods, nucleic acids, and systems that can be used to manipulate and engineer genomes and other nucleic acids, particularly large nucleic acids, are provided herein.

Similarly, prior to the present application, transfer of large nucleic acids, including genomes, into host cells, by available methods was limited. While conventional methods for cloning nucleic acids are well known (bacteria and yeast having good genetic systems have been used as hosts for cloning nucleic acid segments from a number of organisms), limitations associated with these methods can make them undesirable for manipulating and engineering genomes and large nucleic acids. For example, the size of nucleic acid that can be cloned into a host cell using conventional methods is limited. Nucleic acids cloned by conventional methods generally contain no more than a few genes.

Incompatibility and toxicity issues can also limit available cloning methods. For example, donor nucleic acids can be toxic to host cells (e.g., if toxic proteins are expressed from the donor nucleic acid) and can becomes unstable during events such as host cell replication and/or modification using the host's genetic system. Such events may limit the ability to manipulate the nucleic acids within the host cells. Further, the fact that unwanted modifications to a donor genome, which may occur during the modification process, often have no negative impact on host cell viability can make donor genomes and other nucleic acids unstable in host cells.

Incompatibility issues also can impair efficient transplant of the donor genomes from the host cells back into a more natural environment for expression of gene products, such as into recipient cells of the same or closely related species as the donor. Among the provided embodiments are modification methods that overcome such issues for successful propagation and modification of donor nucleic acids, including genomes, in genetically distinct host cells, such as yeast host cells for transplantations into recipient cells more distinct from the species of the original donor genome.

Recovery of donor genomes from a host cell and further introduction of the donor genome into a recipient cell, where the donor, host and recipient cells are less closely related (such, as from different branches of life), may pose additional challenges. For example, introduction of donor genomes propagated in eukaryotic hosts into prokaryotic recipients may be limited by incompatibility and toxicity issues. Restriction-modification systems that are present in recipient cells (and perhaps also in donor cells), but not in host cells can cause incompatibility upon transplantation if the donor genome has been propagated within the host cell. Although some host cells, such as yeast, do not contain restriction-modification systems, they can express DNA methyltransferases that can modify the donor nucleic acids being propagated in the host cell, thereby inhibiting activation of the donor nucleic acid (e.g., genome) upon transplantation into a recipient cell. The structure and confirmation of donor genomes isolated after propagation and modification in host cells can also differ from the confirmation and structure of the same genome propagated in a cell more closely related to the donor organism. Such differences can negatively impact transplantation.

Described herein are methods that overcome such limitations for successful cloning of donor genomes, modification and/or propagation of donor genomes in host cells, recovery of the donor genomes and introduction of donor genomes into recipient cells. In one aspect, donor genomes recovered from host cells are introduced into genetically distinct recipient cells (such as from eukaryotic hosts to prokaryotic recipients).

Donor nucleic acid sequences, e.g., donor genomes, are selected and synthesized, assembled, and/or isolated (e.g., from donor cells) and cloned in host cells. The methods comprise obtaining a donor genome from a donor cell or synthesizing a donor genome as one or more fragments and introducing the donor genome and a host vector into a heterologous host cell, wherein the donor genome and the host vector are optionally joined prior to introduction into the host cell, thereby generating a host cell comprising the donor genome comprising the host vector, and further wherein the donor genome is an essentially intact cellular, viral, or organelle genome that is at least a minimal genome, and is greater than about 300 kb in length.

A first embodiment typically involves introduction of a host vector into a cell containing a donor genome, joining of the donor genome to the host vector, recovering the donor genome comprising the host vector and transforming a host cell such that the donor genome comprising the host vector is maintained within the host cell during host cell replication.

In a second embodiment, a host vector and a linearized donor genome are cotransformed in a host cell where the host vector and donor genome are joined by homologous recombination in the host cell.

In a third embodiment, overlapping DNA fragments (natural or synthetic) and a host vector are cotransformed in a host cell where the host vector and DNA fragments are joined by homologous recombination in the host cell.

A donor genome to be used in the present methods can be an essentially whole cellular, viral or organelle genome.

The donor genome and the host vector can be introduced into the host cell simultaneously or sequentially in either order. In one embodiment, the host vector is joined with the donor genome prior to introduction into the host cell by transforming the host vector into a donor cell containing the donor genome.

A host cell for use in the present embodiments can be a eukaryotic cell or a prokaryotic cell. Host cells include, but are not limited to, a bacterial cell, a fungal cell, an insect cell, a plant cell, or an algal cell. Host cells also include yeast cells.

A host vector is a vector useful for homologous recombination. A host vector for use in the present embodiments can be a centromeric plasmid. In one embodiment, the host vector is a yeast centromeric plasmid and the host cell is a yeast cell.

A donor genome contemplated for use in the present embodiments can be, for example, a bacterial genome, a fungal genome, a yeast genome, an archeal genome, a cyanobacterial genome, an algal genome, a bacteriophage genome, a mitochondrial genome, a chloroplast genome, viral genome, an organelle genome, or a synthetic genome.

In another aspect, the methods further comprise modifying the donor genome within the host cell.

In another aspect, the methods further comprise recovering the donor genome comprising the host vector from the host cell.

In another aspect, the methods further comprise introducing the recovered donor genome into a recipient cell.

In yet another aspect, the methods further comprise degrading or removing the endogenous genome of the recipient cell.

Optionally, a recovered donor genome can be methylated prior to introduction into the recipient cell.

Optionally, a recipient cell's restriction endonuclease function is absent, removed or inactivated.

A recipient cell contemplated for use in the present embodiments can be, for example, a bacterial cell, a yeast cell, a fungal cell, an insect cell, a plant cell, or an algal cell.

In yet another aspect, the methods further comprise introducing a second donor genome into the host cell, wherein the second donor genome is different from the first donor genome, thereby producing a host cell containing two different donor genomes. Introducing the second donor genome can comprise mating the host cell containing the first donor genome with a second host cell containing the second donor genome. Introducing the recovered donor genome into the recipient cell can phenotypically transform the recipient cell to a phenotype corresponding to the donor genome incorporating any modifications thereto.

Provided herein is an isolated, synthetic or recombinant cell produced by any of the methods described herein.

Provided herein is a process for making a cell which exhibits a phenotype encoded by a donor genome, said process comprising: (a) introducing into a host cell, the donor genome and a host vector suitable for cloning the donor genome in the host cell such that a product comprising the donor genome comprising the host vector is obtained; (b) recovering the product comprising the donor genome comprising the host vector obtained in step (a) from the host cell; (c) introducing the product of (b) into a recipient cell under conditions such that the recipient cell exhibits a phenotype encoded by the product; and (d) recovering the cell resulting from step (c); wherein the donor genome is an essentially intact cellular, viral, or organelle genome that is at least a minimal genome, and is greater than about 300 kb in length and comprises the minimal components of nucleic acid material necessary for the recipient cell to exhibit the phenotype encoded by the donor genome. In one aspect, the method further comprises modifying the donor genome of (a) within the host cell. In another aspect, the method further comprises degrading or removing an endogenous genome of the recipient cell. In yet another aspect, the method further comprises modifying the donor genome of (a) within the host cell and degrading or removing an endogenous genome of the recipient cell.

Provided herein is a cell which exhibits a desired phenotype encoded by a donor genome and not otherwise exhibited by the cell, wherein the cell is produced by the processes described herein.

Also provided herein is a cell which comprises a donor genome and exhibits a desired phenotype encoded by the donor genome and not otherwise exhibited by the cell, wherein the donor genome comprises greater than 300 kb of foreign genomic nucleic acid material and the minimal components of a genome necessary for the cell to exhibit the desired phenotype.

The modification methods and tools include aspects that minimize the risk of instability of the donor nucleic acid sequence within the host cell during modification. In a third embodiment, donor nucleic acid sequences are transplanted from host cells into recipient cells, which can be of a different species and/or different branches of life than the donor cells and the host cells, or of the same species as the donor cells. The transplant methods include aspects that minimize the risk of incompatibility and toxicity among the donor genome, host cells, and the recipient cells.

The transfer, modification, and transplantation methods can be performed separately, and can also be performed sequentially, in combination. Thus, in one embodiment, the three steps can be combined in a method by which donor genomes are transferred into a host cell, modified within the host cell, and transplanted into a recipient cell to generate a new cell, thereby generating a genome or cell not previously existing in the laboratory or in nature. The recipient cells can be further grown into, or transferred into, a non-human organism not previously existing. Thus, the provided methods, nucleic acids and systems can be used to produce new organisms. Also provided are newly created organisms and nucleic acid sequences thereof.

The provided methods and compositions are particularly useful for manipulating and engineering genomes from organisms that are genetically intractable. In one example, the methods, nucleic acid sequences, and systems are used to clone whole bacterial genomes from *Mycoplasma genitalium*, *Mycoplasma pneumoniae*, and *Mycoplasma mycoides* LC as circular centromeric plasmids in yeast, to modify the donor genomes within the yeast using the yeast genetic systems with modifications to minimize incompatibility and, further, to transplant the modified bacterial genomes into recipient cells of a different species, thereby generating genomes and organisms not previously existing in the lab or in nature.

The provided methods, nucleic acid sequences, systems, and organisms can be used to engineer organisms that synthesize biofuels. For example, although bacteria such as *Escherichia coli* can be genetically modified, many prokaryotes having the potential to produce industrially useful compounds or to function in extreme environments have very poor or non-existent genetic systems. *Prochlorococcus marinus* is among the most abundant photosynthetic organisms on earth. While it is desirable to manipulate and engineer this and other such organisms to produce biofuels, the ability to manipulate and engineer such organisms is limited by the lack of available methods to genetically alter them. The provided methods can be used to carry out such manipulations. For example, in one embodiment, nucleic acid sequences encoding components of new metabolic pathways can be introduced into the genomes of such organisms by transfer and modification within host cells. Such re-engineered genomes can be transplanted into suitable recipient cells to produce new cells, e.g., new cells that can convert sunlight and carbon dioxide into a biofuel. Such engineered cells and organisms also are provided herein.

The provided method also can be useful for engineering archea, cloning new organelles into eukaryotes and adding chromosomes to cells and organisms. For example, eukaryotic mitochondria and chloroplasts are remnants of endosymbiotic bacteria that have become trapped in their hosts. The provided methods can be used to engineer such organelle genomes in hosts, e.g., in yeast using plasmids, using homologous recombination, thereby creating new mitochondria and chloroplast genomes having improved energy production efficiency and/or metabolism, such as in yeast or algae.

In another embodiment, the provided methods can be used to manipulate viruses, such as those with large genomes that are too large for manipulation in simple plasmids, to produce viruses and bacteriophages having therapeutic uses. In one aspect, viral genomes are cloned and manipulated to improve their immunogenicity and other therapeutic advantages.

In another embodiment, the provided methods can be used to manipulate fungi to produce fungi useful in the production of, for example, wine, bread, beer and medicine. In one aspect, fungal genomes are cloned and manipulated to improve their resistance to temperature, disease-causing organisms, and other advantages. In another embodiment, the provided methods can be used to manipulate yeast to produce yeast useful in ethanol fuel, nutritional supplements, probiotics, fermentation for production of beverages (alcoholic and non-alcoholic) or for use in baking.

Although certain embodiments are provided herein, the methods and processes of the present invention are universal tools that can be used to produce any desired phenotype or product of interest.

Methods and processes of the invention are amenable to automation and to adaptation to high throughput methods, for example, allowing for the joining of multiple nucleic acid molecules and transformation into host or recipient cells simultaneously by computer-mediated and/or robotic methods that do not require human intervention.

The present invention, thus, is directed to systematic methods and the products thereof that permit efficient and extensive assembly, cloning, modification, and transformation of nucleic acid molecules comprising genomes in a high-throughput manner, and readily adaptable to robotic implementation. In alternative embodiments, nucleic acid assembly reactions can be performed on a solid surface as opposed to in a reaction tube, for example, on a chip using microfluidics.

C. Selection and Isolation of Donor Genomes and Nucleic Acids

In a first step of the provided methods, a donor genome or other nucleic acid sequence is selected for transfer, modification, and/or transplantation. The nucleic acid sequences that are transferred, modified, transplanted, and generated by the methods described herein can be of any natural or synthetic organism. Thus, the donor genome is derived from any desired cell or any nucleic acid-containing subunit thereof, either by isolation or chemical synthesis. For example, the nucleic acid sequences include genomes (such as whole genomes, portions of whole genomes that are at least minimal genomes and/or at least minimal replicating genomes, cellular genomes, organelle genomes, and viral genomes), chromosomes, and other large nucleic acid sequences from known organisms and new organisms. The nucleic acid sequences, including genomes, can be of any source within the organisms, including organelle genomes, such as mitochondrial and chloroplast genomes, chromosomes, portions of genomes or chromosomes of plants and animals, algal sources, and any genomic material that supports cell viability, including the whole and minimal cellular genome of bacteria and other prokaryotes, and eukaryotic organisms.

It is apparent, from a review of the examples below and discussion provided herein that the applicability of the described methods are not limited to constructing synthetic genomes that mimic those present in nature. The methods can be used, for example, to join portions of genomes of various organisms in the same DNA molecule to generate new genomes and organisms not present in nature or in the laboratory. The donor genomes and other nucleic acids can be cloned, propagated and/or isolated from cells, such as cells or tissues (including genetically engineered organisms), or can be chemically synthesized in vitro. Methods for isolating and preparing the nucleic acids and genomes are described below.

i. Donor Organisms, Genomes and Other Nucleic Acids

Genomes and other nucleic acid sequences used and generated in the provided methods (e.g., the donor nucleic acids) include those derived from fungi, yeast, bacteria, other prokaryotes, and algae but are not limited to such organisms. They can be of any organism, natural or synthetic, e.g., organisms of the kingdoms Protista, Archaebacteria, Eubacteria, Fungi, Plantae, and Animalia, and viruses, including bacteriophages.

Exemplary nucleic acid sequences are those derived from bacteria, archea, cyanobacteria (e.g., *Prochlorococcus marinus*, *Synechocystis* PCC6803, etc.), algae, viruses (e.g., *Haemophilus influenzae* genomes), fungi (e.g., *Saccharomyces cerevisiae*, *Saccharomyces bayanus*, *Saccharomyces boulardii*, *Neurospora crassa*, etc.), and bacteriophages. Exemplary *Mycoplasma* strains include *Mycoplasma genitalium* (e.g., *M. genitalium* strain MS5, described in Example 1, *M. geni-* talium G37 (GenBank No. L43967)), *Mycoplasma mycoides* (e.g., *M. mycoides* subspecies *mycoides* Large Colony (LC) strain GM12 (Example 1), *Mycoplasma capricolum* subsp. *capricolum* (strain California Kid™) (ATCC 27343), *Mycoplasma mycoides* subsp. *mycoides* (strain GM12) (Damassa et al., 1983), *Mycoplasma capricolum* subsp. *capricolum* (*M. capricolum*), such as wt *M. capricolum* and a *M. capricolum* mutant (*M. capricolum*-ΔRE) and *Mycoplasma pneumonia* (e.g., *M. pneumoniae* strain M129-B 170 (ATCC 29343); *M. pneumoniae* M129, GenBank Accession Number U00089.2 (GI: 26117688)), *Mycoplasma gallisepticum* (ATCC 15302), *Mycoplasma pneumoniae* Eaton (ATCC15531), and derivatives thereof.

Exemplary genomes and nucleic acids include full and partial genomes of a number of organisms for which genome sequences are publicly available and can be used with the disclosed methods, such as, but not limited to, *Aeropyrum pernix; Agrobacterium tumefaciens; Anabaena; Anopheles gambiae; Apis mellifera; Aquifex aeolicus; Arabidopsis thaliana; Archaeoglobus fulgidus; Ashbya gossypii; Bacillus anthracis; Bacillus cereus; Bacillus halodurans; Bacillus licheniformis; Bacillus subtilis; Bacteroides fragilis; Bacteroides thetaiotaomicron; Bartonella henselae; Bartonella quintana; Bdellovibrio bacteriovirus; Bifidobacterium longum; Blochmannia floridanus; Bordetella bronchiseptica; Bordetella parapertussis; Bordetella pertussis; Borrelia burgdorferi; Bradyrhizobium japonicum; Brucella melitensis; Brucella suis; Buchnera aphidicola; Burkholderia mallei; Burkholderia pseudomallei; Caenorhabditis briggsae; Caenorhabditis elegans; Campylobacter jejuni; Candida glabrata; Canis familiaris; Caulobacter crescentus; Chlamydia muridarum; Chlamydia trachomatis; Chlamydophila caviae; Chlamydophila pneumoniae; Chlorobium tepidum; Chromobacterium violaceum; Ciona intestinalis; Clostridium acetobutylicum; Clostridium perfringens; Clostridium tetania Corynebacterium diphtheriae; Corynebacterium efficiens; Coxiella burnetii; Cryptosporidium hominis; Cryptosporidium parvum; Cyanidioschyzon merolae; Debaryomyces hansenii; Deinococcus radiodurans; Desulfotalea psychrophila; Desulfovibrio vulgaris; Drosophila melanogaster; Encephalitozoon cuniculi; Enterococcus faecalis; Erwinia carotovora; Escherichia coli; Fusobacterium nucleatum; Gallus gallus; Geobacter sulfurreducens; Gloeobacter violaceus; Guillardia theta; Haemophilus ducreyi; Haemophilus influenzae; Halobacterium; Helicobacter hepaticus; Helicobacter pylori; Homo sapiens; Kluyveromyces waltii; Lactobacillus johnsonii; Lactobacillus plantarum; Legionella pneumophila; Leifsonia xyli; Lactococcus lactis; Leptospira interrogans; Listeria innocua; Listeria monocytogenes; Magnaporthe grisea; Mannheimia succiniciproducens; Mesoplasma florum; Mesorhizobium loti; Methanobacterium thermoautotrophicum; Methanococcoides burtonii; Methanococcus jannaschii; Methanococcus maripaludis; Methanogenium frigidum; Methanopyrus kandleri; Methanosarcina acetivorans; Methanosarcina mazei; Methylococcus capsulatus; Mus musculus; Mycobacterium Bovis; Mycobacterium leprae; Mycobacterium paratuberculosis; Mycobacterium tuberculosis; Mycoplasma gallisepticum; Mycoplasma genitalium; Mycoplasma mycoides; Mycoplasma penetrans; Mycoplasma pneumoniae; Mycoplasma pulmonis; Mycoplasma mobile; Nanoarchaeum equitans; Neisseria meningitidis; Neurospora crassa; Nitrosomonas europaea; Nocardia farcinica; Oceanobacillus iheyensis; Onions yellows phytoplasma; Oryza sativa; Pan troglodytes; Pasteurella multocida; Phanerochaete chrysosporium; Photorhabdus luminescens; Picrophilus torridus; Plasmodium falciparum; Plasmodium yoelii yoelii; Populus trichocarpa; Porphyromonas gingivalis Prochlorococcus marinus; Propionibacterium acnes; Protochlamydia amoebophila; Pseudomonas aeruginosa; Pseudomonas putida; Pseudomonas syringae; Pyrobaculum aerophilum; Pyrococcus abyssi; Pyrococcus furiosus; Pyrococcus horikoshii; Pyrolobus fumarii; Ralstonia solanacearum; Rattus norvegicus; Rhodopirellula baltica; Rhodopseudomonas palustris; Rickettsia conorii; Rickettsia typhi; Rickettsia prowazekii; Rickettsia sibirica; Saccharomyces cerevisiae; Saccharomyces bayanus; Saccharomyces boulardii; Saccharopolyspora erythraea; Salmonella enterica; Salmonella typhimurium; Schizosaccharomyces pombe; Shewanella oneidensis; Shigella flexneria; Sinorhizobium meliloti; Staphylococcus aureus; Staphylococcus epidermidis; Streptococcus agalactiae; Streptococcus mutans; Streptococcus pneumoniae; Streptococcus pyogenes; Streptococcus thermophilus; Streptomyces avermitilis; Streptomyces coelicolor; Sulfolobus solfataricus; Sulfolobus tokodaii; Synechococcus; Synechocystis; Takifugu rubripes; Tetraodon nigroviridis; Thalassiosira pseudonana; Thermoanaerobacter tengcongensis; Thermoplasma acidophilum; Thermoplasma volcanium; Thermosynechococcus elongatus; Thermotagoa maritima; Thermus thermophilus; Treponema denticola; Treponema pallidum; Tropheryma whipplei; Ureaplasma urealyticum; Vibrio cholerae; Vibrio parahaemolyticus; Vibrio vulnificus; Wigglesworthia glossinidia; Wolbachia pipientis; Wolinella succinogenes; Xanthomonas axonopodis; Xanthomonas campestris; Xylella fastidiosa; Yarrowia lipolytica; Yersinia pseudotuberculosis; and Yersinia pestis* nucleic acids.

The term "algae" includes cyanobacteria (Cyanophyceae), green algae (Chlorophyceae), yellow-green algae (Xanthophyceae), golden algae (Chrysophyceae), brown algae (Phaeophyceae), red algae (Rhodophyceae), diatoms (Bacillariophyceae), and "pica-plankton" (Prasinophyceae and Eustigmatophyceae). Also included in the term algae are members of the taxonomic classes Dinophyceae, Cryptophyceae, Euglenophyceae, Glaucophyceae, and Prymnesiophyceae. Microalgae are unicellular or colonial algae that can be seen as single organisms only with the aid of a microscope. Microalgae include both eukaryotic and prokaryotic algae (e.g., cyanobacteria). Photosynthetic bacteria include cyanobacteria, green sulfur bacteria, purple sulfur bacteria, purple nonsulfur bacteria, and green nonsulfur bacteria.

Exemplary genomes and nucleic acids include full and partial genomes of a number of algal organisms for which genome sequences are publicly available and can be used with the disclosed methods, such as, but not limited, *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Platymonas, Pkurochrysis, Pleurococcus, Prototheca, Pseudochlorella, Pyramimonas, Pyrobotrys, Scenedesmus, Schizochytrium, Skeletonema, Spyrogyra, Stichococcus, Tetraselmis, Thraustochytrium, Thalassiosira, Viridiella*, or *Volvox* species. In some embodiments, photosynthetic bacteria, including for example, green sulfur bacteria, purple sulfur bacteria, green nonsulfur bacteria, purple nonsulfur bacteria, or cyanobacteria may be used. Cyanobacterial species that can be used include, without limitation, *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Tolypothrix, Trichodesmium, Tychonema*, or *Xenococcus* species.

The genomes and other nucleic acid sequences include modified and synthetic nucleic acid sequences derived from such genomes. The presently described methods are equally applicable to yet unpublished nucleic acid sequences, as they become available, including those that characterize multicellular organisms such as higher plants, such as corn and rice, mammals such as rodents (mice, rats, rabbits, etc.), pigs, cows, bulls, horses, primates, sheep, and companion animals (e.g., dogs, cats, etc.). In one embodiment, cells isolated from a human can be used to obtain a donor genome. Many of these are available at the present time. The nucleic acid sequences and genomes include those that do not mimic those present in nature.

In one embodiment, the genomes and other nucleic acid sequences selected for manipulation by the methods are derived from intractable organisms or other organisms with poor genetic systems or genetic systems that are less desirable than those of host organisms, including certain prokaryotes and other non-yeast organisms, such as those in which common genetic techniques are inefficient, such as double crossover homologous recombination and transposon mutagenesis. These techniques are inefficient, for example, in certain bacterial organisms, such as *Mycoplasma* species. Although integration of plasmid DNA by single crossover events has been carried out for targeted addition and disruption of genes in *M. mycoides* LC (Janis, C., et al. 2005, *Appl Environ Microbiol* 71:2888-93), this organism contains a paucity of selection markers, limiting the number of genetic modifications that can be performed in a single *M. mycoides* LC cell.

Of interest are organisms such as prokaryotes, including those with poor genetic systems, with the potential to produce industrially useful compounds and/or to function in extreme environments (e.g., elevated temperatures, elevated pressure, etc.). Exemplary organisms include those that can be used to produce biofuels. Other exemplary organisms include those that undergo photosynthetic processes. Genomes and organisms can be genetically modified using the methods described herein and known in the art to generate novel genomes and organisms for the production of biofuels. For example, genes involved in photosynthesis and other metabolic processes can be modified to generate organisms that produce oils, e.g., biofuels, in place of glucose or another carbon source. Thus, included herein are genomes are those of organisms engineered with the capacity to convert sunlight and carbon dioxide into a biofuel. One such exemplary organism is *Prochlorococcus marinus*, which is among the most abundant photosynthetic organisms on earth but has an inefficient genetic system.

In one embodiment, the methods are carried out to modify and engineer genomes, such as whole (complete) genomes (e.g., whole cellular, viral, and organelle genomes), and portions of whole genomes containing genetic material sufficient to effect and/or sustain viability of a cell (minimal cellular genome), viability, within a host cell, of an organism that depends on a host cell for viability (e.g., minimal viral genome), or organelle function within a host cell (minimal organelle genome), under at least one set of environmental conditions. In one aspect, the genome is a minimal genome or a minimal replicative genome. In another aspect, the genome contains additional nucleic acid sequences beyond those found in a minimal genome or in a whole genome.

The genome can be naturally-occurring or synthetic, such as genetically engineered genomes including modified genomes and hybrid genomes that contain nucleic acid sequences and/or portions of genomes from more than one species.

In one aspect, the genomes are cellular genomes, containing nucleic acid sequences sufficient to cause and/or sustain viability of a cell, e.g., those encoding molecules required for replication, transcription, translation, energy production, transport, production of membranes and cytoplasmic components, and cell division.

In another aspect, the genome is a viral or organelle genome.

In one embodiment, the nucleic acid sequences are organelle nucleic acid sequences, e.g., organelle genomes, such as plastid, e.g., chloroplast, and mitochondrial genomes. Eukaryotic organelles, such as mitochondria and chloroplasts, are cytoplasmic DNA-containing, membrane-bound compartments thought to be remnants of endosymbiotic bacteria that became trapped in their hosts. Generally, mitochondria are found naturally in all eukaryotic cells and chloroplasts and other plastids are found naturally in plants and algae. Plastid genomes vary in size from 35 to 217 kb, with the majority being between 115 and 165 kb. Mitochondrial genomes vary greatly in size among different species, and can be from below 20 kb to over 350 kb. The methods of the present application allow for engineering of organelle genomes in host cells using nucleic acids and genetic systems within the host cells. For example, organelles can be modified in yeast hosts using yeast plasmids and homologous recombination. The provided methods can be used to generate novel mitochondria or chloroplast genomes, for example, to increase energy production or metabolism in eukaryotic cells, such as yeast and algae.

In another embodiment, the nucleic acids are viral and bacteriophage nucleic acids, such as viral and bacteriophage genomes. For example, viral and bacterial nucleic acids and genomes can be modified and engineered by the provided methods to generate viruses with therapeutic uses. As another example, viral genomes can be cloned and manipulated using the methods described herein. Viruses have been used for gene therapy, vaccines, and as Trojan horses in medical applications; however, viral genomes are too large for manipulation in simple plasmids. Similarly, bacteriophages have been used as antibiotics for decades; yet genomes of the T-phage are too large to be worked with easily.

In another embodiment, the nucleic acid sequences modified, engineered and generated by the provided methods are not genomes. For example, the nucleic acids include chromosomes and other nucleic acid sequences.

Typically, the nucleic acid sequences and genomes are large nucleic acid sequences. In one aspect, the genome or other nucleic acid sequence is at least at or about 100 kb, 150 kb, 200 kb, 250 kb, 300 kb, 350 kb, 400 kb, 450 kb, 500 kb, 550 kb, 600 kb, 650 kb, 700 kb, 750 kb, 800 kb, 850 kb, 900 kb, 950 kb, 1 megabase (MB), 1.1 MB, 1.2 MB, 1.3 MB, 1.4

MB, 1.5 MB, 1.6 MB, 1.7 MB, 1.8 MB, 1.9 MB, 2 MB, 2.1 MB, 2.2 MB, 2.3 MB, 2.4 MB, 2.5 MB, 2.6 MB, 2.7 MB, 2.8 MB, 2.9 MB, 3 MB, 3.1 MB, 3.2 MB, 3.3 MB, 3.4 MB, 3.5 MB, 3.6 MB, 3.7 MB, 3.8 MB, 3.9 MB, 4 MB, 4.5 MB, 5 MB, 6 MB, 7 MB, 8 MB, 9 MB, 10 MB, 15 MB or 20 MB in length, or any specific number or range therein. The provided methods are also useful in manipulating and cloning smaller nucleic acid sequences such as, for example, those smaller than about 100 kb.

ii. Propagation, Isolation, and Synthesis of Donor Genomes and Other Nucleic Acids Prior to transfer, the nucleic acid sequences can be propagated in and/or isolated from cells or tissues. The donor nucleic acid sequences can be isolated from donor cells or tissues (e.g. cells and tissues from a donor organism) or can be transformed into and propagated within other cells, using well-known cloning, cell, and plasmid techniques and systems. The nucleic acid sequences in the cells can be natural or synthetic, including partially synthetic. In some cases, the nucleic acid sequences are amplified, such as by PCR, after isolation from cells or tissues.

Donor nucleic acids can also be chemically synthesized in vitro using chemical synthesis and assembly methods and, thus, are not isolated from any particular tissue or cell prior to use in the described methods. Methods for chemical synthesis of DNA and RNA and assembly of nucleic acids are known, and include oligonucleotide synthesis, assembly, and polymerase chain reaction (PCR) and other amplification methods (such as, for example, rolling circle amplification, whole genome amplification), such as those described herein and in U.S. application Ser. No. 12/247,126, to Gibson et al., filed Oct. 7, 2008. Synthesis of DNA, for example, can be from DNA (e.g., by PCR) or from RNA, e.g., by reverse transcription. Among the nucleic acids are synthetic genomes. Synthetic genomes can be produced, for example, as described herein and in U.S. application Ser. No. 12/247,126, by Gibson et al., filed Oct. 7, 2008).

iii. Nucleic Acid Sequences, Vector-Host Systems, and Culture Conditions

The nucleic acid sequences can be isolated from a variety of sources, genetically engineered, amplified, and/or expressed/generated recombinantly. Recombinant polypeptides generated from these nucleic acid sequences can be individually isolated or cloned and tested for a desired activity. Any recombinant expression system can be used, including bacterial, mammalian, fungal, yeast, insect or plant cell expression systems.

Alternatively, the nucleic acid sequences can be synthesized in vitro, such as by well-known chemical synthesis techniques, and/or obtained from commercial sources, and optionally assembled, such as for large nucleic acids and genomes, for example, as described in U.S. application Ser. No. 12/247,126, to Gibson et al., filed Oct. 7, 2008.

Techniques for the manipulation of nucleic acid sequences, such as, e.g., subcloning, labeling probes (e.g., random-primer labeling using Klenow polymerase, nick translation, amplification), sequencing, hybridization and the like are well described in the scientific and patent literature.

Another useful means of obtaining and manipulating nucleic acid sequences used to practice the provided methods is to clone from genomic samples, and, if desired, screen and re-clone inserts isolated or amplified from, e.g., genomic clones or cDNA clones. Sources of nucleic acid sequences used in the described systems and methods include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) *Nat. Genet.* 15:333-335; yeast artificial chromosomes (YAC); bacterial artificial chromosomes (BAC); P1 artificial chromosomes (see, e.g., Woon (1998) *Genomics* 50:306-316); P1-derived vectors (PACs; see, e.g., Kern (1997) *Biotechniques* 23:120-124); cosmids, recombinant viruses, phages or plasmids.

Methods for isolation of nucleic acid sequences, such as genomic DNA, are well-known. As will be apparent to the skilled artisan, the method of isolation depends upon the type and size of sequence(s) being isolated, the type of organism, and the type of tissue or cell from which the sequence(s) is being isolated. Methods for isolation of genetic material from a variety of organisms are well known and can be used in the present embodiments to isolate donor nucleic acid sequences (genomes). For example, conventional methods for DNA isolation are well known and can be used with the provided methods, depending upon the size, and can be performed with a number of commercially available kits for isolation of nucleic acid sequences; for example, commercially available kits can be used for isolation of genomic DNA from cells.

Natural and synthetic nucleic acid sequences can be reproduced, e.g., copied, by amplification. Amplification can also be used to clone or modify the provided nucleic acid sequences. Thus, provided are amplification primer sequence pairs for amplifying the provided nucleic acid sequences. One of skill in the art can design amplification primer sequence pairs for any part of or the full length of these sequences. Amplification can also quantify the amount of nucleic acid sequence in a sample, such as the amount of donor genome in a host cell.

One can select and design suitable amplification primers. Amplification methods are also well known in the art, and include, e.g., polymerase chain reaction, PCR, ligase chain reaction (LCR), transcription amplification (see, e.g., Kwoh (1989) *Proc. Natl. Acad. Sci. USA* 86:1173); and, self-sustained sequence replication (see, e.g., Guatelli (1990) *Proc. Natl. Acad. Sci. USA* 87:1874); Q Beta replicase amplification (see, e.g., Smith (1997) *J. Clin. Microbiol.* 35:1477-1491), automated Q-beta replicase amplification assay (see, e.g., Burg (1996) *Mol. Cell. Probes* 10:257-271) and other RNA polymerase mediated techniques (e.g., NASBA, Cangene, Mississauga, Ontario); see also Berger (1987) *Methods Enzymol.* 152:307-316; Sambrook; Ausubel; U.S. Pat. Nos. 4,683,195 and 4,683,202; and Sooknanan (1995) *Biotechnology* 13:563-564.

In one embodiment, nucleic acid sequences are cloned and propagated in bacterial cells, such as *Escherichia coli*, for example, *E. coli* DH10B [F$^-$-mcrA Δ(mrr-hsdRMS-mcrBC) φ80dlacZΔM15 ΔlacX74 deoR recA1 endA1 araD139 Δ(ara, leu)7697 galU galKλ$^-$ rpsL nupG] (Invitrogen) using plasmids. Methods and plasmids for cloning and propagation of nucleic acids in *E. coli* and other laboratory strains are well known and can be used in connection with the provided methods. In one example, *E. coli* cells are grown in medium, e.g., Luria-Bertani (LB) broth medium or in LB agar, at 37° C.

Nucleic acid sequences can be propagated, for example in *Mycoplasma* cells. The *Mycoplasma* cells can be either the donor *Mycoplasma* cells that naturally contain donor nucleic acids or *Mycoplasma* cells into which donor nucleic acids, e.g., synthetic genomes, have been transformed. Exemplary *Mycoplasma* species include, for example, *Mycoplasma capricolum* subsp. *capricolum* (strain California Kid™) (ATCC 27343) and *Mycoplasma mycoides* subsp. *mycoides* (strain GM12) (Damassa et al., 1983), *Mycoplasma capricolum* subsp. *capricolum* (*M. capricolum*), such as wt *M. capricolum* and a *M. capricolum* mutant (*M. capricolum*-ΔRE), obtained by inactivation of the CCATC-restriction enzyme gene in wt *M. Capricolumn* as described below in the Examples. Methods for growth of these and other *Mycoplasma* cells and other cells are known. In one example, *Mycoplasma* donors are grown at 37° C. in liquid or solid SP4 medium (Tully et al. 1977), containing 17% of fetal bovine serum (Invitrogen).

Cell culture and plasmid systems can be engineered in order to facilitate selection of cells containing the desired nucleic acid cloned and propagated using known methods. In one example, growth of bacterial cells such as *E. coli* is carried out in medium supplemented with antibiotic or other selection agent, e.g., 50 μg/ml of ampicillin, 5 μg/ml of tetracycline or 125 μg/ml of puromycin, depending on resistance genes located within nucleic acids, e.g., plasmids used for cloning and propagation. Similarly, *Mycoplasma* cells that have been transformed with plasmid, donor genomes, or other nucleic acids can be grown in medium, e.g., SP4 medium, supplemented with 5 μg/ml of tetracycline or 8 μg/ml of puromycin.

Expression of desired gene products within cells can be detected using well-known methods. For example, β-galactosidase activity can be detected by plating *Mycoplasma* or other cell types on solid medium containing 150 μg/ml of 5-bromo-4-chloro-3-indolyl-β-D-galactopyranoside (X-gal, Promega). One would understand that other conditions and methods can for expression of gene products are contemplated herein using conventional techniques.

a. Isolation of Nucleic Acid Sequences in Agarose Plugs

Nucleic acid sequences can be isolated in agarose plugs to minimize damage. Large nucleic acid sequences, such as DNA ranging from a few kilobase pairs to 10 MB and larger (e.g., genomes), can be sheared by mechanical force (e.g., pipetting) during conventional isolation procedures, resulting in damage. Isolation of such nucleic acid sequences in agarose can minimize damage. In this embodiment, cells containing the donor DNA are embedded in agarose and lysed. Methods for isolating genomic nucleic acid sequences in agarose, e.g., low-melting point agarose, are also well known, and can be performed using commercially available kits, such as the CHEF Mammalian Genomic DNA Plug Kit (cat. No. 170-3591), the CHEF Bacterial Genomic DNA Plug Kit (cat. No. 170-3592), and the CHEF Yeast Genomic DNA Plug Kit (cat. No. 170-3593), all from Bio-Rad Laboratories, Hercules, Calif. Preparation of DNA using such kits can be carried out using conditions and protocols recommended by the supplier.

Donor nucleic acid sequences (e.g., bacterial, *Mycoplasma*, yeast, or algal genomes) can also be isolated in agarose plugs using low melting point agarose and the Bio-Rad CHEF Mammalian Genomic DNA Plug Kit, following the protocol suggested by the manufacturer. In one example, cells are suspended in medium without serum or PBS and a number of cells (e.g., $5\times10^7$ or $5\times10^8$ per mL agarose to be made) are centrifuged and resuspended in one-half the final volume of agarose to be made. Meanwhile, low-melting point agarose (e.g., Bio-Rad 2% CleanCut™ agarose) is prepared in sterile water and melted and equilibrated to 50° C. The cell suspension is equilibrated to the same temperature and mixed gently with the agarose. The mixture is transferred to a plug mold and allowed to solidify. In one example, for lysis, a mixture containing proteinase K is added (e.g., in 5 ML Proteinase K Reaction Buffer, containing 100 mM EDTA, pH 8, 0.2% sodium deoxycholate, 1% sodium lauryl sarcosine, and 1 mg/mL proteinase K, per mL plug) and incubated at 50° C. overnight. In another example, for lysis, cells in agarose are incubated for a period between overnight and two days at 50° C. in 0.4 M EDTA, 0.4% N-lauroyl sarcosine, 2 mg/mL proteinase K, followed by a buffer change and a second treatment under the same conditions for the same time.

Following lysis, agarose plugs containing donor nucleic acids can be dialyzed against 10 mM Tris pH 8.0 (optionally containing EDTA at 1 mM or 50 mM), e.g., for 1 hour. In one example, this dialysis is followed by dialysis for two times, two hours each, in 10 mM Tris, 50 mM ETDA, 0.1 mM PMSF, and re-dialysisin 10 mM Tris, 50 mM EDTA for storage. In another example, samples are then dialyzed against 10 mM (6%) PEG6000 (United States Biochemical), 0.6 M NaCl for several hours, as described by Katsura et al., *Electrophoresis* 21, 171 (January, 2000) prior to transfer. In one example, plugs further are melted at 65° C. for 5 min, followed by addition of two volumes of 65° C. TE and gentle stirring, followed by incubation at 65° C. for 5 minutes.

In some aspects, the plugs are melted and digested prior to transformation into host cells using, for example, β-agarase. In one example, plugs are electrophoresed twice by CHEF (Bio-Rad) (e.g., first on a 1% pulse-field agarose gel, with 0.5×TBE and 50-90 second switch time over 20 hours, and second on a 1% low melting point gel, with 1×TAE and 60-120 second switch time, over 24 hours), to remove broken DNA but leave genomes intact, followed by dialysis against sterile 1×TAE and melting at 73° C., equilibration to 42° C., and digestion with β-agarase (New England Biolabs), for example for 1.5 hours.

b. Isolation of Organelle Genomes

Donor nucleic acid sequences can be an organelle genome, for example, an organelle genome isolated from a donor cell. Methods for isolating organelle genomes are known in the art. Kits for isolating organelles from cells are available from a variety of manufacturers, including Pierce (Rockford, Ill.), Sigma-Aldrich (St. Louis, Mo.) and others.

Organelle genomes and other nucleic acid can be isolated from various cell types, such as eukaryotic and prokaryotic cells, including yeast cells, plant cells, algae, and mammalian cells. It is understood, as is known in the art, that the isolation procedure may vary depending upon the organism of the cell from which the organelle nucleic acid is isolated and the type of organelle isolated. The organelle nucleic acid isolation procedure can include separation of organelle DNA from nuclear DNA in a total genomic DNA sample, for example, based on molecular weight by fractionation or gel separation. In certain embodiments, organelles can be purified from total cellular fractions prior to extracting DNA.

Methods are known for isolation of chloroplasts (and other plastid) genomes from plants. Isolation is typically carried out by (1) separating plastids from other organelles, (2) lysing chloroplasts, and (3) purifying nucleic acid. In one example, sucrose or Percoll step gradients are used to obtain chloroplasts from cell lysates, which then are lysed and used to recover DNA. In a particular example, plants are placed in the dark to reduce chloroplast starch levels, green leaves washed in tap water, and placed (10-100 g) into isolation buffer for homogenization in a prechilled blender, followed by filtration through cheesecloth and centrifugation. Pellets are loaded onto a one-step gradient with 18 mL 52% sucrose, overlayed with 7 mL 30% sucrose, and optionally more sucrose gradients to enhance yield, such as at least six sucrose gradients with 200 g starting material. The step gradients are centrifuged, e.g., at 25,000 rpm for 30-60 minutes at 4° C., and the chloroplast band removed from the 30-52% interface using a wide-bore pipette. Chloroplasts then are lysed as described and centrifuged to remove debris. DNA then is purified, e.g., as described using a CsCl gradient. DNAseI treatment can be used to modify the sucrose gradient method and to destroy nuclear DNA. Alternatively, a high salt (e.g., NaCl 1.25 M)

method can be used for isolation without step-gradient centrifugation as is known in the art. Chloroplasts can be sorted from mitochondria and nuclei using fluorescence activated cell sorter (FACS) separation.

Methods for isolation of mitochondrial DNA (mtDNA), including highly purified mtDNA, are known and can be used in conjunction with the provided methods to isolate a mitochondrial genome. Highly purified mtDNA can be prepared from vertebrate or invertebrate tissues using sucrose pad gradients and cesium chloride gradients. Generally, tissue (e.g., brain, testes, ovary, liver, kidney, heart, skeletal muscle of vertebrates and invertebrate embryos) is prepared from the organism, if necessary, by homogenizing the tissue, followed by repeated centrifugation at low speed to remove cellular debris and nuclei, followed by centrifugation at high speeds and lysis of the pellet. A sucrose step gradient can be performed on the pellet by ultracentrifugation at 25,000 rpm for 1 hour at 4° C., in which the gradient contains a pad of 10 mL of 1.5 M sucrose in TE buffer and a 10 mL layer of 1 M sucrose. For this process, the pellet is resuspended in TE buffer and layered on the gradient, followed by centrifugation for 1-2 hours at 27,000 rpm at 4° C. Highly purified mitochondria, which appear as a milky white band at the interface of the 1 and 1.5 M sucrose pads, is collected with a Pasteur pipette and placed in a tube for further concentration by high-speed centrifugation (e.g., 13,000 rpm at 4° C.).

The pelleted mitochondria are then lysed, for example, by resuspending in TE buffer and adding sodium dodecyl sulfate (SDS) (e.g., 0.3 mL 10% SDS per mL TE). After the solution appears clear, saturated CsCl is added and the mixture incubated on ice for 20 minutes, followed by centrifugation at 12,000 rpm for 10 minutes, saving the supernatant. DNA is purified with a CsCl-propidium iodide (PI) (or ethidium bromide) gradient (e.g., 8 g CsCl and 0.6 mL 2 mg/ml PI per 8 mL supernatant, mixing and adjusting density to 1.56 g/mL). After centrifugation at 36,000 rpm, the upper band contains nuclear DNA and the lower band contains mtDNA, which can be collected and, optionally, followed by further CsCl gradients. Kits are commercially available for isolation of mtDNA. In one example, mitochondrial DNA is prepared from mammalian tissue, such as muscle or liver tissue, using the mtDNA Extractor CT Kit (Wako, Osaka Japan, Catalog No.: 291-55301). Protocols for isolation of fungal (e.g., yeast) mitochondrial DNA, which cannot typically be released efficiently into cell homogenates as supercoiled circular DNAs, are also known. In one example, CsCl density gradient centrifugation on crude DNA preparations is carried out in the presence of a dye that binds preferentially to AT rich DNA (e.g., DAPI or bis-benzimide). In another example, mtDNA is extracted from isolated mitochondria, which are isolated by pelleting nuclei and cellular debris by centrifugation of lysates at 2000 g for 20 minutes, followed by separation of supernatants on sucrose gradients (e.g., 2 mL 60% sucrose, overlayed with 4 mL 50% sucrose, overlayed with 4 mL 44% sucrose, followed by centrifugation at 120,000 g for 90 minutes in a swing-out rotor and collection of the mitochondria from the 44/55% interface).

D. Introducing Donor Genomes and Nucleic Acid Sequences into Host Cells

Among the provided embodiments are methods and nucleic acids for introducing the donor nucleic acids, including the donor genomes, into host cells, for example, for modification within the host cells using host cell machinery. The host cell is a heterologous host cell that provides desired capabilities typically not present in the cell from which the donor genome is derived, e.g., recombination machinery. As described above, the donor nucleic acid can be isolated from a cell or tissue prior to transfer, chemically synthesized and/or assembled in vitro, and/or copied from such an isolated or synthesized nucleic acid by in vitro or in vivo methods.

Typically, transfer of the donor nucleic acid (e.g., donor genome) into the host cell is carried out by first joining the donor nucleic acid (which may be circular, linearized, or fragmented) to a host nucleic acid which, typically, is a host vector, in order to generate a nucleic acid containing the donor nucleic acid and the host vector, which can be propagated and modified within the host cell. Joining of the donor nucleic acid to the host vector can be carried out in vitro or in vivo in the donor cell or in the host cell. In one example, the host vector is transformed into the donor cell, where it is recombined with the donor genome, followed by isolation of the genome with the vector insertion (see, e.g., FIG. 2A). In another example, the donor genome and a host vector are separately cotransformed into the host cell and the donor and host nucleic acids recombine within the host cell. The donor genome may be linearized (see, e.g., FIG. 2B), or fragmented (see, e.g., FIG. 2C) prior to cotransformation with the vector into the host cell.

i. Host Cells

The host cells can be any host cells, and typically are heterologous cells having genetic systems that are desirable for modification of nucleic acids in the laboratory, for example, improved genetic systems compared to the donor organisms or cells. Exemplary aspects of desirable genetic systems are the ability to support homologous recombination, including double crossover homologous recombination, and transposon mutagenesis, a defined and well-characterized set of selection and other markers, and the capacity for cloning large nucleic acids. It is also desirable that the host cell has properties that make it compatible with the donor nucleic acid during cloning, propagation, and modification of the nucleic acid within the host cell.

For example, particular host cells can be selected to minimize gene toxicity. Host/donor combinations can be selected such that gene expression from donor nucleic acids does not occur in the host cell or is reduced in the host cell compared to in the donor cell. In one such aspect, the host and donor contain different translation and/or transcription signals and/or machinery, such as yeast and bacterial organisms. In another aspect, one or more codon is translated as an amino acid by the donor but is treated as a stop codon by the cell machinery. In one example, the donor translates the codon (e.g., UAG) as an amino acid (e.g., tryptophan) while the host cell reads the same codon as a stop codon (e.g., *Mycoplasma* versus eukaryotic organisms). In these aspects, donor genomes and other nucleic acids can be maintained, replicated, and modified within host cells having desirable genetic systems without (or with minimal) expression of gene products encoded by the donor genome.

The host cell can include any cell compatible with the cloned donor genome or nucleic acid. Thus, for example, genomes from algae may be cloned into yeast and manipulated to provide more favorable characteristics when re-introduced into the same or different algal recipient cell. To the extent the systems are compatible, these algal genes can also be manipulated and provided to plant cell cultures. Similar manipulations are feasible for vertebrate and invertebrate cells.

In one preferred embodiment, the host cell is a yeast cell. Yeast hosts include the "workhorse species," *Saccharomyces cerevisiae*, and other yeast species such as *Saccharomyces pombe*, which can be used to clone even larger genomes.

Yeast hosts are particularly suitable for manipulation of donor genomic material because of their unique set of genetic manipulation tools. The natural capacities of yeast cells, and decades of research have created a rich set of tools for manipulating DNA in yeast. These advantages are well known in the art. For example, yeast, with their rich genetic systems, can assemble and re-assemble nucleotide sequences by homologous recombination, a capability not shared by many readily available organisms. Yeast cells can be used to clone larger pieces of DNA, for example, entire cellular, organelle, and viral genomes that are not able to be cloned in other organisms. Thus, one embodiment of the described methods utilizes the enormous capacity of yeast genetics to advance synthetic biology and synthetic genomics by using yeast as host cells for manipulation of genomes of intractable and other organisms and synthetic genomes.

Exemplary of the yeast host cells are yeast strain VL6-48N, developed for high transformation efficiency parent strain: VL6-48 (ATCC Number MYA-3666TM), the W303a strain, and recombination-deficient yeast strains, such as the RAD54 gene-deficient strain, VL6-48-Δ54G (MATα his3-Δ200 trp1-Δ1 ura3-52 lys2 ade2-101 met14 rad54-Δ1::kanMX), which can decrease the occurrence of a variety of recombination events in yeast artificial chromosomes (YACs).

There is a large set of verified, substantiated, and reliable selectable markers for selection and counter-selection of yeast mutants, making it possible to carry out multiple, e.g., infinite iterative rounds of seamless nucleic acid alterations within yeast host cells. Thus, yeast can be used to introduce a number of different genetic modifications, including single nucleotide changes (e.g., insertions, deletions, mutations), modification of target nucleic acid portions and regions, and construction of entirely new chromosomes. Serial modifications to a cloned copy of an otherwise intractable genome or other large nucleic acid can be performed in yeast in rapid succession. The mating capacity of yeast is favorable for modifying genomes and other large nucleic acids. Yeast recombination machinery, when activated during yeast mating, can be used to generate libraries, e.g., combinatorial libraries containing variants of cloned genomes or nucleic acids.

For example, Yeast Artificial Chromosome (YAC) libraries have been constructed for several different bacteria (Azevedo et al., *PNAS USA* 90, 6047 (1993); Heuer et al., *Electrophoresis* 19, 486 (1998); Kuspa et al., *PNAS USA* 86, 8917 (1989). Large prokaryotic DNA segments can be cloned in yeast using the universal genetic code. Toxic gene expression typically is not a barrier to cloning donor nucleic acids in yeast. Studies with bacterial and archeal genomes, for example, indicate that because eukaryotes use different protein expression machinery than these bacteria, there is little risk of harm to yeast hosts by proteins expressed from the cloned genomes. The transcription (Kozak, *Gene* 234, 187 (1999)) and translation (Kornberg, *Trends Cell Biol* 9, M46 (1999) signals in yeast are different from those in bacteria. In fact, most prokaryotic genes likely are not expressed in yeast. There is no restriction barrier in yeast (Belfort and Roberts, *Nucleic Acids Res* 25, 3379 (1997). If there is a barrier, it may be a replication barrier, rather than a gene expression barrier (Stinchcomb et al., *PNAS USA* 77, 4559 (1980)). Gene toxicity is minimized because regulation of gene expression in a eukaryote such as yeast is different from that in prokaryotes. Also, *Mycoplasmas* use the codon UGA for tryptophan rather than as a translation stop signal. Thus, most *Mycoplasma* genes, if expressed, would produce truncated proteins in yeast. This largely avoids the possibility of toxic gene products.

Donor may be obtained in their native form from donor organisms and modified with yeast vectors prior to transformation into yeast, or may be assembled from natural or synthetic fragments together with yeast vectors prior to transformation into yeast cells or simultaneously co-transformed into yeast cells. New organisms are created by transferring these genomes, which have been optionally manipulated as desired, into compatible recipient cells. Thus, one embodiment provides, for the first time, suitable techniques for transferring genomes to yeast host cells, modifying the genomes within host cells while maintaining their stability and integrity, and transplanting the cloned and manipulated genomes from yeast host cells back into recipient cells that more closely resemble the original donors, thus creating organisms which previously did not exist and/or could not have been created through genetic manipulation of their original cells with available genetic engineering and cloning tools.

ii. Host Vectors

Typically, donor nucleic acids are transformed into and propagated within host cells using host vectors. Thus, the host cell generally contains, or will support introduction of, a host vector for transfer, maintenance, and modification, of the donor nucleic acid within the host cell. In one embodiment, the host vector contains nucleic acid sequences to facilitate transfer of the donor nucleic acid to and from a donor cell, a host cell, and a recipient cell, and other cells, such as bacterial cells used for cloning and propagation (e.g., *E. coli*), such as the tri-shuttle vectors described in the examples herein (see, e.g., FIG. 3).

In one aspect, the vector contains any nucleic acids (e.g., origin of replication) needed to promote replication of the vector within one or more desired cell type and selection and/or resistance markers for use with the different cell type(s).

Resistance markers are well known. The skilled artisan will be able to determine appropriate resistance markers for different host/donor combinations. In some cases, it can be desirable to use markers that are not clinically relevant. In other cases, the choice of resistance marker depends on properties of the donor, host, and/or recipient cells. For example, antibiotics that target the cell wall may not be useful in *Mycoplasma* and other organisms lacking cell walls. Among the resistance markers are genes encoding antibiotic resistance, such as ampicillin, kanamycin, and tetracycline resistance, such as the tetracycline resistance protein (TetM), and chloramphenicol acyltransferase (CAT), aminoglycoside resistance protein (aacA/aphD), and combinations thereof. For example, tet-resistance markers are useful in bacteria, such as *Mycoplasma*, in which tetracyclines have a potent effect and which exhibit low levels of spontaneous resistance. Genes conferring Puromycin resistance also can be used, for example, for cloning and modifying *Mycoplasma* nucleic acids and using *Mycoplasma* cells.

Puromycin is an antibiotic that mimics the 3'-terminal end of aminoacylated tRNA and attaches to the carboxyl-terminus of growing protein chains to stop protein synthesis. Because puromycin conscripts rRNA recognition elements used by all of the various tRNAs in a cell, it is unlikely that spontaneous antibiotic resistance can be acquired via a simple point mutation, which can happen with other markers in some cases. Puromycin is readily available, relatively inexpensive, is not used in the clinic and it is a potent inhibitor of translation in both prokaryotes and eukaryotes. No known rRNA based resistance exists.

A codon-optimized cassette has been developed to confer puromycin resistance in five different *Mycoplasma* species and can function in *E. coli*, making it functional in shuttle vectors. To make this cassette, the 597 bp puromycin N-acetyltransferase 85 gene (PAC) is synthesized using overlapping oligonucleotides as described by Smith et al., *PNAS USA* 100:15440-5 (2003). Briefly, 5' phosphorylated oligonucleotides encoding both strands of a codon optimized version (for expression in *M. genitalium*) are ordered from IDT (Coralville, Iowa). The oligos are 48 bases 88 long with an overlap of 24 bases. The top-strand and bottom-strand oligos are mixed, heated to 95° C., and slow cooled to allow annealing of the overlaps. The reactions are ligated for 12 hours and used as a template for PCR. The PCR amplicon is cloned into pGEM-3Zf(+) (Promega, Madison, Wis.) and sequenced to identify correct PAC clones. The optimized PAC gene is then cloned under the control of the *Spiroplasma citri* spiralin promoter (Ps) and used to replace the tetM gene in a derivative of Mini-Tn4001tet, as well as the tetM gene in pMyco1 (Lartigue et al. (2003), *Nucleic Acids Res* 31: 6610-8). The new plasmid (Mini-Tn4001PsPuro) can be used to transform *M. genitalium, M. gallisepticum* and *M. pneumoniae*, while the pMyco1 derivative (pMycoPuro) can be used to transform *M. mycoides* LC and *M. capricolum*.

The vectors further include nucleic acids that allow joining of the vectors with the donor nucleic acids. In one example, the host vector contains regions of homology to portions of the donor genome or nucleic acid, such as regions of homology at the 3' and 5' termini of a linear vector that are homologous to adjacent regions within the donor nucleic acid, to facilitate joining by homologous recombination. In another example, the host vector contains nucleic acid encoding a transposase and/or inverted repeats, to facilitate joining, e.g., insertion, into the donor nucleic acid, such as within a donor cell. The host vectors can additionally contain restriction enzyme recognition sites and nucleic acids to support replication and segregation within host cells and other cells.

In one aspect, a yeast host vector contains an origin of replication (e.g., high copy origin from pUC19); one or more resistance markers and/or selection markers (e.g., antibiotic resistance genes and selectable host cell (e.g., yeast) markers), such as markers for selection in the host cell, in donor cells and in recipient cells. Exemplary of resistance/selection markers are antibiotic resistance genes (e.g., ampicillin-resistance genes, kanamycin resistance genes and other well-known antibiotic resistance genes), and other antibiotic resistance genes; selectable yeast or other host cell markers, e.g., HIS3) and/or selection markers; nucleic acids to facilitate insertion into donor nucleic acid, e.g., transposase and inverted repeats, such as for transposition into a *Mycoplasma* genome; nucleic acids to support replication and segregation in the host cell, such as an autonomously replicated sequence (ARS), centromere sequence (CEN). In one embodiment, the vector contains a telomere sequence.

Exemplary vectors include yeast vectors, including yeast centromeric plasmids, e.g., Yeast Artificial Chromosome (YAC) vectors, such as pmycYACTn, described in Example 1A(i)(a), below, and illustrated in FIG. 3A; and the miniTn-Puro-JCVI-1.7 vector constructed shown in FIG. 3B. Features of the pmycYACTn vector include: (i) a high copy origin from pUC19 and an ampicillin resistance marker for propagation in *E. coli*, (ii) the IS256 (iii) tetM and lacZ markers, both expressed from spiralin promoters (16, 17), for selection and screening in *E. coli* and *Mycoplasmas*, and (iv) an ARS and a CEN for replication and segregation in yeast, and HIS3 as a selectable yeast marker. The miniTn-Puro-JCVI-1.7 vector differs from pmycYACTn as follows: (i) it does not contain lacZ and substitutes a puromycin resistance marker for tetM and (ii) it contains a bacterial artificial chromosome (BAC) vector, for possible cloning in *E. coli.* iii. Cloning Strategies: Joining of Host and Donor Nucleic Acids and Transfer of Donor Genomes and Nucleic Acids into Host Cells In the provided transfer methods, the donor genome or other nucleic acid is joined to a host nucleic acid, typically a host vector, to generate a nucleic acid containing the donor nucleic acid and host nucleic acid that can be propagated and manipulated in the host cell. Joining the host and donor nucleic acids can be carried out using a number of approaches, drawing on well-known cloning methods. Three general approaches are described in more detail below.

As noted above, yeast cells are exemplary host cells. Large DNA molecules have been stably cloned in yeast by the addition of a yeast centromere (CEN), which allows the molecules to be segregated along with the yeast chromosomes. Such molecules have been cloned both in the linear form by the addition of telomeres to the ends, and also as circles. Because bacterial genomes are generally circular, and circles can be readily separated from linear yeast chromosomes, it can be advantageous to clone bacterial genomes as circular.

In a first approach for joining donor genomes and nucleic acids with host vectors, the donor genome is joined to the host vector within a donor cell, or other cell type that is similar to the donor, followed by isolation of the nucleic acid containing the donor genome and host vector and subsequent transfer into the host cell. An example is illustrated in FIG. 1. This approach can be used, for example, to transfer genomes and other large nucleic acids into host cells. In one example, the host vector contains inverted repeats and/or nucleic acids encoding a transposase, to facilitate insertion into the donor genome or other nucleic acid within the cell.

Joining the donor and host nucleic acids within a donor cell or a cell that is similar to the donor (e.g., a different species of the same genus) provides advantages. For example, it allows selection of vector insertions (e.g., sites of vector insertion along the length of the donor nucleic acid) that do not or are unlikely to impair or otherwise affect donor cell viability. This approach does, however, require that the donor or similar cell is amenable to introduction of foreign nucleic acid (e.g., transformation), so that the vector can be integrated into the donor nucleic acid, e.g., genome. Various approaches for introduction of nucleic acids into a variety of cell types are well known. In one example, as described in Example 1A, below, yeast host vectors are transformed into bacterial cells in the presence of PEG. Donor cells containing the host vector integrated into the donor nucleic acid are selected, for example, based on a resistance or other selective marker in the host vector. Nucleic acids can be isolated from the donor cells, such as in agarose plugs as described above, for confirmation of host vector insertion, for example by PCR or Southern blot as described herein. In one aspect, before transfer into the host cell, the nucleic acid containing the donor genome and host vector is transplanted into a recipient cell to confirm that the nucleic acid can be transplanted and is compatible with a particular recipient cell. For example, transplantation of genomic DNA from one bacterial species to another can be carried out as described in Lartigue et al., *Science* 317, 632 (2007) and as described in Example 1A(ii)(b), below.

In the example illustrated in FIG. 2A, a linear yeast host vector is joined to a circular bacterial genome within the bacterial cell. The resulting circular nucleic acid is isolated, for example, in agarose plugs as described above, and transformed into yeast host cells. An example of this process is described in Example 1A, below.

In a second approach, an example of which is illustrated in FIG. 2B, the donor genome and the host vector are co-transformed, together or separately, into the host cell, whereupon they join, e.g., by homologous recombination, within the host cell. This approach is advantageous in its simplicity, with minimal sample handling and number of steps. Typically, as shown in FIG. 2B, the vector is inserted into the donor genome or nucleic acid by homologous recombination.

Figure 2A:
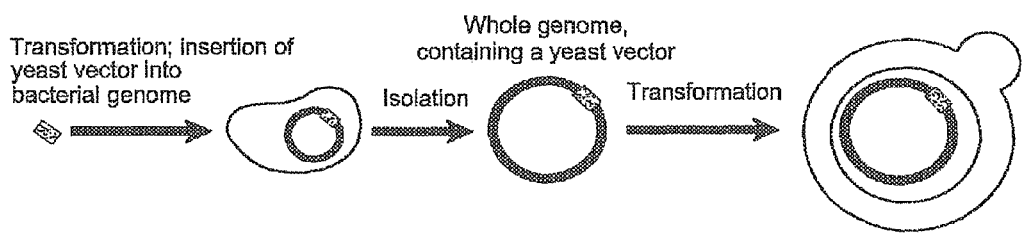
FIGS. 2A-2C illustrate three methods for cloning bacterial genomes in yeast. (A) In order to be propagated by yeast upon transformation, a host vector can be incorporated into a bacterial genome by transformation of the bacterium; the recombined genome and host vector can be isolated and used to transform a yeast host cell. Alternatively, (B) a whole genome and an optionally linearized host vector can be cotransformed into a yeast host cell, where the yeast host cell combines the vector and the bacterial genome by homologous recombination genome. In another scenario (C), a bacterial genome can be cloned by assembling multiple overlapping fragments and co-transforming the fragments into yeast host cell with a host vector where the bacterial genome fragments and host vector are combined by homologous recombination in the yeast host cell.
Figure 2B:
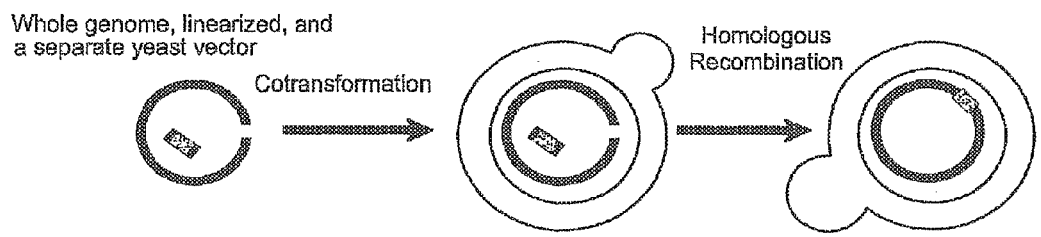

In the example illustrated in FIG. 2B, a linear yeast host vector is co-transformed into a yeast host cell along with a circular bacterial genome, for example, a synthetic genome or one that has been isolated from a donor cell, e.g., in agarose plugs as described above. Typically, the host vector contains region(s) of homology to the donor genome or nucleic acid. In the example shown in FIG. 2B, the linear yeast vector contains, at each terminus, a region of homology to a portion of the bacterial genome. In one example, as shown in FIG. 2B, the bacterial genome is cut with a restriction enzyme that cuts near the region of homology to the host vector, prior to transformation into the host cell. This process generates a double-strand break near the insertion site of the vector, greatly improving efficiency of the joining of the host vector and donor genome (by insertion of the vector into the genome) within the host cell. Typically, a restriction enzyme recognition site is chosen within the donor genome or other nucleic acid that is compatible with maintaining genome or nucleic acid integrity after insertion of the vector at that site. An example of this process is described in Example 1B, below.

Figure 2C:
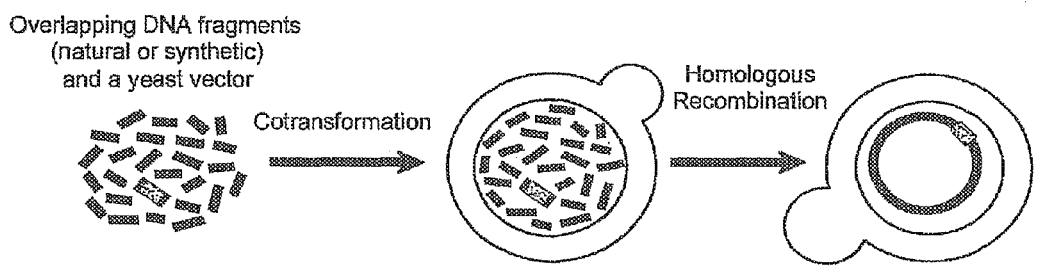

An example of a third approach, which a modification of the second approach, is illustrated in FIG. 2C. This approach is carried out by co-transforming into the host cell, along with the host vector, a plurality of overlapping nucleic acid fragments, which are fragments of the donor genome or nucleic acid. In other words, each of the fragments contains homology to a region of the donor genome or nucleic acid and the regions of homology overlap along the length of the donor genome or nucleic acid. The fragments and vector recombine upon transformation into the host cell, for example by homologous recombination through regions of homology.

In the example illustrated in FIG. 2C, overlapping fragments of a circular bacterial donor genome are co-transformed into a yeast host cell along with a linear yeast vector. Again, the yeast vector contains regions of homology at its termini to portions of the bacterial genome. Upon introduction of the donor genome fragments and yeast host vector into the host cell, the fragments and vector recombine, thereby joining the donor genome and host vector. An example is described in Example 1C, below.

In some embodiments, either after (e.g., first approach) or before (e.g., second and third approaches) joining with the host vector, the donor nucleic acids are isolated from the donor cells or similar cells, as described above. For example, large donor nucleic acids including genomes can be isolated from donor and other cells in agarose plugs, as described above. After isolation or synthesis and assembly, donor nucleic acids are transformed into host cells. When the host vector is not previously joined to the donor nucleic acid, it can be transformed into the host cell simultaneously, or sequentially in any order, using the same transformation methods.

Transformation methods are well known in the art and will vary depending upon the host cell. In one example, when the host cell is a yeast host cell, yeast spheroplasts are prepared from the yeast host cells, for example, as described below, and the nucleic acids are transformed by mixing with the spheroplasts. In some cases, the transformation is performed in the presence of PEG. For example, donor nucleic acids and/or host vectors can be incubated with the spheroplasts for 10 minutes at room temperature, followed by addition of 800 µL PEG 8000 and gentle mixing by inversion and another 10 minute incubation at room temperature.

In one example, spheroplast preparation and transformation is carried out as described by Kouprina and Larionov, Nat Protoc 3, 371 (2008). The OD to which cells are grown can be modified. With these methods, prior to transformation, yeast medium is inoculated with single-cell colonies of yeast hosts, and grown overnight at 30° C. with vigorous shaking to ensure good aeration until an appropriate OD660 is reached. Samples can be centrifuged and resuspended in sorbitol by vortexing, centrifuged and resuspended, e.g., in SPE solution (1 M sorbitol, 0.01 M sodium phosphate, 0.01 M $Na_2EDTA$, pH 7.5). Yeast cell walls are removed, for example using Zymolase™. The level of spheroplasting can be evaluated by comparison of optical densities of the cell suspension in sorbitol solution versus 2% SDS solution (in which spheroplasts are lysed). Spheroplasts can be centrifuged and resuspended in 1 M sorbitol by very gentle rocking, and washed and resuspended in STC solution (1 M sorbitol, 0.01 M Tris-HCl, 0.01 M $CaCl_2$, pH 7.5). Transformation is carried out by mixing the nucleic acids with the spheroplasts, as described above, optionally in the presence of PEG.

After transformation, a selection procedure typically is performed to select cells into which donor nucleic acids and host vectors have been successfully transformed. For example, in the above process, after transformation, the spheroplasts can be centrifuged and resuspended in SOS solution and incubated for 40 minutes at 30° C. without shaking. The spheroplasts can be placed in selection medium, such as melted SORB-TOP-His selection medium as described herein, and equilibrated at 50° C., and plated on plates containing selection medium and grown, e.g., at 30° C. until transformants are visible.

iv. Isolation and Analysis of Donor Nucleic Acids from Host Cells

With the provided methods, donor nucleic acids transformed into host cells can be isolated and analyzed, both before and after modification within the host cells by the provided modification methods. As with isolation from donor and other cells, isolation methods will vary depending on the cell type. In some examples, native host nucleic acids are removed or reduced from isolated nucleic acid samples, e.g., to isolate or enrich for donor nucleic acids. This process can be carried out by pre-electrophoresis to remove chromosomal host DNA, or by digestion with restriction enzymes that digest host, but not donor, nucleic acids.

In one example, the donor nucleic acids are isolated in agarose plugs, for example, using the protocol "Preparation of Agarose Embedded Yeast DNA" from the Bio-Rad CHEF-DR III manual, and as described in the Examples herein. In some examples, agarose plugs containing DNA from the host cells are pre-electrophoresed at constant voltage for several hours to remove yeast host chromosomal DNA. In one aspect, the removal of host DNA can be carried out by first digesting DNA in the plugs with AsiSI, FseI, and RsrII, or other enzymes that cleave yeast chromosomes but do not have recognition sites in donor nucleic acids, such as *M. genitalium* or *M. mycoides* LC.

Analysis of donor nucleic acids can be carried out by any of a number of well-known methods for analyzing DNA. Typically, it is desired to carry out methods to confirm the size and/or sequence of the nucleic acids, and the correct insertion and orientation of the vector and other nucleic acids, including the confirmation of any modifications. In one example, isolated DNA is subject to linearization by heating and/or restriction digestion, followed by separation by gel electrophoresis, such as field-inversion (Bio-Rad FIGE Mapper) or pulsed-field (Bio-Rad CHEF-DR II or III system) electrophoresis.

Analysis can be, for example, by PCR, such as multiplex PCR, with primers designed to bind various regions along the length of the desired donor nucleic acid or modified donor nucleic acid. Typically, primers also are designed to recognize the host vector. In other examples, the analysis is carried out by visualization of the size of the isolated nucleic acid on a gel, or by restriction digestion and performing a Southern blot or other hybridization method, for example, as described in Gibson et al., *Science* 319, 1215 (2008). Specific examples of MPCR and Southern blot analysis of isolated donor genomes are described in the Examples. Modifications of the analysis methods will be apparent to the skilled artisan. Sequencing methods are well known and also can be used to analyze the donor nucleic acids transferred into and propagated within host cells.

v. Generation of Host Cells Containing a Plurality of Donor Genomes

In one embodiment, a plurality of donor nucleic acids, such as a plurality of genomes from different donors, are introduced into a single host cell. In one aspect, a host cells containing one donor genome or other donor nucleic acid is crossed to another such host cell containing transferred nucleic acid from a different donor, generating a host cell containing both nucleic acids. For example, a diploid yeast strain containing two donor genomes from different donors, such as two *Mycoplasma* genomes from different species, can be generated by crossing two different haploid strains, each carrying one of the donor genomes. Crossing haploid yeast strains can be carried out using well-known methods. Multiple distinct selection markers can be used in the respective haploid strains, to allow for selection of cells containing both genomes after the cross. For example, a HIS3 and TRP marker can be introduced into two different haploid cells, respectively, carrying different donor genomes, followed by selection of diploid cells on medium lacking histidine and tryptophan, as described in the Examples herein.

E. Modification of Donor Genomes in Host Cells

Also among the provided embodiments are methods and nucleic acids for modifying the donor genomes and other nucleic acids within the host cells. In one embodiment, the methods are carried out by introducing one or more targeting construct into the donor nucleic acid. The constructs contain portions of homology to the donor nucleic acid, resistance genes, selectable markers, nucleic acids encoding enzymes, such as restriction enzymes, restriction sites, and/or other nucleic acids used in cloning and homologous recombination. Typically, the constructs are introduced into host cells containing the donor nucleic acids.

To design the constructs, a target region of the donor nucleic acid (e.g., the donor genome) is selected for modification. It is not necessary that the methods modify each residue of the target region. For example, one or more target portions or target positions within the target regions can be modified. The modifications include insertions, deletions, mutations, substitutions, and/or other modifications of one or more nucleotides within the target region. In one aspect, the donor nucleic acid is seamlessly modified.

Typically, the target region or a portion thereof first is replaced with a nucleic acid construct containing a marker, such as a counter-selectable marker. The marker is then removed from the nucleic acid, by deleting the marker or replacing it with another nucleotide sequence. In one aspect, the marker and surrounding portions are replaced by introducing a second nucleic acid construct having homology to portion(s) of the target region near or adjacent to the marker. This second construct need not be less than 100% homologous to the portion(s) of the target region. For example, the constructs can contain one or more mutation, deletion, or insertion, compared to the portion of the target region, whereby the target region is modified upon replacement with the construct. The methods typically include one or more homologous recombination step.

In one aspect, removal of the marker is facilitated by introducing a break (e.g., double-strand break) in the nucleic acid sequence of the donor nucleic acid containing the construct with the marker. The break is introduced near, e.g., adjacent to, or within the target region. Typically, the break is generated by inducibly expressing an enzyme, such as an endonuclease, that recognizes and cleaves the desired nucleic acid sequence. Typically, the enzyme is encoded by a nucleic acid within the target region or the construct inserted into the target region.

In one aspect, removal of the marker is facilitated by introducing a nucleic acid sequence into the donor nucleic acid, whereby insertion of the nucleic acid sequence generates tandem repeat regions flank the target region or portion thereof. Typically, the nucleic acid sequence is included as part of the targeting construct.

In one embodiment, the methods include both introduction of a break and introduction of a sequence generating tandem repeat regions. In one aspect, the method is a Tandem Repeat with Endonuclease Cleavage (TREC) method, in which double-strand breaks, generated by an inducibly expressed enzyme, and tandem repeats are used to facilitate recombination events and avoid damage and unwanted mutation.

The provided methods provide advantages compared to conventional and other available methods, particularly for modification of donor nucleic acids in hosts of different species, genera, and orders. In one aspect, the donor nucleic acids, which may come from a donor organism having a poor genetic system, are modified within a host having a rich genetic system, such as a yeast host cell, for example, by homologous recombination methods. For example, nucleic acid fragments several hundred kb in length can be cloned and manipulated in yeast (*Saccharomyces cerevisiae*) host cells using well-known methods and standard genetic tools, including linear and circular forms of yeast artificial chromosomes (YAC). Transplantation of modified donor nucleic acid to recipient cells, including original cells and cells of different species, can be used, for example, for functional studies of genes and gene regulation, and for production of modified gene products. The provided methods can be used to successfully modify donor genomes within host cells, to engineer and modify genomes from organisms that are genetically intractable.

As discussed below, the modification methods can be used to produce genomes, organisms, and gene products produced by the organisms that are commercially useful, such as for production of vaccines, drugs, biological proteins and chemicals, biofuels, and protein therapeutics such as enzymes and antibodies. In one example, donor genomes are modified to produce new immunological compositions to elicit an immune response, such as live viruses and other immunogens. In another example, donor genomes are modified for the production of biofuels, for example, by introducing DNA encoding for enzymes involved in the oil synthesis pathways, for example, by replacing metabolism pathway genes with those for biofuel production. In one example, the donor genome (e.g., of a photosynthetic bacteria) is modified such that, upon transplant into a recipient cell, the recipient cell produces biofuels in place of normal photosynthesis products, such as glucose. Other uses are discussed hereinbelow.

Thus, the provided methods can be used to directly engineer or redesign a synthetic bacterial genome in viva, for example, in yeast host cells.

The provided modification methods include aspects for overcoming incompatibility issues between donor and host organisms of different species, which could otherwise cause instability and unwanted mutation of donor nucleic acids that are manipulated in host cells of different species. For example, when a donor nucleic acid, such as a donor genome, is introduced into a host cell, the donor nucleic acid does not typically contribute to the viability of the host cell, or does not contribute to the viability of the host apart from individual selection marker(s) present in the cloning vector. This is particularly true when the donor and host are different types of organisms, such as of different orders or kingdoms, for example, when the donor is a prokaryote and the host is a eukaryote, such as a yeast. For example, as discussed in the study described in Example 4, below, the *M. genitalium* genome, propagated as a circular YAC (with a histidine marker) in yeast does not have functional complementation with its host, except histidine prototrophy. Any deletion and rearrangement in the bacterial genome is likely neutral for the yeast host.

With available methods, because the host cell does not depend on the integrity of donor nucleic acids for viability, there is a high risk of unwanted mutations and damage to the donor nucleic acid while it is being manipulated in the host cell. The provided methods overcome these problems and can be used to propagate and modify donor genomes within host cells, while minimizing the risk of unwanted mutations within the donor genome. The provided methods can accurately modify a donor genome, such as a bacterial genome, cloned in yeast host cells, with high efficiency The provided methods further can be used in seamless modification of the donor nucleic acids within the host cells, including mutation, deletion, and/or insertion of nucleotides within a target region of the donor nucleic acid, where no unwanted additional nucleic acid sequence is added or removed.

i. Counter-Selectable Markers

Typically, a first step of the methods includes introduction of counter-selectable markers into the donor nucleic acid. The markers typically are inserted by homologous recombination, whereby a portion of the target region is replaced with the counter-selectable marker. Counter-selectable markers are advantageous in that both the presence and the absence of the marker can be selected for. The presence of the marker is selected for with one set of growth conditions, while the absence is selected for with a different set of growth conditions. An exemplary, well-known counter-selectable marker is the URA3 yeast gene. The presence of the URA3 gene in a yeast host allows its growth on medium lacking uracil. Thus, successful replacement of the donor nucleic acid target region with this marker can be selected for by growth on uracil- medium. By contrast, the absence of the URA3 gene, such as following replacement by another homologous recombination event, can be selected by counter-selection on medium with 5-fluoroorotic acid (5-FOA).

For example, the genetic marker URA3 can be integrated, e.g., through homologous recombination, into a target region within the donor nucleic acid cloned in a host cell. Integration of the marker is selected for by growth on medium lacking uracil. Removal of the marker, e.g., by deletion or replacement with another nucleotide sequence, for example in a second round of homologous recombination, is selected for by counter-selection, e.g., on 5-FOA.

Methods employing counter-selectable markers are desirable in that they can be used for seamless modification. Further, replacement or removal of the counter-selectable marker restores auxotrophy (e.g., dependence on uracil), such that the host cells can be modified using the same method in further rounds of modification.

Methods are available for introducing and replacing counter-selectable markers in yeast host cells. For example, methods are known for introduction of a URA3 marker by a first round of homologous recombination and replacement of the marker with a second round of homologous recombination. An example of such a method is described in Example 4A, below, in which a site-specific mutagenesis was performed to correct a single base cytidine deletion (309,388) found in the CDS139 locus of a donor synthetic *M. genitalium* genome maintained in yeast using this conventional method involving two sequential homologous recombination events. As described in that example, yeast hosts containing the mutant bacterial donor genome were transformed with a cassette containing the URA3 marker and 50 bp terminal portions homologous to portions of the target region, replacing a target region containing the single-base deletion CDS139 locus. The second round of transformation introduced a construct containing the non-mutant DNA sequence back to the same locus, replacing the marker.

Conventional methods employing counter-selectable markers are limited in their ability to efficiently modify certain donor nucleic acids in certain host cells. For example, these methods can be insufficient for modifying donor genomes within host cells that do not depend on integrity of the donor genome for viability. When the host cell does not depend on the integrity of the donor genome, a high number of spontaneous deletions can occur during modification. These deletions typically result in loss of the counter-selectable marker and thus are selected. The provided methods overcome this problem and provide increased efficiency compared to conventional methods.

ii. Inducible Enzyme Expression and Introduction of Breaks

In one embodiment, after the selectable marker is introduced, a break, such as a double-strand break (DSB), is introduced near (e.g., adjacent to) or within the target region. This process typically is carried out by inducibly expressing an enzyme, such as an endonuclease, e.g., I-SceI, that recognizes and cleaves a nucleotide sequence located in proximity to or within the target region. Typically, the enzyme is an endonuclease or other enzyme that generates double-strand breaks. The introduction of a double-strand breaks near a site of homologous recombination reportedly increases the efficiency of homologous recombination by about twenty-fold (Leem et al., *Nucleic Acids Res* 31, e29 (2003)). Thus, introduction of a double-strand break near the target region is carried out to increase the efficiency of the modification methods and reduce unwanted background mutations.

In a typical example, the targeting construct containing the selectable marker further contains a gene encoding the enzyme, under the control of an inducible promoter. Typically, the construct further includes a recognition sequence of the enzyme. This construct is introduced into the donor nucleic acid within the host cell. Expression of the enzyme is induced by growth of the host cells under particular conditions that induce expression from the inducible promoter. In one example, the promoter is the GAL1 promoter, expression from which can be induced by growth on medium containing galactose as the only carbon source.

Figure 10A:
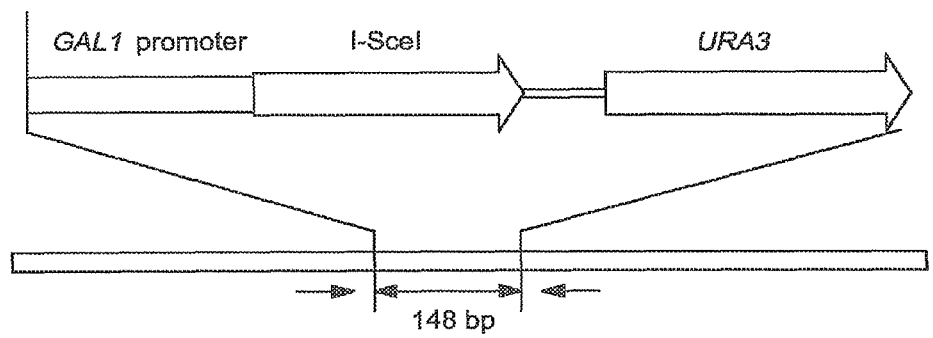
FIG. 10C: a TREC positive control and lane N is the no-genome negative control. Molecular weight markers are in lane M. The results shown are representative of the 40 samples analyzed. All 40 clones appear to contain complete genomes, demonstrating that the bacterial genome is stable during routine propagation in yeast.

Available methods include inducible introduction of double-strand breaks for the purpose of improving efficiency of recombination-based modification in yeast. One such method, Delitto perfetto, is described in Storici et al., *Nat Biotechnol*, 19, 773-776 (2001). An example of this method is described in Example 4B(i), below. The method is based on the showing that introduction of a double-strand break (DSB) in a target nucleic acid stimulates recombination by several orders of magnitude (Storici et. al, *PNAS USA*, 100, 14994-99 (2003)). In Example 4B(i), Dilletto perfetto was used in attempt to correct the same single-base deletion in the CDS139 locus of the *M. genitalium* donor genome. The process is illustrated in FIG. 10A.

It is demonstrated herein that inducible introduction of DSB, in combination with conventional recombination methods in yeast, is limited for modification of certain donor nucleic acids. See Example 4B(i), below. This limitation is due to a high background of spontaneous loss of the negative (counter-) selection marker. The provided methods improve efficiency and reduce unwanted background mutations (e.g., spontaneous deletions).

iii. Tandem Repeats

In one embodiment, removal of the selectable marker by homologous recombination is facilitated by the presence of tandem repeat regions, flanking a region containing the marker. In one aspect, the targeting construct for introducing the marker further contains a nucleic acid sequence, the introduction of which results in tandem repeat regions flanking the target region or portion thereof containing the inserted marker. The construct initially is inserted, either upstream or downstream of the target region or portion thereof, and contains a nucleic acid portion having homology to a portion downstream or upstream of the target region or portion, respectively. Insertion of this portion near the homologous portion in the target nucleic acid generates the tandem repeats.

In one example, insertion of the construct generates a portion within the target nucleic acid, 5' of the marker, having homology to a portion 3' of the target region. In another example, insertion of the construct generates a portion within the target nucleic acid, 3' of the marker, having homology to a portion 5' of the target region. Thus, upon introduction, the modified donor nucleic acid (e.g., modified donor genome) contains tandem repeat sequences flanking a nucleic acid containing a selectable marker.

Figure 10B:
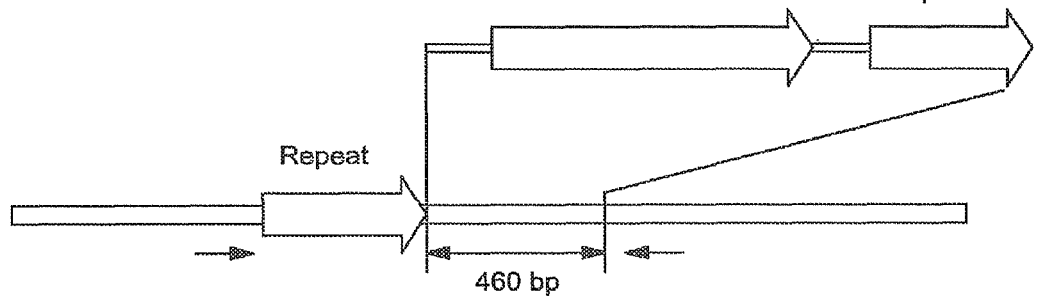

The presence of tandem repeat sequences facilitates homologous recombination between the two sequences, for example, for removal of a portion of the construct containing the counter-selectable markers. Such methods are well known and based on a precise excision of a nucleic acid segment by homologous recombination (HR) between two tandem repeat sequences. An example, known as the "Tandem repeat pop-out" method is described in Akada, R. et al., *Yeast*, 23, 399-405 (2006). An example of such an approach is described in Example 4B(ii), below, used to delete a region of the CDS139 locus in the *M. genitalium* donor genome. The process is illustrated in FIG. 10B. This technique can be adapted for use in gene replacement.

Unlike more conventional homologous recombination methods using selectable markers, methods using tandem-repeat induced BR can introduce and subsequently remove a cassette containing a counter-selectable marker via a single transformation event. For example, a cassette carrying the counter-selectable marker and the sequence that generates the tandem repeat can be introduced into a donor genome in a yeast host by transformation, followed by selection for spontaneous homologous recombination between homologous regions in the cassette and the genome.

Selection for the initial introduction of the marker can be carried out as described above, e.g., by growth in the absence of histidine in the case of URA3. Subsequent transfer of cells into counter-selection medium (e.g., 5-FOA) selects for spontaneous "pop-out" of the marker by homologous recombination between the tandem repeat sequences. Such methods can be adapted for deletion, point mutation, and gene replacement, by varying the portions of the cassette sharing homology with the target nucleic acid.

It is demonstrated herein that introduction of tandem repeats, for "pop-out" in combination with conventional recombination methods, is limited for modification of certain donor nucleic acids in yeast. See Example 4B(ii), below. The limitations are due to a high background of spontaneous loss of the negative (counter-) selection marker. The provided methods improve efficiency and reduce unwanted background mutations (e.g., spontaneous deletions) and can be used to modify bacterial genomes in yeast host cells.

iv. Tandem Repeat—Endonuclease Cleavage (TREC)

Both tandem repeats and enzymatic cleavage near the target region can be used to facilitate removal of the selectable marker. One such embodiment, deemed the "Tandem Repeat Endonuclease Cleavage" (TREC) method, combines conventional homologous recombination replacement using a counter-selectable marker, inducible introduction of double-strand break near or at the target region by expression of an endonuclease, and introduction of tandem-repeat sequences flanking a nucleic acid sequence containing the marker. The methods can be used to accurately modify bacterial donor genomes and large nucleic acids cloned in yeast host cells with high efficiency.

Figure 10C:
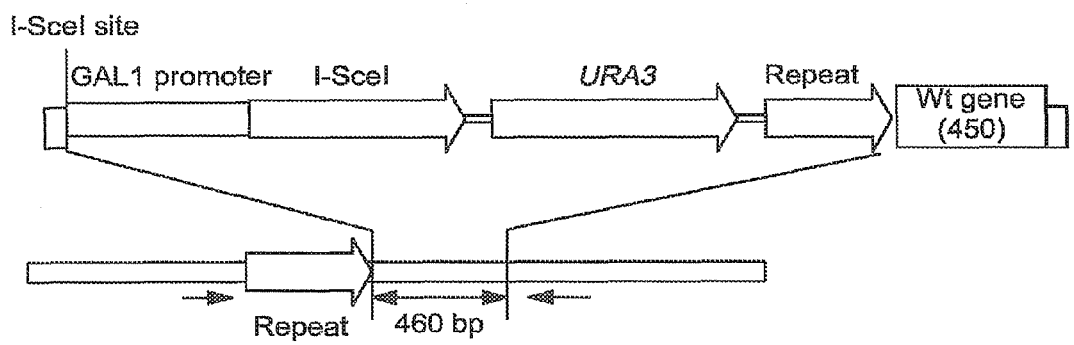
Figure 10D:
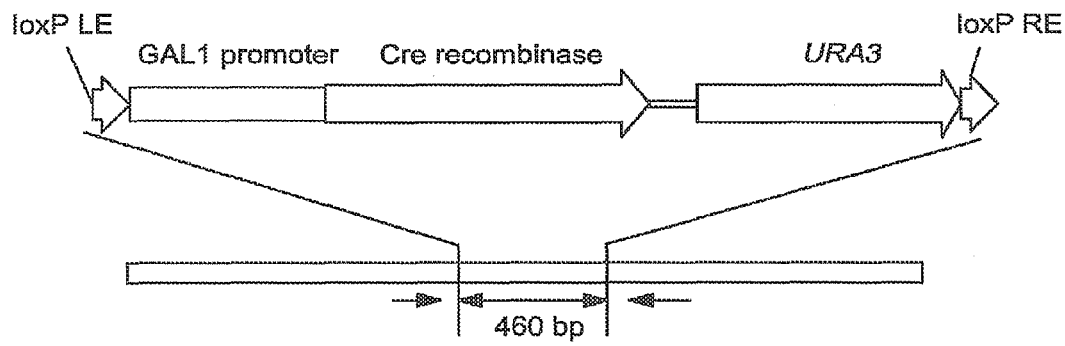

With the TREC method, the combination of flanking tandem repeat sequences and proximal or adjacent double-strand break greatly enhances the efficiency of target-specific recombination and allows genetic engineering of bacterial genome in yeast hosts. An example in which this method was used to successfully seamlessly delete the CD139 locus in the *M. genitalium* genome grown in yeast is described in Example 4C, below. The method is illustrated in FIG. 10C.

The methods described herein can be used to introduce any modification, such as point mutations (e.g., nucleic acid and codon substitution, including conservative and non-conservative substitutions), deletions, insertions, and other modifications to target regions of donor nucleic acids within host cells, such as bacterial genomes within yeast host cells.

v. Targeting Cassettes and Generation of the Cassettes

Provided are methods for designing and generating nucleic acids (e.g., targeting cassettes) for use in the modification methods. Also provided are the constructs and other nucleic acids for use in the methods. Typically, the target cassette for introducing the selectable marker contains a portion of homology to a portion of the donor target region (which optionally contains one or more mutations, deletions, insertions, substitutions, or other modifications compared to the homologous portion) and a selectable marker, typically a counter-selectable marker, such as URA3. Typically, the cassette contains a portion homologous to a 5' portion of the target region and a portion homologous to a 3' portion of the target region.

In some embodiments, a second targeting construct is generated, to replace the selectable marker with nucleic acid having homology to the target nucleic acid. This second targeting construct contains homology to the target region or portion thereof, and optionally contains one or more mutations, deletions, insertions, substitutions, or other modifications compared to the homologous portion within the target region.

In some embodiments, for introduction of a double-strand break near, within, or adjacent to the target region, the targeting cassette further includes a gene encoding an enzyme, such as an endonuclease, which cleaves nucleic acid such as dsDNA at a particular sequence, and further contains a nucleotide sequence recognized by the enzyme, typically at or near a terminus of the cassette. Typically, the gene encoding the endonuclease is under the control of an inducible promoter, such as the GAL1 promoter, such that expression of the gene can be induced by growth of the host cells under particular environmental conditions, such as in the presence of galactose as the only carbon source.

In some embodiments, for generation of tandem-repeat sequences, the targeting cassette includes a further portion of homology to the target nucleic acid, which is upstream or downstream of the target region, along the length of the target nucleic acid, such that upon integration of the cassette through homologous recombination, a tandem-repeat sequence will be present in the target nucleic acid.

When cleavage and tandem repeat sequences are used, the cassette contains a first portion of homology to a portion of the target nucleic acid that is upstream or downstream of the target region along the length of the target nucleic acid (to generate tandem repeats), a second and third portion of homology to 3' and 5' portions of the target region, respectively (for insertion of the cassette by homologous recombination), a nucleic acid encoding an enzyme (e.g., endonuclease) under the control of an inducible promotor, a nucleotide sequence recognized by the endonuclease, and the selectable marker, typically a counter-selectable marker. Typically, the second and third portions of homology (to 3' and 5' portions of the target region) flank a sequence containing the first portion of homology (which generates the tandem repeat). In one aspect, the second and third portions of homology further flank a sequence containing the nucleic acid encoding the enzyme (e.g., endonuclease). They typically also flank a sequence containing the selectable marker.

In one aspect, the nucleotide sequence recognized by the enzyme is located adjacent to the second or third homologous portion and is on the opposite terminus of the construct relative to the first portion of homology (which generates the tandem repeat region).

In one aspect, one or both of the second or third portions of homology (for integration of the cassette) contains one or more nucleotide mutations, insertions, or deletions, compared to the homologous portion in the target nucleic acid.

An exemplary targeting cassette, used in TREC in the Examples below, is illustrated in FIG. 10C. This exemplary construct contains an I-SceI recognition site, a nucleic acid encoding a I-SceI endonuclease under the control of a GAL-1 promoter, a URA3 counter-selectable marker, and a portion (labeled “Repeat”) that is homologous to a portion of the target nucleic acid sequence upstream of the target region (labeled “Repeat” in the target nucleic acid, also pictured). The cassette further contains a 50 bp portion of homology to the target region that is 5' of the I-SceI site and a 50 bp portion of homology to the target region that is 3' of the “Repeat” portion of homology. The portion of the targeting cassette containing the recognition site, the endonuclease-encoding gene and inducible promoter, and the selectable marker is termed the “CORE” cassette. This cassette was used, as described in Example 4C, below, to modify a *M. genitalium* donor genome, which had been transferred into a yeast host using the provided methods, within the host cell, by deleting a 450 base-pair portion of a target region of the genome. A similar construct, was used to delete the Type II Restriction Enzyme gene in a *M. mycoides* LC genome within a yeast host cell using the provided methods.

Variations of these targeting cassettes, such as those described in FIGS. 10A-D and described elsewhere herein, also can be used with the provided methods. For example, variations of the cassettes can be used to introduce mutations, substitutions, insertions, and other modifications such as modified nucleotides, into the target nucleic acid. Such modifications of the provided cassettes and methods will be apparent to the skilled artisan.

The cassettes can be generated using any of a number of well-known nucleic acid synthesis, amplification, joining, and assembly methods, such as those described herein and commercially available methods. In one embodiment the cassettes are by amplification and/or assembly of nucleic acid fragments making up portions of the cassettes. The fragments can be generated using well-known methods, such as chemical synthesis or amplification (e.g., PCR) from a plasmid, genomic DNA or other nucleic acid containing the desired nucleotide sequence.

In one aspect, the fragments are assembled to form the cassette using fusion PCR, using a recombinant PCR technique, as described in Shevchuk, N. A. et al., *Nucleic Acids Res*, 32, e19 (2004).

With this method, chimeric fusion primers are used to amplify two different fragments to be joined, which then are joined in a primer-less polymerase reaction (e.g., primer-less PCR). The chimeric primers each contain a portion of homology to the first fragment to be joined, and a portion of homology to the second fragment to be joined. Thus, amplifying both fragments using the primers generates regions of overlapping homology among the products of the amplification, such as 40 bp homology at the termini of the products.

These products then are used in a number (e.g., 10, 11, 12, 13, or more) cycles of PCR in the absence of primers, with a low annealing temperature, such as at or about 56° C., to join the products by overlap extension. Multiple products joined in this manner then can be joined in subsequent fusion PCR steps. Typically, the fusion products are re-amplified in an additional PCR reaction, such as with primers containing additional sequence to be added at the termini of the desired cassette.

Other assembly methods are known and can be used to generate cassettes. For example, the cassettes can be prepared using conventional synthetic methods as described, or can be purchased from commercial suppliers. Other assembly methods can be used, such as a one-step isothermal DNA assembly method is described in Gibson et al., *Nature Methods* 6, 343-345 (2009), and in U.S. patent application Ser. No. 12/371,543, filed Feb. 19, 2009, by the concerted action of a 5' exonuclease, a DNA polymerase, and a DNA ligase. With this method, DNA fragments are first recessed by the 5' exonuclease, yielding single-stranded overhangs, which then specifically anneal, followed by gap-filling and covalent joining using the polymerase and the ligase. Other assembly methods are described in U.S. patent applications, Publication Nos: US2007/0037197A1 and US2007/0037196A1.

vi. Transformation and Analysis of Modification

For modification, the cassettes are transformed into host cells containing the donor genomes, such as those produced according to the provided methods. Transformation methods are well known. In one example, the cassettes are introduced into yeast host cells containing the donor genome using lithium acetate integrative transformation, according to a published method (Gietz, D. et al., *Nucleic Acids Res*, 20, 1425 (1992)), with 2-3 μg PCR product and 25 μg carrier DNA (Salmon testis DNA, Sigma, St. Louis, Mo.).

For selection of cells in which the cassette has been integrated into the target nucleic acid, cells are grown in medium lacking uracil and individual URA$^+$ transformants are selected and optionally analyzed by PCR, using diagnostic primers that specifically bind to portions of the target donor nucleic acid flanking the region at which the cassette is inserted. Whether the cassette is correctly inserted is determined by evaluating the presence and size of amplicon using such primers, which produce different sized amplicons depending on whether the cassette is inserted. An example is described in Example 4C(ii) below. Cells containing the correct insertion are used in subsequent rounds of homologous recombination.

When inducible expression of an enzyme to generate ds breaks is carried out, cells containing the counter-selectable marker then are grown under conditions that induce expression of the enzyme from the inducible promoter, such as growth in galactose-containing medium. In one example, cells are grown on SG (synthetic galactose)-His medium, containing galactose as the only carbon source, for example, for 4 hours or 24 hours, to induce expression of the enzyme that introduces the ds break. Growth on glucose-containing medium can be carried out as a control.

In some embodiments, a second nucleic acid, containing a sequence homologous to the target nucleic acid that will replace the selectable marker is transformed into the cells. In some cases, this second nucleic acid contains one or more mutations, deletions, insertions, or substitutions compared to the target nucleic acid. See Examples 4A and 4B. In other cases, the second homologous recombination event occurs spontaneously, through the tandem repeats generated in the target nucleic acid after insertion of the vector. With the TREC method, a combination of these methods is used for removal of the selectable marker.

Loss of the counter-selectable marker is selected for by growth under conditions that favor the loss. In some aspects, when URA3 is used as the marker, before such a selection (e.g., after a second round of transformation), cells are grown in the presence of uracil, overnight at 30° C., to deplete residual orotidine-5'-phosphate decarboxylase (encoded by URA3 gene) in yeast cells having lost URA3 gene. Cells having lost the counter-selectable marker are then selected in an environment that favors the loss, such as in the presence of 5-FOA, such as on HIS plates containing 5-FOA, to select loss of the URA3 gene. PCR analysis using the same or different diagnosis primers, flanking the site of insertion, can be carried out to verify deletion of the cassette.

Multiplex PCR can be carried out to analyze the integrity of donor nucleic acids, such as genomes, modified using the provided modification methods. For example, Multiplex PCR (MPCR) can be performed as described in D. G. Gibson et al., *PNAS USA,* 105:20404-9 (2008).

Isolation of total DNA from the host cells for PCR and MPCR analysis can be performed using the isolation methods described herein, depending on the type of host cell. In one example, isolation of genomic DNA from yeast host cells is carried out as described in Example 3. MPCR primer sets can be designed with homology at various portions along the length of the donor genome, such as around the circular bacterial genome in yeast, with varying sizes, such that presence of each amplicon can be verified. See, e.g., D. G. Gibson et al., *PNAS USA,* 105:20404-9 (2008)). Multiplex PCR can be carried out using well-known methods, including commercially available kits, such as Qiagen Multiplex PCR Kit. An exemplary reaction is described in Example 4A, below. The presence of each amplicon indicates that the modified genome is complete and is typically carried out to assure that spontaneous unwanted recombination events have not occurred, generating unwanted modifications.

Other modification methods can be used in connection with the provided methods, depending upon donor, host, and recipient cell types. For example, the well-known Cre-LoxP system can be used. The Cre-loxP system is a known efficient site-specific recombination method that has been successfully used to remove selection markers and large genomic DNA segment in a large number of different organisms. A Cre-loxP mutagenesis construct with mutant loxP genes can be produced, e.g., by two rounds of PCR reactions, as described for other methods. Mutations of loxP prevent reverse recombination events, as described in Araki, K. et al., *Nucleic Acids Res,* 25, 868-872 (1997). An example is described in Example 4D, below. In one example, the modification method is as efficient, substantially as efficient, or more efficient than modification by the Cre-LoxP system.

F. Transplantation of Modified Donor Genomes and Nucleic Acids into Recipient Cells Provided herein are methods for transplantation of donor nucleic acids, including donor chromosomes and/or donor genomes into host cells or recipient cells. The donor nucleic acids can be transplanted from host cells to recipient cells. Donor nucleic acids include those modified within host cells. In another embodiment, the donor genomes are transplanted directly from donor cells into recipient cells, for example by transplantation of native genomes into recipient cells. Transplantation methods are useful for efficiently transplanting donor genomes, which have been propagated and modified within host cells, back into an environment in which gene products can be expressed from the genomes. The recipient cells can be cells of the same species or a closely related species compared to donor cell or organism.

Methods for cloning small nucleic acid fragments, such as gene segments, into host cells and transplanting them back into the original or closely related cells are known, but have generally been restricted to manipulation of small nucleic acids, for example, modification of a single nucleic acid fragment, which then is isolated and inserted back into the genome of the original donor cell. As described by Lartigue et al., *Science* 317, 632 (2007), whole *Mycoplasma* genomes have successfully been transplanted directly from a donor *Mycoplasma* cell to a closely related recipient *Mycoplasma* cell of a different species, with successful gene product expression upon transplant.

Available transplantation methods are limited, however, in their ability to transplant large nucleic acids (e.g., genomes and chromosomes), from host cells to recipient cells that are less closely related, such as cells of a different branch of life compared to the host cell in which the genome has been propagated. For example, available methods are limited for transplantation from eukaryotic hosts to prokaryotic recipients.

For example, transplantation of prokaryotic donor genomes, propagated in eukaryotic hosts, into prokaryotic recipients can be limited by nucleic acid recovery, methylation, incompatibility and toxicity issues. Methods are needed in which a sufficient amount of purified, intact, donor nucleic acid is recovered from the host cells to generate a sufficient number of recipient cells containing transplanted donor nucleic acids, such as a detectable number.

Restriction-modification systems that are present in recipient cells (and perhaps also in donor cells), but not present in host cells, can cause incompatibility upon transplantation of donor nucleic acids that have been propagated within the host cells. For example, because *Saccharomyces cerevisiae* yeast host cells do not contain the restriction-modification systems present in some bacterial cells, bacterial genomes isolated after growth in yeast hosts can be susceptible to restriction-modification system(s) of bacterial recipient cells (Holt et al., *Bioessays* 29, 580 (2007). Thus, transplanting bacterial genomes that have been modified and propagated in yeast cells into cells in which donor gene products can be expressed (such as donor cells and other bacterial recipient cells) carries the risk that the transplanted genomes will be incompatible with the recipient cells.

Further, such yeast hosts which do not contain restriction-modification systems can nonetheless express DNA methyltransferases that can modify donor nucleic acids (such as bacterial genomes) inhibiting their activation (e.g., gene product expression) upon transplantation into a recipient cell such as a bacterium.

Further, the structure and confirmation of donor genomes isolated after propagation and modification in host cells can differ from the confirmation and structure of the same genome propagated in a cell more closely related to the donor organism. Such differences can negatively impact transplantation of the donor nucleic acids back into recipient cells. The transplantation methods described herein include aspects to overcome such limitations for successful transplantation of donor genomes, modified and/or propagated in host cells, into genetically distinct recipient cells, such as from eukaryotic hosts to prokaryotic recipients. Among these aspects are in vitro methylation, treatment with enzymes to degrade host cell protein, and transplantation into recipient cells lacking restriction-modification systems, such as by mutation of these systems in recipient cells. Exemplary studies, demonstrating success of the provided transplantation methods, are described in detail in Example 3 and Example 5, below.

Figure 8:
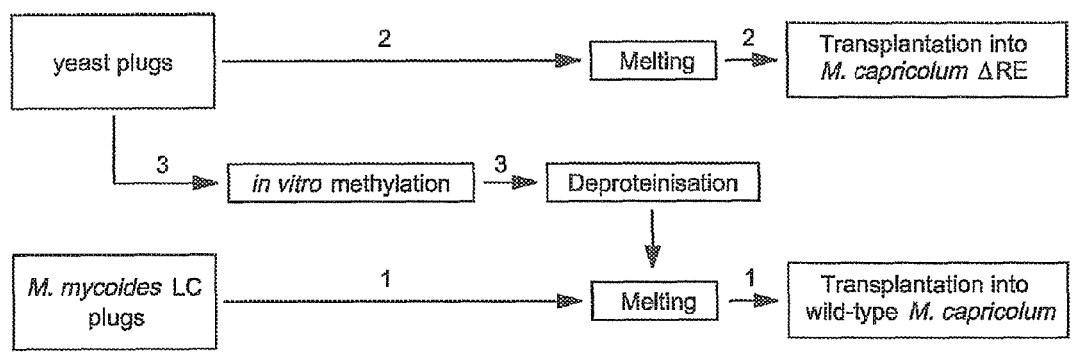

FIG. 8 schematically illustrates three aspects of the provided transplantation methods. In the first approach (denoted with "1" labeling the arrows), donor DNA is isolated in agarose plugs which are melted, such as with β-agarase treatment, and transplanted directly into recipient cells. This first approach is typically used when nucleic acids are transplanted between similar cells and incompatibility issues are not a concern. In the second approach (denoted "2"), recipient cells are modified to mutate restriction enzymes prior to transplantation of the donor nucleic acids, as in the first method. In the third approach (denoted "3"), donor nucleic acid in agarose plugs is subjected to methylation and deproteinisation reactions, prior to melting and transplantation, in order to protect the donor nucleic acid from recipient R-M systems and conformational changes. In another aspect, methylation is performed without deproteinisation.

FIG. 16 schematically illustrates additional aspects of the provided transplantation methods. A bacterial genome can be moved into yeast, engineered, and installed back into a bacterium by genome transplantation. A yeast vector can be inserted into a bacterial genome by transformation; that bacterial genome is cloned into yeast. After cloning, the repertoire of yeast genetic methods is used to create one or more insertions, deletions, rearrangements, or any combination thereof in the bacterial genome. This engineered genome can then be isolated and transplanted into a recipient cell to generate an engineered bacterium. Before transplantation, in some cases, it may be necessary to methylate the donor bacterial DNA in order to protect it from a recipient cell's restriction system(s). This cycle can be repeated in an iterative fashion starting from the newly engineered genome (dashed arrow).

i. Isolation of Donor Nucleic Acids from Host Cells or Donor Cells

In a first step, donor nucleic acids (e.g., donor genomes) are isolated from a host cell or donor cell. Methods for isolation of nucleic acids from cells are well known, including methods for isolation of genomic DNA, including whole genomes, and methods for isolating organelle genomes. Any such method, including those described herein, can be used to isolate the donor nucleic acids. One will understand that the choice of method depends on the type of nucleic acid to be isolated and the type of cell from which it is isolated.

Typically, isolation of large nucleic acids, such as genomes, is carried out in agarose plugs, as described below in the Examples.

Several aspects of the described transplantation methods provide efficiency and high yield of high quality transplanted nucleic acid. In one aspect, cells containing the donor nucleic acids are grown in the presence of Chloramphenicol or similar substance prior to isolation of the donor nucleic acids. Chloramphenicol is used to obtain compact and fully replicated donor genomes and chromosomes in the isolated nucleic acid samples (such as agarose plugs). It is known to synchronize ongoing rounds of replication, inhibit further rounds of replication (Drakulic and Errera, *Biochim Biophys Acta* 31, 459 (1959); Skarstad et al., *EMBO J* 5, 1711 (1986); Bernander et al., *J Bacteriol* 177, 1670 (1995); Skarstad et al., in *Flow cytometry applications in cell culture* A. N. E. Mohamed Al-Rubeai, Ed. (CRC Press, New York, 1996) pp. 241-255) and compact nucleoids (Murphy and Zimmerman, *J Struct Biol* 133, 75 (2001); Seto and Miyata, *J Bacteriol* 181, 6073 (1999)). Presence of chloramphenicol in *Mycoplasma* cultures might help to get compact and fully replicated genomes in the agarose plugs.

a. Isolation from Host Cells

Where donor nucleic acids are isolated from host cells, the donor nucleic acids can be isolated in agarose plugs using a protocol compatible with the host cells. In one aspect, when the host cells are yeast, agarose plugs can be prepared, for example, with the CHEF mammalian Genomic DNA Plug Kit (Bio-Rad), following the instructions recommended by the manufacturer for yeast DNA extraction, with optional modifications. In one non-limiting example, cultures of yeast host cells containing bacterial donor nucleic acids are grown at 30° C. in selective medium until the $OD_{600}$ reaches approximately 1.5. In one example, $6 \times 10^9$ yeast cells are used per mL of plugs (instead of $6 \times 10^8$ cells recommended by the manufacturer) to increase the amount of donor nucleic acid available per plug. Cell walls of the yeast hosts embedded in the agarose plugs are digested. Cell wall digestion can be carried out using lyticase (Biorad), as recommended by the CHEF kit manufacturer, or using 100T (β-1,3-glucan laminaripentaohydrolase; USB, Cleveland, Ohio). In one example, Zymolase™ enzyme is added inside and outside of the plugs at a concentration of 5 mg/mL. The mixture is allowed to stand for 2 hours at 37° C.

In one example, after a washing 1×TE buffer (20 mM Tris-HCl, pH 8; 50 mM EDTA), embedded yeast cells are lysed and proteins digested by two incubations of 24 h at 50° C. with 5 ml of Proteinase K Reaction Buffer [100 mM EDTA; 0.2% Sodium Deoxycholate; 1% Sodium Lauryl Sarcosine; pH 8.0] supplemented with 200 µl of Proteinase K, per ml of plug. The agarose plugs are washed at room temperature four times, for one hour each, with 40 ml of 1×TE buffer, with agitation. Samples then are stored in the same buffer at 4° C. In some cases, it is desired to digest the isolated nucleic acids in subsequent steps, such as for removal of host DNA or linearization of donor genomes. In such cases, 1 mM of phenylmethanesulfonylfluoride (PMSF) is added during the second wash.

When the donor nucleic acid is an organelle genome, the isolation protocol is modified in order to isolate organelle genomes, as in the organelle genome isolation methods discussed herein.

b. Removal of Host Nucleic Acids

For isolation of donor nucleic acids from host cells, it may be desirable to remove host nucleic acids. In one example, for isolation of bacterial donor genomes from yeast host cells, yeast genomic DNA is also isolated along with the bacterial nucleic acid that is extracted from the host cell. In one aspect, isolation includes a "clean-up" step, in which contaminant host nucleic acids are removed, such as with restriction enzymes that recognize host nucleic acids but not donor nucleic acids. In one example, to remove contaminant yeast genomic DNA, plugs are treated with a cocktail of restriction enzymes that specifically digests yeast genomic DNA.

In one example, removal of endogenous host DNA plugs is carried out by incubation of the plugs overnight at 37° C. with restriction enzymes (e.g., 50 units of AsiSI, RsrII, and FseI enzymes (New England Biolabs, Ipswich, Mass.) in a 500 μL reaction volume) that specifically cut host genomic DNA but leave donor DNA intact. Plugs then are washed at room temperature for 1 hour with 1 ml of 1×TE buffer and loaded on 1% TAE agarose gel (120 minutes, 120 volts), to remove digested host DNA fragments from the plugs.

In another example, where the host genomic DNA is linear and the donor genomes are circular, host genomic DNA is removed by Pulse Field agarose gel electrophoresis, whereby host genomic DNA is retained in the wells and donor genomic DNA is electrophoresed out of the wells. (Lartigue et al., *Science* 317, 632 (2007)). In one such example, yeast plugs are subjected to electrophoresis in a 1 LMP gel in 1×TAE buffer, with a contour-clamped homogenous electric field (Chu et al., *Science* 234, 1582 (1986)), using the CHEF DR III, from Bio-Rad. Typically, pulse times are ramped from 60 to 120 seconds for 24 hours at 3.5 V/cm. After electrophoresis, plugs are removed from the wells and stored in 1×TE buffer at 4° C.

Following separation of host DNA by either method, agarose plugs can be removed from wells for further processing. In one example, the removed plugs are washed two times for one hour in 1 mL 0.1×TE buffer and equilibrated for one hour in 1 mL of 1×NEB buffer 2 (New England Biolabs, Ipswich, Mass.) supplemented with BSA (100 μg/mL). To linearize the donor genomic DNA to run it on an agarose gel, plugs can be incubated with a restriction enzyme. In one example, plugs are incubated overnight at 37° C. with 50 units of PspXI restriction enzyme. Following the incubation, plugs are washed for 1 hour at room temperature with 1 mL of 1×TE buffer and loaded onto a pulse-field gel.

In another example, host DNA is not removed prior to transformation.

c. Isolation from Donor Cells

In another embodiment, where the donor nucleic acids (e.g., donor genomes) are transplanted directly from donor cells into recipient cells, isolation methods are used that are compatible with the donor cells. In one example, for isolation of donor bacterial genomes from donor cells, agarose plugs containing genomic DNA are prepared using the CHEF mammalian Genomic DNA Plug Kit (Bio-Rad), with modifications.

In one example, cells (e.g., *M. mycoides* LC cells containing donor genomes or yeast cells containing the donor genomes) are grown in the appropriate medium until a desired OD and then incubated with 100 μg/μl chloramphenicol for 90 minutes before harvesting.

An exemplary protocol for isolation of whole intact genomic DNA from *Mycoplasma* donor cells is performed as described by Lartigue et al., *Science* 317, 632 (2007) with optional modifications, such as modifications to cell culture prior to isolation. One such example is described in Example 2B(ii).

d. Quantification of Isolated Donor Nucleic Acid

The amount of isolated donor nucleic acid can be quantified or estimated prior to transplantation. In one embodiment, donor nucleic acids isolated from host cells are run on agarose gel and compared to donor nucleic acids isolated from known quantities of donor cells. An example is described in Example 2B. In another embodiment, the amount of isolated donor nucleic acid is quantified, such as by UV spectrophotometry. One such example is described in Example 2B(iv).

ii. Treatment of the Isolated Donor Genomes and/or Recipient Cells

The provided methods include steps for overcoming incompatibility barriers between host, donor, and recipient cells/nucleic acids. Such barriers are described herein, and can limit the transplantation of large nucleic acids such as donor genomes from host cells into recipient cells in which donor gene products can be expressed. This is particularly the case when the host cells are not closely related (e.g., from a different branch of life) to the donor and recipient organisms. Such barriers are relevant for transplantation of prokaryotic genomes, propagated in eukaryotic hosts, into prokaryotic recipients.

The barriers can be caused by a number of factors including incompatibility and toxicity. For example, restriction-modification (R-M) systems present in recipient cells (and perhaps also in donor cells), but not present in host cells, can cause incompatibility upon transplantation of donor nucleic acids that have been propagated within the host cells. Restriction-modification systems are well known and are used, typically by bacterial organisms, to protect the organism from foreign DNA. Restriction modification systems generally include proteins for recognizing and cleaving particular nucleic acid sequences in foreign DNA, and enzymes for modifying (e.g., methylating), and thereby protecting, those sequences in the organism's own nucleic acids. Restriction-modification systems include Type I, Type II, and Type III systems. Type I systems generally contain a complex of three proteins that individually recognize (specificity), cleave (restriction) and modify (modification) nucleic acid sequences. Thus, the same complex methylates and cuts DNA. Type II systems generally contain two separate modification and restriction enzymes, which methylate and cut DNA sequences, respectively. Type III systems contain restriction and modification enzymes that form heterodimer complexes for modification and cleavage. The modification enzymes also can methylate their own DNA.

Further, expression of DNA methyltransferases by host cells (including those that do not contain restriction-modification systems) can modify donor nucleic acids and inhibit their activation (e.g., gene product expression) after transplantation into recipient cells. Structural and conformational changes in donor nucleic acids following propagation and modification in host cells can negatively impact transplantation of the donor nucleic acids back into recipient cells.

The provided transplantation methods include steps for overcoming such limitations in order to successfully transplant donor genomes, modified and/or propagated in host cells, into genetically distinct recipient cells, such as from eukaryotic hosts to prokaryotic recipients. The steps include (1) treatment of the isolated donor nucleic acids and (2) modifications to the recipient cells.

a. In Vitro Assays to Assess Restriction-Modification System Incompatibility

In vitro assays can be utilized to determine whether incompatibility issues exist between host cells, donor nucleic acids, and recipient cells, for example, due to inconsistency in restriction-modification systems among the various organisms. Restriction-modification systems expressed by the donor genome or by the recipient cell may have the potential to impair successful transplantation and activation of the donor genome in the host cell.

To examine the issue of a possible restriction-modification problem for donor genomes propagated in host cells of a different type of organism, such as bacterial genomes propagated in yeast, the donor, host, and/or recipient cells are assessed with respect to restriction-modification systems. The presence of restriction-modification systems in donors and/or recipients (and recognition site specificities of the systems) can be identified from donor genome sequences, using known methods. See also REBASE, The Restriction Enzyme Database, available at the World Wide Web address: rebase.neb.com/rebase/rebase.html.

To further confirm the presence of a R-M system, the presence of a modifying enzyme can be tested in vitro. For this process, the methylation status of predicted recognition sites can be probed using commercially available restriction enzymes that recognize the predicted sites. For example, commercially available restriction enzyme isoschizomers corresponding to the predicted restriction enzyme systems can be used in digestion reactions to determine whether donor and recipient genomes are methylated at appropriate restriction sites. Genomic DNA that is methylated at the predicted sites can be protected from cleavage by the commercially available enzymes that recognize the sites. If recipient genomic DNA is protected from cleavage, the presence of the modifying enzyme of the R-M system is confirmed. This process also can be carried out on genomic DNA isolated from donor cells in order to assess whether the donor genome is likely to be protected from the system. An example is described in Example 2D, below.

Additionally, cell-free extracts prepared from the recipient and donor cells can be used to determine whether predicted restriction enzymes are present and active in the cells. Methods for making cell-free extracts are well known and any can be used with the provided methods, depending upon the cell type. In one non-limiting example, *Mycoplasma* cell-free extracts are prepared as described in Example 2D(ii)(b), below. DNA containing the predicted restriction sites is incubated with the cell-free extract in a restriction digest to determine the presence in the extracts of enzymes that recognize and cut DNA at the sequence. Digested samples are run on an agarose gel to determine cleavage. If desired, DNA that is or is not methylated at particular sites can be compared in the assay. Cell-free extracts also can be used as a source of methyltransferase activity, by the addition of EDTA, such as 10 mM EDTA, to inhibit nucleases. Alternatively, recombinant methyltransferases, such as *E. coli* dam methyltransferase (New England Biolabs, Ipswich, Mass.) can be used to methylate DNA prior to digest assays. Methyltransferases can also be purified An example of such a digest assay is described in Example 2D(ii)(b), below.

b. Methylation of Donor Nucleic Acids

Donor nucleic acids can be methylated in vitro following isolation from the donor cells and prior to transplantation into recipient cells. Methylation of the donor genomes, such as those that have been propagated in host cells, can protect them from restriction modification systems of the host cell and/or those encoded by the donor genome. In one aspect, provided is a method of protecting the donor nucleic acid, which has been propagated in host cells, from R-M systems of the recipient and also those encoded by the donor. In other aspects, provided are methods of protecting the donor genome from R-M systems of one of these organisms. For example, in many cases it possible to methylate the donor genome with enzymes that will protect it from the recipient R-M systems. This is the case when donor nucleic acids become methylated by donor methyltransferases before a lethal concentration of corresponding donor restriction enzyme is reached.

As described in Example 2 below, it was unnecessary to protect *M. mycoides* LC donor genomic DNA from its own restriction systems upon transplantation into *M. capricolum* recipient cells, implying that the donor genome becomes methylated before a lethal level of restriction enzyme activities is reached. This is not surprising because most endonuclease and methyltransferase gene pairs can be cloned simultaneously in *E. coli*. See Holt et al., *Bioessays* 29, 580 (2007). One would understand that donor cells, host cells and recipient cells can be assessed with respect to their restriction-modification systems to assess whether a donor genome is to be protected prior to transplantation.

When transplanting other bacterial genomes from yeast it may be necessary to methylate the donor genome in vitro to protect it from its own restriction enzymes, such as by in vitro methylation using cell-free extracts or purified methyltransferases from the donor or by inactivation of restriction endonuclease genes in the donor genome as described below. In vitro methylation and restriction digests, as described below, can be used to determine which methylation reactions may be needed in particular transplantation studies.

Typically, methylation is performed using methyltransferases that are the same as, or similar to, those of the R-M system from which protection is desired. Methylation can be carried out using methylases isolated from cell extracts (e.g., recipient cell extracts) or recombinantly produced and purified methylases.

In one aspect, methylases of the R-M systems of the recipient and/or donor cells are exogenously expressed and purified using recombinant methods. The coding sequences for all methyltransferases identified by R-M prediction can be codon optimized for expression in a desired system, such as yeast or bacterial cells. Fragments containing the coding sequences can be constructed using any of a number of well-known synthesis and/or assembly methods, such as those described herein. One non-limiting example is described in Example 2E(i)(a) in which methyltransferase-encoding nucleic acids were generated using a one-step isothermal DNA assembly method. After construction, the fragments are cloned into expression vectors, for expression in a cell of choice.

Vectors can be used to transform cells for expression of gene products. Exemplary expression systems include the BL21 (DE3) codon plus cells (Stratagene, La Jolla, Calif.). Expression of the methyltransferases can be induced in the cells, such as by incubation with IPTG. Methyltransferases can be purified from the cells, using well-known methods. In one example, cell lysates are clarified, column-purified, and fractions containing the methyltransferases dialyzed against an enzyme buffer for use in subsequent methylation reaction, such as 50 mM HEPES-NaOH pH 7.2, 50 mM NaCl, 0.1 mM EDTA, 10% glycerol). The samples can then be concentrated if needed. Exemplary expression and purification protocols are described in detail in Example 2E(i)(b), below.

In another aspect, crude extracts from cells having the R-M systems (such as the recipient cells or donor cells) are used to methylate the donor nucleic acids isolated from the host cells. This aspect can be advantageous if it is not certain that all the R-M systems of the recipient or host cell have been determined. For example, if the R-M systems of a recipient cell are unknown, methylation using a crude extract from the recipient cell will ensure that all the relevant methyltransferases are present in the methylation reaction. Any well-known method for preparing the appropriate cell extract can be used. An example is described in Example 2E(ii), below, for preparation of crude cell extracts containing methyltransferases from *Mycoplasma* recipient cells. Nucleases in the cell extracts can be inhibited, such as by the addition of 10 mM EDTA, to allow their use in methylation reactions.

Purified methyltransferases or crude cell extracts containing methyltransferases can be used to methylate donor nucleic acids isolated from host cells. In one example, agarose plugs containing the donor nucleic acid can be washed and equilibrated in methylation buffer (e.g., 100 mM Tris-HCL pH 7.5; 10 mM EDTA; 3 µM DTT, 200 µM S-adenosylmethionine (SAM)). Plugs then can be incubated in methylation reactions, including methylation buffer and either crude cell extracts or purified methyltransferases. Parallel reactions without SAM can be used as controls. In one aspect, methylation reactions can be carried out in the presence of dam methyltransferase (New England Biolabs, Ipswich, Mass.). Following methylation, each yeast plug can be incubated for 4 hours at 50° C. in 1 ml of Proteinase K Reaction Buffer supplemented with 40 µl of Proteinase K. The plugs can then be washed 4 times for 45 minutes each with 1 ml of 1×TE buffer and 2 times for 30 minutes each on 0.1×TE buffer with gentle agitation at room temperature. After removing the final wash buffer, the plugs can be melted. An example is described in Example 3A(iii). The effectiveness of methylation reactions on protecting donor nucleic acids from recipient R-M systems can be tested in vitro prior to the transplantation studies. Adjustments can be made depending upon the results of the R-M system assessments. This process can be carried out by performing methylation reactions on donor genomic DNA or plasmids containing donor nucleic acids. The methylation reaction can be followed by a restriction digest reaction, using restriction enzymes of the recipient cell, to ensure protection of the donor nucleic acids by methylation. An example is described in Example 2E.

c. Deproteinisation

Incubation with crude extract can change the confirmation of donor DNA which, in turn, can cause incompatibility upon transplantation. Such conformational changes can be assessed by visualizing donor genomic DNA incubated in the presence or absence of cell extracts, such as described in Example 2B(iv). Thus, in some embodiments, donor nucleic acids can be subjected to a deproteination step after methylation and prior to transplantation to remove the proteins in the crude extract. In one aspect, the proteins can be removed using a proteinase, such as proteinase K. In an exemplary treatment, agarose plugs that have been subject to methylation reactions can be further incubated for 4 hours at 50° C. in proteinase K reaction buffer and proteinase K. The plugs can be washed before proceeding with melting of the plugs and transplantation. See Examples 2B(iv) and 3A(iii).

d. Genetic Modification of Recipient Cell R-M Systems

In some cases, the restriction-modification system of a recipient cell may need to be inactivated prior to transplantation of a donor nucleic acid or genome; modification of a R-M system can occur in vitro or in vivo. Instead of in vitro methylation, restriction modification systems can be removed or inactivated from at least the recipient cell, and possibly the donor genome or nucleic acid.

One or more restriction enzyme(s) of the recipient cell R-M system can be inactivated by mutation of the gene encoding the enzyme. This process typically can be used as an alternative to in vitro methylation of the donor nucleic acids prior to transplantation.

Restriction modification system inactivation of donor genomes, however, may not be practical in some cases. For example, expression of restriction endonucleases encoded by the donor genome immediately following transplantation can help drive transplantation by degrading the resident genome of the recipient cell. Thus, removal of the donor restriction modification systems is undesirable in such cases and methylation should be used. One would understand that each of the donor, host and recipient cells can be assessed in this regard prior to transplantation to identify the best system for inactivation of a R-M system.

Any mutation process can be used to inactivate a R-M system. One example is described in Example 2F, below, in which the gene encoding the single restriction enzyme in a *Mycoplasma* recipient cell was inactivated prior to transplantation of donor nucleic acids. In that example, the gene was mutated by interruption with a puromycin resistance marker, allowing selection of cells containing the mutated gene. Other methods of inactivation are contemplated herein and include a variety of resistance markers that can also be used for selection of cells containing a mutated gene; such markers are described herein and are also known in the art. Cell extracts prepared from such mutant recipient cells can be used as controls in methylation reactions as described herein.

Alternatively, a donor genome can be methylated in vivo, for example, while still in the host cell. In vivo methylation inside a host cell can be carried out by expression of donor or recipient methylases that are cloned into the host vector. This aspect may be less desirable as it may lead to unwanted changes in the donor genome. For example, expression of bacterial methylases in yeast has been shown to increase yeast homologous recombination, which could lead to alteration of a donor bacterial genome housed in either a yeast artificial chromosome (YAC) or yeast centromeric plasmid (YCp). This result can occur because the yeast host cell is under no selective pressure to maintain the integrity of the bacterial genome except for the inserted yeast vector sequence region of said bacterial genome. It would be understood that one can assess whether in vitro methylation, in vivo methylation, or inactivation of the R-M system by insertion of, for example, a resistance marker is to be used to inactivate a R-M system of a recipient cell.

iii. Transplantation into Recipient Cells

Following isolation and treatment, the donor nucleic acids can be further transplanted into recipient cells using methods described herein or known in the art. One exemplary transplantation protocol is described in Example 3, below. One method used to transplant *Mycoplasma* genomes from donors to *Mycoplasma* recipients is described by Lartigue et al., *Science* 317, 632 (2007). Such methods can be used to modify genomes or nucleic acids from intractable cells or organisms in a separate host to confer a specific property upon the donor genome. The modified genome can then be transplanted back into the same donor cell or into a donor cell, thereby conferring the phenotype of the modified genome upon the recipient cell.

Recipient cells typically are chosen based on their ability to support gene expression from the donor nucleic acids, such as the donor genomes. The transfer of a bacterial genome into a eukaryotic host is provided herein as an exemplary method and is not intended to be limiting. For example, after a bacterial genome has been transferred into, and modified within, a eukaryotic host cell having a preferred genetic manipulation system (e.g., yeast), it may be necessary to transplant the genome back into a bacterial recipient cell in order to express gene products from the modified genome. As discussed herein, differences in translation and transcription and different codon usage, among other factors, can prevent expression of the donor gene products within the host cell. The recipient cell, therefore, may be of the same species or a similar species as a donor cell or organism. It is often of the same order or kingdom as the donor. One will be able to determine an appropriate recipient cell based on the donor genome or other nucleic acid from which expression is desired.

Following isolation of donor nucleic acids in agarose plugs, host DNA can optionally be removed (e.g., by digest and/or electrophoresis), and optionally treated with methyltransferases and/or proteinase.

Agarose plugs can be melted, for example, by incubation with β-Agarase I (New England Biolabs) as described in Example 3A(ii)(b) below.

Transplantation can be performed in the presence of polyethylene glycol (PEG), such as PEG-6000 or PEG-8000 or other PEG to facilitate transformation. The source, amount, and size of the PEG can be varied to determine the optimal PEG. In one example, the PEG is PEG-2000, PEG-4000, PEG-6000, PEG-8000, PEG-10000, PEG-20000, or other. The concentration of PEG can be varied depending upon the conditions of the transplantation; concentrations include those, for example, at or about 5% or at or about 10%. An example is described in Example 3A(ii)(c), below. Melted plugs can be added to the recipient cells in the presence of PEG with gentle rocking to mix. Cells are allowed to recover, centrifuged, and grown in medium containing appropriate selection medium to select for recipient cells containing the transplanted donor nucleic acid. In one aspect, cells are plated on the medium and grown under appropriate conditions for the recipient cell type until colonies appear. Colonies can be picked and further grown in selection medium to produce a desired quantity of recipient cells containing the transplanted genome or other donor nucleic acid.

A particular ratio of recipient cells to donor nucleic acid can be maintained as needed. In one example, a ratio of between at or about $10^7$ and at or about $10^8$ recipient cells per 2 μg genomic DNA can be maintained. The provided transplantation methods can be used to achieve approximately 30 transformants for 200 ng of endogenous genomic DNA, or between 500 and 1500 transplants per reaction, or other appropriate amount that is obtained from the host or donor cell. In one non-limiting example, transplantation is carried out with ~$10^7$ recipient cells, 20 μl of melted of agarose plug containing donor genome at 100 ng/μl. One would understand that the ratio of recipient cells to donor nucleic acid may vary depending upon the cell types and that empirical assessment can be used to optimize the ratio.

An exemplary transplantation method is illustrated in FIG. 8 ("3"): in this method, genomic DNA containing appropriate markers and elements for propagation in host and recipient cells is isolated from host cells in agarose plugs, methylated with crude extract or purified methyltransferases and deproteinized with Proteinase K. The agarose plugs are melted, DNA incubated with recipient cells, which then are plated on selection medium. By way of example, whole intact M. mycoides LC donor genomic DNA containing a YCp element, a tetracycline marker and a β-galactosidase gene can be isolated from yeast hosts in agarose plugs, methylated with a M. mycoides LC crude extract, and then deproteinized with Proteinase K. The agarose plugs containing the methylated genomic DNA were melted and incubated with M. capricolum recipient cells and then plated onto SP4 medium containing tetracycline to select for transformants.

G. Iterative Methods

The methods described herein can be used for multiple rounds of genome or other nucleic acid modification out in an iterative fashion.

In one embodiment, an engineered cell produced by the methods (such as a recipient cell containing a transplanted, modified, genome that has been modified by the provided methods, e.g., in a host cell) can be used as a source of donor nucleic acid in subsequent rounds of transformation, modification, and transplantation, thereby generating a further modified genome and organism.

In one non-limiting example, as illustrated in FIG. 1, an engineered bacterial cell produced by the methods (such as a recipient cell containing a transplanted, modified, bacterial genome that has been modified by the provided methods, e.g., in yeast) can be used as a source of donor nucleic acid in subsequent rounds of transformation, modification, and transplantation, thereby generating a further modified genome and organism.

In an alternative iterative embodiment of moving a donor genome into a host cell, engineering it, and installing it back into a donor by genome transplantation, a host vector is inserted into a donor genome by transformation. That genome is cloned into a host cell; after cloning, the repertoire of host genetic methods is used to create insertions, deletions, rearrangements, or any combination of modifications in the donor genome. This engineered genome is then isolated and transplanted into a recipient cell to generate an engineered recipient cell with an altered phenotype. Before transplantation it may be necessary to methylate the donor DNA in order to protect it from the recipient cell's restriction system(s). This cycle can be repeated starting from the newly engineered genome.

Provided in FIG. 16 is a non-limiting example of moving a bacterial genome into yeast, engineering it, and installing it back into a bacterium by genome transplantation, a yeast vector is inserted into a bacterial genome by transformation. That genome is cloned into yeast; after cloning, the repertoire of yeast genetic methods is used to create insertions, deletions, rearrangements, or any combination of modifications in the bacterial genome. This engineered genome is then isolated and transplanted into a recipient cell to generate an engineered bacterium. Before transplantation it may be necessary to methylate the donor DNA in order to protect it from the recipient cell's restriction system(s). This cycle can be repeated starting from the newly engineered genome (dashed arrow).

The large number of available, verified, substantiated, and reliable selectable markers for selection and counter-selection of yeast mutants enables use of the provided methods to carry out multiple, e.g., infinite iterative rounds of seamless nucleic acid alterations within yeast host cells. Serial modifications to a cloned copy of an otherwise intractable genome or other large nucleic acid can be performed in yeast in rapid succession. The mating capacity of yeast is favorable for modifying genomes and other large nucleic acids. Yeast recombination machinery, when activated during yeast mating, can be used to generate libraries, e.g., combinatorial libraries containing variants of cloned genomes or nucleic acids. Although the embodiments described herein utilize yeast cells as host cells, it would be understood that the provided methods encompass other host cells which are already understood with respect to, for example, selectable markers for selection and counter-selection of host cell mutants, or which are assessed in this regard. A number of variations of this embodiment are contemplated and within the scope of the application.

H. Uses of the Provided Methods and Compositions

The provided methods and compositions can be used to solve problems related to the environment, energy production and medicine. The provided methods and compositions are useful in producing, engineering and modifying genomes and organisms and other products for commercial use, such as immunogens, biological proteins and chemicals, vaccines, biofuels, and useful proteins such as enzymes. For example, the provided methods can be used to manipulate and engineer nucleic acids from any organisms, particularly those having poor genetic systems, such as those whose genomes are not easily manipulated by conventional methods. The provided methods are useful in building synthetic genomes and transplanting the genomes into recipient cells to generate synthetic cells. Thus, the methods can be used to produce medically useful proteins, including enzymes, protein and nucleic acid therapeutics, antibodies, immunogens, vaccines, and other cellular products.

A vaccine generally refers to an immunogenic preparation that improves immunity to a particular microorganism (bacterial or viral) associated with a disease. A vaccine typically contains a small amount of an agent that resembles a microorganism. The agent stimulates the body's immune system to recognize the agent as foreign, destroy it, and remember it, so that the immune system can more easily recognize and destroy any of these microorganisms that it later encounters. Vaccines can be prophylactic (e.g., to prevent or ameliorate the effects of a future infection by any natural or "wild" pathogen), or therapeutic (e.g., cancer vaccines). Vaccines may be monovalent (also called univalent) or multivalent (also called polyvalent). A monovalent vaccine can be designed to immunize against a single antigen or single microorganism. A multivalent or polyvalent vaccine can be designed to immunize against two or more strains of the same microorganism, or against two or more microorganisms. In certain cases, a monovalent vaccine may be used for rapidly developing a strong immune response. Vaccines are used to try to reduce risk of illness, while retaining the ability to induce a beneficial immune response. Vaccines can contain dead or inactivated organisms or purified products derived from them. Immunogenic compositions are useful for treating human and non-human populations (e.g., primates, veterinary animals, etc.).

The provided technology is useful for production of immunological compositions to elicit an immune response from an organism, such as immunogenic compositions, such as those including live cells and viruses, including, but not limited to, modified Adenoviridae (e.g., adenovirus), Picornaviridae (e.g., coxsackievirus, hepatitis A virus, poliovirus), Herpesviridae (e.g., various types of Herpes simplex virus, Epstein-barr virus, Human cytomegalovirus), Hepadnaviridae (e.g., Hepatitis B virus), Flaviviridae (Hepatitis C virus, yellow fever virus, dengue virus, West Nile virus, etc.), Retroviridae (e.g., Human immunodeficiency virus (HIV)), Orthomyxoviridae (e.g., influenza virus), Paramyxoviridae (e.g., Measles virus, Mumps virus, Parainifluenza virus, Respiratory syncytial virus, Human metapneumovirus, etc.), Papillomaviridae (e.g., Papillomavirus), Rhabdoviridae (e.g., Rabies virus), Togaviridae (e.g., Rubella virus), and Parvoviridae (e.g., Human bocavirus, Parvovirus B19), influenza (e.g., H1N1 influenza, *Haemophilus influenzae* type B, etc.), polio, vaccinia, varicella zoster, reovirus, retroviruses, poxviruses, Parvoviruses, Picornaviruses, paramyxoviruses, and BCG.

The provided technology is useful for production of immunological compositions to elicit an immune response from an organism, such as immunogenic compositions, such as those including live cells and bacteria, including, but not limited to, modified *Bordetella* (e.g., *Bordetella pertussis*), *Borrelia* (e.g., *Borrelia burgdorferi*), *Brucella* (e.g., *Brucella abortus, Brucella canis, Brucella melitensis*, and *Brucella suis*), *Campylobacter* (e.g., *Campylobacter jejuni*), *Chlamydia* (e.g., *Chlamydia pneumonia, Chlamydia psittaci*, and *Chlamydia trachomatis*), *Clostridium* (e.g., *Clostridium botulinum, Clostridium difficile, Clostridium perfringens*, and *Clostridium tetani*), *Corynebacterium* (e.g., *Corynebacterium diphtheria*), *Enterococcus* (*Enterococcus faecalis* and *Enterococcus faecum*), *Escherichia* (e.g., *Escherichia coli*), *Francisella* (e.g., *Francisella tularensis*), *Haemophilus* (e.g., *Haemophilus influenza*), *Helicobacter* (e.g., *Helicobacter pylori*), *Legionella* (e.g., *Legionella pneumophila*), *Leptospira* (e.g., *Leptospira interrogans*), *Listeria* (e.g., *Listeria monocytogenes*), *Mycobacterium* (e.g., *Mycobacterium leprae* and *Mycobacterium tuberculosis*), *Mycoplasma* (e.g., *Mycoplasma pneumonia*), *Neisseria* (e.g., *Neisseria gonorrhoeae* and *Neisseria meningitides*), *Pseudomonas* (e.g., *Pseudomonas aeruginosa*), *Rickettsia* (e.g., *Rickettsia rickettsii*), *Salmonella* (e.g., *Salmonella typhi* and *Salmonella typhimurium*), *Shigella* (e.g., *Shigella sonne*), *Staphylococcus* (e.g., *Staphylococcus aureus, Streptococcus pneumonia, Staphylococcus epidermidis* and *Staphylococcus saprophyticus*), *Streptococcus* (e.g., *Streptococcus agalactiae, Streptococcus pneumoniae* and *Streptococcus pyogenes*), *Treponema* (e.g., *Treponema pallidum*), *Vibrio* (e.g., *Vibrio cholera*), and *Yersinia* (e.g., *Yersinia pestis*) have immunogenic features that make them attractive vaccine candidates.

Available vaccine preparation methods have been unable to effectively rid many organisms of their pathogenicity while retaining their immunogenicity. The provided methods and compositions, which can be used to engineer and manipulate large nucleic acids and genes, e.g., combinatorially, can be used to engineer such vaccines.

The methods described herein can be used to produce compositions effective to treat, prevent, or substantially reduce the biological impact of: chicken pox, shingles, influenza, polio, measles, mumps, rubella, toxic shock, cholera, bubonic plague, Hepatitis A, Hepatitis B, Hepatitis C, yellow fever, malaria, tuberculosis, tetanus, encephalitis, Acquired Immune Deficiency Syndrome (AIDS), leprosy, canine distemper, canine parvovirus, infectious canine hepatitis, adenovirus-2, leptospirosis, bordatella, canine parainfluenza virus, Dengue fever, Lyme disease and another other disease for which a vaccine is useful in treating and/or managing one or more symptoms.

Additional viruses types, families and associated diseases contemplated for use in the methods described herein are provided in the following table.

| Virus Type | Family | Associated Disease(s) |
|---|---|---|
| adenovirus | adenoviridae | Acute febrile pharyngitis, pharyngoconjunctival fever, epidemic keratoconjunctivitis, and infantile gastroenteritis |
| Coxsackievirus | Picornaviridae | Coxsackie infections |
| Epstein-Barr virus | Herpesviridae | Infectious mononucleosis and Burkitt lymphoma |
| Hepatitis A virus | Picornaviridae | Acute hepatitis |
| Hepatitis B virus | Hepadnaviridae | Acute hepatitis, chronic hepatitis, hepatic cirrhosis and hepatocellular carcinoma |
| Hepatitis C virus | Flaviviridae (e.g.,) | Acute hepatitis, chronic hepatitis, hepatic cirrhosis and hepatocellular carcinoma |
| Herpes simplex virus, type 1 | Herpesviridae | Primary HSV-1 infection (e.g., gingivostomatitis in children, tonsillitis & pharyngitis in adults, keratoconjunctivitis) and latent HSV-1 infection (herpes labialis, cold sores) |
| Herpes simplex virus, type 2 | Herpesviridae | Primary HSV-2 infection, latent HSV-2 infection, and aseptic meningitis |
| cytomegalovirus | Herpesviridae | Infectious mononucleosis and Cytomegalic inclusion disease |
| Human herpesvirus, type 8 | Herpesviridae | Kaposi sarcoma, multicentric Castleman disease, and primary effusion lymphoma |
| HIV | Retroviridae | AIDS |
| Influenza virus | Orthomyxoviridae | influenza and Reye syndrome |
| measles virus | Paramyxoviridae | Measles and postinfectious encephalomyelitis |
| Mumps virus | Paramyxoviridae | Mumps |
| Human papillomavirus | Papillomaviridae | Hyperplastic epithelial lesions (common, flat, plantar and anogenital warts, laryngeal papillomas, epidermodysplasia verruciformis) 55+ (hands/feet) 30+ (anogenital/some are oral/throat/respiratory) and malignancies for some species (cervical carcinoma, squamous cell carcinomas) |
| Parainfluenza virus | Paramyxoviridae | Croup, pneumonia, bronchiolitis, and common cold |
| Poliovirus | Picornaviridae | Poliomyelitis |
| Rabies virus | Rhabdoviridae | Rabies |
| Respiratory syncytial virus | Paramyxoviridae | Bronchiolitis, pneumonia, influenza-like syndrome, and severe bronchiolitis with pneumonia |
| Rubella virus | Togaviridae | German measles and congenital rubella |
| Varicella-zoster virus | Herpesviridae | Chicken pox |

Additional bacterial species and associated diseases contemplated for use in the methods described herein are provided in the following table.

| Species | Diseases |
|---|---|
| *Bacillus anthracis* | Cutaneous anthrax, pulmonary anthrax, and gastrointestinal anthrax |
| *Bordetella pertussis* | Whooping cough and complications such as secondary bacterial pneumonia |
| *Borrelia burgdorferi* | Lyme disease |
| *Brucella abortus*, *Brucella canis*, *Brucella melitensis* and *Brucella suis* | Brucellosis |
| *Campylobacter jejuni* | Acute enteritis |
| *Chlamydia pneumoniae* | Community-acquired respiratory infection |
| *Chlamydia psittaci* | Psittacosis |
| *Chlamydia trachomatis* | Nongonococcal urethritis (NGU), Trachoma, Inclusion conjunctivitis of the newborn (ICN), and Lymphogranuloma venereum (LGV) |
| *Clostridium botulinum* | Botulism |
| *Clostridium difficile* | Pseudomembranous colitis |
| *Clostridium perfringens* | Gas gangrene, acute food poisoning and anaerobic cellulitis |
| *Clostridium tetani* | Tetanus |
| *Corynebacterium diphtheriae* | Diphtheria |
| *Enterococcus faecalis* and *Enterococcus faecum* | Nosocomial infections |
| *Escherichia coli* (generally) | Urinary tract infections (UTI), Diarrhea and Meningitis in infants |
| Enterotoxigenic *Escherichia coli* (ETEC) | Traveller's diarrhea |
| Enteropathogenic *E. coli* | Diarrhea in infants |
| *E. coli* O157:H7 | Hemorrhagic colitis and Hemolytic-uremic syndrome |
| *Francisella tularensis* | Tularemia |
| *Haemophilus influenzae* | Bacterial meningitis, Upper respiratory tract infections, and Pneumonia, bronchitis |
| *Helicobacter pylori* | Peptic ulcer and Risk factor for gastric carcinoma and gastric B-cell lymphoma |

-continued

| Species | Diseases |
| --- | --- |
| *Legionella pneumophila* | Legionnaire's Disease and Pontiac fever |
| *Leptospira interrogans* | Leptospirosis |
| *Listeria monocytogenes* | Listeriosis |
| *Mycobacterium leprae* | Leprosy (Hansen's disease) |
| *Mycobacterium tuberculosis* | Tuberculosis |
| *Mycoplasma pneumoniae* | Mycoplasma pneumonia |
| *Neisseria gonorrhoeae* | Gonorrhea, Ophthalmia neonatorum and Septic arthritis |
| *Neisseria meningitidis* | Meningococcal disease including meningitis and Waterhouse-Friderichsen syndrome |
| *Pseudomonas aeruginosa* | Localized or systemic Pseudomonas infections. |
| *Rickettsia rickettsii* | Rocky mountain spotted fever |
| *Salmonella typhi* | Typhoid fever type salmonellosis (dysentery, colitis) |
| *Salmonella typhimurium* | Salmonellosis with gastroenteritis and enterocolitis |
| *Shigella sonnei* | Bacillary dysentery/Shigellosis |
| *Staphylococcus aureus* | Localized skin infections, Diffuse skin infection (Impetigo), Deep, localized infections, Acute infective endocarditis, Septicemia, Necrotizing pneumonia and Toxinoses (e.g., Toxic shock syndrome and Staphylococcal food poisoning) |
| *Staphylococcus epidermidis* | Infections of implanted prostheses, e.g. heart valves and catheters |
| *Staphylococcus saprophyticus* | Cystitis in women |
| *Streptococcus agalactiae* | Meningitis and septicemia in neonates, Endometritis in postpartum women and opportunistic infections with septicemia and pneumonia |
| *Streptococcus pneumoniae* | Acute bacterial pneumonia & meningitis in adults and Otitis media and sinusitis in children |
| *Streptococcus pyogenes* | Streptococcal pharyngitis, Scarlet fever, Rheumatic fever, Impetigo and erysipelas, Puerperal fever and Necrotizing fasciitis |
| *Treponema pallidum* | Syphyllis and Congenital syphilis |
| *Vibrio cholerae* | Cholera |
| *Yersinia pestis* | Plague such as Bubonic plague and Pneumonic plague |

The methods described herein can also be used to produce compositions effective to treat or prevent the disease contagious bovine pleuro pneumonia (CBPP), which is caused by the bacterium *Mycoplasma mycoides* Small Colony. This disease, also known as lung plague, is a major pathogen of cattle, yaks, buffalo, and zebu. The disease is widespread in Africa, the Middle East, Southern Europe, as well as parts of Asia. There is a real need for an improved vaccine. The disease organism is a close phylogenetic relative of the bacterium used here to demonstrate aspects of the provided methods, *M. mycoides* Large Colony strain GM12. Antigen genes and/or the genome of *M. mycoides* Small Colony bacterium can be cloned and manipulated using the provided technology, to generate cells, e.g., mutants, to function as live vaccines.

The provided methods can be used, for example, with *M. mycoides* LC and closely related species as model systems for exploring the pathogenicity and biology of *Mycoplasmas*. The *mycoides* group of *Mycoplasmas* causes major diseases of ruminants and there is an urgent need for vaccines. The provided methods can accelerate the construction of live vaccine strains. The methods also can be used to determine the minimal gene complement required for life, particularly in small genomes such as the *M. mycoides* genome.

Methods of administering vaccines are known in the art and include injection and aerosol delivery of an immunogenic vaccine composition to a subject. Compositions can be formulated and administered with any pharmaceutically acceptable carrier or excipient. Also provided here are compositions comprising an immunogenic vaccine formulated in a medicament for the treatment of a disease or condition identified herein. Effect of an immunogenic vaccine composition following administration to a subject can be measured with respect to one or more aspects of an immune response. Immune responses include, for example, induction of antibody responses (increased antibody titers), cytokine responses, induction of T helper ($T_H1$ and $T_H2$) cell differentiation and proliferation, etc. Each of such responses can be quantified. Immune responses also include reduction of overall bacterial or viral load in a patient.

The presently disclosed methods are also useful for developing biofuels.

Biocrudes are biologically produced compounds or a mix of different biologically produced compounds that are used as a feedstock for refineries in replacement of, or in complement to, crude oil or other forms of petroleum. In general, but not necessarily, these feedstocks have been pre-processed through biological, chemical, mechanical or thermal processes in order to be in a liquid state that is adequate for introduction in a petroleum refinery.

Microorganisms can be modified using the methods described herein to produce a biocrude, which can be further processed to a biofuel composition. The biofuel can then perform as a finished fuel or a fuel additive.

"Finished fuel" refers to as a chemical compound or a mix of chemical compounds (produced through chemical, thermochemical or biological routes) that is in an adequate chemical and physical state to be used directly as a neat fuel or fuel additive in an engine. In many cases, but not always, the suitability of a finished fuel for use in an engine application is determined by a specification which describes the necessary physical and chemical properties that need to be met. Some examples of engines are: internal combustion engine, gas turbine, steam turbine, external combustion engine, and steam boiler. Some examples of finished fuels include: diesel fuel to be used in a compression-ignited (diesel) internal combustion engine, jet fuel to be used in an aviation turbine, fuel oil to be used in a boiler to generate steam or in an external combustion engine, ethanol to be used in a flex-fuel engine. Examples of fuel specifications are ASTM standards, mainly used ion the US, and the EN standards, mainly used in Europe.

"Fuel additive" refers to a compound or composition that is used in combination with another fuel for a variety of reasons, which include but are not limited to complying with mandates on the use of biofuels, reducing the consumption of fossil fuel-derived products or enhancing the performance of a fuel or engine. For example, fuel additives can be used to alter the freezing/gelling point, cloud point, lubricity, viscosity, oxidative stability, ignition quality, octane level, and flash point. Additives can further function as antioxidants, demulsifiers, oxygenates, thermal stability improvers, cetane improvers, stabilizers, cold flow improvers, combustion improvers, antifoams, anti-haze additives, icing inhibitors, injector cleanliness additives, smoke suppressants, drag reducing additives, metal deactivators, dispersants, detergents, demulsifiers, dyes, markers, static dissipaters, biocides, and/or corrosion inhibitors.

Some eukaryotic algae synthesize as much as 70% of their dry weight as oils. These oils, which are the product of photosynthesis, are ideal biofuel candidates. Organisms that produce these oils can be grown in ponds in deserts so no arable croplands will be lost to biofuel production. Use of such algae is typically limited by their slow growth. However, the provided methods can be used to manipulate the genomes of organisms, for example, to engineer new organisms, e.g., prokaryotic organisms, that express enzymes involved in the oil synthesis pathways, for example, by manipulating transcriptional promoters, translation signals, and codon optimization. The methods can be used to modify genomes of photosynthetic bacteria to engineer new bacteria having chimeric genomes that produce biofuels, such as the oils produced by algae, instead of the normal products of photosynthesis (glucose).

Recombinant microorganisms made using the disclosed methods can contain an engineered biosynthetic pathway capable of converting glucose and other sugars derived from lignocellulosic biomass to geraniol.

Recombinant microorganisms (e.g., strains of photosynthetic microorganisms) made using the disclosed methods can be used to biologically produce branched-chain alcohols, including, for example, 2-methyl-1-butanol, 3-methyl-1-butanol, and isobutanol. One aspect involves the production of recombinant photosynthetic microorganisms via introduction of heterologous genes that encode enzymes that enhance the production and decarboxylation of 2-keto branched-chain acids, leading to the production of the corresponding branched-chain aldehydes. Additional gene introductions can then be carried out for efficient reduction of the branched-chain aldehydes to the corresponding branched-chain alcohols. In addition, the microorganisms can be engineered such that branched chain alcohols are enzymatically dehydrated in vivo to produce various branched-chain alpha-olefins.

Recombinant microorganisms made using the disclosed methods to encode plant acyl-ACP thioesterases. Such nucleic acid molecules can be used to transform organisms, such as photosynthetic organisms and prokaryotic organisms, for synthesizing fatty acids and fatty acid products such as fatty aldehydes, fatty alcohols, fatty esters, including wax esters, and hydrocarbons. Also included are organisms transformed using the methods provided herein.

Recombinant microorganisms (e.g., recombinant photosynthetic microorganisms) made using the disclosed methods to contain a nucleic acid molecule comprising at least one recombinant expression system that produces at least one exogenous acyl-ACP thioesterase, wherein said acyl-ACP thioesterase liberates a fatty acid chain that contains 6-20 carbons, and the microorganism secretes the fatty acid liberated by the acyl-ACP thioesterase into the medium. A thioesterase can be used to liberate a fatty acid chain that contains 6, 7, 8, 9, 10, 11, 12, 13, 14, 15, 16, 17, 18, 19 or 20 carbons. The fatty acids thus recovered can be further modified synthetically or used directly as components of biofuels or chemicals.

In such constructions, it may be desirable to remove the portion of the gene that encodes the plastid transit peptide region, as this region is inappropriate in prokaryotes. Alternatively, if expression is to take place in eukaryotic cells, the appropriate plastid transit peptide encoding region to the host organism may be substituted. Preferred codons may also be employed, depending on the host.

Genomes of microbes can be further modified to include an expression system for a heterologous gene that encodes a β-ketoacyl synthase (KAS) that preferentially produces acyl-ACPs having medium chain lengths. Such KAS enzymes would serve to increase the availability of acyl-ACP molecules of the proper length for recognition and cleavage by the heterologous medium-chain acyl-ACP TE. Another example is that a photosynthetic host cell containing a heterologous acyl-ACP TE gene may be further modified to include an expression system for a heterologous gene that encodes a multifunctional acetyl-CoA carboxylase or a set of heterologous genes that encode the various subunits of a multi-subunit type of acetyl-CoA carboxylase. Other heterologous genes that encode additional enzymes or components of the fatty acid biosynthesis pathway could also be introduced and expressed in acyl-ACP TE-containing host cells.

The photosynthetic microorganism may also be modified such that one or more genes that encode beta-oxidation pathway enzymes have been inactivated or downregulated, or the enzymes themselves may be inhibited to prevent the degradation of fatty acids released from acyl-ACPs, thus enhancing the yield of secreted fatty acids. In cases where the desired products are medium-chain fatty acids, the inactivation or downregulation of genes that encode acyl-CoA synthetase and/or acyl-CoA oxidase enzymes that preferentially use these chain lengths as substrates would be beneficial. Mutations in the genes encoding medium-chain-specific acyl-CoA synthetase and/or medium-chain-specific acyl-CoA oxidase enzymes such that the activity of the enzymes is diminished would also be effective in increasing the yield of secreted fatty acids. An additional modification inactivates or downregulates the acyl-ACP synthetase gene or inactivates the gene or protein.

Photosynthetic microorganisms may also be modified such that one or more genes that encode storage carbohydrate or polyhydroxyalkanoate (PHA) biosynthesis pathway enzymes have been inactivated or down-regulated, or the enzymes themselves may be inhibited. Examples include enzymes involved in glycogen, starch, or chrysolaminarin synthesis, including glucan synthases and branching enzymes. Other examples include enzymes involved in PHA biosynthesis such as acetoacetyl-CoA synthase and PHA synthase.

The disclosed methods are also useful for production of industrial enzymes and industrial organisms. The disclosed methods can be used to generate new organisms with chimeric genomes, e.g., a genome that is a chimera of *Clostridium acetobutylicum* and *Clostridium cellulolyticum* that has the genes from the former species that encode the enzymes needed to synthesize ethanol from glucose and genes from the latter species that encode cellulases that can efficiently degrade cellulose. Thus, the provided methods and compositions can be used to produce cells and organisms that efficiently degrade cellulose to produce the ethanol.

Other uses are described below and are contemplated herein. The methods are also useful generally in cloning of whole and partial genomes, which facilitates the study of genomes from organisms that are difficult to culture and aids in the construction and propagation of synthetic genomes. Although certain preferred industrial applications have been described herein, the methods and processes of the present invention are broadly applicable tools for the production of any phenotype or product of interest from an engineered genome.

I. Examples

The following examples are offered to illustrate provided embodiments and are not intended to limit the scope of the application.

Example 1

Transfer of Bacterial Donor Genomes into Yeast Host Cells

This example describes the successful cloning of bacterial genomes in yeast host cells, using three different cloning approaches provided herein (FIG. 2). As described below, each approach yielded a host cell having a nucleic acid containing the donor bacterial genome joined to a yeast host vector. Transfer of donor genomes to host cells by these approaches can be used with the provided methods for propagation and modification of donor genomes in host cells, and transplantation of donor genomes from host cells into recipient cells (FIG. 1).

The first cloning approach, shown in FIG. 2A, was carried out by inserting the yeast host vector into the donor bacterial genome prior to transformation of yeast, thereby producing the joined molecule that then was transformed into yeast. The second and third approaches, shown in FIGS. 2B and 2C, respectively, were carried out by joining the donor bacterial genome and yeast vector using homologous recombination, within the host cell. With the second approach, the bacterial genome and yeast (host) vector were co-transformed into the yeast host cell (FIG. 2B). The host vector was a linear yeast vector containing terminal regions of homology to a site in the bacterial donor genome and was thereby inserted by homologous recombination. With the third approach (FIG. 2C), multiple overlapping fragments of the bacterial genome were transformed into the yeast host cell along with the yeast vector. Homologous recombination within the yeast cell effected recombination, joining the fragments and yeast vector to produce a molecule containing the donor bacterial genome joined to the yeast vector (FIG. 2C). A study employing each approach is described in detail below.

With each approach, the *M. genitalium* genome was cloned into yeast host cells. Additionally, the *Mycoplasma mycoides* LC and *Mycoplasma pneumoniae* genomes were transferred into yeast using the first approach, as shown in FIG. 2A. The *M. genitalium* and *M. mycoides* LC genomes further were transferred as separate molecules (each joined with a yeast host vector) into a single yeast cell, using the first approach (FIG. 2A).

Example 1A

Transfer of Whole *Mycoplasma* Donor Genomes into Yeast Host Cells Using Integrated Yeast Vectors This example describes successful cloning (transfer and propagation) of three different *Mycoplasma* donor genomes (*M. genitalium* strain MS5; *M. mycoides* subspecies *mycoides*, Large Colony strain GM12; and *M. pneumoniae* strain M129-B170 (ATCC 29343)) in host yeast cells, using the first approach for introduction of a donor genome into a host cell. The *M. genitalium* strain MS5 was a derivative of *M. genitalium* G37 (GenBank No. L43967). It was created by interruption of a gene in the G37 strain, as described in Dhandayuthapani et al., *J Bacteriol* 183, 5645 (2001). The *M. mycoides* subspecies *mycoides*, Large Colony strain GM12 (genome sequence having Genbank Accession no. NZ_AAZK01000004.1 (GI: 149364882)) is described in DaMassa et al., Am J Vet Res 44, 322 (1983) and Lartigue et al., *Science* 317, 632 (2007). The *M. pneumoniae* strain M129-B170 (ATCC 29343) was a derivative of *M. pneumoniae* M129, GenBank Accession Number U00089.2 (GI: 26117688).

Transfer of each *Mycoplasma* donor genome was carried out by inserting a yeast vector into the donor genome to generate a nucleic acid molecule containing the genome and the host vector, and then introducing that molecule into the host cell via transformation.

i. Construction of Tri-Shuttle Host Vectors for Cloning of *Mycoplasma* Genomes in Yeast Two tri-shuttle yeast host vectors were designed for cloning of *Mycoplasma* genomes into yeast host cells using the method shown in FIG. 2A. These vectors, pmycYACTn and miniTn-Puro-JCVI-1.7, are illustrated schematically in FIG. 3.

a. Construction of pmycYACTn Vector

The vector pmycYACTn (FIG. 3A) was 10 kb in length and contained: (i) a high copy origin (ori) from pUC19 and an ampicillin resistance marker for propagation in *E. coli*; (ii) the IS256 transposase gene and inverted repeats for transposition into a *Mycoplasma* genome; (iii) tetM and lacZ markers, both expressed from spiralin promoters, as described in Lartigue et al., *J. Bacteriol* 164, 1094 (1985), for selection and screening in *E. coli* and *Mycoplasmas*; and (iv) an autonomously replicated sequence (ARS) and a centromere sequence (CEN), for replication and segregation in yeast; and (v) HIS3, a selectable yeast marker.

Figure 3A:
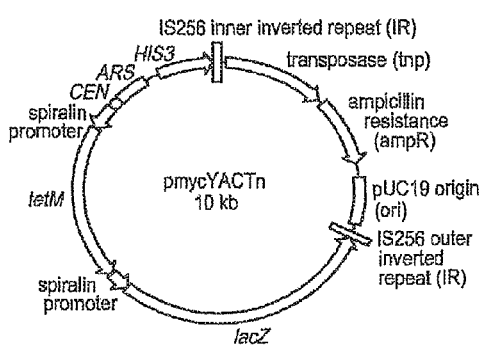
FIGS. 3A-3F illustrate yeast vector insertions in each of the *M. genitalium*, *M. mycoides* LC, and *M. pneumoniae* genomes, using the approach of FIG. 2A. FIGS PCR, using diagnostic primers Seq-F and Seq-R (shown as small, single-head arrows flanking the insertion site. A fusion product was generated that contained the URA3 marker and a 358 bp fragment ("repeat" fragment) homologous to a portion just upstream of the target locus (large arrow labeled as "repeat". To generate the final mutagenesis cassette (FIG. 10B), the fusion product was PCR-reamplified: the resulting cassette contained, in the following order, 50 bp of homology to a 5' portion of the target region (upstream of the single-base deletion), the URA3 marker, the repeat cassette, and 50 bp of homology to a 3' portion of the target region. The cassette was designed in this orientation so that upon transformation into the yeast host cells, replacement of a 450 base pair target region within the CDS139 locus of the M. genitalium genome with this cassette (by HR) would result in a region in the genome containing two tandem repeat sequences (large arrows in labeled as "repeat") flanking the URA3 selection marker.
Figure 3B:
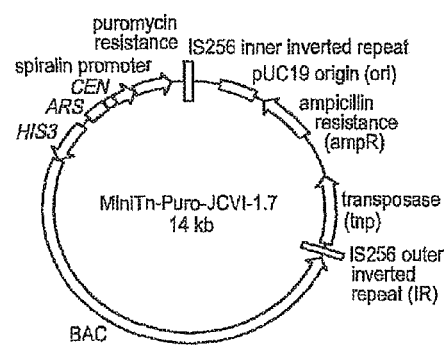
Figure 3C:
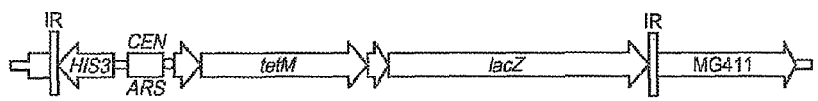
Figure 3D:
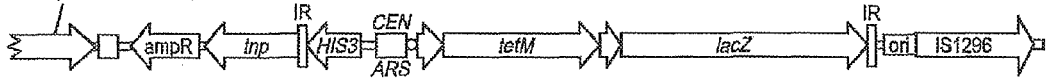
Figure 3E:
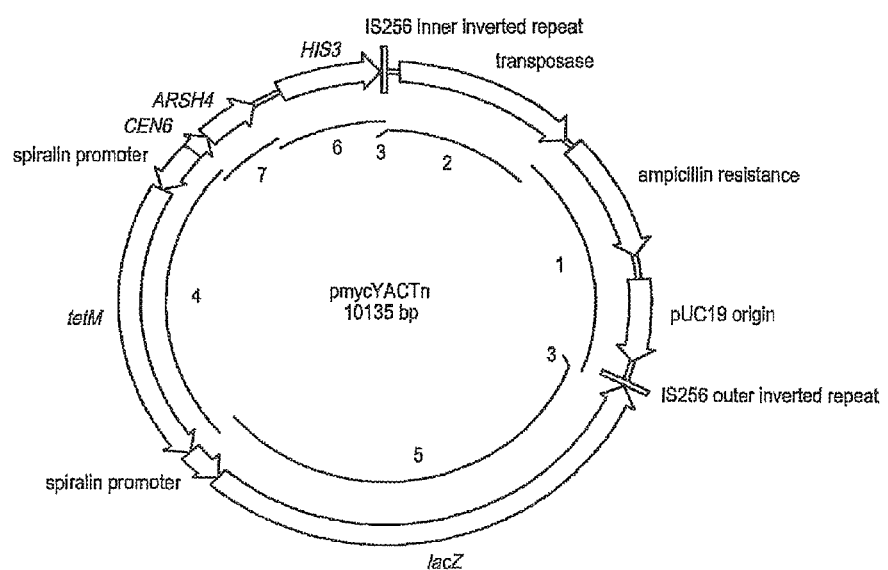
Figure 3F:
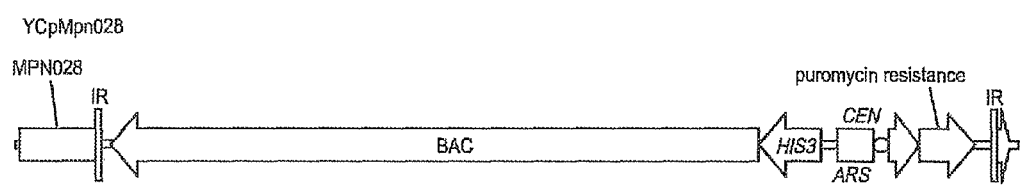

The vector was constructed from overlapping fragments, illustrated in FIG. 3E (labeled as fragments 1, 2, and 4-7), using a published in vitro assembly method (Gibson et al., *Science* 319, 1215 (2008), U.S. patent application Ser. No. 12/247,126, and WO09/048,885, all herein incorporated by reference). Fragment 1 (1846 base pairs (bp)) contained the *E. coli* Ampicillin resistance (bla), pUC19 origin, which was included to facilitate high yield plasmid isolation. Fragment 2 (1256 bp) contained the *Mycoplasma* IS256 transposase and promoter and an IS256 inverted repeat (labeled as "3" in FIG. 3E), which was included to facilitate vector insertion by transposition. Fragments 4 (2294 bp) and 5 (3335 bp) each contained the *Mycoplasma* Spirulin promoter, and contained *Mycoplasma* tetracycline resistance (tetM) and LacZ genes, respectively, which were included to facilitate selection for vector insertion into the donor genome. Fragment 5 additionally contained an IS256 inverted repeat, to facilitate insertion by transposition. Fragment 6 (847 bp) contained the *S. cerevisiae* HIS3 gene and promoter, which was included to facilitate selection of transformation into host cells. Fragment 7 (505 bp) contained the *S. cerevisiae* ARSH4 and CEN6 genes, which was included to facilitate replication and segregation. See FIG. 3E.

These overlapping fragments were constructed by PCR, using the primers listed in Table 1 (Integrated DNA Technologies, Coralville, Iowa). In Table 1, regions of overlap with other fragments are underlined; IS256 inverted repeats (labeled as "3" in FIG. 3E) are in bold type. The following plasmids were used as templates in the PCRs of individual fragments. For fragments 1, 4, and 5, the template was the pBS+ (Stratagene, San Diego, Calif.) portion of the pMYCO1PSlacZ plasmid, which was modified from the pMYCO1 plasmid, described in Lartigue and Blanchard, et al. (2003), *Nucleic Acids Res* 31 (22): 6610-8. For fragment 2, the template was a 3.7 kb PciI-SalI fragment of the pISM31.1 vector, described in Pour-El et al., *Plasmid* 47(2): 129-37 (2002). For fragments 6 and 7, the template was the pARS-VN plasmid, described in Noskov et al., *BMC Genomics* 4(1): 16 (2003).

TABLE 1

Primers for PCR of fragments used in construction of *E. coli-Mycoplasma*-Yeast shuttle vector pmycYACTn.

| Fragment | Forward Primer | Reverse Primer |
|---|---|---|
| 1 | GATTTATTCTTCAAGAAAAAT ACATCAATTTTGATAAGTAGT TCAAATATGTATCCGCTC (SEQ ID NO: 1) | GCTGCGCTCGGTCGTT CGGC (SEQ ID NO: 2) |
| 2 | TACCAACGATGTTCCCTCCAC CAAAGGTGTTCTTATGTAGTT TTACACAGGAGTCTGGACTTG ACTGTGTAAAAGTAAAAGGC CA (SEQ ID NO: 3) | CTACTTATCAAAATTG ATGT (SEQ ID NO: 4) |
| 4 | TTCTTAAAAAAACAAAAAAAG ATTTTCCAAATAAATTGCGTC AGATCTTTATATAACAAC (SEQ ID NO: 5) | AATTAAAAGTTAGTGA ACAA (SEQ ID NO: 6) |
| 5 | AGCTGATACCGCTCGCCGCAG CCGAACGACCGAGCGCAGCGA TAAAGTCCGTATAATTGTGTA AAATTATTATTATTTTTGACA CC (SEQ ID NO: 7) | CGCAATTTATTTGGAA AATC (SEQ ID NO: 8) |
| 6 | GATACGAGGCGCGTGTAAGTT ACAGGCAAGCGATCCTAGTAC ACTCTATATTTTTTATG (SEQ ID NO: 9) | CTACATAAGAACACCT TTGG (SEQ ID NO: 10) |
| 7 | ACTGGTGCTTCACTGTTTTCT TGTTCACTAACTTTTAATTAT CACGTGCTATAAAAATAA (SEQ ID NO: 11) | GGATCGCTTGCCTGTA ACTT (SEQ ID NO: 12) |

To produce each fragment (amplicon), PCR was carried out in a 100 μL reaction volume, using 10 ng of the plasmid template. Primers indicated in Table 1, Phusion DNA polymerase, HF buffer (New England Biolabs, Ipswich, Mass.) were included in amounts according to the manufacturer's protocol, with extra $MgCl_2$ added for a final concentration of 2.0 or 3.0 mM. Cycling conditions were as follows: 98° C. for 30 seconds, followed by 30 cycles of incubation at 98° C. for 10 sec, annealing for 30 seconds, and incubation at 72° C. for 90 seconds, followed by 72° C. for 5 minutes. Annealing temperatures varied among the cycles and among PCRs for different fragments, as follows. Annealing temperature was between 46° C. and 59° C. for cycles 1-5, and increased by 5° C. (to between 51° C. and 64° C.) for cycles 6-30. Specifically, cycle 1-5 annealing temperatures were 56° C. and 59° C. for fragment 1; 46° C. and 48° C. for fragment 5; 46° C. and 50° C. for fragment 4; 46° C. for fragment 2; and 48° C. and 52° C. for fragments 6 and 7. For cycles 6-30, each temperatures was 5° C. higher than the temperature for cycles 1-5. For each fragment, PCR products were pooled and amplicons gel-purified using β-agarase (New England Biolabs, Ipswich, Mass.).

For fragment, 2, which contained the transposase gene, amplified from the template pISM31.1, one of the PCR primers contained the standard 20 base pairs of homology to the template at the desired location, but further contained 26 base pairs of homology to 2 additional copies of the IS256 inverted repeat, which were also present in other parts of the plasmid. In order to facilitate specific amplification of the correct fragment, these IS256 copies were separated from the desired template portion of pISM31.1 with a double restriction enzyme digest with PciI and SalI, followed by agarose gel-purification of the correct resulting 3.7 kb fragment, which then was used as the template in the PCR amplification of fragment 2.

The purified fragments were assembled to generate the pmycYACTn vector, using the published in vitro assembly method, described in D. G. Gibson et al., *Science* 319, 1215-1220 (2008), U.S. patent application Ser. No. 12/247,126 and WO 09/048,885, all incorporated by reference herein. The entire "chew back assembly" (CBA) reaction was repaired as described (Gibson et al., *Science* 319, 1215-1220 (2008); U.S. patent application Ser. No. 12/247,126; and WO 09/048, 885) by incubating the assembly with Taq DNA ligase and Taq DNA polymerase at 45° C. for 15 min in the presence of 5% PEG-8000, 50 mM Tris-Cl, pH 7.5, 10 mM $MgCl_2$, 10 mM DTT, 25 ug/ml BSA, 200 uM each dNTP, and 1 mM NAD. The reaction was then was phenol extracted, isopropanol precipitated, resuspended, and electroporated into EPI300 cells (Epicentre Biotechnologies, Madison, Wis.). Transformants were selected with carbenicillin. DNA from selected clones was screened for the correct sized plasmid using three separate restriction digests. The presence of the various elements of the plasmid was tested phenotypically, as follows. Propagation in *E. coli* ensured functionality of the pUC19 origin; selection in *E. coli* with carbenicillin and tetracycline and screening with X-gal verified that intact copies of the bla, tetM, and lacZ markers were present; and successful transformation of yeast with the isolated vector demonstrated that the HIS3, ARSH4, and CEN6 markers were viable. Presence of a functional transposon was confirmed by transformation into *Mycoplasma*, as described below.

b. Construction of miniTn-Puro-JCVI-1.7 Vector

The miniTn-Puro-JCVI-1.7 vector (FIG. 3B) was 14 kb in length, and was identical to the pmycYACTn, with the following exceptions: (i) it did not contain lacZ; (ii) instead of a tetM marker, it contained a puromycin resistance marker; and (iii) it contained a bacterial artificial chromosome (BAC) vector.

ii. Insertion of Host Vectors into Donor Genomes a. *M. genitalium* MS5

In preparation for transfer of the *M. genitalium* strain MS5 donor genome into yeast host cells, the vector pmycYACTn vector was inserted into the donor genome by electroporation into the *M. genitalium* donor cells, as described in J. I. Glass et al., *PNAS USA* 103, 425 (2006). Transformants were selected by growth in the presence of tetracycline and a single clone chosen for further analysis. Direct genomic sequencing (as described in J. I. Glass et al., *PNAS USA* 103, 425 (2006)), using primers internal to the vector, was performed to determine the site of vector insertion. The chosen clone contained the sequence between and including the two IS256 inverted repeats of pmycYACTn, indicating that transposition had occurred, as designed (FIG. 3C). The transposase, pUC19 origin, and ampicillin resistance gene were lost during transposition. The host vector inserted into the donor genome within the nonessential MG411 gene (J. I. Glass et al., *PNAS USA* 103, 425 (2006); C. A. Hutchison et al., *Science* 286, 2165 (1999)).

b. *M. mycoides* Subspecies *mycoides*, Large Colony Strain GM12

Figure 4A:
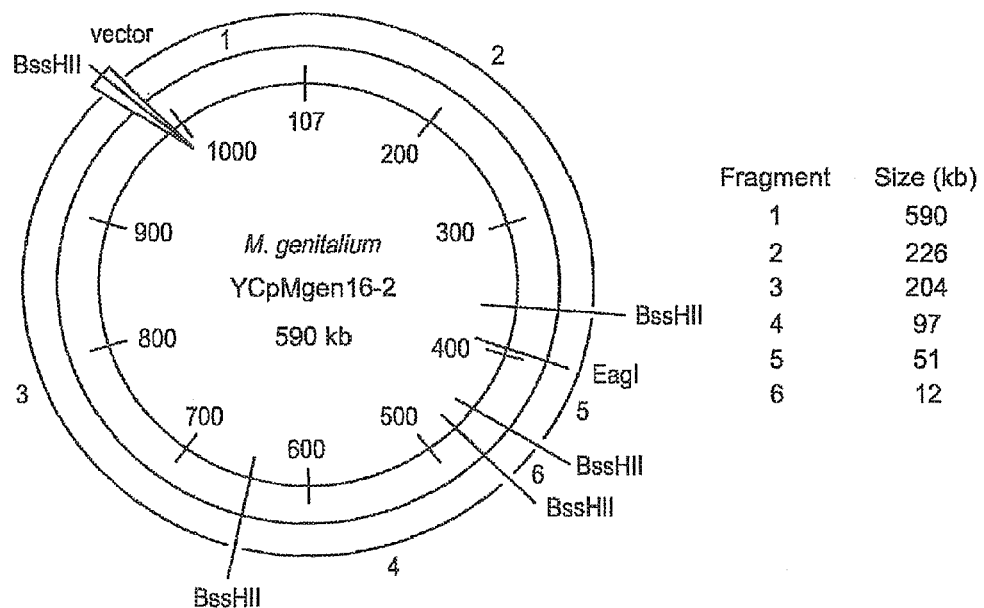

In preparation for transfer of the *M. mycoides* subspecies *mycoides*, Large Colony strain GM12 genome into yeast hosts, the *Mycoplasma* donor cells were transformed with pmycYACTn using PEG, as described in K. W. King and K. Dybvig, *Plasmid* 26, 108 (1991). Transformants were selected by growth on plates supplemented with tetracycline.

Four selected clones were analyzed by direct genomic sequencing to locate the site of insertion of the host vector into the donor genome. The results revealed that in each of the four clones, instead of integration of a portion of the pmycYACTn construct by transposition, the entire host plasmid had integrated into the donor genome. In three of the four clones, the vector (pmycYACTn) had been inserted by a crossover event within or very close to the pUC origin. In the fourth clone, the crossover had occurred within the yeast HIS3 gene, and thus was not used for subsequent transformation of the genome into yeast. In all cases, insertion of the host vector had occurred at a location adjacent to an IS1296 element.

Clone 1.1, which is illustrated schematically in FIG. 3D, grew robustly. To confirm that the genome of this clone could be efficiently transplanted, the calcium chloride transformation procedure described in C. Lartigue et al., *Science* 317, 632 (2007) was carried out to transplant it from the *M. genitalium* donor cells into *M. capricolum* recipient cells. The genome of clone 1.1 was efficiently transplanted into *M. capricolum* host cells. Thus, this clone was chosen for genome transfer from donor *Mycoplasma* into yeast host cells.

c. *M. pneumoniae* Strain M129-B170 (ATCC 29343)

In preparation for transfer of the *M. pneumoniae* strain M129-B170 donor genome into yeast host cells, the *Mycoplasma* were transformed with MiniTn-Puro-JCVI-1.7 by electroporation as described in J. I. Glass et al., *PNAS USA* 103, 425 (2006). A pool of puromycin resistant transformants was selected in liquid culture.

iii. Isolation of Donor Genomes Containing Inserted Yeast Vectors

In order to minimize breakage, the donor genomes containing yeast vector insertions were isolated in agarose plugs using low melting point agarose and the Bio-Rad CHEF Mammalian Genomic DNA Plug Kit (Bio-Rad Laboratories, Hercules, Calif.), following the protocol suggested by the manufacturer. Agarose plugs containing the *Mycoplasma* genomes with insertions were dialyzed against 10 mM Tris pH 8.0 (in some cases with 1 mM EDTA) for 1 hour. Plugs were then dialyzed against 10 mM (6%) PEG 6000 (United States Biochemical), 0.6 M NaCl for several hours, as described in S. Katsura et al., *Electrophoresis* 21, 171 (2000). This PEG/NaCl treatment was not carried out for isolation of *M. mycoides* LC genomes containing vector for transfer into W303a cells (see below), or for isolation of *M. pneumoniae* genomes containing vector for transfer into VL6-48N cells (see below).

Plugs then were melted at 65° C. for 5 min, after which 2 volumes of 65° C. TE was added and the mixture was stirred gently and incubated at 65° C. a further 5 min. Twenty microliters were used for transformation.

iv. Transfer of Donor Genome with Yeast Vector into Yeast Host Cells

For introduction of the donor genomes into host cells, yeast spheroplasts were transformed with DNA from the plugs, using the published method described by N. Kouprina and V. Larionov, *Nat Protoc* 3, 371 (2008), except that cultures were sometimes grown to less than the recommended OD.

Using this method, all three genomes containing yeast vector inserts were transformed into the yeast strain VL6-48N, developed for high transformation efficiency (V. Larionov et al., *PNAS USA* 94, 7384 (1997)). The *M. genitalium* cl16-2 and *M. mycoides* LC cl1.1 genomes with inserts also were transformed into the commonly used W303a strain (MATa his3 leu2 ura3 trp1 ade2). The *M. mycoides* LC cl1.1 genome with insert also was transferred into a recombination-deficient yeast strain, VL6-48-Δ54G, which is defective in the RAD54 gene (MATα his3-Δ200 trp1-Δ1 ura3-52 lys2 ade2-101 met14 rad54-Δ1::kanMX). Transformation into the VL6-48-Δ54G strain was done to address the possibility that the genome would be unstable in other yeast, due to recombination among the multiple nearly-identical 1.5 kb IS1296 copies. Yeast strains defective in the RAD54 gene can decrease the occurrence of a variety of recombination events in yeast artificial chromosomes (YACs) (Y. Le and M. J. Dobson, *Nucleic Acids Res* 25, 1248 (1997)). The rad54 mutant strain, which was nearly isogenic with VL6-48N, was a gift from Vladimir Larionov (Laboratory of Molecular Pharmacology, National Cancer Institute, National Institutes of Health).

v. Analysis and Confirmation of Whole Genome Transfer

DNA from each of the transformed yeast host cells was analyzed to confirm transfer of complete host vector-containing donor genomes into the host cells. *Mycoplasma* genomes cloned in yeast were screened by multiplex PCR (MPCR) to confirm completeness. MPCRs were carried out using 1 or 2 sets of 10 amplicons each, using primers from IDT with the Multiplex PCR Kit from Qiagen (Valencia, Calif.). Individual reactions are described in more detail below.

To confirm the size of genomes containing inserts, total DNA from individual yeast clones containing *Mycoplasma* genomes was isolated and analyzed by gel electrophoresis as described below. In general, DNA was isolated in agarose plugs using the protocol "Preparation of Agarose Embedded Yeast DNA" from the Bio-Rad CHEF-DR III manual. Where indicated, plugs were pre-electrophoresed at constant voltage for several hours to remove yeast chromosomal DNA. Where indicated, to increase the efficiency of this step, plugs were first digested with AsiSI, FseI, and RsrII, which cleave yeast chromosomes but do not have recognition sites in *M. genitalium* or *M. mycoides* LC. Isolated DNA was subject to restriction digestion (with indicated enzyme(s)), followed by field-inversion (Bio-Rad FIGE Mapper) or pulsed-field (Bio-Rad CHEF-DR II or III system) electrophoresis, as indicated, or linearization by heating at 55° C. for 1 hr. Where indicated, Southern blots were performed on the gels. Southern blotting was carried out as described in D. G. Gibson et al., *Science* 319, 1215 (2008), except in some cases where probe labeling and detection used the Amersham AlkPhos Direct Labeling and Detection System with CDP-Star (GE Healthcare, Piscataway, N.J.).

a. Isolation and Analysis of *M. genitalium* Genomes from Yeast Host PCR

Genomic DNA from 24 individual clones recovered after transfer of *M. genitalium* cl16-2 genomes containing yeast vectors to strain VL6-48N and 8 individual clones recovered after transfer of *M. genitalium* into the W303a strain was isolated in agarose plugs and analyzed by PCR to confirm completeness. An *M. genitalium* synthetic genome (sMgTARBAC37, generated as described in (D. G. Gibson et al., *Science* 319, 1215 (2008)) and a native *M. genitalium* genome were used as positive controls.

The PCR primers listed in Table 2, below, were used in MPCR reactions to generate amplicons evenly spaced around the *M. genitalium* genome containing the yeast vector insert. The locations of the amplicons along the length of the genome are shown in FIG. 4A, in which amplicons are indicated with black bars and numbers representing sizes of the amplicons. The results of the PCR for DNA recovered from clones in VL6-48N and W303a (data not shown) are summarized in Table 5. Twenty-two (22) of the 24 clones isolated from the 24 VL6-48N strain and 5 of the 8 clones isolated from the W303a strain appeared complete (correctly sized product for each amplicon) by PCR analysis (data now shown).

TABLE 2

*M. genitalium* Multiplex PCR Primer Sequences (Set 1)

| Amplicon size (bp) | Forward Primer | Reverse Primer |
|---|---|---|
| 107 | CGATCTTATTAATGGCATAAAAG (SEQ ID NO: 13) | CATTAATTGTGTTTA AATTAATACTTG (SEQ ID NO: 14) |
| 200 | ATCGTGCGCATAACGATG (SEQ ID NO: 15) | GCTTGATCTAAGAAT TGC (SEQ ID NO: 16) |
| 300 | ATATTAAAGCTACCTTAT TTGATG (SEQ ID NO: 17) | AAGAGCGTAAATCAG TGGC (SEQ ID NO: 18) |
| 400 | TTTTTGTTTGGTGCTAAT (SEQ ID NO: 19) | CAATTTTCTATAAGC GTTGC (SEQ ID NO: 20) |
| 500 | TGGGGATACTGAAAATATTAC (SEQ ID NO: 21) | CTGAAATGATCCCTT TAA (SEQ ID NO: 22) |
| 600 | AAAAACAAGCTTTACAAGAG (SEQ ID NO: 23) | CATCTTGATCCAACT TATTTA (SEQ ID NO: 24) |
| 700 | AGCTATTGGTCCTGAAACAC (SEQ ID NO: 25) | ACCCCTTTTTTTGCT AAAAGG (SEQ ID NO: 26) |
| 800 | TTAACTTCGTTAAAAGTGAAT (SEQ ID NO: 27) | AATGGATTACTAATG AGCTTG (SEQ ID NO: 28) |
| 900 | ATCCAGTAAAAACCTTGA (SEQ ID NO: 29) | AAATGATTTTATTGC TGTTAC (SEQ ID NO: 30) |
| 1000 | TTTGCGTTCCTTAGCACG (SEQ ID NO: 31) | TATAAAACAACAATT ACTGAAG (SEQ ID NO: 32) |

Size Analysis

To confirm that the *M. genitalium* cl16-2 genomes containing yeast vectors in the complete clones from the VL6-48N strain were the correct size, CHEF gel analysis was performed on 3 clones (11, 16, and 24) that were deemed complete by the MPCR. For this process, DNA was isolated from the clones in agarose plugs, using the protocol "Preparation of Agarose Embedded Yeast DNA" from the Bio-Rad CHEF-DR III manual. To remove chromosomal DNA, plugs were pre-electrophoresed at constant voltage for several hours to remove yeast chromosomal DNA. To increase the efficiency of this step, the plugs were first digested with AsiSI, FseI, and RsrII, which cleave yeast chromosomes but do not have recognition sites in *M. genitalium*.

After pre-electrophoresis, DNA was digested with either EagI or BssHII. The fragments of the *M. genitalium* genome with vector insert that are produced by these enzymes and their sizes are indicated on the map in FIG. 4A and in columns next to the map. The digested DNA was separated by field-inversion (Bio-Rad FIGE Mapper) gel electrophoresis. The results are summarized in Table 5 (gel not shown). Two of these three clones (11 and 16) were the expected size.

To confirm that the *M. genitalium* cl16-2 genomes containing yeast vectors in the complete clones from the W303a strain were the correct size, CHEF gel analysis was performed for 5 complete clones. For this process, DNA from these clones was isolated in agarose plugs as described for the VL6-48N strain above, with pre-electrophoresis for several hours at constant voltage to remove yeast genomes, as described above. Isolated DNA then was linearized with EagI.

Samples were separated by pulsed-field electrophoresis. The synthetic sMgTARBAC37 genome (see above) was cut with NotI and used as a positive control. The results are summarized in Table 5 (gel not shown). Four of the five clones were of the expected size; clone 4 contained a faint extra band of about 300 kb.

b. Isolation and Analysis of *M. mycoides* cl1.1 from Yeast Hosts by PCR

Genomes isolated from 48 individual clones recovered after transfer of *M. mycoides* LC cl1.1 genome containing yeast vector insert to strain VL6-48N were analyzed by multiplex PCR, as described above, to confirm completeness. DNA was isolated from the clones in agarose plugs, using the protocol "Preparation of Agarose Embedded Yeast DNA" from the Bio-Rad CHEF-DR III manual.

The PCR primers listed in Table 3 were designed and used to generate amplicons to assess completeness of the transferred *M. mycoides* genomes. As shown in FIG. 5, an amplicon was located between most pairs of IS1296 elements, indicated by arrowheads on the map of the genome with insert illustrated in FIG. 5. An additional 230 bp amplicon was a region of the HIS3 marker of the yeast vector. Another primer set (NSF1179/18 and NSR1642/16; see Table 3) produced a 464 bp amplicon (region of *S. cerevisiae* rDNA), and was used as a positive control for the assay. The sets of primers and sizes of amplicons produced thereby are listed in Table 3.

A similar result was obtained with multiplex PCR analysis of *M. mycoides* LC cl1.1 genome containing yeast vector insert transformed into the Δ54 recombination-deficient strain (gel not shown).

Multiplex PCR analysis of DNA from W303a cells transformed with *M. mycoides* LC cl1.1 genome containing yeast vector insert revealed that eight of 15 clones were complete (gel not shown).

TABLE 3

*M. mycoides* LC Multiplex PCR Primer Sequences

| Amplicon size (bp) | Forward Primer | Reverse Primer |
|---|---|---|
| 89 | CAACTGATACACCA ACCATC (SEQ ID NO: 33) | TTATGGTAGTGGTTT TCACAT (SEQ ID NO: 34) |
| 159 | GCTTTGGTTATCATA TGTGAAC (SEQ ID NO: 35) | CAAATCCTTGATCTT TAATTACTTG (SEQ ID NO: 36) |
| 309 | TATTGGTGAACCAGT GGG (SEQ ID NO: 37) | CCTTGTTCAACACGT AATACTG (SEQ ID NO: 38) |

TABLE 3-continued

| *M. mycoides* LC Multiplex PCR Primer Sequences | | |
|---|---|---|
| Amplicon size (bp) | Forward Primer | Reverse Primer |
| 392 | GTGAGCAACAATGTT TTGAG (SEQ ID NO: 39) | CAACTCCACCAAGTA CTCC (SEQ ID NO: 40) |
| 608 | CTAAACCATCAGAAT TAGGTTC (SEQ ID NO: 41) | GCAAAGTCACAGATCA ACAA (SEQ ID NO: 42) |
| 708 | CAACTCCAGAAGGTG CTC (SEQ ID NO: 43) | CTAAACTAATTCTAAT AGCACCC (SEQ ID NO: 44) |
| 777 | TCGATCATTATTTTA TATGTTGTG (SEQ ID NO: 45) | TATAATTCTTACTCCA GCATTTC (SEQ ID NO: 46) |
| 884 | GCTCATCAGCTTGAC TAATTTG (SEQ ID NO: 47) | CTAATCTCAGATATTC AAGCAG (SEQ ID NO: 48) |
| 1020 | TTAATTTTGGCATCA AGTGCTG (SEQ ID NO: 49) | AGAACAATAACTAGTC TATACAC (SEQ ID NO: 50) |
| 203 (HIS3) | TGAAACCAAGATTCA GATTGC (SEQ ID NO: 51) | GGTCGTCTATGTGTAA GTCACC (SEQ ID NO: 52) |
| 464 ("Y") | AATTTGACTCAACACGGG (primer NSF1179/18) (SEQ ID NO: 53) | GACGGGCGGTGTGTAC (primer NSR1642/16) (SEQ ID NO: 54) |

Size Analysis

To confirm that the *M. mycoides* cl1.1 genomes containing yeast vectors in the complete clones from the VL6-48N strain were the correct size, Southern blot analysis of a CHEF gel analysis was performed for 6 of the complete clones, revealing that five of the six were the correct size.

A CHEF gel analysis of three of these five clones recovered after transformation of the VL6-48N strain with *M. mycoides* cl1.1 genomes containing yeast vectors was performed as follows: DNA from clones (07, 14, and 38) was isolated in agarose plugs as described above, without pre-electrophoresis. The isolated DNA was digested with BssHII and then separated by pulse-field gel electrophoresis (CHEF). For each clone, the parent clone and 3-4 subclones were analyzed (gel results not shown). Markers and controls used in the analysis were: (1) Low Range PFG Marker (New England Biolabs, Ipswich, Mass.); (2) *S. cerevisiae* marker (Bio-Rad); VL6-48N (undigested (3) and BssHII-digested (4)); and *M. mycoides* LC cl1.1 (undigested (5) and BssHII-digested (6)). Results indicated that all three clones were the correct size and were stable.

A CHEF gel analysis was performed on eight complete clones recovered after transformation of the W303a cells with *M. mycoides* LC cl1.1 genome containing yeast vector insert to confirm size. For this process, DNA from the clones was isolated in agarose plugs as described above, with pre-electrophoresis as described above to remove yeast genome. DNA was either left untreated (−) or digested (+) with BssHII. DNA then was separated by pulsed-field gel electrophoresis. *M. mycoides* LC cl1.1 DNA was run as a positive control. Results are summarized in Table 5 (gel results not shown). The results indicated that each of the eight clones contained the correct size genome.

c. Isolation and Analysis of *M. pneumoniae* from Yeast Hosts by PCR

Genomes isolated from 20 individual clones recovered after transfer of *M. pneumoniae* genomes containing yeast vectors to strain VL6-48N were analyzed by multiplex PCR as described above to confirm completeness. Two different multiplex PCRs were performed. Primers for set 1 and set 2 and the size of amplicons produced thereby are listed in Table 4 (gel results not shown). As shown in FIG. 4A, amplicons (indicated with black bars and numbers; inside: set 1, outside: set 2) were evenly spaced around the *M. pneumoniae* genome containing the vector insert. The results indicated that thirteen of the twenty transformants were complete.

TABLE 4

| *M. pneumoniae* Multiplex PCR Primer Sequences | | | |
|---|---|---|---|
| SET | Amplicon size (bp) | Forward Primer | Reverse Primer |
| 1 | 100 | TATTTACCGACGAAATTAATACC (SEQ ID NO: 55) | ATTTTCCTATATACCACTTTCTTTT TC (SEQ ID NO: 56) |
| 1 | 200 | CTTAGAACTTTACAGCTCCAAAC (SEQ ID NO: 57) | CTGGTTATTGGCCACCAAC (SEQ ID NO: 58) |
| 1 | 300 | ATGGTGGGATTGCCC (SEQ ID NO: 59) | ATATTTGGACAGTTTTTCGCC (SEQ ID NO: 60) |
| 1 | 400 | CCGAAAGTTGAGAAGTTAAAGG (SEQ ID NO: 61) | AGAAATATTTGAAATTTTTATCTAA AAAGC (SEQ ID NO: 62) |
| 1 | 500 | AATCTCCTCTTGTTTTAATGGAG (SEQ ID NO: 63) | TTGCAAGCGATTTTGTG (SEQ ID NO: 64) |
| 1 | 600 | AAACCTATGCAAATATTTTAACGAT (SEQ ID NO: 65) | ACTTGTAAAAGTAAAGAACCACTGC (SEQ ID NO: 66) |
| 1 | 700 | CATGGTAATGGCCAAAGC (SEQ ID NO: 67) | GTTGATCGGGTTGATGTTTTAT (SEQ ID NO: 68) |
| 1 | 800 | TAAGGCTGATAAAAGTGGTAATTC (SEQ ID NO: 69) | CTTTAGTATGTTCTAAGCGAAAGC (SEQ ID NO: 70) |

TABLE 4-continued

*M. pneumoniae* Multiplex PCR Primer Sequences

| SET | Amplicon size (bp) | Forward Primer | Reverse Primer |
|---|---|---|---|
| 1 | 900 | GGGTCAAACGTGAACTTTAAG (SEQ ID NO: 71) | AACGGAAGGTAACTATGAAGCT (SEQ ID NO: 72) |
| 1 | 1000 | AGTTTGGCTCGTGCAAAAATAG (SEQ ID NO: 73) | TTTTCGGTTTTATGAACCGTTC (SEQ ID NO: 74) |
| 2 | 100 | TATTTACCGACGAAATTAATACC (SEQ ID NO: 75) | ATTTTCCTATATACCACTTTCTTTTTC (SEQ ID NO: 76) |
| 2 | 125 | AGTAGTCTTTGATAATGGCTAAGG (SEQ ID NO: 77) | CCTGTATGAGGGCTTTCAG (SEQ ID NO: 78) |
| 2 | 225 | GTGCTTGACTGTGAGACATACA (SEQ ID NO: 79) | AATCGGCGAACAGCC (SEQ ID NO: 80) |
| 2 | 325 | TGCACCAACTCCAGCA (SEQ ID NO: 81) | ATATCCAATAGTTCATTCTTATTGG (SEQ ID NO: 82) |
| 2 | 425 | GAAGCGGAAAAACGGC (SEQ ID NO: 83) | CAATTAATGGAAGAATTTTTATTTTCATT (SEQ ID NO: 84) |
| 2 | 525 | ACAAAACAAACACCACCACG (SEQ ID NO: 85) | CGGCGTGATGATTCATC (SEQ ID NO: 86) |
| 2 | 625 | AATGCTACCCCAAACGGT (SEQ ID NO: 87) | TGAGCTTTATTGCCATCCTTT (SEQ ID NO: 88) |
| 2 | 725 | TAGATAATGAAGCGTCTTCATTACCACTTCTACTAGCGTCAATTTAACTC (SEQ ID NO: 89) | AAC (SEQ ID NO: 90) |
| 2 | 825 | AACCTCTTTCAGAAAGGAGG (SEQ ID NO: 91) | AACTTTAATTGGTTTGGAGATTATTCTTTAG (SEQ ID NO: 92) |
| 2 | 925 | ACTTTTAACACCATCACTCGCTA (SEQ ID NO: 93) | CAAACAACTAGAGGGTAAATACTTTATTGT (SEQ ID NO: 94) |
| 2 | 1025 | CAACCTTTTGTTCGATACTAAAGAGAATTTCTTTCTCATTTTTGGTTTAG (SEQ ID NO: 95) | TCC (SEQ ID NO: 96) |

Size Analysis

Figure 4B:
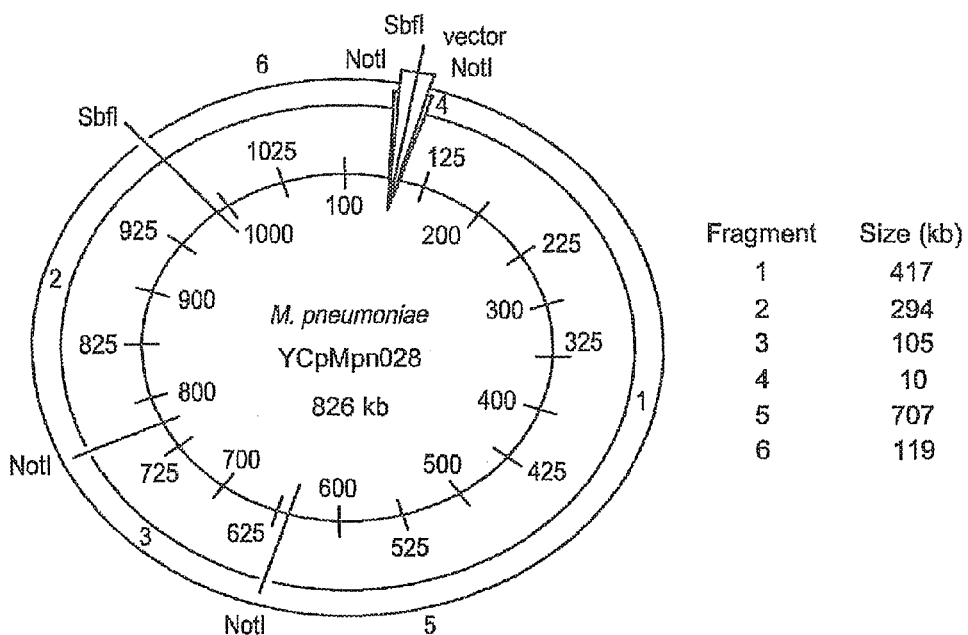

CHEF gel analysis was performed on nine of these complete transformants. For this process, DNA from these clones was isolated in agarose plugs using the protocol "Preparation of Agarose Embedded Yeast DNA" from the Bio-Rad CHEF-DR III manual. To remove chromosomal DNA, plugs were pre-electrophoresed at constant voltage for several hours to remove yeast chromosomal DNA. The DNA then was digested with NotI or SbfI. The fragments (numbered 1-6) of the *M. pneumoniae* genome with vector insert that are produced by these enzymes are indicated on the map in FIG. 4B, with the fragments and their sizes listed in columns next to the map.

The digested DNA was separated by pulsed-field electrophoresis (Bio-Rad CHEF-DR II or III system). The results are summarized in Table 5 (gel results not shown). Restriction fragments are numbered as in FIG. 4B. Yeast clone 8 was not completely digested (data not shown).

Table 5 summarizes results from Example 1(A), in which three *Mycoplasma* genomes containing integrated yeast vectors were transferred into yeast. Clones were screened for completeness by multiplex PCR with 1 or 2 sets of 10 amplicons each. Clones were tested for size by restriction digestion and gel electrophoresis, followed in some cases by southern blot.

TABLE 5

Cloning 3 *Mycoplasma* genomes containing an integrated yeast vectors in yeast

| Genome (species, strain, clone) | Size (Mb) | Percent GC | Host yeast strain (mating type) |
|---|---|---|---|
| *M. genitalium* cl16-2 | 0.6 | 32 | VL6-48N (α) W303a(a) |

TABLE 5-continued

Cloning 3 Mycoplasma genomes containing an integrated yeast vectors in yeast

| | | | |
|---|---|---|---|
| M. mycoides LC cl1.1 | 1.1 | 24 | VL6-48N (α) |
| | | | VL6-48N-Δ54G (α) |
| | | | W303a (a) |
| M. pneumonia, pool of transformants | 0.8 | 40 | VL6-48N (α) |

| Genome (species, strain, clone) | No. transformants | No. of PCR amplicons tested | Fraction of clones complete by PCR | Fraction of clones correct size by gel or blot |
|---|---|---|---|---|
| M. genitalium cl16-2 | 172 | 10 | 22/24/ | 2/3 |
| | 421 | 10 | 5/8 | 4/5 |
| M. mycoides LC cl1.1 | 174 | 10 | 20/48 | 5/6 |
| | 54 | 10 | 19/48 | Not done |
| | 57 | 10 | 8/15 | 8/8 |
| M. pneumonia, pool of transformants | 67 | 20 | 13/20 | 5/9 |

Example 1B

Transfer of the M. genitalium Genome to Yeast Host Cells by Homologous Recombination of Whole Genome and Yeast Host Vector The linearized, whole M. genitalium genome was transferred into yeast cells using the method depicted in FIG. 2B, by homologous recombination of the genome with a yeast vector within the host cells. The M. genitalium genome contains 3 single-cut restriction sites, 2 of which lie within its rRNA operon. The third lies at the 3' end of a tRNA coding sequence. Because the cloning could be designed to preserve the integrity of the tRNA, a vector was inserted by homologous recombination adjacent to this AscI site.

The yeast cloning vector pARS-VN (described in V. N. Noskov et al., BMC Genomics 4, 16 (2003)) was used as template for PCR with a pair of primers, each containing 60 bp homologous to the region flanking the insertion site in the M. genitalium genome, and 20 bp of homology to the vector. Primers were supplied by IDT PAGE-purified. Their sequences are as follows, with the vector sequence in bold and the ClaI (first primer) or XhoI (second primer) site underlined:

(SEQ ID NO: 97)
TTAATAACAAAAAAATCTCTATTAAAAAAACCAACTTTAAAGTTGGTTTG

AAATTCTAAAATCGATGTCGAAAGCTACAT
and (SEQ ID NO: 98)
GGATAGAGTGTCTGGCTTCGGACCAGAAGGTTATGGGTTCAAGTCCTATT

GGGCGCGCCACTCGAGCCACTATTTATACC.

PCR of the vector with these primers amplified the entire vector except for 9 bp between the unique ClaI and XhoI restriction sites, producing a 6.5 kb product.

A mixture of this linear vector DNA and DNA from M. genitalium strain MS5 was prepared for co-transformation into yeast strain VL6-48N spheroplasts. M. genitalium DNA was isolated in agarose plugs, as follows, to minimize breakage. M. genitalium genomic DNA was isolated in two batches in low melting point agarose plugs from strain MS5 grown in SP-4 medium. The culture for batch 2 was supplemented with gentamicin to 200 μg/ml. Adherent cells were rinsed twice with PBS and then scraped into a buffer containing 8.0 mM HEPES, pH 7.4, 272 mM sucrose, and 10% glycerol. Each plug contained DNA from about 6 (batch 1) or 10 (batch 2) cm$^2$ of confluent cells. For lysis, cells in agarose were incubated for a period between overnight to 2 days at 50° C. in 0.4 M EDTA, 0.4% N-lauroyl sarcosine, and 2 mgs/ml proteinase K, followed by a buffer change and a second treatment under the same conditions for the same time range. Plugs were dialyzed thoroughly against 10 mM Tris, 50 mM EDTA, then dialyzed 2 times for 2 hours each in 10 mM Tris, 50 mM EDTA supplemented with PMSF to 0.1 mM, and then re-dialyzed and stored in 10 mM Tris, 50 mM EDTA.

Figure 6A:
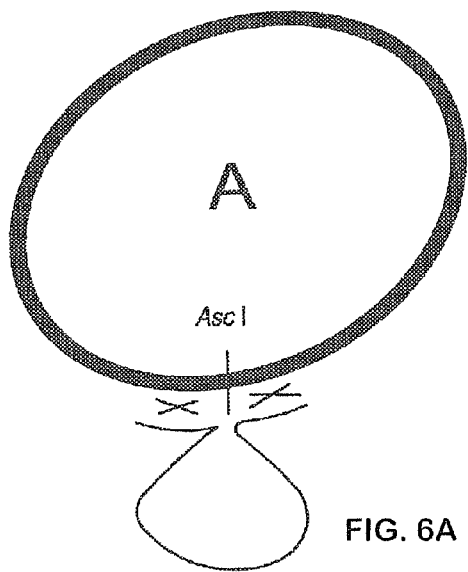
Figure 6C:
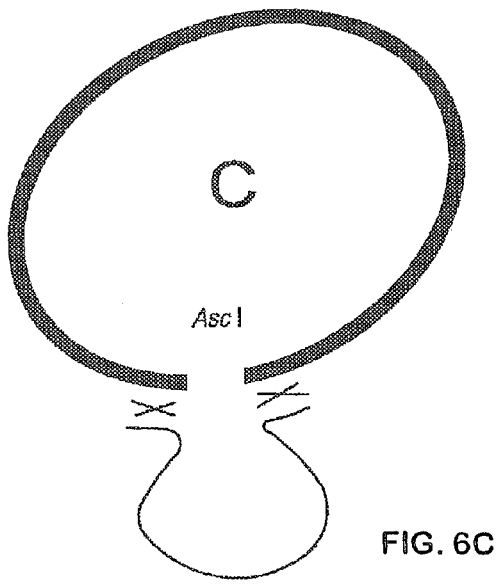

Before transformation, the plugs were melted and digested with agarase, as follows. The first batch of plugs was electrophoresed twice by CHEF (Bio-Rad), which removed broken DNA, while leaving circular genomes intact (to increase the frequency of intact circular genomes in the plugs). The first electrophoresis was carried out on a 1% pulsed-field agarose gel, with 0.5×TBE and a 50-90 second switch time, over 20 hrs. The second electrophoresis was carried out on a 1% low melting point gel, with 1×TAE and a 60-120 sec switch time, over 24 hrs. Both gels were run at 120°, 6 V/cm, at 14° C. Three plugs from each of the two batches were dialyzed thoroughly against sterile 1×TAE, melted for several minutes at 73° C., equilibrated to 42°, then digested with β-Agarase I (New England Biolabs, Ipswich, Mass.) for 1.5 hrs. One-half of each volume was moved to a fresh Eppendorf tube. Prior to transformation, the genomes were digested overnight at 37° C. with 20 U AscI (in 1×NEB buffer 4; New England Biolabs, Ipswich, Mass.), which resulted in a double-strand break near the site of intended recombination with the host vector, as illustrated in FIG. 6A.

For introduction of the donor genomes (by co-transformation with yeast vector) into host cells, yeast spheroplasts were transformed with DNA from the plugs, using the published method described by Kouprina and Larionov, Nat Protoc 3, 371 (2008), except that cultures were sometimes grown to less than the recommended OD. With this published method, as described above, yeast cells were suspended in 1M sorbitol and treated with Zymolyase™ (β-1,3-glucan laminaripentao-hydrolase) before transformation to remove cell walls. DNA recovered from agarose plugs was incubated with the spheroplasts. After recovery in growth medium, cells were plated in selective medium.

Clones were picked and evaluated by multiplex PCR and gel electrophoresis as described in Example 1A(v)(a), above, except that two sets of 10 amplicons, instead of one set, were used. The primers used to generate the first set of amplicons were those listed in Table 2, above. The primers used to generate the second set of amplicons, and the sizes of amplicons produced thereby, are listed in Table 6, below.

TABLE 6

M. genitalium Multiplex PCR Primer Sequences (Set 2)

| Amplicon size (bp) | Forward Primer | Reverse Primer |
|---|---|---|
| 146 bp: | TTTCTATGAACTACATGATCTT (SEQ ID NO: 99) | GTTGTAGAATTGCCAGGT (SEQ ID NO: 100) |
| 250 bp: | AAGGGAAGGATAGTAGTGGG (SEQ ID NO: 101) | AGGTGTTGGTGGTTTGGT (SEQ ID NO: 102) |
| 348 bp: | TAAGACTTGGCAAGGTAG (SEQ ID NO: 103) | TCTTGATAGGAAAGTCCT (SEQ ID NO: 104) |
| 450 bp: | GAACCACCCTTAGAAAGG (SEQ ID NO: 105) | GATAATTGTTAAATTCTTAATTG (SEQ ID NO: 106) |
| 550 bp: | GGTCAAACTAGAACTTGA (SEQ ID NO: 107) | AGCATTAGCTTCATTACTAAAG (SEQ ID NO: 108) |
| 650 bp: | TAACATTTATGAAAAACGAA (SEQ ID NO: 109) | ACCATTTTAATAATGTACATAG (SEQ ID NO: 110) |
| 750 bp: | TTGCCATTACTACTACTACTACT (SEQ ID NO: 111) | TCTTCATCAACTTCATCA (SEQ ID NO: 112) |
| 850 bp: | TATGTTCATCCCTTCAGG (SEQ ID NO: 113) | CTCTCTAATGCAGGGAGA (SEQ ID NO: 114) |
| 950 bp: | TGAACTCACAAAAACAAC (SEQ ID NO: 115) | TGCAGAAGAAGTTGTTAC (SEQ ID NO: 116) |
| 1050 bp: | ACAAAATCACCTAAAGAAACAAT (SEQ ID NO: 117) | GGTTAATTTGAGAAGAACATATTG (SEQ ID NO: 118) |

Transformation with AscI-digested DNA yielded forty-five transformants. All of these were examined by multiplex PCR, with the primers to produce the twenty amplicons as discussed above (Table 2, Table 6). Twenty-one appeared to be complete. These twenty-one transformants were examined by Southern Blot of a CHEF gel and fifteen appeared to be the correct size. Transformation with undigested *M. genitalium* genomes yielded fifty transformants. All of these were examined by the same multiplex PCR, and seven appeared to be complete. One of these was the correct size. These results demonstrate successful transfer of a whole donor *Mycoplasma* genome by digestion with a restriction enzyme at the recombination site and co-transformation with a yeast host vector, followed by in vivo recombination within the yeast host cell.

Example 1C

Transfer of *M. genitalium* Genome to Yeast Host Cells by Assembly of Overlapping Fragments of Genome and Yeast Host Vector by In Vivo Recombination in Yeast Host Cells This example describes successful transfer to and propagation of *M. genitalium* donor genomes in yeast host cells, using the method illustrated in FIG. 2C. In this method, genomes are assembled in the host cell (yeast) by homologous recombination of multiple overlapping fragments of the genome.

This strategy has been performed using pieces derived from *E. coli* BAC clones (See Gibson et al., *Science* 319, 1215 (2008), including supplemental online materials; Gibson et al., *PNAS USA*, (2008) 105:20404-9; and U.S. patent application Ser. No. 12/247,126, naming as inventors: Gibson et al.).

Figure 6B:
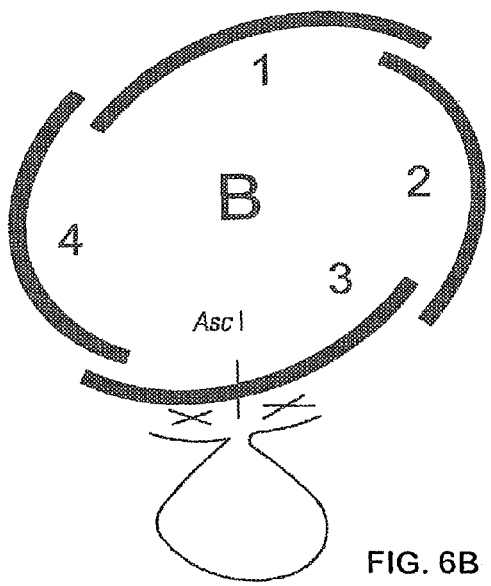
Figure 6D:
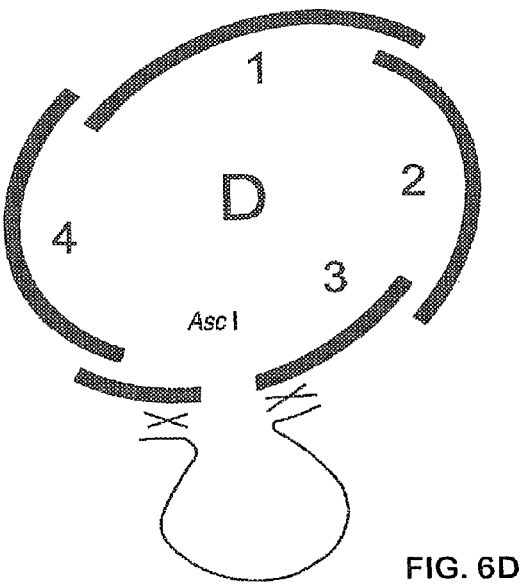

In the present study, a synthetic *M. genitalium* genome was assembled from six pieces, using the first published method described above (the multi-stage process described in Gibson et al., *Science* 319, 1215 (2008) and supplemental online materials), by first generating quarter-genomes (approximately 144 kb each) by three stages of assembly using in vitro recombination and cloning in *E. coli* using BAC vectors. These four "quarter genomes" (1-4) are illustrated in FIG. 6B.

Isolation of genomic DNA from host yeast cells was carried out as described in Example 1A, without pre-electrophoresis and without digestion with yeast-specific enzymes to deplete yeast genomic DNA. Samples were analyzed using CHEF analysis, as described above. Southern blots also were performed (data not shown).

TABLE 7

Primers for analyzing *M. genitalium* genome transfer to yeast cells using homologous recombination using overlapping fragments

| Amplicon name | Forward Primer | Reverse Primer |
|---|---|---|
| Quarter 1: | AACCAATCAGTACCCTTGC (SEQ ID NO: 119) | AGCAAACTTAATTAGTGGGAC (SEQ ID NO: 120) |

TABLE 7-continued

Primers for analyzing M. genitalium genome transfer to yeast cells using homologous recombination using overlapping fragments

| Amplicon name | Forward Primer | Reverse Primer |
|---|---|---|
| Quarter 2: | CAAACACTTTCGTGAAACAGG (SEQ ID NO: 121) | GTTTCAACTCCAATAATAGTAGGG (SEQ ID NO: 122) |
| Quarter 3 | CACCGCTTCAGTCACTACAAG (SEQ ID NO: 123) | GCTATTGAATCACCTGATCCTG (SEQ ID NO: 124) |
| Quarter 4: | GGCACCTAAGTTTTGAGA (SEQ ID NO: 125) | CTTGAAATGCTAATTTGGTG (SEQ ID NO: 126) |
| HIS3: | TGAAACCAAGATTCAGATTGC (SEQ ID NO: 127) | GGTCGTCTATGTGTAAGTCACC (SEQ ID NO: 128) |
| rDNA: | AATTTGACTCAACACGGG (SEQ ID NO: 129) | GACGGGCGGTGTGTAC (SEQ ID NO: 130) |

The results revealed that 6 of these transformants contained the correct sequences. With the non-digested samples, only two transformants were obtained, neither of which showed a complete *M. genitalium* genome in the PCR and southern analyses. Another study was performed, using the same process as described above, except that instead of AscI-digestion, quarter 3 was cut at the unique BsmBI site in that quarter. The same transformation and analysis methods were used. The study with BsmBI digestion produced 73 transformants, 44 of which were correct when assayed by PCR. Five (5) out of 28 of these clones examined by Southern Blot were correct. These results revealed that this method for transferring donor genomes into yeast host cells (by in vivo recombination of overlapping fragments and vectors within the host) is more efficient when one of the fragments is cut with a restriction enzyme prior to transformation, likely due to higher efficiency of homologous recombination at DNA ends (Orr-Weaver et al., *PNAS USA* 78, 6354 (1981).

Example 1D

Construction of a Diploid Yeast Strain Carrying Two Donor *Mycoplasma* Genomes (*M. genitalium* and *M. mycoides*)

This example describes production of a diploid yeast host strain, carrying two donor *Mycoplasma* genomes that were transferred in using the method depicted in FIG. 2A (see Example 1A, above). For this process, two haploid strains were crossed as described in D. C. Amberg et al., *Methods in Yeast Genetics: A Cold Spring Harbor Laboratory Course Manual*. (Cold Spring Harbor Laboratory Press, Cold Spring Harbor, N.Y., ed. 2005, 2005), pp. 230, each of which carried one of the genomes.

The W303a strain (mating type a) containing the *M. genitalium* cl16-2 was mated with the VL6-48 strain (mating type α) containing *M. mycoides* LC cl1.1 (see Example 1A and Table 1, above). Prior to mating, the HIS3 marker in the *M. genitalium* genome was replaced with a TRP marker, as follows, to allow selection of diploids carrying both genomes on medium lacking histidine and tryptophan.

For replacement of the HIS3 marker with TRP1, a 1059 bp TRP1 fragment was amplified by PCR from the plasmid pRS304 (described by Sikorski and Hieter, *Genetics* 122, 19 (1989), Genbank Accession No. U03436.1, gi number 416305). The fragment, which had homology to *M. genitalium* MS5 cl16-2, was amplified from the plasmid using primers with the following sequences:

(SEQ ID NO: 131)
TACGAGGCGCGTGTAAGTTACAGGCAAGCGATCCTAGTACACTCTATATC

AGAGCAGATTGTACTGAGAGTGCACC and (SEQ ID NO: 132)
CTACATAAGAACACCTTTGGTGGAGGGAACATCGTTGGTACCATTGGGCG

CGCATCTGTGCGGTATTTCACACCGC.

In each primer sequence, the portion homologous to the *M. genitalium* cl16-2 sequence is in bold. The 1059 bp fragment was transformed into yeast using lithium acetate, using techniques described by Gietz et al., *Nucleic Acids Res* 20, 1425 (1992).

Replacement of HIS3 with TRP1 was confirmed by amplification with two primers (sequences: ATTATTCCATCATTAAAAGA (SEQ ID NO:133) and AGTCAAGTCCAGACTCCTGT (SEQ ID NO:134)), amplification with which produced a 1207 bp fragment when HIS3 is replaced with TRP1 and a 927 bp fragment when replacement has not occurred. The results revealed correct replacement.

After replacement, the haploid strains carrying the two different donor genomes were crossed as described by Amberg et al., *Methods in Yeast Genetics: A Cold Spring Harbor Laboratory Course Manual*. (Cold Spring Harbor Laboratory Press, Cold Spring Harbor, N. Y., ed. 2005), pp. 230. Following cross, DNA from individual clones was isolated in agarose plugs using the protocol "Preparation of Agarose Embedded Yeast DNA" from the Bio-Rad CHEF-DR III manual. Plugs were preelectrophoresed at constant voltage for several hours to remove yeast chromosomal DNA. Isolated DNA was subject to linearization by heating at 55° C. for 1 hour; control samples were left unheated (data not shown). The results demonstrated that five out of five diploids generated in this study contained both *M. genitalium* and *M. mycoides* genomes, confirming successful generation of a diploid yeast host cell containing two full donor *Mycoplasma* genomes of different species.

Example 1E

Maintenance of a *Mycoplasma* Donor Genome in Yeast Host Cells without the Presence of an ARS Sequence The yeast vector in the synthetic *M. genitalium* genome generated as described by Gibson et al., *Science* 319, 1215 (2008) and in Example 1C, above, was transferred from its original site within the RNaseP gene to a new site in MG411 so as not to interrupt an essential gene. For this process, the yeast clone containing the synthetic *M. genitalium* as described in Example 1C, above, was co-transformed with two (2) fragments. The first fragment, which was 1842 bp in length, inserted yeast vector sequence containing URA3, the GAL1 promoter, and a centromere into MG411. This fragment was generated by PCR using primers with the sequences:

(SEQ ID NO: 135)
CAGATGGTATTCCTGAAAGGATATCAATAATAAGTGAAAGTTTTTTTCTT

ATTTTTGGTTGCGGCCGCTTGATTTCGGTTTCTTTGAAAT
and (SEQ ID NO: 136)
TTAATTATTGCTAGTTATATAGGGGTTAGAACTTCATTTTTCCTTGTTTA

TCGATGCAGCGGCCGCGGGTCCTTTTCATCACGTG (*M. genitalium* sequence is in bold; NotI sites are underlined). The template for this PCR was a construct having the sequence provided in SEQ ID NO:137 (Table 8).

TABLE 8

Sequence of PCR template for generating yeast vector sequences (SEQ ID NO: 137)
TTGATTTCGGTTTCTTTGAAATTTTTTTGATTCGGTAATCTCCGAACAGA

AGGAAGAACGAAGGAAGGAGCACAGACTTAGATTGGTATATATACGCATA

TGTAGTGTTGAAGAAACATGAAATTGCCCAGTATTCTTAACCCAACTGCA

CAGAACAAAAACCTGCAGGAAACGAAGATAAATCATGTCGAAAGCTACAT

ATAAGGAACGTGCTGCTACTCATCCTAGTCCTGTTGCTGCCAAGCTATTT

AATATCATGCACGAAAAGCAAACAAACTTGTGTGCTTCATTGGATGTTCG

TACCACCAAGGAATTACTGGAGTTAGTTGAAGCATTAGGTCCCAAAATTT

GTTTACTAAAAACACATGTGGATATCTTGACTGATTTTTCCATGGAGGGC

ACAGTTAAGCCGCTAAAGGCATTATCCGCCAAGTACAATTTTTTACTCTT

CGAAGACAGAAAATTTGCTGACATTGGTAATACAGTCAAATTGCAGTACT

CTGCGGGTGTATACAGAATAGCAGAATGGGCAGACATTACGAATGCACAC

GGTGTGGTGGGCCCAGGTATTGTTAGCGGTTTGAAGCAGGCGGCAGAAGA

AGTAACAAAGGAACCTAGAGGCCTTTTGATGTTAGCAGAATTGTCATGCA

AGGGCTCCCTATCTACTGGAGAATATACTAAGGGTACTGTTGACATTGCG

AAGAGCGACAAAGATTTTGTTATCGGCTTTATTGCTCAAAGAGACATGGG

TGGAAGAGATGAAGGTTACGATTGGTTGATTATGACACCCGGTGTGGGTT

TAGATGACAAGGGAGACGCATTGGGTCAACAGTATAGAACCGTGGATGAT

GTGGTCTCTACAGGATCTGACATTATTATTGTTGGAAGAGGACTATTTGC

TABLE 8-continued

Sequence of PCR template for generating yeast vector sequences

AAAGGGAAGGGATGCTAAGGTAGAGGGTGAACGTTACAGAAAAGCAGGCT

GGGAAGCATATTTGAGAAGATGCGGCCAGCAAAACTAAAAAACTGTATTA

TAAGTAAATGCATGTATACTAAACTCACAAATTAGAGCTTCAATTTAATT

ATATCAGTTATTACCCACGGATTAGAAGCCGCCGAGCGGGTGACAGCCCT

CCGAAGGAAGACTCTCCTCCGTGCGTCCTCGTCCTCACCGGTCGCGTTCC

TGAAACGCAGATGTGCCTCGCGCCGCACTGCTCCGAACAATAAAGATTCT

ACAATACTAGCTTTTATGGTTATGAAGAGGAAAAATTGGCAGTAACCTGG

CCCCACAAACCTTCAAATGAACGAATCAAATTAACAACCATAGGATGATA

ATGCGATTAGTTTTTTAGCCTTATTTCTGGGGTAATTAATCAGCGAAGCG

ATGATTTTTGATCTATTAACAGATATATAAATGCAAAAACTGCATTAACC

ACTTTAACTAATACTTTCAACATTTTCGGTTTGTATTACTTCTTATTCAA

ATGTAATAAAAGTATCAACAAAAAATTGTTAATATACCTCTATACTTTAA

CGTCAAGGAGAAAAAACCGGCCTGAGAGCAGGAAGAGCAAGATAAAAGGT

AGTATTTGTTGGCGATCCCCCTAGAGTCTTTTACATCTTCGGAAAACAAA

AACTATTTTTTCTTTAATTTCTTTTTTTACTTTCTATTTTTAATTTATAT

ATTTATATTAAAAAATTTAAATTATAATTATTTTTATAGCACGTGATGAA

AAGGACCC

The second fragment was 302 bp in length, having the following sequence:

(SEQ ID NO: 138)
TTAAAGTCAGTTATTTATCTACAGCAATTGCTGTCATTACTTTAATTATT

TGTTCTTAAAGCAACATTCCCTTACCAAAATTTAGGTTTCTTGCTTGTGG

AGTTTACCGCGTTTCATACCTGGTTTTCACCAAGCTCGTCTCTGTGGCAC

TTTCAAAACATCATCATAGTATTAACCTTAGACTAGTTATGTCGTTATGG

CTATCACATCCTAAATCTTATCGCTTTGATTTACACAAACACTACTTGCA

TTCCAGCAAGTGCAAGCATGGACTTTCCTCTACTTTAAATATATCTTTAA

AG.

This fragment was used to replace the yeast vector insertion in RNaseP with *M. genitalium* sequence such that the coding region of this gene was restored. This fragment was generated by PCR from *M. genitalium* DNA using primers with the sequences TTAAAGTCAGTTATTTATCTACAGC (SEQ ID NO:139) and CTTTAAAGATATATTTAAAGTAGAGG (SEQ ID NO:140).

Before cotransformation, TRP1 was inserted into MG411, as follows: an 1177 bp TRP1 gene fragment with homology to MG411 was amplified from the plasmid pRS304 (Genbank Accession No. U03436.1, gi number 416305), using two primers with the following sequences:

(SEQ ID NO: 141)
CAGATGGTATTCCTGAAAGGATATCAATAATAAGTGAAAGTTTTTTTCTT

ATTTTTGGTTCAGAGCAGATTGTACTGAGA
and

-continued (SEQ ID NO: 142)
TTAATTATTGCTAGTTATATAGGGGT TAGAACTTCATTTTTCCTTGTTT

ATCGATGCACGCATCTGTGCGGTATTTCA.

In each primer, portions of homology to *M. genitalium* genome are set forth in bold. TRP1 gene insertion was confirmed by PCR using a set of primers (sequences GCCATTGTTTCACTAATTGC (SEQ ID NO:143) and TAATCCTATCTTTGGAGCTT (SEQ ID NO:144)) that amplified 1739 bp (if insertion occurred) and 680 bp if it did not. Cotransformants, which were His− Trp− Ura+, were selected. Restoration of RNaseP was confirmed by PCR amplification of a 513 bp product using primers with sequences CTCCATCATGCGCAGTAATA (SEQ ID NO:145) and CTTTAAA GATATATTTAAAGTAGAGG (SEQ ID NO:146). Replacement of TRP1 with yeast vector sequence was confirmed by PCR amplification of an 1841 bp product using primers with sequences TTGATTTCGGTTTCTTTGAA (SEQ ID NO:147) and CAGGCAGGAATTTGATTCCC (SEQ ID NO:148).

The vector inserted in the new site did not contain an ARS. The results of these studies confirmed that the vector containing the *M. genitalium* donor genome did not require the presence of the ARS sequence for maintenance in yeast host cells. The *M. genitalium* is AT-rich and thus is likely to contain sequences that can function as ARS in yeast. ARS-like sequences are frequent in eukaryotic AT-rich DNA (See Montiel et al., *Nucleic Acids Res* 12, 1049 (1984); Stinchcomb et al., *PNAS USA* 77, 4559 (1980)).

Collectively, the studies described in this Example confirm that three different whole donor *Mycoplasma* genomes (the largest being 1.1 MB in size) were successfully transferred, propagated and maintained in yeast host cells, using the provided methods. In each case, complete clones were recovered and no sign of instability was detected. Additionally, in several of the studies, molecules as large as about 2 MB were recovered and detected by Southern blotting. These molecules likely represented clones of concatamers, and reveal that the provided methods can be used to clone and transfer larger genomes and nucleic acid molecules into yeast host cells. Such methods can be used to generate host cells containing donor genomes, which then can be propagated and modified in the host cells and transplanted into recipient cells using the provided methods.

Example 1F

Figures 18A, 18B, 18C:
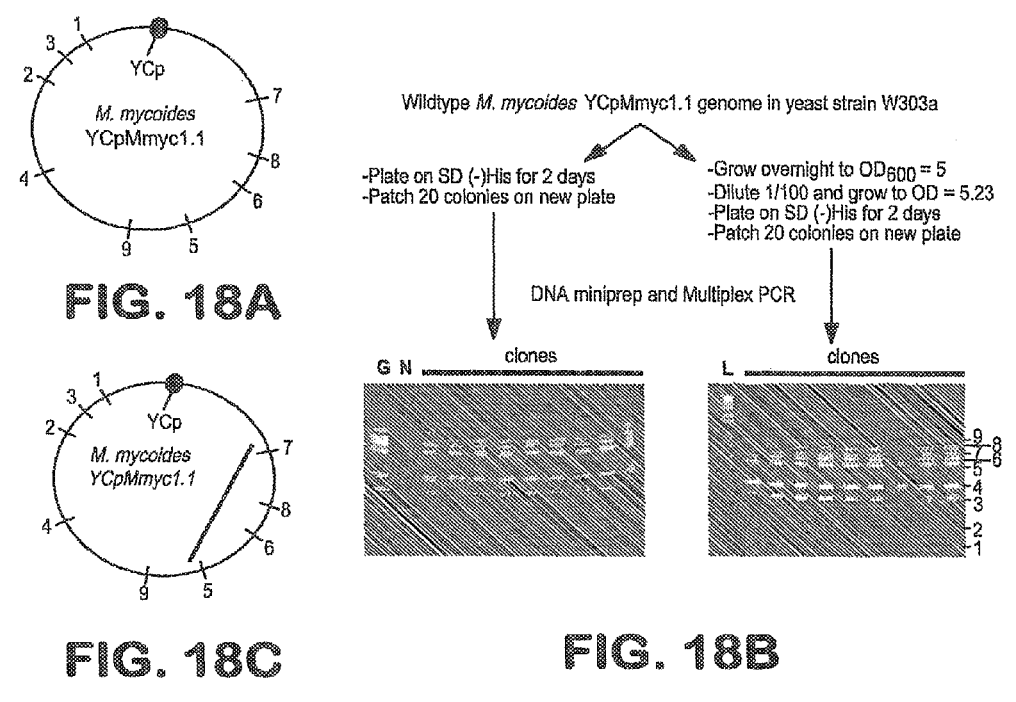

Stability and Evaluation of the *M. mycoides* MCpMmyc1.1 Genome During Propagation in Yeast The stability of the *M. mycoides* YCPMmyc1.1 genome during propagation in yeast was assessed. FIG. 18A provides a schematic of the YCpMmyc 1.1 genome and the position of the integrated YCp is shown. The nine (9) individual primer pairs used in the PCR amplifications are shown at their approximate locations in the genome and are numbered corresponding to the amplicons in FIG. 18B. The stability of the *M. mycoides* genome during propagation in yeast was tested by two methods. In the first, a yeast culture of a clone containing the genome was plated on solid synthetic media lacking histidine for two days and then individual colonies were patched onto a new plate. In the second, a yeast culture of a clone containing the genome was grown to saturation, diluted to a 1/100 fraction and again grown to saturation. The culture was then plated on solid synthetic media lacking histidine for two days and then individual clones were patched onto a new plate. In both methods, genomic DNA was isolated and used as template in multiplex PCR amplification using the nine individual primer pairs shown in FIG. 18A. The resulting amplicons were analyzed by gel electrophoresis. The numbers on the right side of the gel correspond to the individual primer pair amplicons as shown in FIG. 18B. Lane G is a positive control and lane N is the no-genome negative control. Molecular weight markers are shown in lane M. The results shown are representative of the 40 samples analyzed. All 40 clones appear to contain complete genomes, demonstrating that the bacterial genome is stable during routine propagation in yeast (FIG. 18B).

The *M. mycoides* YCP genomes in yeast manipulated at the type III restriction enzyme locus was evaluated. A schematic of the *M. mycoides* YCpMmyc1.1 genome is shown in FIG. 18C; the position of the integrated YCp is shown. The 9 individual primer pairs used in the PCR amplifications are shown at their approximate locations in the genome and are numbered corresponding to the amplicons (gel results not shown). The diagonal line in FIG. 18C represents the missing amplicons in clone 3 (gel results not shown). After transformation of a *M. mycoides* YCpMmyc1.1 yeast clone with a cassette containing URA3, genomes of Ura+ clones were evaluated by multiplex PCR and the resulting amplicons were analyzed by gene electrophoresis (gel results not shown). Amplicons 5 to 8 were missing in Clone 3, suggesting that there is a large deletion in this genome. The other four clones appeared to contain complete genomes.

Example 2

Transplantation of Whole *Mycoplasma* Donor Genomes, Propagated in Yeast Host Cells, into *Mycoplasma* Recipient Cells Provided are methods for transfer of large nucleic acids, such as genomes, are transferred among different organisms and cell types (e.g., donor, host, and recipient), which can be of different species, kingdoms, and/or orders (e.g., different bacterial species and bacterial versus eukaryotic yeast cells). Thus, in some embodiments, the methods include steps for overcoming potential incompatibilities among the different cell types, such as methods for successfully transplanting into recipient cells donor genomes that have been propagated in host cells.

Example 3, below, describes the successful transplantation of a whole donor genome (*M. mycoides* LC (Genbank accession NZ_AAZK00000000.1 (GI: 149364883), which had been propagated in yeast host cells, into recipient cells of a different species (*M. capricolum*), using the provided methods. This Example describes analysis of differences among these three different organisms (donor, host, and recipient), and the development of various processes that can be used to overcome these differences using the provided methods.

Example 2B demonstrates that sufficient amounts of purified, intact donor *Mycoplasma* genomic DNA can be recovered from yeast host cells for transplanting into the recipient cells. Example 2C demonstrates a provided transplantation method for transplanting native bacterial donor genomes into recipient cells with high efficiency. Example 2D describes evaluation of restriction-modification systems (not present in yeast) in the host and recipient cells, and of methyltransferase (which are expressed in yeast) expression and effects of methyltransferases on the donor genomes and activation. Example 2E describes treatments used in the provided methods to overcome host-donor-recipient incompatibility issues associated with restriction-modification (R-M) systems. Example 2F describes mutation of the R-M system of recipient cells, and Example 2G demonstrates successful transplantation of donor genomes (transferred from *Mycoplasma* to yeast host cells) from the yeast host cells to recipient bacteria of different species.

Example 2A

Bacterial Strains, Culture Conditions and Vectors

For the studies described in this Example and in Example 3, below, *Escherichia coli* DH10B [F⁻-mcrA Δ(mrr-hsdRMS-mcrBC) φ80dlacZΔM15 ΔlacX74 deoR recA1 endA1 araD139 Δ(ara, leu)7697 galU galKλ⁻ rpsL nupG] (Invitrogen, Carlsbad, Calif.) served as the host strain for cloning procedures and plasmid propagation. *E. coli* cells were grown in Luria-Bertani (LB) broth medium or in LB agar at 37° C. Depending upon the selection markers present in a given plasmid, *E. coli* transformants were grown in LB medium supplemented with 50 μg/ml of ampicillin, 5 μg/ml of tetracycline, or 125 μg/ml of puromycin.

Two *Mycoplasma* species were used in the studies described in this Example and in Example 3, below: *Mycoplasma capricolum* subsp. *capricolum* (strain California Kid™) (ATCC 27343) and *Mycoplasma mycoides* subsp. *mycoides* (strain GM12) (Damassa et al., 1983; described above). The *Mycoplasma* cells were grown at 37° C. in liquid or solid SP4 medium (Tully et al. 1977), containing 17% of fetal bovine serum (Invitrogen, Carlsbad, Calif.). *Mycoplasma* transformed with plasmid or whole-genome were grown at 37° C. in SP4 medium supplemented with 5 μg/ml of tetracycline or 8 μg/ml of puromycin. Beta-galactosidase activity was detecting by plating *Mycoplasma* on solid medium containing 150 μg/ml of 5-bromo-4-chloro-3-indolyl-β-D-galactopyranoside (X-gal, Promega, Madison, Wis.).

Two strains of *Mycoplasma capricolum* subsp. *capricolum* (*M. capricolum*) were used as recipient cells in the following Examples: wild-type (wt) *M. capricolum* and a restriction-free *M. capricolum* mutant (*M. capricolum*-ΔRE) that was obtained by inactivation of the CCATC-restriction enzyme gene in wt *M. Capricolum* (described in Example 2F, below). Donor genomic DNA for transplantation was from a *Mycoplasma mycoides* subsp. *mycoides* LC (*M. mycoides* LC) clone (cl1.1), described in Example 1, above, the genome of which contained the tetracycline resistance marker, the lacZ gene, and the yeast centromere plasmid integrated between ORF04334 (lppA) and ORF04335 (transposase B of IS1296). As described in detail, below, *Mycoplasma* genomic DNA was prepared in agarose plugs either directly from *M. mycoides* LC cells clone 1.1 (native genomic DNA) or from yeast host cells carrying *M. mycoides* clone 1.1 genome, generated as described in Example 1, above.

Some vectors used in the following Examples derived from oriC plasmids, which are able to replicate in *M. mycoides* LC (pMYCO1 (SEQ ID NO:149)) and in *M. capricolum* (pMYCO1 (SEQ ID NO:149); pSD4 (SEQ ID NO:150)) (Lartigue et al., *Nucleic Acids Res* 31, 6610 (2003)). Those plasmids were based on the pBS(+) plasmid (Stratagene) and contain the tetM gene from transposon Tn916 driven by the spiralin promoter, as a resistance marker (Lartigue et al., *Plasmid* 48, 149 (2002). Restriction buffers were from New England Biolabs, Ipswich, Mass.

Example 2B

Isolation of *M. mycoides* LC Donor Genomes from Host Yeast Cells, Confirmation of Quantity of Recovered Whole Genomic DNA and Development of Transplantation Methods In order to isolate and analyze intact *Mycoplasma* donor genomes from yeast cells, yeast W303a cells that had been transformed with the *Mycoplasma mycoides* Large Colony (*M. mycoides* LC) GM12, clone 1.1, genome, as described in Examples 1A(ii)b and 1A(iv), above, were embedded in agarose plugs as described below. This genome carried the tetracycline resistance gene (tetM) and β-galactosidase gene (lacZ). DNA from the plugs was isolated and evaluated. Genomic DNA from native yeast not carrying donor genomes and native donor *Mycoplasma* cells isolated were evaluated in a similar manner for comparison.

i. Yeast Agarose Plugs Containing Donor Genomes

Yeast cultures were grown at 30° C. in selective medium until the $OD_{600}$ reached approximately 1.5. Yeast cells were embedded in agarose plugs and DNA isolated from the plugs, using the CHEF mammalian Genomic DNA Plug Kit from Bio-Rad Laboratories (Valencia, Calif.), following the manufacturer's suggested protocol with the following details/modifications. To increase the amount of *M. mycoides* LC genomic DNA available per plug, $6\times10^9$ yeast cells (instead of $6\times10^8$ cells) were used per mL of plugs to be made, to yield $6\times10^8$ cells per plug. After embedding in plugs, rather than treatment with lyticase (Bio-Rad Laboratories), digestion with Zymolyase™ 100T enzyme (USB Corporation, Cleveland, Ohio) was used to digest yeast cell walls. The enzyme was added inside and outside of the plugs at a concentration of 5 mg/mL; the mixture was let stand for 2 hours at 37° C. After a wash in 1×TE buffer (20 mM Tris-HCL pH 8; 50 mM EDTA), embedded yeast cells (spheroplasts) were lysed and proteins degraded using two incubations with proteinase K Reaction Buffer (100 mM EDTA; 0.2% Sodium Deoxycholate; 1% Sodium Lauryl Sarcosine; pH 8.0), supplemented with 200 μL Proteinase K per mL of plug, 24 hours each, at 50° C. The agarose plugs were then washed at room temperature 4 times, 1 hour each, in 1×TE buffer (20 mM Tris-HCL pH 8; 50 mM EDTA), with agitation, and stored in the same buffer at 4° C. For yeast plugs that would be digested with restriction enzymes (see below), phenylmethanesulfonylfluoride (PMSF) was added during the second wash, for a final concentration of 1 mM.

The yeast agarose plugs carrying *M. mycoides* LC genomic DNA and those containing control yeast DNA were prepared for analysis using the CHEF mammalian Genomic DNA Plug Kit from Bio-Rad (Valencia, Calif.). A series of 3 agarose plugs (A, B, and C) was made for the yeast containing the donor genomes (A2, B2, and C2) and for the native yeast (A1, B1, and C1). The plugs were washed at room temperature, two times for one hour in 1 mL of 1×TE buffer, and equilibrated for one hour at room temperature in 1 mL of 1×NEB buffer 2 supplemented with BSA (100 μg/mL).

In order to remove endogenous yeast genomic DNA (which migrated at a similar position as the *M. mycoides* LC genomic DNA in CHEF gel analysis described below), plugs B and C (for each set of yeast) were incubated overnight at 37° C. with 50 units of AsiSI, RsrII, and FseI restriction enzymes (New England Biolabs) in a 500 μL reaction volume, which specifically cut yeast genomic DNA and left the donor DNA intact. Plug A was incubated without these enzymes under the same conditions. All 3 plugs then were washed at room temperature for 1 hour with 1 ml of 1×TE buffer and loaded on 1% TAE agarose gel (120 minutes, 120 volts), to remove digested yeast genomic DNA fragments from the plugs.

After migration, agarose plugs were removed from the wells and washed two times for one hour in 1 mL 0.1×TE buffer and equilibrated for one hour in 1 mL of 1×NEB buffer 2 (New England Biolabs, Ipswich, Mass.) supplemented with BSA (100 µg/mL). To linearize the *M. mycoides* LC genomic DNA, which allows entry of the DNA into the gel, plugs C were incubated overnight at 37° C. with 50 units of PspXI restriction enzyme. Plugs A and B (for each set of yeast) were incubated for a mock-digestion with no enzyme under the same conditions. Following the incubation, all plugs were washed for 1 hour at room temperature with 1 mL of 1×TE buffer and loaded onto a pulse-field gel.

ii. Native *M. mycoides* LC Agarose Plugs

For comparison of amount of DNA recovered, native donor *M. mycoides* LC agarose plugs containing different amounts of genomic DNA also were prepared from *M. mycoides* cells, using the CHEF mammalian Genomic DNA Plug Kit from Bio-Rad (Valencia, Calif.). Whole intact genomic DNA isolation from *M. mycoides* LC was performed as described by Lartigue et al., *Science* 317, 632 (2007), with some modifications, in particular in the way the cells were cultured prior to isolation. Five hundred (500) mL *M. mycoides* LC (tetM, lacZ YCp) cells were grown in SP4 medium, supplemented with 10 μg/μl tetracycline and 10 μg/μl streptomycin, until the pH of the medium reached 6.5 (approximately $10^9$ cells/mL). Prior to the collection of the cells, 100 μg/μl chloramphenicol was added to the medium and the cells were incubated another 90 minutes at 37° C. at this cell concentration, in order to synchronize ongoing rounds of chromosomal replication and inhibit further rounds of replication.

The cells were washed once in 10 mM Tris pH 6.5, 0.5 M sucrose, and resuspended in 2 mL of the same buffer. From this cell suspension, 8 series of *M. mycoides* LC genomic DNA (MLC gDNA) agarose plugs were prepared by 2-fold serial dilutions of the *M. mycoides* LC cells. Plugs from series 1 contained approximately $10^{10}$ native *M. mycoides* LC cells per plug; plugs from series 7 contained approximately $1.5\times10^8$ per plug; and plugs from series 8 contained approximately $7\times10^7$ cells per plug. For comparison to the genomic DNA from yeast, the plugs containing native DNA and the plugs containing *M. mycoides* LC genomic DNA isolated from yeast (see above) were digested with PspXI to linearize MLC genome as described above for analysis on a pulse-field gel.

iii. Comparison of Recovered Genomic DNA on Pulse Field Gel

The amount of *M. mycoides* LC genomic DNA in yeast cells was estimated by comparing the amount of isolated genomic DNA from yeast cells in agarose plugs to the various amounts of native genomic DNA isolated from 2-fold serial dilutions of *M. mycoides* LC cells in agarose plugs. For this process, the yeast agarose plugs (Example 2B(i), plugs A1, B1, and C1 and A2, B2, and C2) and the eight *M. mycoides* LC agarose plugs (Example 2B(ii) were subjected to electrophoresis in a 1% certified pulse-field agarose gel (Bio-Rad, Valencia, Calif.) in TAE 1×, with contour-clamped homogeneous electric field (Chu et al., *Science* 234, 1582 (1986)) (CHEF DR III; Bio-Rad). Pulse times were ramped from 60 to 120 over 27 h at 4.5 V/cm. After migration, the gel was stained with SYBR® GOLD nucleic acid stain (Invitrogen, Carlsbad, Calif.) (1/10,000 dilution) and PFGE patterns were scanned with a GE Typhoon 9410 imager. The *S. cerevisiae* CHEF DNA size marker was used to evaluate DNA size; this marker contained *Saccharomyces cerevisiae* chromosomes and is used for sizing in the 0.2-2.2 Mb range.

Lanes with plugs A2-C2 (from yeast containing *M. mycoides* donor genomes) and A1-C1 (native yeast) (Example 2B(i)) were run on a gel with a marker lane. Plugs (series 7 and 8) contained increasing concentrations of *M. mycoides* native DNA (Example 2B(ii)). The 1.12 Mb *M. mycoides* LC genome was detected at the expected position on the pulse-field gel in certain lanes. In the case of yeast host cells containing *M. mycoides* donor genomes, selective digestion of yeast genomic DNA with the enzyme cocktail (AsiSI, RsrII FseI restriction enzymes), followed by electrophoresis (samples B2 and C2; see Example 2B(i), above) improved recovery of *M. mycoides* donor genomic DNA (data not shown). Further, linearization of the *M. mycoides* LC genome (C2) greatly improved recovery of the 1.2 Mb *M. mycoides* (C2). No 1.2 Mb band was detected in the parallel samples from native (wild-type) yeast cells, which contained no *M. mycoides* genome (B1, C1), confirming that the band at 1.2 Mb indeed represented the presence of *M. mycoides* genome in the yeast cells. The same band appeared in lanes containing native *M. mycoides* genomic DNA.

The amount of *M. mycoides* LC genomic DNA recovered from yeast cells was compared to that recovered from native *M. mycoides* LC genomic DNA standards, which had also been treated with PspXI as described above. The amount of *M. mycoides* LC genomic DNA obtained from $6\times10^8$ yeast cells was similar to the amount of genomic DNA recovered from native *M. mycoides* LC plugs from series 7 (approximately $1.5\times10^8$ native *M. mycoides* LC cells per plug).

iv. Quantification of Recovered DNA

A UV spectrophotometer was used to determine the amount of native *M. mycoides* LC genomic DNA present in melted plugs prepared from native *M. mycoides* cells as described in Example 2B(ii) above. Results are listed in Table 9, below. As shown in this table, plugs from series 7 contained approximately 12 ng/μl of genomic *M. mycoides* LC DNA (L2 μg per 100 μL plug). As noted above, the pulse-field gel revealed comparable 1.2 Mb band intensity in the lane with this sample (7) and the lane containing DNA recovered from yeast sample (C2) (see Example 2B(iii) above)). Thus, it was determined that that quantity of *M. mycoides* LC genomic DNA per 100 μL plug in recovered from the host cells containing donor genomes was equal roughly to 1 μg.

TABLE 9

Quantification and transplantation of native *M. mycoides* LC genomic DNA
Transplantation of native *M. mycoides* LC genomic DNA into wt *M. capricolum* recipient cells

| Plug series | Quantity (μg) genomic DNA recovered from 1/5 plug (20 μl) | Number of transplants after transfer of 1/5 plug to recipient cells |
|---|---|---|
| 1 | 5.7 | 237 |
| 2 | 2.9 | 405 |
| 3 | 1.5 | 236 |
| 4 | 0.96 | 215 |
| 5 | 0.64 | 113 |
| 6 | 0.4 | 64 |
| 7 | 0.24 | 29 |
| 8 | Below detection limit | 12 |

Example 2C

Transplantation of DNA Recovered from Plugs into Recipient Cells

For each sample from the series of melted native *M. mycoides* LC agarose plugs (Example 2B(iv); Table 9), 1/5 of a plug (20 µL) was transplanted into *M. capricolum* recipient cells, using a protocol similar to that described by Lartigue et al., *Science* 317, 632 (2007), with some modifications, as follows:

i. Culture and Preparation of Recipient Cells

Six (6) mL of *M. capricolum* recipient cells were grown in SOB(+) medium (Bacto SOB medium (Becton Dickinson; Franklin Lakes, N.J.), supplemented with fetal bovine serum (17%), glucose (10 g/L), 2 ml of phenol Red (1%) and 100 μl of Penicillin G (5 mg/ml)) until the pH of the culture reached pH 5.7 to 5.85 (approximately $5\times10^7$ cells/ml). The recipient cells were centrifuged at 4575 g for 15 minutes at 10° C., washed once in S/T buffer (10 mM Tris-HCl, pH 6.5; and 250 mM NaCl), resuspended in 200 μl of $CaCl_2$ (0.1 M) and incubated on ice for 30 minutes.

ii. Preparation of Isolated Donor Genomic DNA in Agarose Plugs

Before transplantation, the agarose plugs (series 1-7) containing *M. mycoides* LC genomic DNA were washed 2 times, for 30 minutes each, in 0.1×TE buffer [2 mM TRIS-HCl, pH 8.0-5 mM EDTA] under gentle agitation at room temperature. The buffer was completely removed and the agarose plugs were melted with 1/10 volume of 10×β-Agarase Buffer [10 mM Bis Tris-HCl pH 6.5; 1 mM $Na_2EDTA$] at 65° C. for 10 minutes. The molten agarose was cooled down to 42° C. for 10 minutes and incubated overnight at this temperature with 3 units of β-Agarase I (New England Biolabs, Ipswich, Mass.) per 100 μl of plug.

iii. Transplantation Using 5% PEG

After 30 minutes on ice, 200 μl of the recipient cells were gently mixed with 400 μl of SP4 (−) medium [0% fetal bovine serum, 0.45% NaCl], containing 20 μl of melted donor genomic DNA agarose plugs (1/5 of the plug) as generated in Example 2B(ii) above. The plugs were added immediately before proceeding with the next step, as follows.

An equal volume (620 μl) of 2× fusion buffer (20 mM Tris-HCl pH 6.5, 250 mM NaCl, 20 mM $MgCl_2$, 10% Fluka PEG-6000 (Sigma-Aldrich, St. Louis, Mo.)) was immediately added to the mixture of SP4(−), genomic DNA and cells and the mixture homogenized by rocking the tube gently for 30 seconds. After 50 minutes at 37° C., 5 ml of pre-warmed SP4 was added and cells were gently mixed. After another 3 hours at 37° C., cells were centrifuged at 4,575 g for 15 minutes at 10° C., resuspended in 0.6 ml of SP4 and plated on SP4 plates containing 4 μg/ml of tetracycline and 150 μg/ml of X-gal. After 3-4 days, individual colonies were picked and grown in broth medium containing 10 μg/ml of tetracycline.

The results are presented in Table 9, above, which indicate that the number of transplants (colonies of recipient cells with donor DNA) recovered increased proportionally with the amount of native *M. mycoides* LC genomic DNA present in the transplantation reaction. A decrease in number of transplants was observed at the highest DNA concentration tested (series 8). Thirty (30) transplants were obtained with 200 ng genomic DNA. Approximately 200 transplant colonies per 1 μg native *M. mycoides* LC donor genomic DNA was routinely obtained using this method in subsequent experiments. These data demonstrated that the protocol efficiency was high enough that the quantity of donor *M. mycoides* LC DNA obtained from yeast host cells would not be a limiting factor in genome transplantation using this method.

The transplantation method described above can also be used to transform *M. capricolum* recipient cells with plasmid DNA (not in agarose plugs) by substituting 10 μg of plasmid DNA in solution for the 20 μL of melted agarose plugs.

Example 2D

Evaluation of Restriction-Modification (R-M) Systems

Because differences in restriction-modification systems between donor cells, host cells, and recipient cells could lead to difficulty in genome transplantation, these systems were investigated. This Example demonstrates components of restriction-modification systems that are present and active in some of the *Mycoplasma* cells used in transplantation herein, and demonstrates aspects of the provided methods used to subvert these systems for successful transplantation.

i. Identification of Predicted R-M Systems in Donor and Recipient Cells

The *M. mycoides* LC genome, which has been sequenced (Genbank Accession No.: NZ_AAZK00000000; GI: 149364883), was predicted to contain six different restriction-modification systems (five Type II systems and a single Type III system). The *M. capricolum* genome sequence showed the presence of a single Type II system. The recognition site specificities of the Type II enzymes were predicted from the gene sequences (Dr. R. Roberts, personal communication), as described in Roberts R J et al., *Nucleic Acids Res.* 35(Database issue): D269-70 (2007). See also REBASE, The Restriction Enzyme Database, available at the World Wide Web address: rebase.neb.com/rebase/rebase.html. These recognition sites and commercially available restriction enzymes that cleave at these sites are listed in Table 10, below. The specificity of the Type III system was not predicted.

TABLE 10

Restriction-modification (R-M) systems predicted from *M. capricolum* and *M. mycoides* LC sequences

| | operon | Specificity Type II | Specificity Type III | RE Isoschizomer |
|---|---|---|---|---|
| Wt *M. capricolum* (1 system) | M1-M2-RE | CCATC | — | BccI |
| Wt *M. mycoides* LC (6 systems) | M1-M2-RE | CCATC | — | BccI |
| | M-RE | CCTTC | — | HpyAV |
| | M-RE | GANTC | — | HinFI |
| | M-RE | GATC | — | MboI |
| | M1-M2-RE | GCATC | — | SfaNI |
| | M-RE | — | Unknown | — | ii. Confirmation of R-M Systems a. Methylation Status of Restriction Sites Commercially available restriction enzyme isoschizomers corresponding to the predicted Type II restriction enzyme systems were used to confirm that the native genomes of *M. mycoides* LC and *M. capricolum* were methylated at the predicted sites listed in Table 10. Digestion of the *M. mycoides* LC and *M. capricolum* genomic DNA with the isoschizomers indicated that the native genomic DNAs were methylated at the predicted sites (data not shown). These results showed that *M. capricolum* and *M. mycoides* LC both contain a CCATC restriction-modification system.

For this study, genomic DNA from *M. mycoides* LC and *M. capricolum* was purified using the Wizard® Genomic DNA Purification Kit (Promega, Madison, Wis.), following the manufacturer's directions. Approximately 1 μg each of *M. mycoides* LC and *M. capricolum* genomic DNA was incubated with BccI, HinfI, HpyAV, MboI and SfaNI, respectively, as described by the manufacturer (New England Biolabs, Ipswich, Mass.). The DNA was then analyzed by agarose gel electrophoresis (data not shown).

As expected based on the predicted R-M systems (see Table 10), *M. mycoides* LC genomic DNA was resistant to cleavage by all 5 restriction enzyme isoschizomers tested, indicating the DNA was methylated at each of these sites. On the other hand, *M. capricolum* genomic DNA was resistant only to cleavage by the restriction enzyme isoschizomer (BccI), the restriction-modification system identified in both organisms. These results confirmed the presence of these respective R-M systems (Table 10) in the *Mycoplasma* species and showed, for example, that *M. mycoides* LC and *M. capricolum* both contained a CCATC restriction-modification system.

The availability of a commercial restriction enzyme isoschizomer corresponding to the predicted restriction enzyme system from *M. capricolum* enabled us to test whether the two genomes were methylated at the appropriate restriction site. Genomic DNA from *M. mycoides* and *M. capricolum* was purified using the Wizard Genomic DNA Purification Kit. Approximately 1 μg each of *M. mycoides* and *M. capricolum* genomic DNA was incubated with BccI. The DNA was then analyzed by agarose gel electrophoresis. As expected, both *M. mycoides* and *M. capricolum* genomic DNA were resistant to cleavage by BccI, the enzyme that corresponds to the homologous R-M system of the two organisms (data not shown).

b. Restriction Enzyme Activity

Cell-free extracts from *M. mycoides* LC and *M. capricolum* were prepared to demonstrate that restriction enzymes were active in both species. As described below, the extracts were used in restriction enzyme assays to test their ability to cleave *M. mycoides* LC, *M. capricolum*, and *M. genitalium* genomic DNA.

c. Preparation of Cell Extracts

For *M. mycoides* LC, a 1 liter culture of the cells in SP4 medium was grown at 37° C. until a pH of 6.2-6.3 was reached. The culture was harvested by separating the cells into five 200 mL fractions and centrifuging at 5,000×g in a SLA-1500 Sorvall rotor at 4° C. for 15 minutes. Each *M. mycoides* LC pellet was then washed with 200 mL of 8 mM Hepes, pH 7.4, and 272 mM sucrose and centrifuged at 5,000×g in a SLA-1500 Sorvall rotor at 4° C. for 15 minutes. Each resulting pellet was resuspended in 1 ml Extract buffer (20 mM Tris-HCl, pH 7.5, 0.1 mM EDTA, 150 mM NaCl, 1 mM DTT, and 10% glycerol) and subsequently sonicated on ice 5 times with 10-12 seconds bursts, using a microtip, at an output control of three. Each solution was clarified by microcentrifugation at 18,000×g for 30 minutes at 4° C. Each resulting soluble fraction was combined, tested for protein concentration, aliquoted into 200 μl fractions, and stored at −80° C. Protein concentration of extracts prepared in this manner typically ranged from 15 to 25 mg/ml.

For *M. capricolum*, extracts were prepared using the same method described for *M. mycoides* LC, except that the 1 liter culture was grown in SP4 medium containing 10 μg/ml of tetracycline.

d. Restriction Enzyme Activity Assay

Restriction enzyme activity of the *M. mycoides* LC extract was tested as follows. Two (2) μg of genomic DNA, isolated using a WIZARD® Genomic DNA purification kit (Promega Corporation, Madison, Wis.) from *M. capricolum, M. mycoides* LC and *M. genitalium*, individually in separate reactions, was incubated in 1× of NEB restriction enzyme buffer 4 plus 100 μM deoxynucleotides with 8 μg of the extract, in a total volume of 100 μl, at 37° C. Protein was added last and at 0, 5, 10 and 15 minutes time intervals, a 20 μl aliquot was removed and added to 20 μl of 2× Stop buffer (2% SDS, 20 mM EDTA). The solution was extracted with 40 μl of phenol/chloroform/isoamylalcohol (25:24:1) and centrifuged at 18,000×g for 2 minutes at room temperature. The aqueous phase was placed into a fresh tube with 4 μl of 10× Blue Juice (Invitrogen, Carlsbad, Calif.) and 18 μl of each solution was loaded onto a 0.8% 1×TAE agarose gel and run under FIGE conditions of 120V, 0.1-0.6 linear and 80V, 0.1-0.6 linear for 16 hrs. The agarose gel was then stained with SYBR® GOLD nucleic acid stain (Invitrogen, Carlsbad, Calif.) (1/10,000dil.) for 30 minutes and scanned with a GE Typhoon 9410 imager.

Restriction enzyme activity of the *M. capricolum* extract was tested in the same manner, with the exception that 1×NEB restriction enzyme buffer 1 and 12 μg of *M. capricolum* extract was used in each reaction, and aliquots were removed and processed at 0, 15, 30 and 45 minutes intervals.

Results from the study described in Example 2D(ii)(a) (gel results not shown) suggested that *M. mycoides* LC genomic DNA should be protected from cleavage by the restriction-modification system of *M. capricolum* but that the *M. capricolum* genomic DNA should be readily cleaved by the restriction-modification systems of *M. mycoides* LC. Indeed, as predicted by the homologous restriction-modification system, genomic DNA from *M. mycoides* LC and genomic DNA from *M. capricolum* were not cleaved, while genomic DNA from *M. genitalium*, which does not contain any restriction-modification systems, was readily cleaved. Cleavage of *M. genitalium* genomic DNA was due to the activity of restriction enzyme in *M. capricolum*. This was evidenced by the fact that a crude extract derived from a strain of *M. capricolum*, in which the predicted restriction enzyme gene was disrupted (See Example 2F), did not cleave genomic DNA from any of the three *Mycoplasma* strains tested. Also as expected, genomic DNA from *M. capricolum* but not *M. mycoides* LC was cleaved when incubated with *M. mycoides* LC crude extracts. These results demonstrated that *M. capricolum* and *M. mycoides* LC contain active restriction-modification systems, which have the potential to affect activation of unmethylated *M. mycoides* LC donor genomes isolated from yeast. Lambda DNA was digested by wild-type *M. capricolum* extract. Incubation of the DNA with the extract made from the *M. capricolum* RE(−) strain did not result in the appearance of bands indicating the absence of the restriction activity from this strain.

e. Genome Sequencing and Genome Comparison of *M. mycoides* Donor and Transplant Clones.

Two *M. mycoides* clones were sequenced. One was the donor genome described by Lartigue et al. in the 2007 "Genome transplantation in bacteria: changing one species to another" paper published in *Science* (317, 362) (1,088,905 bp, GenBank #CP001621). The other was the transplanted *M. mycoides* clone containing the Type III restriction enzyme gene deletion, (ΔtypeIIIres; FIG. 17) (1,084,586 bp, Genbank #CP001668).). The clone used in the 2007 paper was sequenced using only Sanger DNA sequencing chemistry. The Type III restriction enzyme gene deletion clone described herein was sequenced to 8× coverage by the Sanger method and also with 454 FLX paired-end read pyrosequencing chemistry.

To confirm that the transplants were entirely *M. mycoides* and not chimeras containing either yeast sequences or *M. capricolum* recipient cell sequences, and to determine whether the bacterial genomes were stable when cloned in yeast, the two sequences were compared. All of the assembled ΔtypeIIIres genome matched *M. mycoides*, except for those regions that matched the YCp vector. Additionally, except for differences deliberately built into the genome, the transplant *M. mycoides* genome sequence with the Type III restriction enzyme gene deletion was identical to the previously sequenced *M. mycoides* genome except at 95 sites. It should be noted that these 95 sequence differences are not differences between the donor *M. mycoides* strain used herein and the engineered genome. They are differences between the sequence of the *M. mycoides* strain (Genbank #CP001621) used in the 2007 paper (Id) and the engineered genome herein (Genbank #CP001668). We sequenced each one of those 95 sites in *M. mycoides* YCpMmyc1.1, which was used to generate the original *M. mycoides* yeast clone. In each instance, the transplant sequence matched the YCpMmyc1.1 donor from which it was derived. Thus, none of the 95 sequence differences arose during cloning in yeast, propagation and engineering in yeast, or transplantation out of yeast to create the engineered *M. mycoides* strain. It was concluded that no sequence changes other than those deliberately engineered occurred during cloning and propagation in yeast, and transplantation back in a bacterium based on the assumption that all sequences that are the same in the two completely sequenced *M. mycoides* genomes are also the same in the YCpMmyc1.1 donor strain.

These data indicate there was no recombination of either yeast or recipient cell genomes with the *M. mycoides* donor genome, and that these bacterial genome sequences are stable during propagation, engineering, and storage in yeast as YCps.

Example 2E

Methods for Protecting Donor Genomes and Nucleic Acids from Restriction-Modification System Incompatibility This example describes two methylation methods that were employed to protect *Mycoplasma* (e.g., *M. mycoides* LC) donor genome from cleavage by restriction-modification systems. Methylation assays were performed for each method, to confirm efficacy.

i. Methylation by Constructed and Purified Methyltransferases

First, as described below, the determined sequence of the *M. mycoides* LC genome was used to exogenously express and purify each of the identified methyltransferases (See Table 10, above). Because the only R-M system identified in *M. capricolum* was the same as that identified in *M. mycoides* LC only the *M. mycoides* LC methyltransferases were purified for this study.

a. Methyltransferase Construction

The coding sequences of the five identified methyltransferases (CCATC-M, CCTTC-M, TypeIII-M, GCATC-M and GANTC-M) from potential restriction-modification systems in *M. mycoides* LC were codon optimized for expression in yeast. These sequences were then constructed from multiple overlapping 60 bp oligonucleotides using a one-step isothermal DNA assembly method, described in Gibson et al., *Nature Methods* 6, 343-345 (2009) and in U.S. patent application Ser. No. 12/371,543, filed Feb. 19, 2009, by the concerted action of a 5' exonuclease, a DNA polymerase, and a DNA ligase. Briefly, with this method, DNA fragments are first recessed by the 5' exonuclease, yielding single-stranded overhangs, which then specifically anneal, followed by gap-filling and covalent joining using the polymerase and the ligase. After construction, the CCATC-M, CCTTC-M and TypeIII-M sequences were cloned into the pTYB1expression vector (New England Biolabs, Ipswich, Mass.; SEQ ID NO:156). The GCATC-M and GANTC-M sequences were cloned into an N-terminal His tag expression vector with GATEWAY® recombination cloning technology (Invitrogen, Carlsbad, Calif.).

b. Methylase Purification

CCATC-M CCTTC-M Expression Plasmids

The CCATC-M and CCTTC-M expression plasmids were transformed into BL21(DE3) codon plus cells (Stratagene, La Jolla, Calif.) and transformants were used to separately inoculate 250 ml of ZYM-505 medium (Studier, F W, *Protein Expr Purific* 41:207-34 (2005)) containing 100 mg/ml carbenicillin and 34 mg/ml chloramphenicol and grown at 37° C. with vigorous shaking (315 rpm). After approximately 4 hours, the cultures were transferred to 16° C. and expression was induced by the addition of 0.3 mM IPTG, overnight. The cells were pelleted, suspended in 50 ml Intein lysis buffer (25 mM HEPES-NaOH pH 7.2, 500 mM NaCl, 1 mM EDTA, 10% glycerol, plus protease inhibitors (Complete protease inhibitor cocktail, Roche Applied Sciences, Indianapolis, Ind.)) and lysed by two passages through a high-pressure homogenizer.

The lysates were clarified by centrifuging at 20,000×g for 20 minutes at 4° C. The clarified lysates were purified on a 1.5 ml column of chitin beads as suggested by the manufacturer (New England Biolabs, Ipswich, Mass.). Fractions containing the appropriate methyltransferases were pooled and dialyzed against Enzyme buffer (50 mM HEPES-NaOH pH 7.2, 50 mM NaCl, 0.1 mM EDTA, 10% glycerol). Following dialysis, the methyltransferases were concentrated using an Amicon Ultra Centrifugal Filter Unit (Millipore, Billerica, Mass.).

TypeIII-M

The TypeIII-M protein was purified using the same protocol, with the exception that after purification on the chitin column, the protein was further purified using a HiTrap MonoQ column (GE Healthcare). The protein was loaded in Buffer A (50 mM HEPES-NaOH pH 7.2, 50 mM NaCl, 1 mM EDTA, 10% glycerol) and eluted with a linear gradient from 0-100% Buffer B (50 mM HEPES-NaOH pH 7.2, 1M NaCl, 1 mM EDTA, 10% glycerol). The fractions containing TypeIII-M were pooled, dialyzed into Enzyme buffer containing 100 mM NaCl and concentrated as described for the CCATC-M and CCTTC-M proteins.

GCATC-M and GANTC-M Expression Plasmids

The M.GCATC and M.GANTC expression plasmids were transformed into BL21(DE3) codon plus cells and transformants were used to separately inoculate 2 ml of ZYM-505 medium containing 100 mg/ml carbenicillin and grown at 37° C. with vigorous shaking overnight. One milliliter of the overnight culture was used to inoculate 250 ml of ZYM-5052 media (Studier, F W, *Protein Expr Purific* 41:207-34 (2005)). Cells then were grown for 20 hrs at 27° C. with vigorous shaking. The cells were pelleted, suspended in 50 ml Nickel lysis buffer (50 mM HEPES-NaOH pH 7.2, 500 mM NaCl, 30 mM imidazole, 10% glycerol, plus protease inhibitors (Complete protease inhibitor cocktail, Roche Applied Sciences, Indianapolis, Ind.)) and lysed by two passages through a high-pressure homogenizer. The lysates were clarified by centrifuging at 20,000×g for 20 minutes at 4° C. The clarified lysates were purified using a 5 ml HisTrap column with Nickel lysis buffer as the running buffer and Nickel lysis buffer with 300 mM imidazole as the elution buffer. The M.GCATC protein was pooled, dialyzed into Enzyme buffer containing 100 mM NaCl and concentrated as above. The M.GANTC protein was further purified using a 1 ml HiTrap MonoQ heparin column utilizing Buffers A and B as for the M.TypeIII. The M.GANTC containing fractions were pooled, dialyzed into Enzyme buffer containing 100 mM NaCl and concentrated as described above.

c. Methyltransferase Studies

The purified methyltransferases were used in methylation assays to determine whether they could methylate a plasmid containing *Mycoplasma* DNA. The methylation assays were performed using buffer conditions described by Wilson and Hoffman, *Anal Biochem* 191, 370 (December, 1990). Reactions were performed in 100 μl volumes, at 37° C. Reaction mixtures contained 100 mM Tris-HCl, pH 7.5, 10 mM EDTA, 3 μM DTT, 200 μM S-adenosylmethionine (SAM), 3 μg pSmart-pMYCO1 plasmid DNA (yeast-*E. coli-Mycoplasma* tri-shuttle vector).

To evaluate whether DNA had been methylated by the purified methyltransferases, 4 μl of each sample was cleaved using restriction enzyme isoschizomers, purchased from New England Biolabs, according to the manufacturer's instructions. The restriction enzyme isoschizomer used depended on the sequence being evaluated for methylation (BccI (recognition site, CCATC), HinfI (GANTC), HpyAV (CCTTC), SfaNI (GCATC). Samples were run on 1% 48-well agarose E-gels (Invitrogen, Carlsbad, Calif.) at 70V for 25 minutes. Gels were scanned on a GE Typhoon 9410 imager.

The results demonstrated that the individual purified methyltransferases were capable of completely methylating *Mycoplasma* plasmid DNA, as judged by the complete inability of the corresponding restriction enzyme isoschizomers to cleave the plasmid DNA after incubation with the individual methyltransferases (see Table 10) and S-adenosylmethionine (SAM) (gel data not shown).

In another study, the *M. mycoides* crude extract was used to treat pMYCO1 plasmid DNA with or without SAM. The DNA was then digested by BccI to examine the activity of the methyltransferase in the extract (data not shown). An extract of *M. mycoides* also protected the incoming donor DNA. The additional restriction-modification systems present in the *M. mycoides* donor genome did not affect transplantation.

ii. Methylation by Crude Extracts

In order to eliminate the possibility of cleavage, even after methylation, by enzymes from unidentified restriction-modification systems not identified in the genomic sequences (and thus not addressed by the purified methylases), a protocol was developed for methylating DNA using crude extracts prepared from *M. capricolum* and *M. mycoides* LC. The extracts can be used as a source of methyltransferase activity by the addition of 10 mM EDTA, which inhibits nucleases.

a. Preparation of Cell Extracts

For *M. mycoides* LC, a 1 liter culture of the cells in SP4 medium was grown at 37° C. until a pH of 6.2-6.3 was reached. The culture was harvested by separating the cells into 5×200 ml fractions and centrifuging at 5,000×g in a SLA-1500 Sorvall rotor at 4° C. for 15 minutes. Each *M. mycoides* LC pellet was then washed with 200 ml of 8 mM Hepes, pH 7.4, and 272 mM sucrose and centrifuged at 5,000×g in a SLA-1500 Sorvall rotor at 4° C. for 15 minutes. Each resulting pellet was resuspended in 1 ml Extract buffer (20 mM Tris-HCl, pH 7.5, 0.1 mM EDTA, 150 mM NaCl, 1 mM DTT, and 10% glycerol) and subsequently sonicated on ice 5 times with 10-12 seconds bursts using a microtip at an output control of 3. Each solution was clarified by microcentrifugation at 18,000×g for 30 minutes at 4° C. Each resulting soluble fraction was combined, tested for protein concentration, aliquoted into 200 μl fractions and stored at −80° C. Protein concentration of extracts prepared in this manner typically ranged from 15 to 25 mg/ml.

For *M. capricolum*, extracts were prepared using the same method described for *M. mycoides* LC, except that the 1 liter culture was grown in SP4 medium containing 10 μg/ml of tetracycline.

b. Assessing Methylation by Crude Extracts

Methylation assays were used to demonstrate the ability of the crude extracts to methylate *Mycoplasma* plasmid DNA grown in various host cells, as follows. The methylation assays using crude extracts were performed using buffer conditions described by Wilson and Hoffman, *Anal Biochem* 191, 370 (1990).

c. Evaluating Methylation of CCATC, GANTC, CCTTC, AND GCATC by *M. mycoides* LC Extracts To evaluate methylation (and thus protection) of CCATC, GANTC, CCTTC, and GCATC sites by *M. mycoides* LC extracts, reactions were performed in 100 μl volumes, at 37° C. Reaction mixtures contained 100 mM Tris-HCl, pH 7.5, 10 mM EDTA, 3 μM DTT, 200 μM S-adenosylmethionine (SAM) (absent in control samples, as indicated) 3 μg of pMYCO1 plasmid DNA (SEQ ID NO:149)), isolated from *E. coli* and 20 μg of *M. mycoides* LC extracts.

At 0, 2-, 4-, and 16-hour time intervals, a 20 μl aliquot was removed from each reaction mixture and added to 2× stop buffer (2% SDS, 20 mM EDTA). DNA extraction was performed on each aliquot, using 40 μl phenol/chloroform/isoamylalcohol (25:24:1), followed by centrifugation at 18,000×g for 2 minutes at room temperature. Each aqueous phase was placed into a fresh tube and DNA was precipitated by adding 80 μl of ice-cold 100% ethanol and 1 μl of Ambion® GlycoBlue™ (Invitrogen, Carlsbad, Calif.) and incubating at −20° C. overnight. Each sample was then centrifuged at 18,000×g for 15 minutes at 4° C. and each resulting pellet was washed with 100 μl of ice-cold 70% ethanol. After centrifugation at 18,000×g for 5 minutes at 4° C., each supernatant was discarded, and each pellet dried and resuspended in 20 μl of TE pH 8.0.

To evaluate whether DNA had been methylated by respective Type II methyltransferases, 4 μl of each sample was cleaved using restriction enzyme isoschizomers, purchased from New England Biolabs, appropriate for the particular sequence being evaluated, according to the manufacturer's instructions (BccI (recognition site, CCATC), HinfI (GANTC), HpyAV (CCTTC), SfaNI (GCATC). Samples were run on 1% 48-well agarose E-gels (Invitrogen) at 70V for 25 minutes. Gels were scanned on a GE Typhoon 9410 imager.

d. Evaluating GATC Site Methylation by *M. mycoides* LC Extracts

When testing for GATC methylation by *M. mycoides* LC extracts, the above protocol was modified by using 3 μg of pMYCO1 plasmid DNA isolated from *M. capricolum* in the first step and cleaving with MboI restriction isoschizomer.

e. Evaluating CCATC Site Methylation by *M. capricolum* LC Extracts

Methylation of CCATC sites by *M. capricolum* extracts was tested as above, except that 3 μg each of pSmart-pMYCO1 plasmid DNA (yeast-*E. coli-Mycoplasma* tri-shuttle vector), isolated from *E. coli*, and pMYCO1 isolated from *M. capricolum* and *M. mycoides* LC were used, and the reactions were carried for 4 hours in the presence or absence of S-adenosylmethionine. The methylated DNA was then checked by incubating with BccI as above.

f. Results

The *M. capricolum* crude extract was able to completely methylate the two plasmids isolated from *E. coli*, evidenced by the fact that the corresponding restriction enzyme isoschizomer, BccI, was unable to cleave the plasmids that had been incubated with crude extract and SAM (gel data not shown).

The results of the study assaying for methylation (and thus protection) of CCATC, GANTC, CCTTC, GCATC, and GATC sites by *M. mycoides* LC extracts are as follows: *M. mycoides* LC extract was able to completely methylate *Mycoplasma* plasmid DNA in the case of 4 restriction-modification systems, and only partially in the case of 1 system (the GATC restriction-modification system) (gel results not shown). Because the endogenous *M. mycoides* LC GATC methyltransferase showed low activity in the *M. mycoides* LC extract, the commercially available *E. coli* dam methyltransferase (New England Biolabs, Ipswich, Mass.) was used to successfully supplement its activity.

Methylation of the *Mycoplasma* plasmid DNA by both crude extracts dramatically increased transformation efficiency in *M. capricolum* (data not shown), indicating that incubation with crude extracts in the provided methods can help overcome potential incompatibility of donor genomes propagated in yeast cells that are being transplanted into *M. capricolum* recipients. Effectiveness of Type III methyltransferase was not evaluated in the *M. mycoides* LC crude extract because its site-specificity is unknown.

iii. Increased Transformation Efficiency with Methylation

Unmethylated plasmids, and plasmids methylated with the *M. mycoides* LC extract, as described above, were transformed into *M. capricolum* cells, and compared. The results indicated an increased transformation efficiency of the methylated plasmids, demonstrating a positive effect of DNA modification prior to transformation.

iv. Additional Analysis, Confirmation Effects and Treatment of DNA after Methylation Although crude extracts protected donor plasmid DNA from host restriction-modification system and increased efficiency of transformation, crude extracts also completely inhibited genome transplantation experiments involving native *M. mycoides* LC genomic DNA isolated in agarose plugs and *M. capricolum* cells (See Example 3, below).

To study the inhibition in more detail, endogenous *M. mycoides* LC genomic DNA, isolated in agarose plugs (prepared as described in Example 2B(ii), above), in the absence or presence of *M. capricolum* or *M. mycoides* LC *Mycoplasma* crude extracts (prepared as in Example 2E(ii)(a) above), was analyzed by fluorescence microscopy. *M. mycoides* LC genomic DNA agarose plugs were melted with β-agarase I, as described above (Example 2C(ii)). 2 μl diluted (1/2000) SYBR® Gold nucleic acid gel stain (Invitrogen, Carlsbad, Calif.) was then gently mixed to 5 μl of melted agarose, and let stand for 5 minutes at room temperature. The mixture was dropped onto a glass slide and covered with a coverslip.

*M. mycoides* LC genomic DNA then was visualized using an upright Axioskop® 2 microscope (Carl Zeiss, Inc) (with objective lens (100×); rhodamine filter), equipped with an AxioCam® MRc5 color camera (Carl Zeiss, Inc, Thornwood, N.Y.). Fluorescence microscopic images were acquired and analyzed with AxioVision release 4.7.1 software from Carl Zeiss, Inc. FIG. 7A illustrates initial treatment of the agarose plugs and the result of untreated agarose plugs. Results of methylation and deproteinisation steps are presented in FIGS. 7B-7C, respectively, in which samples and treatment are indicated above pictures.

As shown in FIG. 7B, native genomic DNA treated in the absence of crude extracts (shown to allow transplant into recipient cells) displayed a punctate pattern (right panel), while endogenous genomic DNA treated in the presence of crude extracts (shown to inhibit transplant) formed large aggregates (left two panels). This result suggested that conformation of DNA is important for transplantation experiments.

To confirm that confirmation was important, samples were treated with proteinase K to remove cell extracts after treatment, as follows. Each yeast plug was incubated for 4 h at 50° C. in 1 mL of Proteinase K Reaction Buffer [100 mM EDTA; 0.2% Sodium Deoxycholate; 1% Sodium Lauryl Sarcosine; pH8.0], supplemented with 40 μl Proteinase K. The plugs were then were washed 4 times, 45 minutes each, with 1 ml 1×TE buffer (20 mM Tris-HCl pH 8; 50 mM EDTA) and 2 times, 30 minutes each, in 0.1×TE buffer with soft agitation at room temperature. After removing the final wash buffer, the plugs were melted with β-agarase I and analyzed by fluorescence microscopy as described above. The results are presented in FIG. 7C, which shows that removal of the crude extracts by proteinase K treatment after incubation with the genomic DNA in agarose plugs restored the punctate pattern originally observed with the untreated genomic DNA. Further, as described below (Example 3), proteinase K treatment to some extent restored the transplantation efficiency of native genomic DNA that had been treated with crude extracts. Thus, removal of proteins in crude cell extracts (e.g., by proteinase K treatment) provided a means by which *M. mycoides* LC donor genomic DNA isolated from yeast host cells could be methylated using crude extracts, and still be successfully transplanted into recipient cells.

Example 2F

Mutation of R-M Systems (Generation of *M. capricolum* ΔRE)

Another method was employed as a means to overcome restriction barriers between host cells and recipient cells. In this method, the single restriction enzyme identified in *M. capricolum* (See Example 2D(i) and Table 3, above) was inactivated by interruption of the coding region of the gene. The restriction enzyme gene was interrupted by integration of a puromycin resistance marker into the coding region of the gene.

The heterologous pSD4 *Spiroplasma citri* oriC plasmid (SEQ ID NO:150) has been shown to transform *M. capricolum* (Lartigue, C. et al. *Nucleic Acids Res.* 31:6610-8 (2003)). This plasmid is efficient for integration of foreign sequences and for targeted mutagenesis in the *M. capricolum* genome. To inactivate the potential restriction enzyme gene (MCAP0050) in *M. capricolum*, an internal fragment of the gene was amplified from *M. capricolum* genomic DNA using oligonucleotides RE-Mcap-F (5'-gatc tctagactaatgttcaattggatgatata G-3' (SEQ ID NO:157)) and RE-Mcap-R (5'-gatctctagactcaagtcttgtaggagaatc-3' (SEQ ID NO:158)) that include a XbaI site. The fragment was then cleaved by XbaI and cloned into an XbaI cleaved pSD4 plasmid (SEQ ID NO:150), yielding pSD4-ΔMcap0050.1 (SEQ ID NO:159). Ten micrograms of this plasmid was used to transform wild type *M. capricolum* cells using the 5% PEG mediated protocol, described in Example 2C, above. Transformants were selected on solid SP4 plates containing 4 μg/mL tetracycline. After 7 days of incubation at 37° C., several colonies were picked in liquid medium containing 10 μg/ml tetracycline and cells were propagated for 15 passages (15P). Clones then were analyzed by Southern blot to verify the presence of the plasmid and its possible integration at the target gene by homologous recombination via a single crossing-over.

One clone, *M. capricolum* ΔRE clone 10 15P, was selected because (as evidenced by Southern blot) its hybridization pattern demonstrated the interruption of MCAP0050 gene by the plasmid. No free plasmid was detected. Centrifuge-clarified lysate extracts also were prepared as described in 2D(ii)(b), and used in the restriction enzyme assay described in Example 2D(ii). The results revealed a complete absence of restriction enzyme activity in clone 10 15P clone compared to wild type *M. capricolum* (data not shown).

Using the method described in Example 2E(ii), above, *M. capricolum* ΔRE clone 10 was used as a source to make crude *M. capricolum* cellular extracts for in vitro methylation experiments. The *M. capricolum* ΔRE clone 10 was not, however, a good candidate recipient cell for transplantation of *M. mycoides* LC because it contained the same resistance marker gene (tetM) as the *M. mycoides* LC donor genomic DNA present in yeast. Accordingly, using the cloning strategy described above, another *M. capricolum* ΔRE mutant was constructed, which carried the YCp and puromycin resistance gene instead of the tetM gene. Centrifuge-clarified lysate extracts were prepared from the *M. capricolum* ΔRE clone 17.5 15P, as described in 2D(ii)(b), and used in the restriction enzyme assay described in Example 2D(ii). The results revealed a complete absence of restriction enzyme activity in clone 17.5 15P clone compared to wild type *M. capricolum. Accordingly, this clone was chosen for transplantation.*

These results demonstrate that removal of the *M. capricolum* restriction activity from recipient cells allows donor *M. mycoides* LC genomic DNA, isolated from yeast, to survive within the *M. capricolum* cytoplasm. Alternatively, as described above, the provided methylation methods can be used to treat the donor DNA prior to transplantation to protect it.

Example 3

Transplantation of *M. mycoides* LC-YCp Genomic DNA from Yeast Host Cells into *M. capricolum*

Example 1, above, describes the successful cloning of complete bacterial genomes (including these *Mycoplasma*) in yeast host cells. This example describes the successful transplantation of whole *Mycoplasma* donor genome (*M. mycoides* LC (Genbank Accession No.: NZ_AAZK00000000; GI: 149364883)) DNA, which had been propagated in yeast host cells, into *Mycoplasma* recipient cells of a different species (*M. capricolum*). The donor and recipient were chosen based on their rapid growth. The method could also be performed, however, using other *Mycoplasma* donors and recipients, such as *M. genitalium* genomes/cells, which are described above. Further, the methods described in this Example can be used in conjunction with steps for modifying the donor genomes in vivo while in the host cell (e.g., using the repertoire of yeast tools during propagation of the bacterial donor genome) prior to transfer. Thus, the methods can be used to genetically engineer donor genomes, such as genomes from bacteria with relatively poorly developed genetic systems.

For example, the methods can be used to generate synthetic cells that contain synthetically engineered genomes. A complete synthetic genome of non-pathogenic strain of *Mycoplasma genitalium* has been synthesized (Gibson et al., *Science* 319:1215-20 (2008); Gibson et al., *PNAS USA* 105: 20404-9 (2008)). In that study, the genome was assembled in the final step as a centromeric plasmid in yeast.

Such synthetically produced and natural genomes (e.g., *Mycoplasma* or other bacterial genomes) propagated in host cells (e.g., yeast host cells) can be transplanted into recipient cytoplasm to generate synthetic cells using the provided methods, such as those described in this Example. For example, to express a bacterial synthetic donor genome (propagated in yeast) in a bacterial recipient, the methods can be used to transplant it from yeast into a bacterial (e.g., *Mycoplasma*) recipient.

As described in Example 2, above, different restriction-modification systems can present incompatibility issues when transplanting a donor genome from a host cell in which it has been propagated to a recipient cell of a different species. In particular, it was determined that upon introduction and propagation of the *M. mycoides* LC genome into yeast host cells (See Example 1, above), it was unlikely that the methyltransferases that are endogenously expressed by these *Mycoplasma* (See Example 2B, above) were expressed in the yeast host cells. This determination was based on the fact that the methyltransferase genes contain UGA tryptophan codons, which are treated as stop codons by the eukaryotic yeast host cells. This determination indicated that *M. mycoides* LC donor genomic DNA, isolated from yeast, would be unmethylated and susceptible to the *M. capricolum* recipient cell restriction-modification system upon transfer into that cell. It was also possible that one or more *M. mycoides* LC restriction enzymes could cleave the donor genome, once expressed following transplantation. Various aspects of the provided methods for overcoming R-M incompatibility issues are described in Example 2, above. Such aspects were selected and used in the following study to achieve successful transplant of donor *Mycoplasma* genomes, propagated in yeast, into *Mycoplasma* recipient cells of a different species.

Example 3A

Transplant Methods

This Example describes the use of these techniques to successfully transplant donor *Mycoplasma* genomes from yeast host cells to *Mycoplasma* recipient cells. FIG. 8 shows three alternative transplantation approaches that can be used to transplant whole genomic DNA. Variations on these three approaches were used in the examples, described below. The first approach (denoted with the number "1" labeling the arrows in FIG. 8), includes digestion of agarose plugs containing the genomic DNA (e.g., with β-agarase (melting step)), followed by transplantation directly into recipient cells. This method is typically used, as shown in FIG. 8, for transplantation of donor genomes or nucleic acids from one cell (e.g., donor *Mycoplasma* cell) into a similar cell, such as from a *Mycoplasma* donor cell into a *Mycoplasma* recipient cell.

The second approach (denoted with the numbers "2") is identical to the first method, except that recipient cells had been modified to mutate the restriction enzyme genes (ΔRE; generated as described in Example 2F, above). With this approach, as indicated in FIG. 8, genomic *Mycoplasma* DNA grown in yeast host cells and isolated in yeast plugs can successfully be transplanted into *Mycoplasma* recipient cells. With the third approach (denoted with the numbers "3" in FIG. 8), samples were methylated and subjected to a deproteinisation step (treatment with proteinase K), prior to the melting step (β-agarase digestion) and transplantation into recipient cells. As indicated in the figure, the methylation and deproteinisation steps also facilitate efficient transplant of donor *Mycoplasma* genomes, isolated after propagation in yeast, into *Mycoplasma* recipient cells. As described below, control studies included conditions similar to the third approach, where samples were treated in parallel, under the same conditions, without the presence of methylases ("mock methylation"). These approaches and the results obtained with each are described in detail below.

i. Preparation of Agarose Plugs

In each approach, *M. mycoides* LC genomic DNA was isolated in agarose plugs from yeast strain VL6-48N (described by Larionov et al., *PNAS USA* 94:7384-7 (1997)), as follows.

Yeast cells containing the *M. mycoides* LC genomic DNA (generated as described in Example 1A) were grown at 30° C. in selective medium until the OD reached approximately 1.5; control cells not containing the donor genome were grown under the same conditions. Agarose plugs were prepared from each cell type, using the CHEF mammalian Genomic DNA Plug Kit (Bio-Rad Laboratories, Valencia, Calif.), following the instructions recommended by the manufacturer for yeast (eukaryotic) DNA extraction, with the following modifications. $6\times10^9$ yeast cells were used per plug, (instead of $6\times10^8$ cells, as recommended by the kit), to yield $6\times10^8$ cells per plug, in order to increase the amount of *M. mycoides* LC genomic DNA available per plug. After embedding the cells in the plugs, to digest the cell walls, Zymolyase™ 100T enzyme (USB Corporation, Cleveland, Ohio) was used instead of Lyticase (Bio-Rad Laboratories, Valencia, Calif.). The enzyme was added inside and outside of the plugs at a concentration of 5 mg/ml and let stand for 2 hours at 37° C.

After a wash in 1×TE buffer (20 mM Tris-HCl pH 8; 50 mM EDTA), embedded yeast cells were lysed and proteins digested by two incubations of 24 h at 50° C. with 5 ml of Proteinase K Reaction Buffer [100 mM EDTA; 0.2% Sodium Deoxycholate; 1% Sodium Lauryl Sarcosine; pH8.0] supplemented with 200 μl of Proteinase K, per ml of plug. The agarose plugs then were washed at room temperature, 4 times, 1 hour each, with 40 ml of 1×TE buffer with agitation and stored in the same buffer at 4° C. For yeast plugs that would subsequently be digested with restriction enzymes (see below), 1 mM of phenylmethanesulfonylfluoride (PMSF) was added during the second wash.

Clean-Up

Prior to these studies, it was unknown whether yeast genomic DNA, isolated along with the *M. mycoides* LC donor genomic DNA extracted from yeast, would affect or abrogate transplantation reactions. Accordingly, with each approach, two sets of donor genomic DNA were prepared, one of which was submitted to the optional "clean-up" step after digestion of cell walls and proteinase K treatment. The "clean-up" step was designed to remove yeast genomic DNA from the samples.

The "clean-up" samples were either treated with a cocktail of restriction enzymes that specifically digests yeast genomic DNA and then cleared of small yeast DNA fragments by electrophoresis or directly loaded on Pulse Field agarose gel to separate circular genomes that are being caught into the well, and linear yeast chromosomes that are electrophoresed out of the well (Lartigue et al., *Science* 317, 632 (2007).

For clearing with the cocktail of enzymes, yeast plugs were washed two times, 1 hour each, in 1 ml of 0.1×TE buffer (2 mM Tris-HCl pH 8.0-5 mM EDTA), equilibrated 1 h in 1 ml of 1×NEB buffer 2 (New England Biolabs, Ipswich, Mass.) supplemented with BSA, and the genomic DNA present in the plug was digested over-night with 50 units of restriction enzymes cocktail (AsiSI, RsrII and FseI) in a 500 μl reaction volume. The yeast plugs were washed at room temperature for 1 hour with 1 mL of 1×TE buffer (20 mM Tris-HCl pH 8.0-50 mM EDTA) and loaded on 1% TAE agarose gel (120 minutes, 120 volts). Agarose plugs were removed from the well and stored at 4° C.

For clean-up via electrophoresis alone, the other yeast plugs were subjected to electrophoresis in a 1% LMP gel in TAE 1×, with contour-clamped homogeneous electric field (6) (CHEF DR III; Bio-Rad). Pulse times were ramped from 60 to 120 s over 24 h at 3.5 V/cm. After migration, plugs were removed from the wells and stored in 1×TE buffer at 4° C.

ii. General Transplantation Method

With each approach, transplantation proceeded as follows, with the exception that with the third approach, samples were subject to methylation and proteinase K treatment prior to melting with β-agarase, as described in the Example 3A(iii), below.

a. Recipient Cells

Twelve (12) mL of *M. capricolum* recipient cells (wild-type or ΔRE (as produced in Example 2F)) were grown in SOB(+) medium (Bacto SOB medium (Becton Dickinson, Franklin Lakes, N.J.) supplemented with fetal bovine serum (17%), glucose (10 g/l), 2 ml of phenol Red (1%) and 100 μl of Penicillin G (5 mg/ml)) until the pH of the culture reached pH 5.7 to 5.85 (approximately $5\times10^7$ cells/ml). The recipient cells were centrifuged at 4575×g for 15 minutes at 10° C., washed once in 6 mL S/T buffer (Tris-HCl 10 mM pH 6.5; NaCl 250 mM), resuspended in 400 μl of $CaCl_2$ (0.1 M) and incubated on ice for 30 minutes.

b. Preparation of Isolated Donor Genomic DNA in Agarose Plugs

Before transplantation, the agarose plugs, prepared as described in Example 3A(i)(a), above, containing *M. mycoides* LC genomic DNA from yeast, were washed 2 times, for 30 minutes each, in 0.1×TE buffer [Tris-HCl 2 mM pH 8.0, EDTA 5 mM] under gentle agitation at room temperature. The buffer was completely removed and the agarose plugs were melted with 1/10 volume of 10×β-Agarase Buffer [10 mM Bis Tris-HCl pH 6.5; 1 mM $Na_2EDTA$] at 65° C. for 10 minutes. The molten agarose was cooled down to 42° C., for 10 minutes, and incubated overnight at this temperature with 3 units of β-Agarase I (New England Biolabs, Ipswich, Mass.) per 100 μl of plug. As described in Example 3A(i)(c), below, methylation and proteinase K treatment were performed before β-Agarase treatment in the third approach (FIG. 8 ("3")).

c. Transplantation in the Presence of 5% PEG

After 30 minutes on ice, 400 μl of the recipient cells were gently mixed with 800 μl of SP4 (−) medium [0% fetal bovine serum, 0.45% NaCl], containing 100 µl of melted donor genomic DNA agarose plugs as generated in Example 2B(ii) above. The plugs were added immediately before proceeding to the next step, as follows.

Thirteen hundred (1300) µl of 2× fusion buffer (20 mM Tris-HCl pH6.5, 250 mM NaCl, 20 mM MgCl$_2$, 10% PEG-6000 from Fluka] was immediately added to the mixture of SP4(−), genomic DNA and cells and the mixture homogenized by rocking the tube gently for 30 seconds. After 50 minutes at 37° C., 10 ml of pre-warmed SP4 is added and cells were gently mixed. After another 3 hours at 37° C., cells were centrifuged at 4575×g for 15 minutes at 10° C., resuspended in 1.2 mL of SP4 and plated on SP4 plates containing 4 µg/ml of tetracycline and 150 µg/ml of X-gal (two plates per sample). After 3-4 days, individual colonies were picked and grown in broth medium containing 10 µg/ml of tetracycline.

iii. Methylation and Proteinase K Digestion (Specifics of the Third Approach)

With the third approach (FIG. 8, "3"), prior to melting with β-Agarase, *M. mycoides* LC genomic DNA from yeast agarose plugs was methylated, followed by a deproteination step. For this process, the plugs were washed two times 30 minutes in 200 mM Tris-HCl pH 7.5; 50 mM EDTA and equilibrated two times 30 minutes in methylation buffer (100 mM Tris-HCl pH 7.5; 10 mM EDTA, 3 µM DTT, 200 µM S-adenosyl-methionine) with soft agitation. Following equilibration, each yeast plug was cut into 4 pieces and added to 100 µl methylation reaction (1× methylation buffer plus methyltransferases) and incubated 16 hours at 37° C. For 100 µl of reaction, either 5 µl of wild type *M. mycoides* LC cellular extracts, or 7.5 µl of *M. capricolum* ΔRE (clone 10 15P) cellular extracts (approximately 125 μg protein) or 2.5 μl of each purified *M. mycoides* LC specific methyltransferases (M.GANTC, M.CCATC, M.GCATC, M.CCTTC, M.Type III). Each cell extract was prepared as described in Example 2E(ii), above and purified methyltransferases were prepared as described in Example 2E(i), above. The methylation reactions containing *M. mycoides* LC cellular extracts or purified methyltransferases were also supplemented with 5 μl of dam methyltransferase (New England Biolabs, Ipswich, Mass.).

Following methylation, each yeast plug was incubated for 4 hours at 50° C. in 1 mL Proteinase K Reaction Buffer [100 mM EDTA; 0.2% Sodium Deoxycholate; 1% Sodium Lauryl Sarcosine; pH8.0] supplemented with 40 μl of Proteinase K.

The plugs were then washed 4 times 45 minutes with 1 ml of 1×TE buffer (20 mM Tris-HCl pH 8; 50 mM EDTA) and 2 times 30 minutes in 0.1×TE buffer with soft agitation at room temperature. After removing the final wash buffer, the plugs were melted with β-Agarase I as described in section (b), above, followed by transplantation.

Example 3B

Study Demonstrating Successful Transplantation Using the Provided Methods

Using the general method described in Example 3A, above, transplantation of *M. mycoides* LC genomic donor DNA from yeast host cells into wild-type and restriction enzyme-deficient *M. capricolum* recipient cells was carried out, under the following conditions listed in Table 11. "Untreated" samples were not methylated, nor treated with proteinase K, prior to melting. "Mock-methylated" samples were incubated under the same conditions as methylated samples, without enzymes or cell extracts. Methylation treatments included methylation with donor or recipient cell extract and methylation with purified methylases.

TABLE 11

| Transplantation conditions | | |
|---|---|---|
| Recipient cells | Sample | Methylation Treatment |
| Wild-type *M. capricolum* | 1 | untreated |
| | 2 | *M. mycoides* LC extracts |
| | 3 | *M. mycoides* LC purified methylases |
| | 4 | *M. capricolum* extracts |
| | 5 | Mock-methylated |
| *M. capricolum* ΔRE | 6 | untreated |
| | 7 | *M. mycoides* LC extracts |
| | 8 | *M. mycoides* LC purified methylases |
| | 9 | *M. capricolum* extracts |
| | 10 | Mock-methylated |

Results were scored by selecting for growth of blue colonies on SP4 medium containing tetracycline at 37° C. and are presented in Table 12A, below. As indicated in that table, for methylation with *M. mycoides* extracts and transplanted into wild-type cells (sample 2), some samples were cleaned-up to remove yeast DNA, as described above, either by digestion with yeast-specific enzymes (b) or by electrophoresis (c).

TABLE 12A

| Quantification of transplant colonies with donor phenotype | | | | |
|---|---|---|---|---|
| Yeast strain | Genome | Methylation treatment | Number of transplants from recipient cells (colonies/plugs)[a] *M. capricolum* RE(—) | Wild-type *M. capricolum* |
| VL6-48N | clYCp1.1 | Untreated | 37 ± 3 | 0 |
| | | *M. capricolum* extracts | 32 ± 13 | 9 ± 4 |
| | | *M. mycoides* LC extracts | 15 ± 8 | 22 ± 8 [13 ± 4][b] [10 ± 4][c] |
| | | Mock-methylated | 34 ± 17 | 0 |
| W303a | clYCp1.1 | Untreated | 22 ± 5 | Not done |
| | ΔtypeIIIres::URA3 | Untreated | 52 ± 10 | Not done |
| | ΔtypeIIIres | Untreated | 52 ± 12 | Not done |
| | Δ500kb | Untreated | 0 | Not done |

[a]Average of at least three experiments. The error reported is the mean deviation.

[b]Yeast plugs have been cleared of yeast genomic DNA using AsiSI, RsrII, FseI cocktail restriction enzymes protocol.

[c]Yeast plugs have been cleared of yeast genomic DNA using Pulse field gel electrophoresis protocol.

As shown in Table 12A, above, in the samples that were methylated using the M. mycoides LC extracts or purified methylases, and transplanted into either wild-type or ΔRE recipient cells (samples 2, 3, 7, and 8), colonies were obtained that were phenotypically similar (based on similar appearance and growth rate) to M. mycoides LC (as described by Lartigue et al., (2007) Science 317:632-8.(6)). This result confirmed that the *M. mycoides* LC donor genome that had been propagated in yeast was resistant to both restriction enzymes produced from *M. mycoides* LC, and enzymes produced by the recipient cell system.

On the contrary, transplantation of mock-methylated and untreated *M. mycoides* LC genomes produced donor-phenotype colonies only in the case of *M. capricolum* ΔRE recipient cells (samples 6 and 10) and not in the case of wild-type recipient cells (samples 1 and 5). For example, thirty-four and thirty-seven colonies, respectively, were obtained when the mock-treated and untreated donor genomic DNA was transplanted into the *M. capricolum* ΔRE recipient cells (samples 6 and 10). However, no colonies were obtained when either mock-treated or untreated *M. mycoides* LC genomic DNA were transplanted into wild-type *M. capricolum* recipient cells (Table 12A).

Similarly, colonies were obtained in both recipient cell types with donor genomes treated with the *M. capricolum* extract (samples 4 and 9) (32 and 9 colonies, Table 12A). Because the *M. capricolum* extract provides protection against the *M. capricolum* restriction enzyme, this result demonstrates that avoidance of the *M. capricolum* recipient restriction system was important for successful transformation of the *M. mycoides* LC donor genomes, propagated in yeast cells. The fact that inactivation of the *M. capricolum* restriction system (*M. capricolum* ΔRE recipient cells) was sufficient to allow successful transplantation and activation of the *M. mycoides* donor genome suggested that inactivation of this recipient cell restriction system also was sufficient for these events. Thus, donor *M. mycoides* LC restriction systems (which could have been activated upon transplantation into the recipient cells) did not appear to constitute a barrier to transplantation of the donor genome from yeast into *M. capricolum* recipient cells.

Recovery of colonies in the transplantation experiments was dependent on the presence of *M. capricolum* recipient cells, as no colonies were observed when recipient cells were omitted from the reactions. Moreover, the transplantation experiments were also dependent on a *M. mycoides* LC genome from yeast, as no colonies were obtained when only yeast genomic DNA or YCp plasmid from yeast was used as donor DNA. Southern blots confirmed that the recipient cell colonies having received the donor genomes from yeast were of the *M. capricolum* and *M. mycoides* LC genotype.

Without "clean-up," yeast DNA was present in samples containing genomic DNA. Purifying the donor genomic DNA away from yeast genomic DNA (denoted by "b" and "c" in Table 12A, above) did not substantially alter transplantation results, demonstrating that the recipient *M. capricolum* cells were able to tolerate the presence of non-specific or carrier DNA (Table 12). In addition, positive transplantation results were obtained with donor genomic DNA isolated from two different yeast strains (VL6-48N and W303a), indicating that the genotype and/or phenotype of the host yeast strain may not be important for transplantation experiments.

Taken together, these results demonstrate the capacity of *M. capricolum* cells to activate a phenotypically dormant *M. mycoides* LC genome from yeast, leading to the generation of living *M. mycoides* LC cells, and thus that the provided methods can be used to transplant a whole prokaryotic genome, grown in a eukaryotic host cell, into a recipient prokaryotic cell of a different species than either the donor or the host.

Transplantation of the non-methylated *M. mycoides* LC genome from yeast into the *M. capricolum* ΔRE recipient cells confirmed that the transformed, selected, recipient cells contained donor genomes and were not selected due to the presence of some *M. mycoides* LC component other than genomic DNA. This confirmation was due to the fact that no *M. mycoides* LC cells or components other than genomic DNA were present during transformation.

In another example, YCpMmyc1.1, as well as the engineered YCp genomes (YCpMmyc1.1-ΔtypeIIIres::URA3 and YCpMmyc1.1-ΔtypeIIIres), were also isolated from yeast strain W303a. Transplantation of all three YCp genomes into *M. capricolum* recipient cells resulted in similar numbers of tetracyclineresistant blue colonies (Table 12B). The large deletion clone (YCpMmyc1.1-Δ500 kb) discussed above served as an appropriate control because it lacks many presumed essential genes yet retains the YCp element and tetM. As expected, no colonies were recovered when this genome was transplanted into *M. capricolum* recipient cells.

Recovery of colonies in all these transplantation experiments was dependent on the presence of both *M. capricolum* recipient cells and an *M. mycoides* genome. The experiments described here used donor YCp genome DNA that included yeast genomic DNA. However, purifying the donor YCp genome DNA away from yeast genomic DNA did not substantially alter transplantation results, which indicates that the recipient *M. capricolum* cells are able to tolerate the presence of non-specific or carrier DNA (Table 12B). Positive transplantation results were obtained with donor YCp genome DNA isolated from four independent transformant cultures of strain VL6-48N and four of strain W303a. Thus, bacterial genomes can be stably cloned in both yeast strains. Verification that the recovered colonies were *M. mycoides* was done by Southern blot analysis using an *M. mycoides*-specific IS1296 element as probe (data not shown). It was shown that the Type III restriction gene was deleted in the engineered bacterium by PCR by Southern blot analysis using the Type III restriction gene sequence as probe (data not shown), and by sequencing the locus (FIG. 17).

TABLE 12B

| Yeast strain | Genome | Methylation treatment | Number of transplants (colonies or plugs) *M. capricolum* RE(—) | Number of transplants (colonies or plugs) Wild-type *M. capricolum* |
|---|---|---|---|---|
| VL6-48N | YCpMmyc1.1 | Untreated | 37 ± 3 | 0 |
| | | *M. capricolum* extracts | 32 ± 13 | 9 ± 4 |
| | | *M. mycoides* extracts | 15 ± 8 | 22 ± 8 [13 ± 4]* [10 ± 4]† |
| | | Mock-methylated | 34 ± 17 | 0 |
| | | *M. mycoides* purified methylases | 20 ± 17 | 13 ± 10 |

TABLE 12B-continued

| Yeast strain | Genome | Methylation treatment | Number of transplants (colonies or plugs) M. capricolum RE(—) | Wild-type M. capricolum |
|---|---|---|---|---|
| W303a | YCpMmyc1.1 | Untreated | 22 ± 5 | Not done |
| | YCpMmyc1.1-ΔtypeIIIres::URA3 | Untreated | 52 ± 10 | Not done |
| | YCpMmyc1.1-ΔtypeIIIres | Untreated | 52 ± 12 | Not done |
| | YCpMmyc1.1-Δ500kb | Untreated | 0 | Not done |

*Yeast plugs were cleared of yeast genomic DNA by digestion with a cocktail of Asi St, Rsr II, and Fse I followed by pulsed-field gel electrophoresis.
†Yeast plugs were cleared of yeast genomic DNA by using pulsed-field gel electrophoresis.

Table 12B provides the results of transplantation of *M. mycoides* YCp genomes from yeast into wild-type and RE(−) *M. capricolum* recipient cells. The number of tetracycline-resistant, blue colonies obtained after the transplantation of *M. mycoides* YCp genomes from yeast into *M. capricolum* recipients was counted. Wild-type *M. capricolum* and *M. capricolum* RE(−) transplantation was performed using methods described in FIG. 8. For untreated samples, yeast plugs were digested with β-agarase (melting step) and transplanted into both recipient cells. The treated samples were methylated and treated with proteinase K before the melting step. The mock-methylated sample was treated the same as the methylated samples, except that no extract or purified methyltransferases were added. VL6-48N yeast agarose plugs used in this experiment carried YCpMmyc1.1.W303a yeast agarose plugs carried YCpMmyc1.1, YCpMmyc1.1 that was engineered in yeast (YCpMmyc1.1-ΔtypeIIIres::URA3 or YCpMmyc1.1-ΔtypeIIIres), or YCpMmyc1.1-Δ500 kb. The number of transplants is the average of at least three experiments. The error reported is the absolute mean deviation.

Example 4

Modification of Donor Genomes within Yeast Host Cells

This example describes the use of methods for introducing a seamless modification into a *Mycoplasma* donor genome that has been cloned into a yeast host cell.

The yeast *Saccharomyces cerevisiae* has been developed as a host capable of cloning large DNA fragments, as both linear and circular yeast artificial chromosomes (YACs). Once cloned in yeast, these YACs can be manipulated using standard genetic tools. Transfer of this modified DNA to host cells suitable for expression allows the functional study of genes and their regulation. Cloning of whole bacterial genomes in yeast, and subsequent transplantation of such genomes back into their original cellular environments, has extended this application from the gene to the genome level.

Two-step recombination protocols utilizing counter-selectable markers can be used to modify YACs in yeast (Tucker and Burke (1996) *Nucleic Acids Res,* 24, 3467-3468). In these methods, a counter-selectable marker is first recombined into the YAC and selected for. Next, a new DNA fragment containing the desired alteration is recombined in place of the marker, which is selected against. The most frequently used marker in these procedures is the URA3 gene, which restores Uracil autotrophy in deficient strains. Counter-selection for the replacement of the URA3 gene is performed by treatment with 5-fluoroorotic acid (5-FOA) (Boeke et al., (1984) *Mol Gen Genet,* 197, 345-346). First, the method restores uracil auxotrophy, which can then be used again for a further round of modification. Second, the method creates a seamless modification. This basic method for seamless modification has been improved in a number of ways. The delitto perfetto method introduces a double-strand break (DSB) near the target locus by utilizing the endonuclease I-SceI (Storici et al. (2001) *Nat Biotechnol,* 19, 773-776). The formation of a DSB stimulates the efficiency of homologous recombination repair by several orders of magnitude (Storici et al. (2003) *PNAS USA,* 100, 14994-14999). Another method, referred to as tandem repeat pop-out, creates tandem repeat sequences flanking the target site (Akada et al. (2006) *Yeast,* 23, 399-405). This method requires only one transformation followed by 5-FOA counter-selection, whereas other methods require two transformations. These methods can be adapted for deletions, point mutations, or gene replacement.

The assembling and cloning of a synthetic *M. genitalium* genome as a circular YAC in yeast has been described by Gibson et al. (*Science,* 319, 1215-1220; and Gibson et al. (*PNAS USA,* 105, 20404-20409 (2008)). Yeast can be used as a platform to directly engineer or redesign a synthetic bacterial genome in vivo.

As described in individual sub-sections below, five different site-specific modification methods were performed to modify a target region (target locus) containing a single-based cytidine deletion (309,388) in the CDS139 locus of the synthetic sMgTARBAC37 *M. genitalium* genome that had been introduced into and maintained in yeast host cells, as described by Gibson et al., *Science* 319, 1215 (2008) and U.S. Publication No. 20090275086, by Gibson et al., and as described in Example 1C, above.

The *Saccharomyces cerevisiae* strains VL6-48N (MATα his3-Δ200 trp1-Δ1 ura3-52 lys2 ade2-101 met14) and W303a (MATa ade2-1 ura3-1 his3-11,15 trp1-1 leu2-3,112 can1-100 RAD5), carried the synthetic genome as described by Gibson et al., *Science Id.* and provided in Example 1, above. Yeast cells were grown in standard rich medium (YEPD) and synthetic dextrose (SD) or synthetic galactose (SG) minimal medium (Amberg et al., (2005), "Methods in yeast genetics: A Cold Spring Harbor Laboratory Course Manual," Cold Spring Harbor Laboratory Press, Cold Spring Harbor, N.Y., pp. 230).

The nucleic acid sequences of primers that were used in the various studies described throughout this Example (Example 4) are listed in Table 13. A dash in the primer sequence indicates that the primer was chimeric in structure. Portions of primer sequences that are homologous to *M. genitalium* portions are set forth in lowercase type. Portions of primer sequences that are not homologous to *M. genitalium* are set forth in uppercase type. The I-SceI cleavage site (see below) is set forth in underlined text. In the methods described in this example, all primers were custom-synthesized (Integrated DNA Technologies (IDT)). Primers longer than 60 bp were purified by polyacrylamide gel electrophoresis.

PCR constructs were introduced into the yeast strain containing the *M. genitalium* genome using lithium acetate integrative transformation according to a published method (Gietz et al., *Nucleic Acids Res,* 20, 1425 (1992)), using 2-3 μg PCR product and 25 μg carrier DNA (Salmon testis DNA, Sigma).

TABLE 13

Primers used in mutagenesis studies

| Primer | Sequence (5'-3') | SEQ ID NO: | PCR product or name of primer |
|---|---|---|---|
| Traditional Sequence replacement | | | |
| Ura-F | TTGATTTCGGTTTCTTTGAA (SEQ ID NO: 160) | | 1,066 by URA3 gene fragment |
| Ura-R | GGGTAATAACTGATATAATT (SEQ ID NO: 161) | | |
| Int-Ura-F | gcttctaattactagtgagttaactgataaaatcaaacaacaattaaagt-TTGATTTCGGTTTCTTTGAA (SEQ ID NO: 162) | | URA3 mutagenesis cassette |
| Int-Ura-R | ttaaagcaatggctaaagtacctgaaccacaacaaaggtcaagtgcagt t- GGGTAATAACTGATA (SEQ ID NO: 163) | | |
| Amp-F | caatattggaacactatggt (SEQ ID NO: 164) | | 328 by *M.genitalium* wild-type fragment |
| Amp-R | acatcaagtgtatcacactt (SEQ ID NO: 165) | | |
| Seq-F | gttagtttaccaatccagtc (SEQ ID NO: 166) | | Diagnostic primers |
| Seq-R | aatgcttggatatcaatatc (SEQ ID NO: 167) | | |
| Delitto perfetto | | | |
| Gal-F | ACGGATTAG AAGCCGCCGAG (SEQ ID NO: 168) | | 1,184 by GAL1/I-SceI fragment |
| Sce-R | GATCTGACTTATTATTTCAG (SEQ ID NO: 169) | | |
| Ura-F | TTGATTTCGGTTTCTTTGAA (SEQ ID NO: 160) | | 1,066 by URA3 gene fragment |
| Ura-R | GGGTAATAACTGATATAATT (SEQ ID NO: 161) | | |
| Sce-Ura1 | TTAAAGAAACCGAAATCAA-GATCTGACTTATTATTTCA (SEQ ID NO: 170) | | (GAL1/I-SceI)-URA3 fusion |
| Sce-Ura2 | CTGAAATAATAAGTCGATC-TTGATTTCGGTTTCTTTGAA (SEQ ID NO: 171) | | |
| Sce-Int1 | aagtgtgatacacttgatgtttatggtagtgatattgatatccaagcatt-TAGGGATAACAGGGTAAT-ACGGATTAGAAGCCGCCGAG (SEQ ID NO: 172) | | (GAL1-I-SceI-URA3) mutagenesis cassette |
| Sce-Int4 | aagactagactctgaataactaattaatcccatttgtgtatcagtattta-GGGTAATAACTGATATAATT (SEQ ID NO: 173) | | |
| Seq-F | gttagtttaccaatccagtc (SEQ ID NO: 166) | | Diagnostic primers |
| Seq-R | aatgcttggatatcaatatc (SEQ ID NO: 167) | | |
| Tandem repeat | | | |
| Ura-F | TTGATTTCGGTTTCTTTGAA (SEQ ID NO: 160) | | 1,066 by URA3 gene fragment |
| Ura-R | GGGTAATAACTGATATAATT (SEQ ID NO: 161) | | |
| Amp-F | caatattggaacactatggt (SEQ ID NO: 164) | | 358 by *M. genitalium* fragment |
| Seq-R | aatgcttggatatcaatatc (SEQ ID NO: 167) | | (Repeat sequence) |
| Fus1 | AATTATATCAGTTATTACCC-caatattggaacactatggt (SEQ ID NO: 174) | | (URA3 - Repeat) fusion |
| Fus2 | accatagtgttccaatattg-GGGTAATAACTGATATAATT (SEQ ID NO: 175) | | |
| UM2-70 | aagtgtgatacacttgatgtttatggtagtgatattgatatccaagcatt-TTGATTTCGGTTTCTTTGAA (SEQ ID NO: 176) | | (URA3 - Repeat) mutagenesis cassette |

TABLE 13-continued

Primers used in mutagenesis studies

| Primer | Sequence (5'-3') | SEQ ID NO: | PCR product or name of primer |
|---|---|---|---|
| MUT-70 | aagactagactctgaataactaattaatcccatttgtgtatcagtatttaaatgcttggatatcaatatc (SEQ ID NO: 177) | | |
| Seq-F | gttagtttaccaatccagtc (SEQ ID NO: 166) | | Diagnostic primers |
| M2-det1 | aagtaactagcaatttgttg (SEQ ID NO: 178) | | |

Tandem Repeat Endonuclease Cleavage (TREC)

| Primer | Sequence (5'-3') | PCR product or name of primer |
|---|---|---|
| Gal-F | ACGGATTAG AAGCCGCCGAG (SEQ ID NO: 168) | 2.25 kb (GAL1-I-SceI-URA3) fragment |
| Ura-R | GGGTAATAACTGATATAATT (SEQ ID NO: 161) | |
| Amp-F | caatattggaacactatggt (SEQ ID NO: 164) | 358 by M.genitalium fragment (Repeat sequence) |
| Seq-R | aatgcttggatatcaatatc (SEQ ID NO: 167) | |
| Fus1 | AATTATATCAGTTATTACCC-caatattggaacactatggt (SEQ ID NO: 174) | (GAL1-I-SceI-URA3 - Repeat) fusion |
| Fus2 | accatagtgttccaatattg-GGGTAATAACTGATATAATT (SEQ ID NO: 175) | |
| Sce-Int1 | aagtgtgatacacttgatgtttatggtagtgatattgatatccaagcatt-TAGGGATAACAGGGTAAT-ACGGATTAGAAGCCGCCGAG (SEQ ID NO: 179) | (GAL1-I-SceI-URA3 - Repeat) mutagenesis cassette |
| MUT-70 | aagactagactctgaataactaattaatcccatttgtgtatcagtatttaaatgcttggatatcaatatc (SEQ ID NO: 180) | |
| Seq-F | gttagtttaccaatccagtc (SEQ ID NO: 166) | Diagnostic primers |
| M2-det1 | Aagtaactagcaatttgttg (SEQ ID NO: 178) | |

Cre-loxP recombinase

| Primer | Sequence (5'-3') | PCR product or name of primer |
|---|---|---|
| Gal-F | ACGGATTAG AAGCCGCCGAG (SEQ ID NO: 168) | 450 by GAL1 promoter fragment |
| Gal-R | GGTTTTTTCTCCTTGACGTTAA (SEQ ID NO: 181) | |
| Cre-F | ATGTCCAATTTACTGACCGT (SEQ ID NO: 182) | 1,032 by Cre recombinase ORF fragment |
| Cre-R | CTAATCGCCATCTTCCAGCA (SEQ ID NO: 183) | |
| Cre-Fus1 | AACGTCAAGGAGAAAAAACC-ATGTCCAATTTACTGACCGT (SEQ ID NO: 184) | (GAL1-Cre) fusion |
| Cre-Fus3 | ACGGTCAGTAAATTGGACAT-GGTTTTTTCTCCTTGACGTT (SEQ ID NO: 185) | |
| Ura-F | TTGATTTCGGTTTCTTTGAA (SEQ ID NO: 160) | 1,066 by URA3 gene fragment |
| Ura-R | GGGTAATAACTGATATAATT (SEQ ID NO: 161) | |
| Cre-Fus2 | TGCTGGAAGATGGCGATTAG-TTGATTTCGGTTTCTTTGAA (SEQ ID NO: 186) | (GAL1-Cre-URA3) fusion |
| Cre-Fus4 | TTCAAAGAAACCGAAATCAA-CTAATCGCCATCTTCCAGCA (SEQ ID NO: 187) | |
| Lox-F | TACCGTTCGTATAATGTATGCTATACGAAGTTAT-ACGGATTAGAAGCCGCCGAG (SEQ ID NO: 188) | loxP-site introducing primers: loxP-RE-(GAL1-Cre-URA3)-loxP-LE |
| Lox-R | TACCGTTCGTATAGCATACATTATACGAAGTTAT-GGGTAATAACTGATATAATT (SEQ ID NO: 189) | |
| Int-F2 | aagtgtgatacacttgatgtttatggtagtgatattgatatccaagcatt-TACCGTTCGTATAATGTATG (SEQ ID NO: 190) | loxP-RE-GAL1-Cre-URA3-loxP-LE mutagenesis cassette |
| Int-R2 | aagactagactctgaataactaattaatcccatttgtgtatcagtatttt-TACCGTTCGTATAGCATACA (SEQ ID NO: 191) | |

TABLE 13-continued

Primers used in mutagenesis studies

| Primer | Sequence (5'-3') | SEQ ID NO: | PCR product or name of primer |
|---|---|---|---|
| Seq-F | gttagtttaccaatccagtc (SEQ ID NO: 166) | | Diagnostic primers |
| M2-det1 | aagtaactagcaatttgttg (SEQ ID NO: 178) | | |

Example 4A

Modification Using Conventional Two-Step Homologous Recombination Method

Figure 12A:
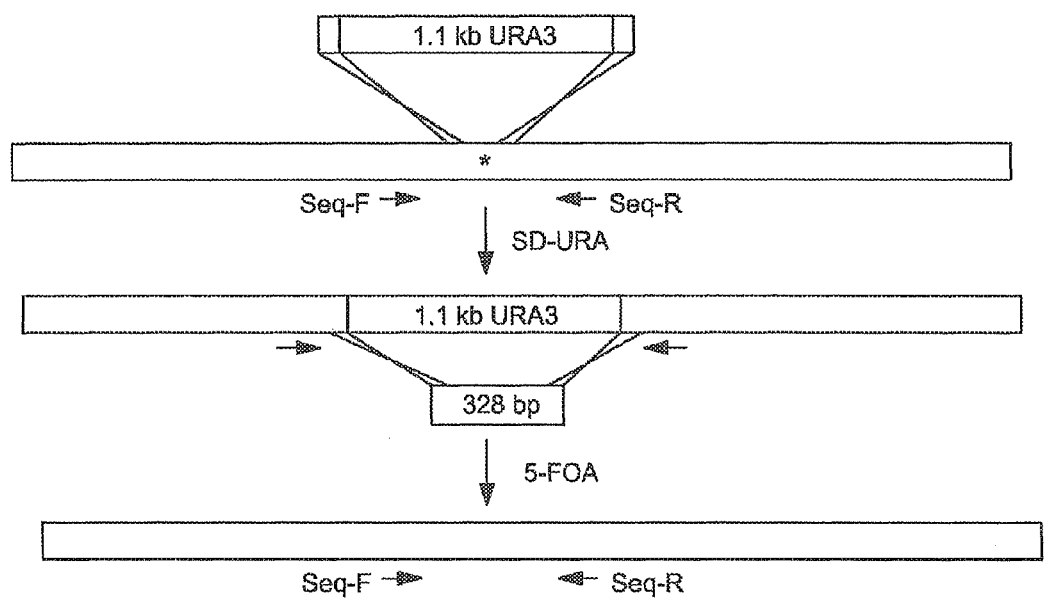
Figure 12B:
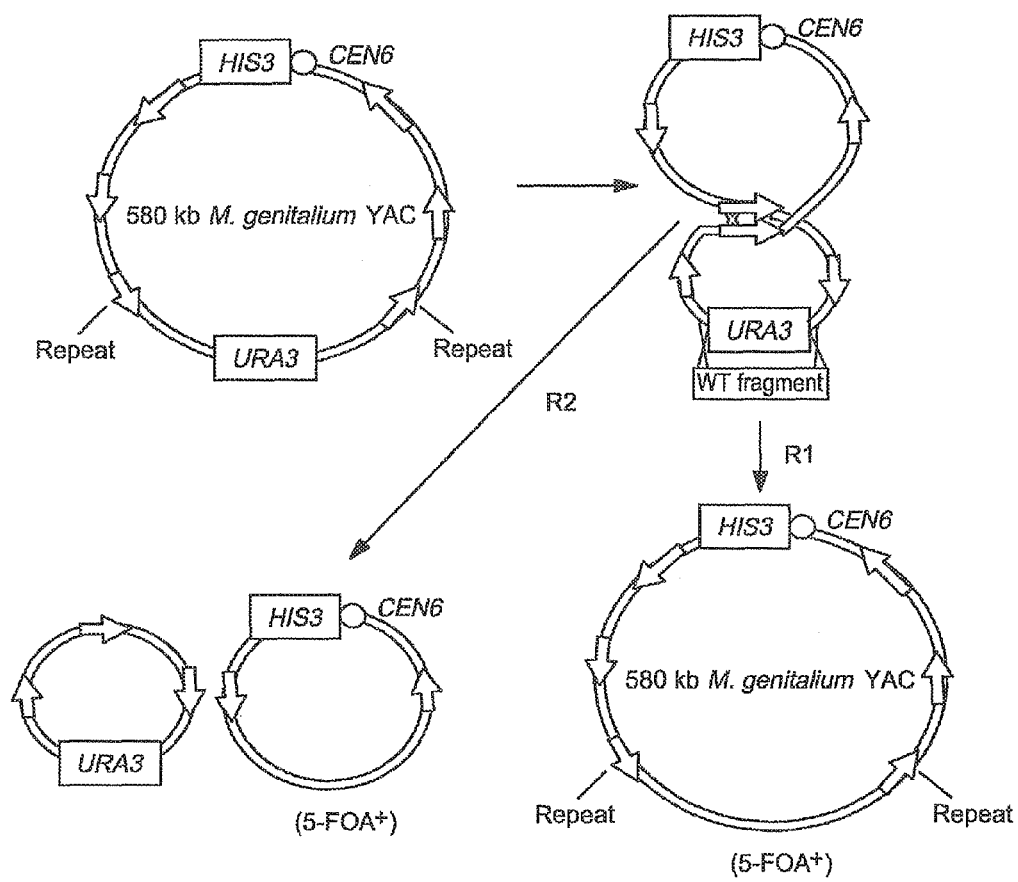

A conventional two-step homologous recombination method (Rothstein, R. *Methods Enzymol,* 194, 281-301 (1991)) was used in to introduce a site-specific mutation to correct the single base cytidine deletion in the synthetic *M. genitalium* genome that had been maintained in yeast. This method is illustrated schematically in FIG. 12A.

i. Introduction of URA3 Gene by Homologous Recombination—Traditional Sequence Replacement Using primers listed in Table 13, the conventional method (traditional sequence replacement) was performed as follows. In the first step, which involved two sequential transformations, a URA3 gene (1,066 bp) was PCR amplified from the plasmid pRS306 (described in R. S. Sikorski and P. Hieter, *Genetics* 122, 19 (1989)) using primers URA-F and URA-R, the sequences of which are listed in Table 13, above. This amplified URA3 gene contained two 50-bp terminal sequences identical to portions of the region of the *M. genitalium* genome that was targeted for mutation. The PCR reaction was performed using DNA polymerase (Takara, Madison, Wis.), under conditions recommended by the manufacturer. The PCR product was introduced into the yeast strain containing the *M. genitalium* genome using lithium acetate integrative transformation.

Individual Ura+ transformants were selected and analyzed by PCR, using diagnosis primers Seq-F and Seq-R, listed in Table 13, above, to confirm that the amplified URA3 gene had been inserted at the correct location within the donor genome. The Seq-F and Seq-R primers flanked the target locus (region of the target genome being modified), and were separated along the genome by 0.4 kb, such that amplification from a genome containing the URA3 marker replacement would produce a 1.35 kb PCR product (shown schematically in FIG. 12A). Products from the PCR reaction were separated on an agarose gel, which was visualized to verify correct insertion of the URA3 gene.

ii. Second Round of Transformation: Introduction of Wild-Type Fragment and Selection For a second round of transformation, a 328 bp wild type DNA fragment (homologous to a portion of the target region but not containing the CDS139 locus single base deletion) was produced by PCR amplification with primers Amp-F, and Seq-R, listed in Table 13, above. This fragment was introduced into the URA3-replaced strains obtained from the first round of transformation using the lithium acetate integrative transformation method.

After the second round of transformation, cells were grown SD-HIS plate at 30° C. overnight, to deplete the residual orotidine-5'-phosphate decarboxylase (encoded by the URA3 gene) in any yeast cells that had lost the URA3 gene. SD medium supplemented with 5-fluoroorotic acid (FOA) (SD-HIS plates containing FOA) was used to select for URA3 gene loss (Boeke et al., *Mol Gen Genet,* 197, 345-346 (1984)).

Correction of the mutation was assessed via PCR of the genomic DNA from selected clones using the diagnosis primers, Seq-F and Seq-R (described above and listed in Table 13). The PCR reaction was performed using Takara DNA polymerase (Takara, Madison, Wis.), under conditions recommended by the manufacturer. PCR products were separated on an agarose gel. Using these primers, amplification of genomic DNA containing the CDS139 locus (either the original locus with the single base deletion or the replaced wild type sequence) would give rise to a PCR product of 0.4 kb DNA fragment (data not shown).

Ninety-seven FOA resistant colonies were tested by this method. Full results are summarized in the first row of Table 14; as shown in Table 14, none of the FOA resistant colonies gave rise to the correct 0.4 kb fragment by PCR amplification of genomic DNA. This result suggested that no precise homologous recombination (BR) had occurred between the incoming wild type DNA fragment and the target site. Instead, loss of the URA3 marker in these FOA-resistant colonies might have been caused by unwanted deletions. This possibility was likely, given that the *M. genitalium* genome, propagated as a circular YAC in yeast, does not have functional complementation with its host, aside from histidine prototrophy. Thus, deletions and rearrangement in donor bacterial genome would likely have been neutral to host cell viability.

iii. Multiplex PCR

To test this possibility by evaluating the integrity of the *M. genitalium* genomes in selected yeast, Multiplex PCR (MPCR) was performed as described by Gibson et al., *PNAS USA,* 105(51):20404-9 (2008) and Gibson et al., *Science* 319, 1215 (2008). Isolation of total DNA from the yeast for PCR analysis was performed according to a published protocol (Kouprina and Larionov, *Nat. Protoc.* 3, 371 (2008)), as described in Example 3, above. The primer set for MPCR (set 3) was designed to produce 10 amplicons (ranging from 125 bp to 1025 bp, in 0.1 kb increments) distributed around the *M. genitalium* genome approximately every 60 kb DNA (Gibson et al., *PNAS USA,* 105(51):20404-9 (2008)). Multiplex PCR was done using Multiplex PCR Kit from Qiagen (Valencia, Calif.). A 1/50 volume (2 µl) of the DNA extract and 1 µl of a 10× primer stock containing 20 oligos at 5 µM each were included in each 10-µl reaction. Cycling parameters were 94° C. for 15 min, then 35 cycles of 94° C. for 30 s, 52° C. for 90 s, and 72° C. for 90 s, followed by a single 3-min incubation at 72° C. Then 2 µl of each reaction was loaded onto a 2% E-gel (Invitrogen) and 72 V was applied for 30 minutes. Bands were visualized using an Amersham Typhoon 9410 Fluorescence Imager.

The results showed that for each of twenty-two FOA-resistant colonies, amplification of total DNA did not give rise to all ten amplicons. Two amplicons, 0.55 and 0.65 kb in length (which cluster together in *M. genitalium* genome), were not produced by MPCR of any of the FOA-resistant clones. The CDS139 target locus locates 3 kb upstream of the 0.65 kb amplicon (gel results not shown).

This result demonstrated that some unspecific deletions or rearrangements had occurred in the *M. genitalium* genome propagated in yeast. Loss of the URA3 marker in these clones (evidenced by their selection with FOA) had likely resulted from homologous recombination among repetitive sequences in *M. genitalium* genome. Cells in which the URA3 marker was deleted as a result of this recombination were able to survive on FOA medium. Thus, with this non-conventional method, there was a higher probability of nonspecific loss of the URA3 gene than replacement of URA3 replacement by the intended recombination event with the introduced wild-type DNA fragment.

This problem with the conventional modification methods is illustrated schematically in FIG. 9, where introduction of the wild-type fragment into yeast carrying the *M. genitalium* with URA3 insertion (FIG. 9A) (as generated in Example 4A(i), above), followed by selection on SD-HIS plates containing FOA, results in selection of two different types of recombination events (P1 (recombination between the wild-type fragment and the genome) and P2 (recombination among repeats within the genome)) (FIG. 9B). These events would produce cells carrying the alternative products illustrated in FIG. 9C. Because the *M. genitalium* genome contains multiple repeats, the probability of nonspecific loss of the URA3 gene (P2) was greater than the probability of loss due to the intended recombination (P1). Prevalent nonspecific loss likely accounts for the observed lack of any clones containing the intended sequence, using this conventional method. These results demonstrate the need for improved methods for modifying donor genomes in yeast host cells.

TABLE 14

Number of correct sequence replacements and complete
*Mycoplasma genitalium* amplicons among FoA+ clones

| System | Fraction clones w/correct sequence replacement | Fraction clones w/complete amplicons by multiplex PCR |
|---|---|---|
| Traditional replacement (Example 4A) | 0/97 | 0/22 |
| Tandem repeat (Example 4B(ii)) | 0/38 | 1/9 |
| Delitto perfetto (Example 4B(i)) | 0/60 | NT |
| Cre-loxP recombinase | 28/30 | 4/4 |
| Tandem repeat endonuclease cleavage (TREC) (Example 4C) | 28/28 | 9/9 |

Example 4B

Alternative Seamless Modification Methods

Two other seamless modification methods, which are reported to be more efficient, were used in attempt to modify the same target region of the synthetic *M. genitalium* donor genome in yeast, described above.

i. Delitto Perfetto

The first of the two reportedly efficient methods, delitto perfetto (Storici, F. et al., *Nat Biotechnol*, 19, 773-776 (2001)), is illustrated schematically in FIG. 10A. In this method, introduction of a double-strand break into a target DNA site stimulates recombination by several orders of magnitude.

The delitto perfetto method used herein used a construct having a 50 bp sequence homologous to the region upstream of the target locus and a 50 bp sequence homologous to the region downstream of the target locus flanking a CORE cassette that includes: a nucleic acid sequence recognized by a particular endonuclease, an inducible promoter, a gene encoding the particular endonuclease under the control of the inducible promoter, and a selectable/counterselectable marker (FIG. 10A). Thus, the cassette is designed such that, upon induction of expression of the endonuclease, the endonuclease cleaves at its recognition site within the cassette, generating a double-strand break and increasing recombination efficiency at the desired site.

a. Generation of Dellitto Perfetto Cassette

The delitto perfetto mutagenesis cassette was generated by fusion PCR to fuse a first fragment, containing the GAL1 promoter (inducible promoter) and the I-SceI gene (endonuclease-encoding gene), to a URA3 (selectable/counterselectable marker) gene fragment. The URA3 gene fragment (1,066 bp) was amplified, as described in Example 4A, above, from plasmid pRS306, using primers URA-F and URA-R, listed in Table 13, above. The 1,184 bp fragment containing the GAL1 promoter and the I-SceI gene (GAL1/I-SceI gene fragment) was amplified from the plasmid pGSKU (described in Storici et al., *PNAS USA*, 100, 14994-14999 (2003)), using the primers Gal-F and Gal-R, listed in Table 13, above. Fusion PCR was carried out using a recombinant PCR technique, essentially as described in Shevchuk et al., *Nucleic Acids Res*, 32, e19 (2004).

b. First Round of Transformation

The cassette was introduced into the yeast strain containing the *M. genitalium* genome, using lithium acetate integrative transformation. Individual Ura+ transformants were selected and analyzed by PCR, using diagnostic primers Seq-F and Seq-R (shown as small, single-head arrows flanking the insertion site in FIG. 10A), listed in Table 13, above, to confirm that the gene had been inserted at the correct location within the donor genome. PCR of genomes containing the inserted cassette using these primers would produce a 2.5 kb product. Products from the PCR reaction were separated on an agarose gel, which was visualized to verify correct insertion of the URA3 gene.

c. Induction of Endonuclease Expression and Second-Round Transformation

Clones testing positive in the PCR reaction with diagnostic primers were grown in SD/galactose/-HIS medium for 4 hours to induce expression of the I-SceI endonuclease, which was controlled by the GAL1 promoter and thus expressed when yeast were grown in medium containing galactose as the only carbon source. Induced expression of the endonuclease was intended to produce a double-strand break by cleaving the 18 bp recognition sequence within the cassette, located just downstream of the region of homology to the genome. After induction, the wild-type DNA fragment was transformed into the cells as described in Example 4A, above.

Cells were grown on SD-HIS plates containing FOA to select for cells that had lost the URA3 marker, as described in Example 4A. Diagnostic PCR using the Seq-F and Seq-R primers was performed to determine whether selected FOA-resistant cells contained genomes in which the cassette had been replace with the wild-type fragment (which would have produced a PCR product of 400 base pairs). As indicated in Table 14, above, none of sixty tested FOA-resistant isolates produced the amplicon of the correct size. The results revealed that the *M. genitalium* genomes from sixty FOA resistant isolates contained imprecise deletion of the CDS139 locus.

ii. Tandem Repeat Pop-Out

The second of the two reported seamless deletion methods, the tandem repeat pop-out, was based on a precise excision of a nucleic acid segment by homologous recombination (HR) between two tandem repeat sequences and is described in Akada et al., *Yeast*, 23, 399-405 (2006). This technique can be adapted for use in gene replacement. With this method, instead of correction of the single-base deletion, a seamless deletion of the CDS139 locus was performed in the same yeast strain harboring the *M. genitalium* genome.

a. Generation of the Tandem Repeat Cassette by Fusion PCR

A fusion product was generated that contained the URA3 marker and a 358 bp fragment ("repeat" fragment) homologous to a portion just upstream of the target locus (large arrow labeled as "repeat" in FIG. 10B). The 1,066 bp URA3 marker fragment was produced by PCR using the Ura-F and Ura-R primers (Table 13), using the same method as described in Example 4A. The 358 bp repeat fragment was produced by PCR amplification with Amp-F and Seq-R primers, listed in Table 13.

The two Portions were joined by fusion PCR, using a recombinant PCR technique, as described in Example 4B(i), above, as follows. First, chimeric fusion primers Fus1 and Fus2, listed in Table 13, above, each containing a portion of homology to the URA3 gene and the "repeat" fragment, were used in a PCR to amplify the URA3 gene and in another PCR to amplify the repeat fragment. The product from each reaction included a region of homology to the product of the other reaction, for a total of 40 base pairs of overlapping homologous sequence shared between the two amplified products. The products then were subjected to cycles of PCR without primers, with a low annealing temperature to join the products, yielding a fusion product containing the joined fragments.

Figure 14A:
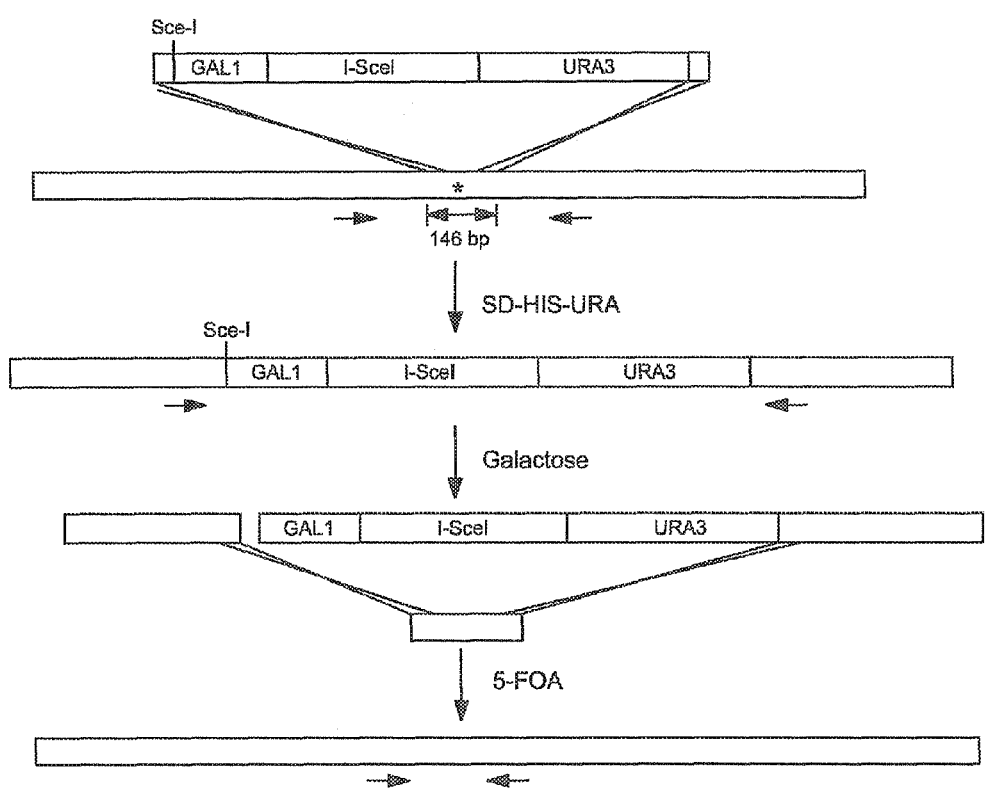
Figure 14B:
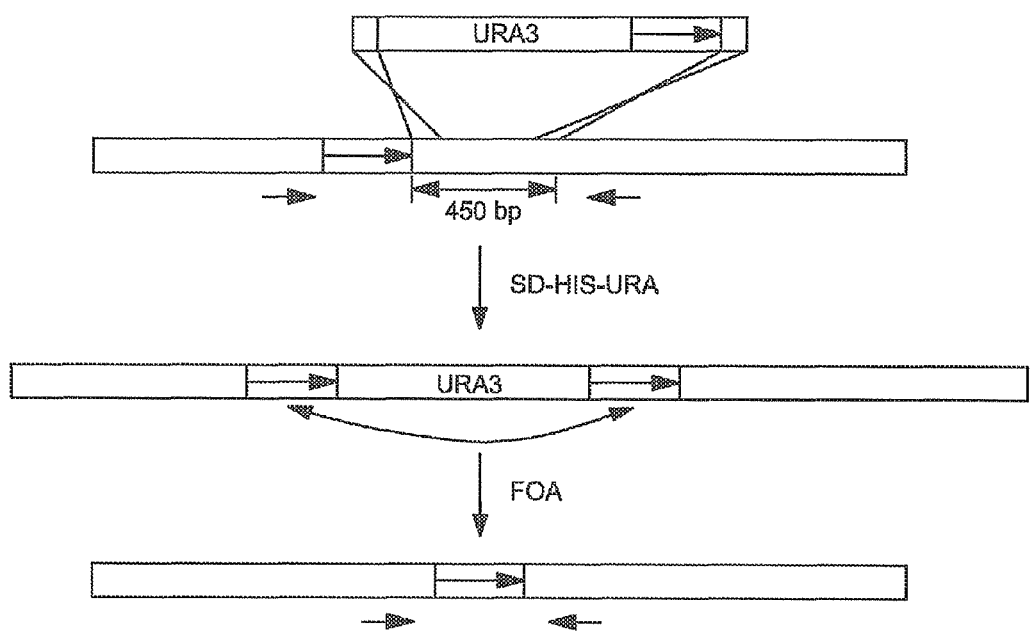

To generate the final mutagenesis cassette (see FIG. 10B), the fusion product was PCR-reamplified, using the chimeric primers UM2-70 and MUT-70, listed in Table 13, above. As shown in that table, each of these primers contained homology to the fusion product and 50 base pairs (bp) of homology to the target region (5' end; lowercase). The resulting cassette (illustrated in FIG. 10B) contained, in the following order, 50 bp of homology to a 5' portion of the target region (upstream of the single-base deletion), the URA3 marker, the repeat cassette, and 50 bp of homology to a 3' portion of the target region. The cassette was designed in this orientation so that upon transformation into the yeast host cells, replacement of a 450 base pair target region within the CDS139 locus of the *M. genitalium* genome with this cassette (by HR) would result in a region in the genome containing two tandem repeat sequences (large arrows in FIG. 14B labeled as "repeat") flanking the URA3 selection marker. The tandem repeat sequences were included to facilitate deletion (pop-out) of the cassette by homologous recombination between the two repeat sequences. Such an event would remove the URA3 marker and could be selected for by growth on FOA-containing medium.

b. Transformation and Analysis

The cassette was introduced into the yeast strain containing the *M. genitalium* genome, using lithium acetate integrative transformation. Individual Ura+ transformants were selected and analyzed by PCR, using the diagnostic primers, Seq-F and M2-det1-R (shown as small, single-head arrows flanking the insertion site in FIG. 10B), listed in Table 13 above, to confirm that the gene had been inserted at the correct location within the donor genome. PCR of wild-type genomes with these primers would produce a 1 kb product. PCR of genomes containing the inserted cassette, on the other hand, produced a 1.973 kb product. Products from the PCR reaction were separated on an agarose gel, which was visualized to verify correct insertion of the URA3 gene.

Cells testing positive by PCR for the correct insertion were grown on SD-HIS plates containing FOA to select for cells losing the URA3 marker, as described in Example 4A. Diagnostic PCR using the primers Seq-F and M2-det1 was performed to determine whether selected FOA-resistant cells contained genomes in which the cassette had been deleted, leaving a seamless deletion of a 450 base-pair portion of the target region. PCR with these primers on genomes in which such precise deletion had occurred would have yielded a 0.55 kb product. As indicated in Table 14, above, none of the thirty-eight FOA-resistant isolates yielded a product in this PCR amplification.

MPCR was performed, as described in Example 4A, on DNA from nine of the FOA-resistant isolates. As indicated in Table 14, above, only one out of these nine isolates generated a complete replicon (all 10 products). Absence of a complete replicon indicated that recombination had occurred between repetitive sequences within the donor genome itself. This result suggested that the frequency of recombination between the tandem repeat sequences flanking the URA3 marker was much lower than recombination among repetitive sequences in *M. genitalium* genome.

Results from the studies described in Examples 4A and this example (4B), collectively indicated that the known methods based on the URA3/FOA system were not sufficient in this particular system to manipulate and engineer the *M. genitalium* donor genome in these yeast host cells and that the majority of FOA-resistant colonies recovered in these studies had nonspecifically lost the URA3 marker via unintended recombination events during the course of manipulation, demonstrating a need for improved methods for modifying donor genomes in yeast host cells.

Example 4C

Modification Method Using Tandem Repeats and Endonuclease Cleavage (TREC)

Based on the results of the studies described in Examples 4A and 4B, it was reasoned that frequency of recombination between the intended tandem repeats in the pop-out method (Example 4B(ii)) might be enhanced by an introduction of a double-strand break near the target locus. Provided is such a method (TREC), which uses tandem repeats and endonuclease cleavage (TREC) and can be used to modify donor nucleic acids in yeast host cells. This Example describes the use of this provided method to modify the same target locus in the *M. genitalium* donor genome in yeast. The results of the study confirm that the introduction of ds break near the target site increases recombination efficiency via tandem repeats in this system.

A method was designed to reduce background of unspecific loss when counter-selecting against the URA3 marker and create both tandem repeat sequences and a double strand break near the target site, which greatly enhances the efficiency and specificity of target-specific recombination. This TREC method is efficient enough to seamlessly engineer an *M. genitalium* genome in yeast.

i. Generation of TREC Cassette

In another example, the TREC mutagenesis construct was generated by fusing the (GAL1/I-SceI)-URA3 fusion product (produced as described in Example 4B(i)) with the 358 bp "repeat" fragment located upstream of the target locus (described in Example 4B(ii)). Fusion of the (GAL1/I-SceI)-URA3 product and the repeat fragment was carried out by fusion PCR, as follows. Chimeric primers, Fus1 and Fus2 (listed in Table 13, above), each having portions of homology to the (GAL1/I-SceI)-URA3 fusion product and the repeat fragment, were used in a PCR amplification with the (GAL1/I-SceI)-URA3 fusion product as a template and in another PCR amplification with the "repeat" fragment as a template. The products then were subjected to a primer-less PCR, as described in Example 4A and 4B, above, to generate a ((GAL1/I-SceI)-URA3)-Repeat fusion product.

The ((GAL1/I-SceI)-URA3)-Repeat fusion product then was amplified using the Sce-Int1 and the MUT-70 primers, listed in Table 13, above. As shown in that table, each of these primers contained homology to the ((GAL1/I-SceI)-URA3)-Repeat fusion product and 5' 50 base pair (bp) portions of homology to portions at the ends of the target region (5' lowercase portion). The Sce-Int1 primer further contained an I-SceI recognition site (underlined).

The resulting TREC cassette (illustrated in FIG. 10C) contained, in the following order, 50 bp of homology to a 5' portion of the target region (upstream of the single-base deletion), a CORE cassette (consisting of the 18 bp I-SceI recognition site, the GAL1 promoter, a gene encoding I-SceI endonuclease and the URA3 marker), the "repeat" (358 bp portion homologous to sequence of the genome just upstream of the target locus), and 50 bp of homology to a 3' portion of the target region (downstream of the single-base deletion being corrected).

Thus, this cassette was designed so that upon transformation into the yeast host cells, replacement of a 450 base pair target region within the CDS139 locus of the *M. genitalium* genome with this cassette (by HR) would result in a region in the genome containing two tandem repeat sequences (large arrows in FIG. 10B labeled as "repeat") flanking the URA3 selection marker and an endonuclease cleavage site that could be inducibly cleaved by promoting endonuclease expression by growth on galactose. As in the tandem repeat pop-out method, the tandem repeat sequences were included to allow seamless deletion by homologous recombination between the two repeat sequences. As in the delitto perfetto method, the inducible endonuclease gene and the endonuclease recognition site were included to allow inducible double-strand break production at the desired site of recombination. Selection of seamless deletion by recombination could be carried out by growth on FOA-containing medium.

ii. Transformation and Selection

The TREC cassette was introduced into the yeast strain containing the *M. genitalium* genome, using lithium acetate integrative transformation. Individual $Ura^+$ transformants were selected and analyzed by PCR, using the diagnostic primers Seq-F and M2-det1 (shown as small, single-head arrows flanking the insertion site in FIG. 10C), listed in Table 13, above, to confirm that the gene had been inserted at the correct location within the donor genome. PCR of genomes containing the inserted TREC cassette using these primers would produce a 2.884 kb product. Products from the PCR reaction were separated on an agarose gel, which was visualized to verify correct insertion of the URA3 gene.

iii. Induction of Endonuclease Expression, FOA Selection, and Evaluation

Clones then were replica-plated onto plates containing SG (synthetic galactose)-His and SD-HIS (containing glucose) and grown for 24 hours. Growth on SG medium, containing galactose as the only carbon source, was done to induce expression of the I-SecI endonuclease, controlled by the GAL1 promoter. Growth on SD-HIS plates under the same conditions was carried out as a control. Expression of the endonuclease was intended to produce a double-strand break by cleaving the 18 bp recognition sequence within the cassette, located just downstream of the region of homology to the genome. After 24 hours of incubation, induced and control (non-induced) cells were replica-plated onto SD-HIS plates containing FOA (SD-HIS+FOA) to select for cells that had lost the URA3 marker, as described in Example 4A.

Cells that had been subjected to galactose induction produced a large number of colonies when grown on SD-HIS+FOA. Control cells, on the other hand, produced few colonies. Cells were re-streaked to obtain FOA-resistant single colonies derived from both induced and uninduced cells. Diagnostic PCR using the Seq-F and M2-det1 diagnostic primers (listed in Table 13, above) was performed to determine whether selected FOA-resistant cells contained genomes in which the TREC cassette had been removed, resulting in seamless deletion of a portion of the target locus. PCR of genomes containing the seamless deletion yielded a product of 0.55 kb. All twenty-four colonies tested from the galactose-induced cells contained the *M. genitalium* genome with the intended modification. Only two positive clones were isolated from uninduced cells.

Integrity of the *M. genitalium* genome was further analyzed by MPCR on the first ten induced and uninduced clones tested by diagnostic PCR analysis, as described in Examples 4A and 4B, above. PCR of DNA from all ten tested galactose-induced colonies yielded a complete replicon (all 10 amplicons); PCR on DNA from the uninduced cells did not generate complete replicons (data now shown). These results are summarized in Table 14, above. The results demonstrate the successful seamless deletion of a portion of a bacterial donor genome within yeast host cells with high efficiency.

iv. Exemplary TREC

The complete synthetic *Mycoplasma genitalium* genome (~583 kb) has been assembled and cloned as a circular plasmid in the yeast *Saccharomyces cerevisiae*. Attempts to engineer the cloned genome by standard genetic methods involving the URA3/5-fluoroorotic acid (5-FOA) counter-selection have shown a high background of 5-FOA resistant clones derived from spontaneous deletions of the bacterial genome maintained in yeast. Here, we report a method that can precisely modify the bacterial genome in yeast with high efficiency. This method involves two sequential homologous recombination events. First, the target region is replaced with a mutagenesis cassette that consists of a knock-out CORE (an 18-bp I-SceI recognition site, the I-SceI gene under the control of GAL1 promoter, and the URA3 gene) and a DNA fragment identical to the sequence upstream of the target site. The replacement generates tandem repeat sequences flanking the CORE. Second, galactose induces the expression of I-SceI which generates a double-strand break (DSB) at the I-SceI site. This DSB promote intra-molecular homologous recombination between the repeat sequences, leading to an excision of the CORE. As a result, it creates a seamless modification. This method can be adapted for a variety of genomic modifications and, therefore, provides an alternative way to modify and design synthetic genomes in yeast.

Materials and Methods

Yeast Strains and Media

Saccharomyces cerevisiae yeast strains VL6-48N (MATα his3-Δ200 trp1-Δ1 ura3-52 lys2 ade2-101 met14) and W303a (MATa ade2-1 ura3-1 his3-11,15 trp1-1 leu2-3,112 can1-100 RAD5) housing a 0.6 Mb Mycoplasma genitalium whole genome YAC were constructed as previously described (Lartigue et al. (2009) Science, 325, 1693-1696; and Gibson et al. (2008) PNAS USA, 105, 20404-20409). Yeast cells were grown in standard rich medium (YEPD) and synthetic dextrose (SD) or synthetic galactose (SG) minimal medium (Amberg et al. (2005) Methods in yeast genetics: A Cold Spring Harbor Laboratory Course Manual, Cold Spring Harbor Laboratory Press, Cold Spring Harbor, N.Y., pp. 230). SD medium supplemented with 5-fluoroorotic acid (5-FOA) was used to select for URA3 gene loss (Boeke et al. (1984) Mol Gen Genet, 197, 345-346).

Production of Mutagenesis Cassettes

All primers were custom synthesized (Integrated DNA Technologies). Primers longer than 60 bp were purified by polyacrylamide gel electrophoresis. Primers used for construction of all mutagenesis cassettes are summarized in Table 13. The URA3 gene (1,066 bp) was amplified from the plasmid pRS306 (Sikorski and Hieter (1989) Genetics, 122, 19-27); the GAL1 promoter (450 bp) was amplified from the plasmid pYES2 (Invitrogen); the 1,184 bp fragment containing the GAL1 promoter and the I-SceI gene was amplified from the plasmid pGSKU (Storici et al. (2003) PNAS USA., 100, 14994-14999); and the Cre recombinase gene (1,032 bp) was amplified from the plasmid pBS185 (Sauer and Henderson (1990) New Biologist 2, 441-449).

All PCRs were performed with Takara Ex Taq DNA polymerase (Takara Bio Inc.) using the conditions recommended by the manufacturer. Gene fusions were performed by a recombinant PCR technique (Shevchuk et al. (2004) Nucleic Acids Res, 32, e19) with minor modifications. In each case of PCR-based fusion, complementary ends overlapped by 40 bp (Table 13). To generate each final mutagenesis cassette, a fusion product was PCR-reamplified by chimeric primers, each containing 50 bp of homology to the target site (Table 13).

Primers containing a dash in the middle are chimeric in structure; lowercase letters indicate M. genitalium homologous sequences; uppercase letters indicate non-homologous sequences; and underlined is I-SceI cleavage site.

Transformation and PCR Analysis

Lithium acetate integrative transformation was performed according to a published method (Gietz et al. (1992) Nucleic Acids Res, 20, 1425). Two to three µg of integrative construct DNA and 25 µg of carrier DNA (salmon testis DNA, Sigma) were used in routine experiments. Isolation of total DNA from yeast for PCR analysis was performed according to a published protocol (Kouprina and Larionov. (2008) Nat Protoc, 3, 371-377). Correct integration of each mutagenesis cassette was verified by PCR using primers located upstream and downstream of the target site (Table 13). Multiplex PCR was used to confirm completeness of M. genitalium clones as described previously (Gibson et al. (2008) PNAS USA, 105, 20404-20409). The primer set used for multiplex PCR (set 3) was designed to produce 10 amplicons (ranging from 125 bp to 1025 bp in 0.1 kb increments) distributed around the M. genitalium genome approximately every 60 kb (Gibson et al. (2008) PNAS USA, 105, 20404-20409).

Results

Engineering a point mutation in the MG259 locus of a synthetic M. genitalium genome maintained in yeast by the classical method involved two homologous recombination events (FIG. 12A). After the first homologous recombination, the exact replacement of a target region in the synthetic genome with the URA3 gene was confirmed by PCR. After the second round of homologous recombination, however, we were not able to identify the correct replacement of the URA3 gene with the DNA segment by PCR screening from 5-FOA resistant colonies (FIG. 12B and Table 15).

TABLE 15

Efficiency of several yeast DNA modification methods in engineering an *M. genitalium* genome in yeast

| Methods | Fraction of clones with correct modification** | Fraction of clones with complete genome*** |
|---|---|---|
| Traditional replacement* | 0/97 | 0/22 |
| Delitto Perfetto | 0/60 | ND |
| Tandem repeat | 0/38 | 1/9 |
| Tandem repeat and endonuclease cleavage (TREC) | 28/28 | 10/10 |
| Cre/loxp recombinase | 28/30 | 4/4 |

Unique PCR primer sets were used to analyze FOA+ clones for the correct replacement. Ten primer pairs were used for multiplex PCR analysis. Production of all ten amplicons was considered a complete genome.

These results suggest that a precise homologous recombination did not occur between the incoming DNA fragment and the target site. The loss of the URA3 marker might be due to unexpected deletions. The *M. genitalium* genome propagated as a circular YAC in yeast does not have functional complementation with its host, except histidine prototrophy. Any deletion and rearrangement in the bacterial genome is likely neutral for the yeast's viability. Multiplex PCR was used to evaluate the integrity of the *M. genitalium* genome in yeast. The primer set was designed to produce 10 amplicons (ranging from 125 bp to 1025 bp in 0.1 kb increments) distributed around the *M. genitalium* genome approximately every 60 kb. Total DNA prepared from 22 5-FOA-resistant colonies did not give rise to all ten amplicons (FIG. 12C). Two amplicons, 0.525 and 0.625 kb (adjacent in the *M. genitalium* genome), were missing in all clones. The MG259 locus is located 3 kb upstream of the 0.65 kb amplicon. This result demonstrates that some spontaneous deletions or rearrangements occurred in the *M. genitalium* genome propagated in yeast. The loss of the URA3 marker may have resulted from homologous recombination among repetitive sequences in the *M. genitalium* genome. As a result, the cells with the URA3 marker deletion could survive on 5-FOA medium. The probability of unspecific loss of the URA3 gene is higher than that of URA3 replacement by the incoming DNA fragment (FIG. 12D). We also employed two other methods to engineer the same locus and produce a point mutation or 450 bp deletion by the delitto perfetto or the tandem repeat pop-out method, respectively (strategies outlined in FIGS. 10A and 10B). However, we were not able to identify any correct modifications by PCR screening 5-FOA resistant colonies (Table 15). Therefore, we concluded that the majority of 5-FOA-resistant colonies were derived from cells that unspecifically lost the URA3 marker during the course of manipulation.

Figure 13:
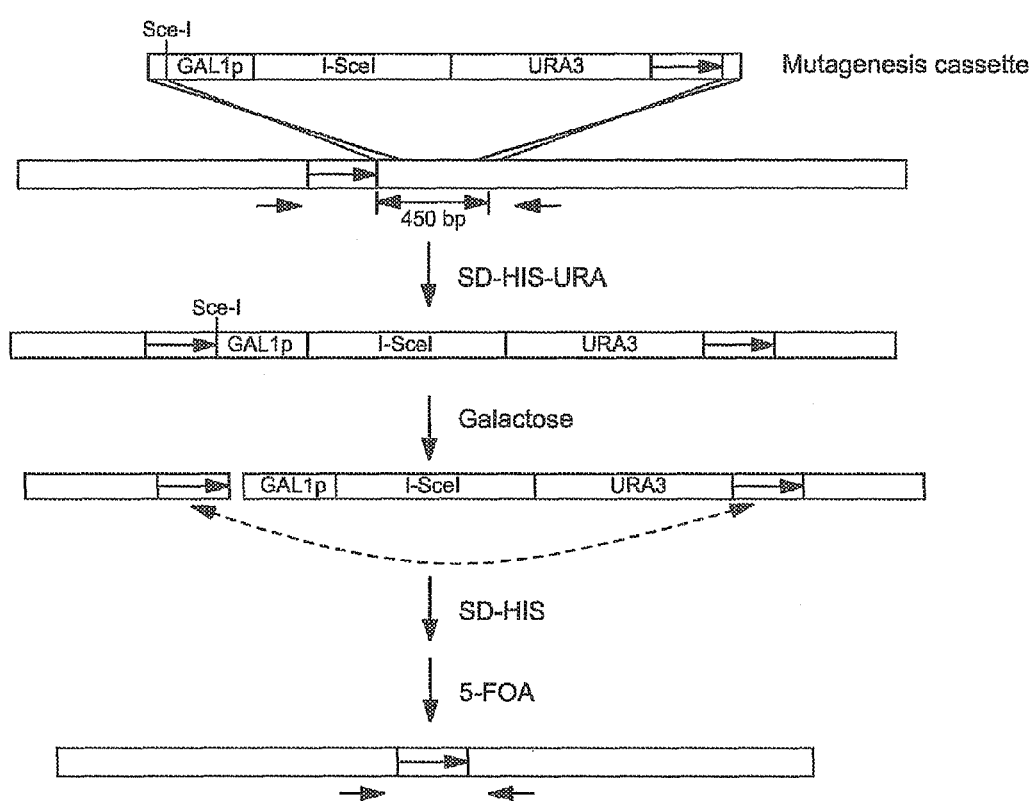

The frequency of recombination between two tandem repeats might be greatly enhanced by the introduction of a DSB near the target site. Therefore, we combined two strategies—the tandem repeat pop-out method and the delitto perfetto method. A mutagenesis construct was generated by fusing a CORE cassette with 358 bp of DNA upstream of the target site. Replacement of the 450 bp target region with this construct would produce two repeat sequences encompassing the CORE, which contains the I-SceI recognition site (FIG. 13). Then, homologous recombination between the repeats would result in a seamless deletion. Following transformation of the mutagenesis construct into yeast, I-SceI endonuclease expression was induced on SG-minus HIS agar. After 24-hours of incubation, cells were replica-plated onto SD-minus HIS+5-FOA agar. Cells with galactose induction produced significantly more colonies on SD-HIS+5-FOA agar than uninduced cells (data not shown). 5-FOA-resistant cells derived from both induced and uninduced cells were re-streaked, and single colonies selected and analyzed. Transformants with the correct deletion were identified by PCR. DNA with precise removal of the CORE cassette would result in the generation of a 0.55 kb amplicon. All 24 colonies derived from the galactose-induced cells contained the correct modification of the M. genitalium genome; only 2 positive clones were isolated from colonies derived from uninduced cells (data not shown). M. genitalium genomic integrity was further evaluated by multiplex PCR. DNA from 10 induced clones that were examined produced the complete set of 10 amplicons. DNA from uninduced cells did not generate the complete set of 10 amplicons data not shown). Hence, results from both PCR analyses demonstrate that the TREC method can perform a seamless deletion on a bacterial genome cloned in yeast with a high efficiency (Table 15).

Figure 15:
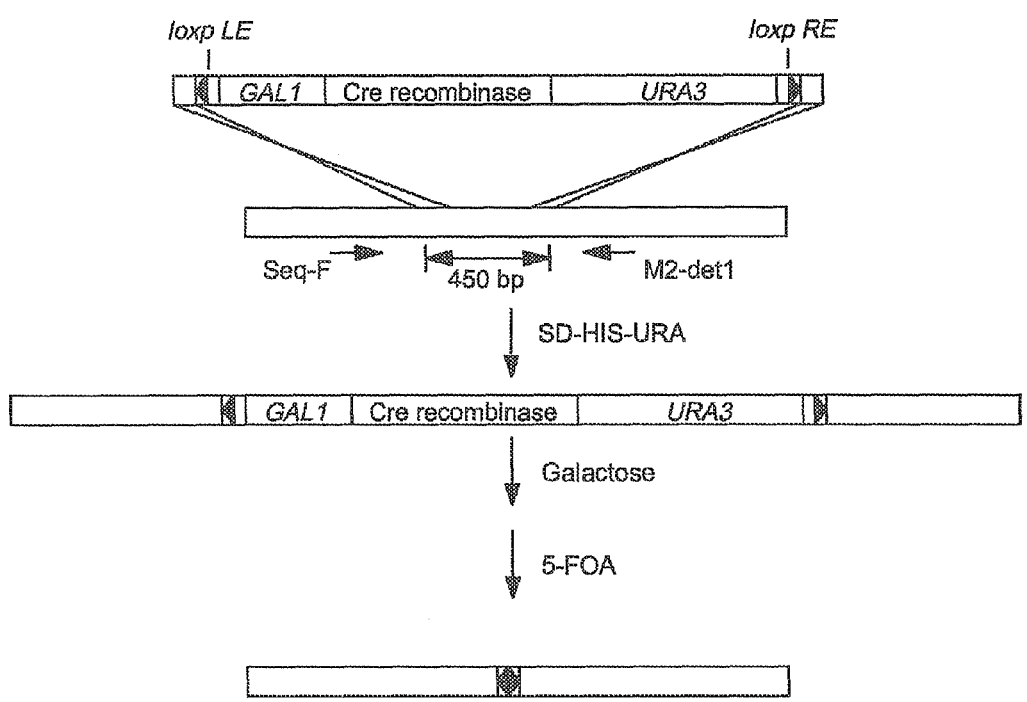

Finally, the efficiency of the TREC method was compared with that of the Cre-loxP system for deletions in a bacterial genome cloned in yeast. The Cre-loxP system is a highly efficient site-specific recombination method. It has been successfully used for removing selection markers and large genomic DNA segments in a wide range of organisms (Gueldener et al. (2002) *Nucleic Acids Res,* 30, e23). A mutagenesis construct was made by two rounds of PCR (Materials and Methods). It consisted of the URA3 marker, the Cre gene under the control of the GAL1 promoter, and two mutant loxP sites flanked by the two terminal sequences homologous to the target site (FIG. 15). The mutant loxP sites prevent a reverse recombination event (Araki, et al. (1997) *Nucleic Acids Res,* 25, 868-872).

The same region that was modified previously was targeted by this construct. A similar procedure and analyses were carried out to produce and detect the site-specific deletions. PCR analysis showed that 93% (28/30) of the 5-FOA resistant isolates contained the desired deletion and multiplex PCR results suggested that 100% (4/4) of isolates with the correct deletion contained the complete M. genitalium genome (Table 15). In conclusion, the efficiency of the TREC method is comparable with that of the Cre-loxP system in engineering an M. genitalium genome cloned in yeast Seamless genome engineering often requires a counter-selectable marker that can be selected against and subsequently removed. Several existing methods that adapt the counter-selection URA3/5-FOA system have been successfully demonstrated for modification in yeast chromosomes (Rothstein (1991) *Methods Enzymol,* 194, 281-301). However, we have shown that those methods are not suitable for engineering an M. genitalium genome episomally maintained in yeast. The synthetic M. genitalium genome was shown to be stably maintained in yeast even though the genome contains up to 4% of repetitive sequences (Peterson et al. (1995) *PNAS USA,* 92, 11829-11833). Thus, spontaneous deletions or rearrangements might still occur in low frequency while maintaining in yeast. This would potentially generate unwanted URA3-negative clones during the course of manipulation and therefore complicate 5-FOA selection for site-specific mutagenesis.

We demonstrated that the TREC method can efficiently generate a seamless modification of the M. genitalium genome in yeast. It is a simple method that only needs a single transformation and is adaptable to other kinds of modifications (insertions, gene replacements, or point mutations). The preparation of the mutagenesis construct takes less than a day. In fact, rather than performing the fusion reaction, we found that co-transformation of the CORE cassette and the repeat fragment with 50 bp of overlap to each other was enough to obtain a correct gene replacement (data not shown). The high frequency of homologous recombination when using the TREC method is mainly attributable to the fact that every cell, in principle, is engaging in repair during the induction of the DSB and that the repair substrates (repeat sequences and DSB) are in close proximity. The performance of TREC is comparable with the Cre/loxP system. However, since TREC does not leave a scar it is more valuable than the Cre/loxP system in genomic engineering. Recently, a new method, called MIRAGE, was shown to produce a seamless modification of the yeast genome with high efficiency. This method is based on the introduction of an inverted repeat near the target site, flanked by two short tandem repeats. The unstable inverted repeat greatly promotes an excision between the two tandem repeats. However, inverted repeat sequences also introduce the potential problem of imprecise deletion due to replication slippage (Gordenin et al. (1992) *PNAS USA,* 89, 3785-3789). Another drawback of using the MIRAGE method is that the generation of the knock out construct is time consuming, as it requires a two day preparation.

Delivering an engineered bacterial genome carried as a YAC back to its original cell can determine the function and regulation of genes and gene clusters (Vrancic et al. (2008) *Food Tech Biotechnol* 46, 237-251). Seamless modification is a favorable means of engineering a YAC, since additional sequences remaining in engineered site could potentially cause unexpected consequences. Additionally, chromosomes of many higher eukaryotic cells contain a high fraction of repetitive sequences. The method described here should be beneficial for modifying their gene(s) cloned in yeast. We have also applied this method to generate a seamless deletion of a Type III restriction enzyme in a Mycoplasma mycoides large colony (M. mycoides LC) genome cloned in yeast. A precise deletion was confirmed by sequencing. Subsequent genome transplantation has created an *M. mycoides* LC strain with a genome deletion that would be difficult to make in the host cell, due to limited genetic tools in this organism (Lartigue et al. (2009) *Science,* 325: 1693). Yeast has been successfully demonstrated as a host for the assembly of the whole *M. genitalium* genome. TREC provides a complementary mean to design synthetic genomes that can be used to create synthetic cells.

The use of yeast provides advantages over *E. coli* because cloning foreign DNA greater than 300 kb in *E. coli* is not very common, which limits its application. Yeast cells, on the other hand, provide the capability of mega-base pair cloning.

Example 4D

Cre-LoxP Modification System

For comparison, a known modification system for bacterial genome modification, the Cre-loxP system, was used to modify the same bacterial genome in yeast host cells. The Cre-loxP system is a known efficient site-specific recombination method that has been successfully used to remove selection markers and large genomic DNA segment in a large number of different organisms. See Gueldener et al., *Nucleic Acids Res*, 30, e23 (2002).

A Cre-loxP mutagenesis construct with mutant loxP genes was produced by two rounds of PCR reactions, as described in the previous examples. Mutations of loxP prevent reverse recombination events, as described in Araki, K. et al., *Nucleic Acids Res*, 25, 868-872 (1997).

i. Generation of Cre-LoxP Cassette

The loxP-RE-GAL1-Cre-URA3-loxP-LE mutagenesis cassette was produced using a Cre recombinase gene ORF fragment (1,032 bp) amplified from the plasmid pBS185 (Sauer and Henderson. *New Biologist* 2, 441-449 (1990)), using Cre-F and Cre-R primers (Table 13), a GAL1 promoter (450 bp) amplified from the plasmid pYES2 (Invitrogen, Carlsbad, Calif.)) using the primers Gal-F and Gal-R (Table 13), and a 1066 bp URA3 gene fragment produced by PCR as described in the previous examples, using the Ura-F and Ura-R primers (Table 13).

A GalI-Cre-URA3 fusion product was generated using PCR fusion using the Cre-Fus2 and Cre-Fus4 primers (Table 13), and mutant loxP sites were introduced by amplification of the fusion product using chimeric primers Lox-F and Lox-R (Table 13) which contained portions of homology to the GAL1-Cre-URA3 fusion product and mutant LoxP sites. This amplification generated LoxP-RE-GAL1-Cre-URA3-loxP-LE fusion product. This fusion product then was amplified using the Int-F2 and Int-R2 primers, listed in Table 13, above. As shown in that table, each of these primers contained homology to the LoxP-RE-GAL1-Cre-URA3-loxP-LE fusion product and 5' 50 base pair (bp) target region homology segments (in lowercase type).

The resulting LoxP-RE-GAL1-Cre-URA3-loxP-LE mutagenesis cassette (illustrated in FIG. 10D) contained, in the following order, 50 bp of homology to a 5' portion of the target region (upstream of the single-base deletion), a first loxP site (loxP-RE), the GAL1 promoter, a Cre recombinase gene ORF, the URA3 marker, a second loxP site (loxP-LE), and 50 bp of homology to a 3' portion of the target region (downstream of the single-base deletion). Thus, this cassette was designed so that upon transformation into the yeast host cells, replacement of a 450 base pair target region within the CDS139 locus of the *M. genitalium* genome with this cassette (by HR) would result in a region in the genome containing loxP sites that could be inducibly targeted for recombination and deletion by inducing Cre expression from the same cassette by growth on galactose. Deletion of the cassette, which contained a URA3 marker, could be selected for by growth on FOA medium.

ii. Transformation and Selection

The loxP-Cre cassette was introduced into the yeast strain containing the *M. genitalium* genome, using lithium acetate integrative transformation. Individual Ura transformants were selected and analyzed by PCR, using the diagnostic primers Seq-F and M2-det1 (shown as small, single-head arrows flanking the insertion site in FIG. 10D and listed in Table 13) to confirm that the gene had been inserted at the correct location within the donor genome. This PCR of genomes containing the inserted loxP-Cre cassette would produce a 3.068 kb product. Products from the PCR reaction were separated on an agarose gel, which was visualized to verify correct insertion of the cassette.

iii. Induction of Endonuclease Expression, FOA Selection, and Evaluation

Clones then were replica-plated onto plates containing SG (synthetic galactose)-His and SD-HIS (containing glucose) and grown for 24 hours. Growth on SG medium, containing galactose as the only carbon source, was done to induce expression of the Cre recombinase, which was controlled by the GAL1 promoter. Expression of the recombinase was intended to induce recombination at the LoxP sites within the cassette. After induction, cells were replica-plated onto SD-HIS plates containing FOA (SD-HIS+FOA) to select for cells that had lost the URA3 marker, as described in Example 4A.

5-FOA resistant colonies were subjected to diagnostic PCR (as described in Examples 4A-C) using the Seq-F and M2-det1 primers (Table 13) to determine whether selected FOA-resistant cells contained genomes in which the cassette had been removed, resulting in seamless deletion of a portion of the target locus. As presented in Table 14, the results indicated that 93% of the 5-FOA-resistant isolates tested (28/30) contained the desired deletion.

Integrity of the *M. genitalium* genome was further analyzed by MPCR on four of the clones testing positive by diagnostic PCR analysis, as described in Examples 4A and 4B, above. As indicated in Table 14, above, 100% (4/4) of these colonies contained all 10 amplicons, evidencing the completeness of the genomes.

Results from the studies presented in Examples 4C and 4D indicated that for modification of *Mycoplasma* genomes in yeast host cells, the efficiency of the provided TREC method (which is a simple method that can be performed with a single transformation and is adaptable to deletion, insertion, gene replacement and point mutation) was equal, if not greater, than that of the well-known cre-loxP modification method. Unlike the Cre-loxP method, however, the TREC method resulted in seamless modification, making it exceptionally advantageous.

Example 5

Transfer of Donor Genome into Host Cells, Modification by TREC within Host Cells, and Transplantation into Recipient Cells This Example describes manipulation of a donor genome using a combination of the provided methods for transferring donor genomes into host cells, modifying donor genomes within host cells (TREC modification), and transplantation of donor genomes into recipient cells. The methods were used to successfully engineer an *M. mycoides* LC genome in yeast that did not previously exist either in the laboratory or in nature. As described below, the Type III restriction enzyme gene was deleted from a donor *M. mycoides* LC genome that had been cloned in a yeast host. The Type III restriction enzyme gene was chosen because it was expected to be non-essential for viability and transplantation. The modified genome then was transplanted into *M. capricolum* recipient cells, generating a new cell containing a modified whole genome.

Example 5A

Transfer of Donor Genome into Host and Modification of the Genome

The *M. mycoides* LC-YCp genome was transferred to and propagated in yeast strain W303a, as described in Example 1A, above.

In one example, the type III restriction enzyme gene was replaced with a cassette containing a URA3 marker, which was subsequently removed by 5-fluoroorotic acid (5-FOA) selection, using the TREC method described in Example 4C, above. For this process, which is illustrated schematically in FIG. 11, a TREC knockout cassette was generated by PCR fusion, as described in Example 4C, above, with the following details. First, a CORE cassette (containing a GAL1 gene, a SceI gene and a URA3 marker, in that order) was generated.

A tandem repeat sequence (TRS) fragment also was generated by PCR. This fragment contained homology to a portion of the *M. mycoides* LC genome, upstream of the TypeIII Restriction enzyme target locus. The TRS fragment and corresponding homologous portion in the genome upstream of the target region are labeled with large horizontal arrows in FIG. 11. The TRS fragment was included so that tandem repeats would be present in the genome after integration of the cassette into the genome by homologous recombination to facilitate pop-out of the cassette by recombination.

The CORE cassette was fused to the TRS fragment by fusion PCR as described in Example 4, above. Fusion primers were used in a PCR using the CORE cassette as a template and in another PCR with the TRS fragment as a template. The products then were combined and subject to primer-less PCR to join the products. The resulting fusion product then was amplified using additional primers which contained homology to the CORE-TRS fusion product and also 50 bp regions of homology to the target region. The primer further contained an 18 bp I-SceI recognition site. Thus, the TREC knockout cassette contained, in the following order: 50 bp of homology to a 5' portion of the target region, an 18 bp I-SceI recognition site, a CORE cassette (consisting of, in this order: the GAL1 promoter, a gene encoding I-SceI endonuclease and the URA3 marker), the TRS repeat fragment, (portion homologous to sequence of the genome just upstream of the target locus; indicated with large horizontal arrow in FIG. 10A), and 50 bp of homology to a 3' portion of the target region.

For modification of the *M. mycoides* LC-YCp donor genome in the yeast W303a host, the TREC knockout cassette was transformed into the host cells, using lithium acetate integrative transformation as described in Example 4C(ii), above. To select for replacement of the TypeR III ORF (target locus) with the TREC knockout cassette (via the 50-bp homologous regions at the termini of the cassette to the target sites, cells were grown, individual URA⁺ transformants were selected and analyzed. This process produced genomes in which the Type III restriction enzyme gene had been replaced by the Cassette (labeled as ΔtypeIIIres::URA3 in FIG. 11).

Cells then were grown on plates containing SG-His medium, such that galactose was the only carbon source. This step induced expression of the I-SceI endonuclease, which was under control of the GAL1 promoter, in order to promote cleavage of the 18-bp I-SceI site (asterisk in FIG. 11), creating a double strand break. The double-strand break then would promote homologous recombination between the tandem repeat sequences (horizontal large arrows), promoted by the double-strand break.

To select for this recombination event, cells were grown on SD-HIS 5-FOA medium to select for cells having lost the URA3 marker, which were presumed to have lost the TREC cassette. This process was carried out to select genomes in which there had been seamless deletion of the typeIIIres gene (labeled as ΔtypeIIIR in FIG. 11).

In another example, a knock-out cassette can be constructed in three steps. First, a 2.3 kb of DNA fragment, referred as the Knock-Out Core (KOC), was produced by PCR using primer RCO293 (CAGGTGGACAAAACAAT-GAGATTAACTAATAAACAAGAATTTGTAGTGCATA-GGGATAACAGGGTAATACGGAT; SEQ ID NO: 152) and primer RCO294 (ATCTTGTCTATTTAATTCTAAAACAG-GGTAATAACTGATATAATTAAATTGAAG; SEQ ID NO: 153). The resulting PCR product contains, starting from 5' end, a 50 bp segment (highlighted in bold in primer RCO293) homologous to the upstream of 5' target site, an 18 bp I-SceI recognition site, the GAL1 promoter, a gene encoding I-SceI homing endonuclease and URA3 marker. Second, a 400-bp upstream of target site was amplified by primer RCO295 (AATTTAATTATATCAGTTATTACCCTGTTTTAGAATT-AAATAGACAAGATAATGG; SEQ ID NO: 154) and primer RCO296 (ATAAGTAATTTTTTATTTTAACAATTTAATA-ATCTTCTTTAACAATATCTTGCACTACAAATTCTTGT-TTATTAGTTA; SEQ ID NO: 155) using *M. mycoides* LC genomic DNA as template. The PCR product, referred as Tandem Repeat Sequence (TRS), contains a 50 bp segment (highlighted in bold in primer RCO296) homologous to the downstream of 3' target site. Third, two PCR products, KOC and TRS, overlapping each other by 50 bp (underlined in primer RCO294 and RCO295) was joined together by PCR-based fusion method. The fusion product, knock-out cassette, was gel-purified by gel extraction kit from Qiagen and re-amplified by primer RCO293 and primer RCO296. The final 2.7 kb fragment was then transformed into yeast 303a strain harboring *M. mycoides* LC genome (Benders et al., *Science*, *submitted* (2009)) using lithium acetate (LioAc) method as described (Gietz et al., *Nucleic Acids Res* 20, 1425 (Mar. 25, 1992)) and selected for both uracil and histidine prototrophy. Total DNA was prepared from transformants as described (Kouprina and Larionov, *Nat Protoc* 3, 371 (2008)). The replacement of knock-out cassette with the type III RE locus was verified by PCR screening using primer 5 (GATTTTTAT-GCTGGATCTGGAACA; SEQ ID NO: 192), located at the upstream of target site and primer 6 (TCCGTATTACCCTGT-TATCCCTA; SEQ ID NO: 193), resided inside the knock-out cassette. To make a mark-less deletion of Type III RE, the PCR-positive strains were grown in medium containing galactose as the sole carbon source, followed by 5-FOA counter-selection as described in Example 4. All PCR amplification experiments described above were carried out using Phusion DNA polymerase (New England Biolabs). Purified *M. mycoides* LC genome from transplants were amplified by PCR using primer 5 and primer 7 (CTACTTCAAATAGTAT-TCTTTTAAGCG; SEQ ID NO: 194) located at the downstream of the target site. The PCR products were purified by kit (Qiagen) and used for sequencing using primer 5 and 7.

Thus, the modification method was designed to produce two modified *M. mycoides* LC genomes in the yeast host cells. The first modified genome was the one obtained after insertion of the TREC cassette but prior to recombination promoted by 1-Sec1 endonuclease digestion and selection on 5-FOA. This first genome contained the URA3-containing (TREC) cassette, which had replaced the wild-type gene at Type III restriction enzyme locus (ΔtypeIIIres::URA). The second genome was the final product obtained after removal of the cassette, which contained a seamless deletion of the Type III restriction enzyme gene (ΔtypeIIIres).

To demonstrate that the modified genomes (ΔtypeIIIres:: URA, ΔtypeIIIres) produced in this study were the correct size, isolated genomic DNA was run on a CHEF gel, as follows, to compare their sizes to the size of unmodified *M. mycoides* LC genome. For this process, yeast plugs were washed and digested over-night with 50 units of AsiSI, RsrII, and FseI restriction enzymes (which specifically cut yeast genomic DNA as described above). The DNA plugs then were loaded on a 1% TAE agarose gel in order to purify the donor DNA by running out the digested yeast genomic DNA fragments. Plugs were removed from the wells and the remaining genomic DNA digested with the PspXI restriction enzyme, which linearized *M. mycoides* LC genomic DNA. After that digestion, all plugs were washed and loaded onto a pulse-field gel. The gel was stained with SYBR Gold (diluted 1:10,000). PFGE patterns were observed after scanning the gel with a GE Typhoon 9410 imager (data not shown).

The samples designed to have ΔtypeIIIres::URA, and ΔtypeIIIres modified genomes correctly exhibited genomes of comparable size to the unmodified genome. This process further revealed that another clone (Δ500 kb) had been produced during the course of the study. Based on the size of the band recovered from this clone, its genome contained a 500 kb deletion. This clone was used in later studies as a control because it presumably lacked many essential genes but retained the YCp (yeast centromeric plasmid) element and the tetM selection marker.

Figure 11:
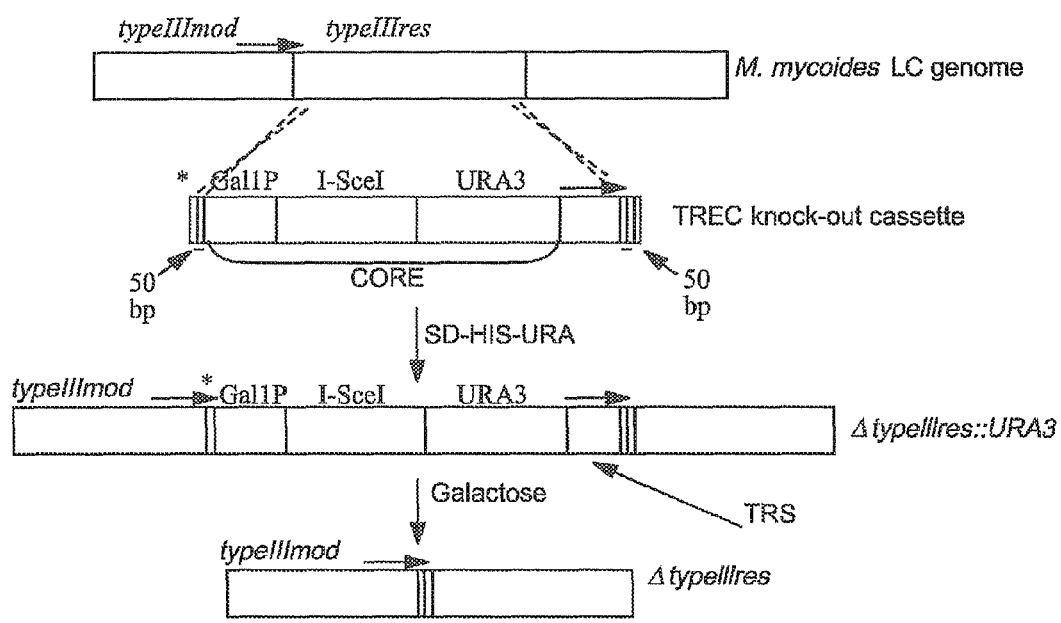
Figure 19:
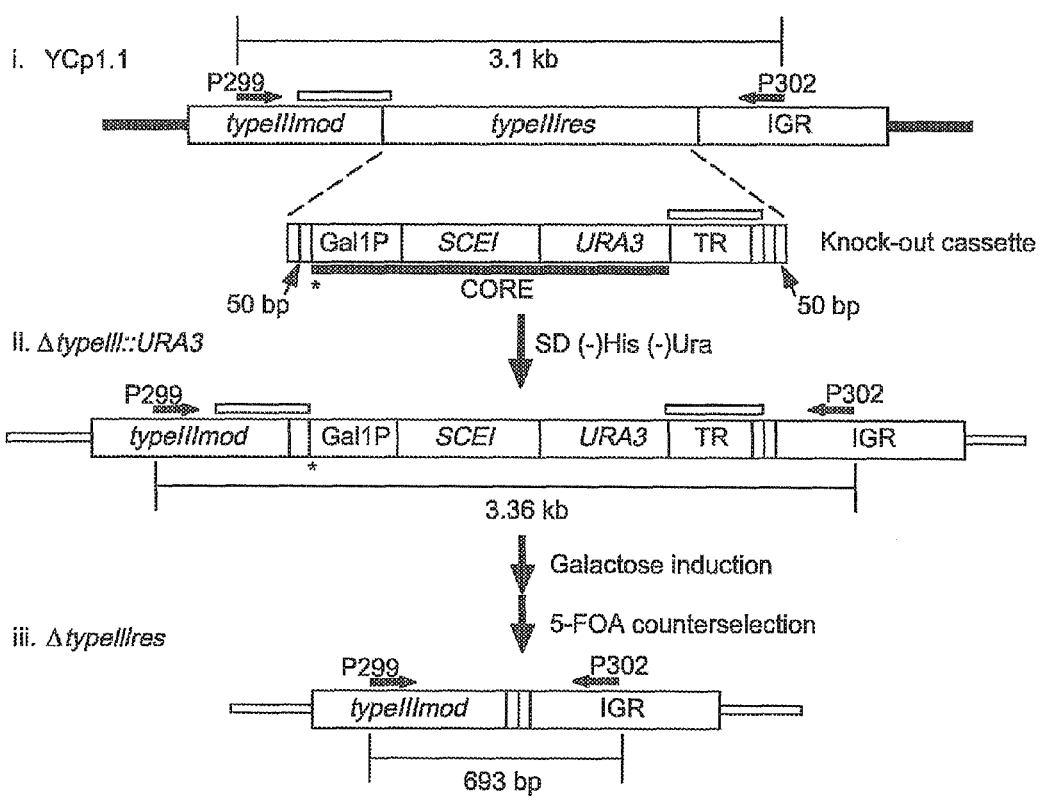

Another example of generation of Type III restriction enzyme deletions is illustrated in FIG. 19. YCpMmyc1.1 was engineered in yeast by creating a seamless deletion in a nonessential Type III restriction endonuclease gene. Briefly, a YCpMmyc 1.1 yeast clone was first transformed with a cassette containing a URA3 marker and the SCEI endonuclease gene under the control of the GAL1 promoter. Insertion of the cassette into the Type III gene was used as a selection criterion; four of five clones contained intact genomes, and one contained a genome with a large deletion (YCpMmyc1.1-Δ500 kb) (FIG. 11). The URA3 cassette was removed by cleavage at an I-Sce I recognition site near one end of the cassette (FIG. 19). Counter selection with 5-fluoroorotic acid (5-FOA) produced clones that had lost the URA3 cassette. Thus, two *M. mycoides* YCp genomes were obtained: one that contained the URA3 cassette and the other that contained a seamless deletion of the Type III restriction enzyme gene (FIG. 19). The changes to the genome were verified by PCR (data not shown).

Example 5B

Transplantation of Modified Genomes into Donor Cells

Each of these *M. mycoides* LC modified genomes (including the Δ500 kb control) and the unmodified *M. mycoides* LC genome were transplanted into *M. capricolum* recipient cells using the methods described in Example 3, above. Transplantation was performed using the third protocol described in Example 3, above, which is illustrated in FIG. 8, indicated with the number "3." As described in Example 3, this method included a methylation step, deproteinisation step (treatment with proteinase K), and a melting step prior the transplantation reaction. Transplantation is into wild-type recipient cells. For this process, agarose plugs were prepared as described in Example 3A(i), and cleaned-up with both the restriction enzyme cocktail and gel electrophoresis, as described in Example 5A, above (see also Example 3A(i)). Transplantation was carried out, as described in Example 3A(ii) and 3A(iii), in the presence of 5% PEG and with methylation using the cell-free *M. mycoides* LC extract and proteinase K digestion. Genomes were transplanted into wild-type (not RE-deficient) *M. capricolum* cells, as described in Example 3, above. Successful transplantation was evaluated by selecting for growth of blue colonies on SP4 medium containing tetracycline at 37° C. Results are presented in Table 17, below.

TABLE 17

Transplantation of modified *M. mycoides* LC genomes into wild-type *M. capricolum* recipient cells

| | Modification | Number of transplants per plug* |
|---|---|---|
| Modified *M. mycoides* LC genome (YCp, tetM, lacZ) | ΔtypeIIIres::URA3<br>ΔtypeIIIres<br>Δ500kb | 28 ± 5<br>33 ± 23<br>0 |
| Unmodified *M. mycoides* LC genome (YCp, tetM, lacZ) | None | 28 ± 16 |

The number of transplants represents an average of at least three studies. The error reported is the mean deviation.

As shown in Table 17, transplantation of the two intended modified genomes (ΔtypeIIIres::URA3 and ΔtypeIIIres) resulted in similar numbers of tetracycline-resistant blue colonies (average of 28 and 33 colonies per plug, respectively) compared to the numbers observed upon transplantation of unmodified *M. mycoides* LC genome (average 28 colonies per plug). As was expected, transplantation of the control clone containing the 500 kb deletion (and presumably lacking essential *Mycoplasma* genes but retaining the YCp element and tetM) into *M. capricolum* recipient cells produced no colonies.

To verify the sequences of selected colonies containing transplanted modified genomes, the Type III locus in those genomes was sequenced. The sequencing results revealed that the expected modifications were present in both modified strains (ΔtypeIIIres::URA3 and ΔtypeIIIres). For example, deletion of the typeIIIres gene in the ΔtypeIIIres genome was verified with the sequence of the nucleic acid containing the junction of the typeIIImod gene (See FIG. 11), adjacent to the typeIIIres gene in the wild-type genome, and the DNA downstream of the native typeIIIres gene, evidencing seamless deletion of that gene in these cells.

To verify that the genotype of the recovered colonies was *M. mycoides* LC, genomic DNA from selected blue colonies was analyzed by Southern blot, using the IS1296 element as probe. Copies of the IS1296 insertion sequence are dispersed throughout the *M. mycoides* LC (donor) genome, but are absent from the *M. capricolum* (recipient) genome. To verify complete loss of the TypeIII restriction enzyme sequence in modified genomes, blots were further probed with a probe containing the *M. mycoides* LC typeIIIres gene sequence. Southern blotting was carried out as follows.

*Mycoplasma* total DNA was extracted from 10 ml cultures of the *M. capricolum* recipient cells transplanted with modified or unmodified *M. mycoides* genomes. Genomic DNA from native *M. mycoides* LC clone 1.1 donor cells and genomic DNA from *M. capricolum* recipient cells were used as controls. Extraction was done using a Wizard genomic DNA purification kit (Promega). For Southern blot hybridization, 1.5 μg of DNA was digested with either HindIII or EcoRV and the resulting samples separated by electrophoresis on a 1% agarose gel. DNA fragments from gels were transferred to positively charged nylon membranes (Nytran Super Charge, Schleicher and Schuell) by alkali transfer. Twenty (20) ng/ml digoxigenin-labeled DNA probes (IS1296 insertion sequence and typeIIIres gene sequence were hybridized to the membranes, to verify *M. mycoides* genotype and donor genome modification, respectively.

The membrane was incubated with Fab fragments of anti-digoxigenin antibodies coupled to alkaline phosphatase. Hybridization then was detected with the fluorescent substrate HNPP (2-hydroxy-3-naphthoic acid-2'-phenylanilide phosphate) (Roche Molecular Biochemicals). Chemifluorescence was detected under UV with a camera and Quantity One software, designed for acquiring images (Bio-Rad Laboratories, Inc.).

Each of the selected transplanted colonies resulted in the same pattern (8 bands) in the blots probed with the IS1296 probe (data not shown). As expected, no IS 1296 pattern was detected in lanes containing samples from recipient cells (r). This result strongly suggests that the recovered colonies indeed were the *M. mycoides* LC genotype. Further, lanes containing control samples from *M. mycoides* donor genomes contained a band recognized by the typeIIIres probe. This band was not detected, however, in the lanes containing samples from transplanted modified genomes.

These results indicated that the donor genomes modified in yeast host cells were successfully transplanted into recipient cells, which were of a different species than the donor. The results further demonstrate that both modified genomes contained the intended modification (loss of the TypeIIIres gene). Thus, the provided methods were successfully used to generate two synthetic recipient cells, containing transplanted synthetic donor *M. mycoides* LC genomes that did not previously exist either in the laboratory or in nature. These results demonstrate the first example of the genetic manipulation of a whole bacterial genome in yeast and its installation into a recipient cell to yield a novel bacterium.

Example 6

Transplantation of a Chemically Synthesized Donor Genome or a Semi-Synthetic Donor Genome, Assembled and Propagated in Yeast Host Cells, into Recipient Cells A 1.08 Mbp *Mycoplasma mycoides* genome was chemically synthesized, and assembled in yeast as a centromeric plasmid; the genome was isolated as naked DNA and transplanted into *Mycoplasma capricolum* to create a new bacterial cell controlled only by the synthetic genome.

Described herein is the design, synthesis and assembly of the 1,077,947-bp *Mycoplasma mycoides* JCVI-syn1 genome from 1,078 1-kb synthetic DNA cassettes. The assembly was facilitated by in vitro and in vivo assembly methods. Cassettes in sets of ten were assembled by yeast recombination and propagated in a yeast/*Escherichia coli* shuttle vector. The 10-kb assemblies were recombined in sets of ten to produce 100-kb assemblies. The resulting eleven 100-kb assemblies were recombined in a single final step into the complete genome. A yeast clone bearing the synthetic genome was selected and confirmed by multiplex PCR and restriction analysis.

The assembled synthetic genome has been propagated in yeast as a centromeric plasmid and successfully transplanted into restriction-minus *Mycoplasma capricolum* cells. The new cells have the phenotypic properties expected for *M. mycoides* and the designed synthetic DNA sequence, including watermark sequences and other designed gene deletions and polymorphisms. We refer to this strain as *M. mycoides* JCVI-syn1. This is the second bacterial chromosome synthesized and the first over one million bp. It is a synthetic bacterial genome successfully transplanted into a recipient cell resulting in new cells that are controlled only by a synthetic chromosome. The new synthetic chromosome cells are capable of continuous self-replication. This study confirms the ability to start with digitized genetic information, synthesize new DNA and transplant that synthetic DNA into cells replacing all of the existing genetic information and, as a result, create new cells controlled only by that synthetic designed DNA. The existing (endogenous) genetic information is lost and as a result new cells are created which are controlled only by the designed synthetic chromosome.

Example 6A

Synthetic Donor Genome Design

Design of the *M. mycoides* JCVI-syn1 genome was based on the highly accurate finished genome sequences of two previously described laboratory strains of *M. mycoides* subspecies *capri* GM12 (Benders et al., *Nucleic Acids Res*, (2010); Lartigue et al., *Science* 325, 1693 (2009)). One was the genome donor used by Lartigue et al. [GenBank accession CP001621] (Lartigue et al., *Science* 317, 632 (2007)). The other was a strain created by transplantation of a genome that had been cloned and engineered in yeast, YCpMmyc1.1-ΔtypeIIIres, [GenBank accession CP001668] (Lartigue et al., *Science* 325, 1693 (2009)). Differences at 95 sites were identified between the *M. mycoides* genomic sequences. We chose to use the sequence of the genome successfully transplanted from yeast (CP001668) as our design reference; all differences between previously synthesized cassettes that appeared to be of biological significance were corrected to match CP001668. Sequence differences between our synthetic cassettes and CP001668 that occurred at 19 sites appeared harmless, and so were not corrected. These provide 19 polymorphic differences between our synthetic genome (JCVI-syn1) and the natural genome that we have cloned in yeast and use as a standard for genome transplantation from yeast, YCpMmyc1.1 (Lartigue et al., *Science* 325, 1693 (2009)).

i. Genomic Sequences

GenBank accession no. CP001621 is the sequence of the *M. mycoides* strain used as the genome donor as described by Lartigue et al. (*Science* 317, 632 (2007)), with a length of 1,089,202 bp.

mmycDRAFT—Design of our synthetic *M. mycoides* genome was begun using a draft genome sequence from the project that produced the above sequence (CP001621), with a length of 1,114,292 bp. This draft was found to contain a large duplication.

GenBank accession no. CP001668 is the sequence of an *M. mycoides* strain engineered in yeast by deleting the gene for a Type III restriction endonuclease, then transplanted to produce a *Mycoplasma* (Lartigue et al., *Science* 325, 1693 (2009)). This sequence has a length of 1,084,586 bp.

First the mmycDRAFT sequence was divided into cassettes 1080 bp in length, with 80 bp overlaps, and a NotI restriction site was added at each end, as follows:

*mmyc*0 = bases 1-1080 preceded and followed by *GCGGCCGC*

*mmyc*1 = bases 1001-2080 preceded and followed by *GCGGCCGC*

*mmyc*2 = bases 2001-3080 preceded and followed by *GCGGCCGC*

⋮

*mmyc*1113 = bases 1113001-1114080 preceded and followed by *GCGGCCGC*

*mmyc*1114 = bases 1114001-1114292 preceded and followed by *GCGGCCGC*

Designed cassettes located within parts of the mmycDRAFT sequence were ordered for synthesis by Blue Heron. This initial order of 1,072 cassettes included all 1,115 designed cassettes except mmyc0-mmyc14 (15 cassettes), mmyc835-mmyc852 (18 cassettes), and mmyc1105-mmyc1114 (10 cassettes).

Assembly of these 1,072 cassettes would yield two contiguous stretches of DNA, with two gaps corresponding to regions where the sequence was uncertain.

Design of the remaining cassettes was based on sequence CP001668 after it was completely finished, because that genome was known to be stably maintained in yeast and to be transplantable from yeast to produce a viable mycoplasma. First, cassettes were designed to fill the two largest gaps:

Cassettes to fill gap 1. "a" designates cassettes that were not part of the initial order from Blue Heron. Cassettes 835a-850a produce a sequence that matches CP001668 and fills the gap left by cassettes mmyc835-mmyc852, which were omitted from the initial Blue Heron order.

Cassettes to fill gap 2. Cassettes 2a-12ax fill the gap left where the cassettes mmyc1105-mmyc1114 and mmyc0-mmyc14 were located in the draft sequence (these were omitted from the Blue Heron order). This sequence matches CP001668 exactly and is considerably shorter than the corresponding region of the draft sequence, mainly due to problems with assembly of that sequence. The sequence of mmyc12ax is longer than most; hence, "x" for extended.

Cassettes to make the synthetic genome match CP001668 near the origin of replication. There were many differences between the mmycDRAFT sequence and CP001668 in this region.

mmyc799a (overlaps mmyc798 bp 80 bp—to 1084586, the end of CP001668)

mmyc811a (−80 to 1074 of CP001668)

mmyc812a (995 to 2074 of CP001668)

Cassettes Synthesized to Match CP001668.

mmyc56a (344335 to 345333 of CP001668), mmyc58a (345252 to 345926 of CP001668), and mmyc938.1a, which goes between mmyc938 and mmyc939.

Cassettes "Fixed" by Oligonucleotide Mutagenesis to Match CP001668.

"f" cassettes had small numbers of sequence differences that could be fixed by oligonucleotide mutagenesis to exactly match CP001668. See below for details on how these cassettes were fixed. The following cassettes were fixed: mmyc1011f, mmyc1028f, mmyc247f, mmyc248f, mmyc342f, mmyc399f, mmyc400f, mmyc528f, mmyc529f, mmyc578f, mmyc579f, mmyc632f, mmyc642f, mmyc759f, and mmyc874f. In addition, for constructing genomes with the "94D" deletion, which is missing mmyc936-mmyc939, cassette mmyc940f was produced to contain a 5' overlap with cassettes mmyc935. This region was demonstrated to be dispensable by deleting it from the natural genome in yeast, then transplanting to produce a viable mycoplasma.

Cassettes Containing Watermark Sequences.

(1) mmycWM1 replaces mmyc282-287 (5' 80 bp overlap from mmyc282; 3' 80 bp overlap from mmyc287), (2) mmycWM2b replaces mmyc447 (both 80 bp overlaps are from mmyc447), (3) mmycWM3 replaces mmyc106 (both 80 bp overlaps are from mmyc106), and (4) mmycWM4 replaces mmyc680 (both 80 bp overlaps are from mmyc680).

Nucleotide 1 is at the Initiation Codon of the dnaA Gene.

Both *M. mycoides* sequences CP001621 and CP001668 use a numbering system in which nucleotide 1 is at the initiation codon of the dnaA gene, in the vicinity of the DNA replication origin. The mmycDRAFT sequence used for the initial cassette design was numbered from a different origin but in the same direction. Consequently, nucleotide 1 of the genome sequence is located in cassette mmyc811a.

Differences Between Cassette Designs and CP001668 that were Not Fixed.

There are 19 differences between cassette designs and the CP001668 sequence that appeared harmless, which we opted not to fix. These were all differences in lengths of homopolymer or dinucleotide runs and were located between annotated genes. Some may affect the spacing between the −35 and −10 sequences of promoters, and so could affect gene expression. Table 18 gives details of these 19 differences. They provide more sequence differences to distinguish the synthetic genome from the natural *M. mycoides* genome that have been cloned in yeast, in addition to the watermark sequences.

DNA Cassette Sequence Corrections

The synthetic cassettes comprising the synthetic genome were ordered based on an imperfect draft sequence. Because of this, there were small differences between the ordered synthetic cassette sequences and the completed base *M. mycoides* subspecies *capri* genome sequence. Forty-three cassettes contained differences. Many of the differences were small insertions or deletions in homopolymer or dinucleotide runs not predicted to be located in genes. These changes were thought to be benign and were not fixed. Sixteen cassettes were chosen to be fixed. The differences were all single base changes except for a deletion of a 12 bp repeat unit in one cassette.

Two strategies were employed to change the synthetic cassette sequences to match the completed *M. mycoides* subspecies *capri* genome sequence. The QuikChange® II site directed mutagenesis kit (Stratagene) was used for some of the single base changes. The remainder of the changes were performed by a combination of PCR and in vitro recombination (Gibson et al., *Nat Methods* 6, 343 (2009)). Primers (BH pUC bckbn For1 and Rev1) were used to amplify the plasmid backbone for use in the recombination reaction. Complements of backbone primers (BH insert For1 and Rev1) were used in conjunction with error correcting primers (Cassette Fix For1 and Rev1) to produce amplicons with regions of homology to each other and the BH backbone amplicon. The three PCR products were used in in vitro recombination to generate the corrected cassette (data not shown). All fixes were performed on the 1,080 bp cassette clones.

Primers BH pUC bckbn For1 (5'-CGTCAAAGCAACCATAGTACGCGCCCTGTAG-3; SEQ ID NO.: #) and BH pUC bckbn Rev1 (5'-CTGACTCGCTGCGCTCGGTCGTTCGGC-3'; SEQ ID NO.: #) were used to amplify the plasmid backbone of a cassette clone. This amplicon (BH backbone) is ~2,600 bp and contains the ampicillin resistance marker and origin of replication. Primers BH insert For1 (5'-GCCGAACGACCGAGCGCAGCGAGTCAG-3'; SEQ ID NO.: #) and BH insert Rev1 (5'-CTACAGGGCGCGTACTATGGTTGCTTTGACG-3'; SEQ ID NO.: #) are the reverse complements of BH pUC bckbn For1 and BH pUC bckbn Rev1 and are used as the forward and reverse primers with the correction primers to amplify the cassette insert and create homology regions with the BH backbone for in vitro recombination.

To change a single nucleotide in a cassette, two oligonucleotides are required. The first primer contains the fixed nucleotide sequence flanked by approximately 20-25 bases and the second is the complement of the first. Examples of primers used to change a nucleotide to a G are shown. Cassette Fix For1 (5'-GAACTGAAAATTATATATCAGGTAGATATGAATAGGAAATAGTATGTC-3' SEQ ID NO.: #) and Cassette Fix Rev1 (5'-GACATACTATTTCCTATTCATATCTACCTGATATATAATTTTCAGTTC-3' SEQ ID NO.: #) with the nucleotide to be changed in bold. PCR is used to change the selected base. Primers BH insert For1 and Cassette Fix Rev1 are used to amplify part of a corrected insert and primers BH insert Rev1 and Cassette Fix For1 are for amplifying the remaining insert also with the correction. Because the Cassette Fix For1 and Cassette Fix Rev1 primers are reverse complements of each other this creates a homology region for in vitro recombination between the amplicons. As mentioned previously, the BH insert primers create homology with the BH backbone piece, allowing a three piece in vitro recombination reaction to create the corrected insert plasmid.

One synthetic cassette contained five repeats of a 12 bp sequence whereas the completed genome sequence showed six repeats of this sequence. PCR and in vitro recombination were used as above to correct the 12 bp deletion with minor changes. The forward primer used to add the 12 bp repeat unit contained four repeat units on the 5' end followed by 27 bases of non-repeat sequence on the 3' end. This primer was used with primer BH insert Rev1 to create an amplicon with four repeat units at the 5' end. The reverse primer used to add the 12 bp repeat unit contained the complement of four repeat units on the 5' end followed by 27 bases of non-repeat sequence on the 3' end. This primer was used with primer BH insert For1 to create an amplicon with four repeat units at the 3' end. Following in vitro recombination, clones were sequenced to identify the clones that recombined between two repeat units on the 3' end and two units on the 5' end of the amplicons resulting in a cassette insert sequence with six 12 bp repeat units.

A further change was made in cassette 940 that was not related to differences between the synthetic and native sequences. Cassettes 936-939 were difficult to assemble. Further work demonstrated that cassettes 936-939 were not essential for the viability of *M. mycoides* subspecies *capri* and could be deleted. In order to delete this region during construction of the synthetic genome, the 5' 80 bp overlap of cassette 940 was changed to match the 80 bp 3' overlap of cassette 935. Upon construction, cassette 935 would then join with cassette 940 deleting cassettes 936-939. To change the overlap region, cassette 940 was amplified with BH insert Rev1 and a forward primer that binds adjacent to the 5' 80 bp overlap region. The 5' overlap from cassette 936 (which is identical to the 3' 80 bp overlap of cassette 935) was obtained by amplifying cassette 936 with BH insert For1 and a reverse primer that binds the 3' 40 bp of the overlap with a 5' extension that is the complement of the forward primer used to amplify cassette 940. In vitro recombination was then used with the BH backbone piece to generate cassette 940 with a 5' 80 bp overlap to cassette 935.

ii. Watermarks

To further differentiate between a synthetic genome and a natural one, four watermark sequences were designed to replace one or more cassettes, added at places where insertion of additional sequence would not interfere with viability.

Watermark-1, 321 unencoded characters, 1246 base pairs

J. CRAIG VENTER INSTITUTE 2009

ABCDEFGHIJKLMNOPQRSTUVWXYZ

0123456789#@( )-+\=/:<;>$&}{*]"[%!'.,

SYNTHETIC GENOMICS, INC.

<!DOCTYPE HTML><HTML><HEAD><TITLE>GENOME TEAM</

TITLE></HEAD><BODY><A HREF="HTTP: //WWW.JCVI.ORG/"

>THE JCVI</A><P>PROVE YOU'VE DECODED THIS

WATERMARK BY EMAILING US <A

HREF="MAILTO: MROQSTIZ@JCVI.ORG">HERE!</A></P></

BODY></HTML>

(SEQ ID NO: #)
TTAACTAGCTAAGTTCGAATATTTCTATAGCTGTACATATTGTAATGCTG

ATAACTAATACTGTGCGCTTGACTGTGATCCTGATAAATAACTTCTTCTG

TAGGGTAGAGTTTTATTTAAGGCTACTACTGGTTGCAAACCAATGCCGTA

CATTACTAGCTTGATCCTTGGTCGGTCATTGGGGGATATCTCTTACTAAT

AGAGCGGCCTATCGCGTATTCTCGCCGGACCCCCCTCTCCCACACCAGCG

GTGTACATCACCAAGAAAATGAGGGGAACGGATGAGGAACGAGTGGGGGC

TCATTGCTGATCATAATGACTGTTTATATACTAATGCCGTCAACTGTTTG

CTGTGATACTGTGCTTTCGAGGGCGGGAGATTCTTTTTGACATACATAAA

TATCATGACAAAACAGCCGGTCATGACAAAACAGCCGGTCATAATAGATT

AGCCGGTGACTGTGAAACTAAAGCTACTAATGCCGTCAATAAATATGATA

ATAGCAACGGCCTGACTGTGAAACTAAAGCCGGCACTCATAATAGATTAG

CCGGAGTCGTATTCATAGCCGGTAGATATCACTATAAGGCCCAGGATCAT

GATGAACACAGCACCACGTCGTCGTCCGAGTTTTTTTGCGCGACGTCTAT

ACCACGGAAGCTGATCATAAATAGTTTTTTTGCTGCGGCACTAGAGCCGG

ACAAGCACACTACGTTTGTAAATACATCGTTCCGAATTGTAAATAATTTA

ATTTCGTATTTAAATTAATGATCACTGGCTATAGTCTAGTGATAACTACA

ATAGCTAGCAATAAGTCATATATAACAATAGCTGAACCTGTGCTACATAT

CCGCTATACGGTAGATATCACTATAAGGCCCAGGACAATAGCTGACTGAC

GTCAGCAACTACGTTTAGCTTGACTGTGGTCGGTTTTTTTGCTGCGACGT

CTATACGGAAGCTCATAACTATAAGAGCGGCACTAGAGCCGGCACACAAG

CCGGCACAGTCGTATTCATAGCCGCACTCATGACAAAACAGC*GGCGCGCC*

TTAACTAGCTAA

Watermark-2 326 unencoded characters, 1081 base pairs

MIKKEL ALGIRE, MICHAEL MONTAGUE, SANJAY VASHEE,

CAROLE LARTIGUE, CHUCK MERRYMAN, NINA

ALPEROVICH, NACYRA ASSAD-GARCIA, GWYN BENDERS,

RAY-YUAN CHUANG, EVGENIA DENISOVA, DANIEL

GIBSON, JOHN GLASS, ZHI-QING QI. "TO LIVE,

TO ERR, TO FALL, TO TRIUMPH, TO RECREATE

LIFE OUT OF LIFE."

- JAMES JOYCE (SEQ ID NO: #)
TTAACTAGCTAACAACTGGCAGCATAAAACATATAGAACTACCTGCTATA

AGTGATACAACTGTTTTCATAGTAAAACATACAACGTTGCTGATAGTACT

CCTAAGTGATAGCTTAGTGCGTTTAGCTATATTGTAGGCTTCATAATAAG

TGATATTTTAGCTACGTAACTAAATAAACTAGCTATGACTGTACTCCTAA

-continued
GTGATATTTTCATCCTTTGCAATACAATAACTACTACATCAATAGTGCGT

GATATCCTGTGCTAGATATAGAACACATAACTACGTTTGCTGTTTTCAGT

GATATGCTAGTTTCATCTATAGATATAGGCTGCTTAGATTCCCTACTAGC

TATTTCTGTAGGTGATATACGTCCATTGCATAATTAATGCATTTAACTAG

CTGTGATACTATAGCATCCCCATTCCTAGTGCATATTTTCATCCTAGTGC

TACGTGATATAATTGTACTAATGCCTGTAGATAATTTAATGCCTGGCTCG

TTTGTAGGTGAAATTTAGTGCCTGTAAAACATATACCTGAGTGCTCGTTG

CGTGATAGTTCGTTCATGCATATACAACTAGGCTGCTGTGATATGGTCAC

TGCCCTTACTGTGCTACATATTACTGCGAGGGGATGACTATAAACCTGT

TGTAAGTGATATGACGTATATAACTACTAGTGATATGACGTATAGGCTAG

AACAACGTGATATGACGTATATGACTACTGTCCCAAACATCAGTGATATG

ACGTATACTATAATTTCATAATAGTGATAAATAAACCTGGGCTAAATACG

TTCCTGAATACGTGGCATAAACCTGGGCTAACGAGGAATACCCATAGTTT

AGCAATAAGCTATAGTTCGTCATTTTTA*AGGCGCGCC*<u>TTAACTAGTAA</u>

Watermark-3 335 unencoded characters, 1109 base pairs

CLYDE HUTCHISON, ADRIANA JIGA, RADHA

KRISHNAKUMAR, JAN MOY, MONZIA MOODIE, MARVIN

FRAZIER, HOLLY BADEN-TILSON, JASON MITCHELL,

DANA BUSAM, JUSTIN JOHNSON, LAKSHMI DEVI

VISWANATHAN, JESSICA HOSTETLER, ROBERT

FRIEDMAN, VLADIMIR NOSKOV, JAYSHREE ZAVERI.

"SEE THINGS NOT AS THEY ARE, BUT AS THEY

MIGHT BE."

(SEQ ID NO: #)
<u>TTAACTAGCTAA</u>TTTAACCATATTTAAATATCATCCTGATTTTCACTGGC

TCGTTGCGTGATATAGATTCTACTGTAGTGCTAGATAGTTCTGTACTAGG

TGATACTATAGATTTCATAGATAGCACACTGGCTTCATGCTAGGCATCCC

AATAGCTAGTGATAGTTTAGTGCATACAACGTCATGTGATACAACGTTGC

TGGCTGTAGATACAACGTCGTATTCTGTAAGTGATACAATAGCTATTGCT

GTGCAAGGCCTATAGTGGCTGTAACTAGTGATATCACGTAACAACCATAT

AAGTTAGATTTAATGCCCTGACTGAACGCTCGTTGCGTGATAGTTTAGG

CTCGTTGCATACAACTGTGATTTTCATAAAACACGTGATAATTTAGTGCT

AGATAAGTTCCGCTTAGCAAGTGATAGTTTCCGCTTGACTGTGCATAGTT

CGTTCATGCGCTCGTTGCGTGATAAACTAGGCAGCTTCACAACTGATAAT

TTAATTGCTGAATTGCTGGCTGTCTAGTGCTAGTGATCATAGTGCGTGAT

AGTTTAAGCTGCTCTGTTTTAGATATCACGTGCTTGATAATGAAACTAAC

TAGTGATACTACGTAGTTAACTATGAATAGGCCTACTGTAATTCAATAGT

GCGTGATATTGAACTAGATTCTGCAACTGCTAATATGCCGTGCTGCACGT

TTGGTGATAGTTTAGCATGCTICACTATAATAAATATGGTAGTTGTAACT

ACTGCGAATAGGGGGAGTTAATAAATATGATCACTGTGCTACGCTATATG

CCGTTGAATATAGGCTATATGATCATAACATATATAGCTATAAGTGATAA

GTTCCTGAATATAGGCTATATGATCATAACATATACAACTGTACTATGAA

TAAGTTAACGAGGA<u>TTAACTAGCTAA</u>

Watermark-4 338 unencoded characters, 1222 base pairs

CYNTHIA ANDREWS-PFANNKOCH, QUANG PHAN, LI MA,

HAMILTON SMITH, ADI RAMON, CHRISTIAN TAGWERKER,

J CRAIG VENTER, EULA WILTURNER , LEI YOUNG,

SHIBU YOOSEPH, PRABHA IYER, TIM STOCKWELL,

DIANA RADUNE, BRIDGET SZCZYPINSKI, SCOTT DURKIN,

NADIA FEDOROVA, JAVIER QUINONES, HANNA TEKLEAB.

"WHAT I CANNOT BUILD, I CANNOT UNDERSTAND." -

RICHARD FEYNMAN (SEQ ID NO: #)
<u>TTAACTAGCTAA</u>TTTCATTGCTGATCACTGTAGATATAGTGCATTCTATA

AGTCGCTCCCACAGGCTAGTGCTGCGCACGTTTTTCAGTGATATTATCCT

AGTGCTACATAACATCATAGTGCGTGAAAACCTGATACAATAGGTGATAT

CATAGCAACTGAACTGACGTTGCATAGCTCAACTGTGATCAGTGATATAG

ATTCTGATACTATAGCAACGTTGCGTGATATTTTCACTACTGGCTTGACT

GTAGTCATATGATAGTACGTCTAACTAGCATAACTAGTGATAGTTATATT

TCTATAGCTGTACATATTGTAATGCTGATAACTAGTGATATAATCCAACT

AGATAGTCCTGAACTGATCCCTATGCTAACTAGGATAAACTAACTGATAC

ATCGTTCCTGCTACGTGATAGCTTCACTGAGTTCCATACATCGTCGTGCT

TAAACATCAGTGATAACACTATAGAGTTCATAGATACTGCATTAACTAGT

GATATGACTGCAATAGCTTGACGTTTTGCAGTCTAAAACAACGTGATAAT

TCTGTAGTGCTAGATACTATAGATTTCCTGCTAAGTGATAAGTCTACTGA

TTTACTAATGAATAGCTTGGTTTTGGCATACACTGTGCGTGCACTGGTGA

TAGCTTTTCGTTGATGAATAATTTCCCTAGCACTGTGCGTGATATGCTAG

ATTCTGTAGATAGGCTAAATTCGTCTACGTTTGTAGGTGATAGTTTAGTT

GCTGTAACTAATATTATCCTGTGCCGTTGCTAAGCTGTGATATCATAGTG

CTGCTAGATATGATAAGCAAACTAATAGAGTCGAGGGGGAGTCTCATAGT

GAATACTGATATTTTAGTGCTGCCGTTGAATAAGTTCCCTGAACATGTGA

TACTGATATTTTAGTGCTGCCGTTGAATATCCTGCATTTAACTAGCTTGA

TAGTGCATTCGAGGAATACCCATACTACTGTTTTCATAGCTAATTATAGG

CTAACATTGCCAATAGTGC*GGCGGCC*<u>TTAACTAGCTAA</u>

Watermarks 1-4 replaced cassettes 282-287, 447, 106, and 680, respectively. The watermarks were inserted in regions experimentally demonstrated (watermarks 1 (1246 bp) and 2 (1081 bp)) or predicted (watermarks 3 (1109 bp) and 4 (1222 bp) to not interfere with cell viability. An all-6 reading frame stop codon is underlined at the beginning and end of each watermark; Afc I restriction sites are shown in bold italics. Since our data indicated that the genome sequence represented by cassettes 936-939 was dispensable, we produced a version of cassette 940 that contained an 80 bp overlap to cassette 935. This would produce a 4-kb deletion and further distinguish the synthetic genome from a natural one.

The synthetic genome design, with this deletion and the four watermark sequences is 1,077,947 bp in length. This sequence was partitioned into cassettes 1,080 bp in length with 80 bp overlaps, and a NotI restriction site (GCGGC-CGC) was added to each end. A map of the genes, the 1,078 cassettes from which it was assembled, expected polymorphisms, unexpected polymorphisms an inserted *E. coli* transposon, and other features of *M. mycoides* JCVI-syn1 was created which provides the genome map of *M. mycoides* JCVI-syn1: Genes, structural RNAs, watermarks, polymorphisms relative to natural *M. mycoides capri* GM12, and the coordinates of the synthetic DNA cassettes were identified. Table 18 lists the differences between the synthetic genome and our control natural genome cloned in yeast, YCpMmyc1.1.

TABLE 18

Differences between *M. mycoides* JCVI-syn1 and the natural genome YCpMmyc1.1.

| designed difference | Coordinate on JCVI-syn1 | JCVI-syn1 | YCp-Mmyc1.1 | Affected cassettes | Search string following difference | SEQ ID NO. |
|---|---|---|---|---|---|---|
| homopolymer run | 59700 | A15 | A16 | mmyc872. | TAATATAATTTGCATAC TATAAAAA | |
| homopolymer run | 118608 | A16 | A17 | mmyc931 | GCAAAAAAACTAGTAAA TATCGTAT | |
| homopolymer run | 120703 | A18 | A17 | mmyc933 | CAAAATAGCTTAGTACA TATCGCAT | |
| homopolymer run | 122656 | A17 | A16 | mmyc935 | GCAACAAGGTGTGATCG CACCATTT | |
| deletion "94D" | 123020 | deletion | 4130 bp | mmyc936-939 | TATTTTGTAAAACAGTT TCATCAAGTT | |
| homopolymer run | 123429 | A18 | A21 | mmyc940f | GCAAACAAACCTAGTAC ACATCGTA | |
| dinucleotide run | 159343 | (TA)10 | (TA)9 | mmyc976 | ATGGAATTAACTATATA CACTAGGT | |
| homopolymer run | 174542 | T16 | T15 | mmyc991 | AATAAAAAGACTCACAT AAGTGAGT | |
| watermark | 388631-389563 | WM3 | 1000 bp | mmyc106 | TGATGCACTGATGTAAC AGAGTTTAAA | |
| snp | 405381 | G | A | mmyc122 | CCAATGCTAAAAAATCA AAATGCTCATT | |
| homopolymer run | 420496 | A22 | A18 | mmyc137 | CTAAAAACAAACTCTAT TTCTTAAA | |
| homopolymer run | 421365 | A19 | A20 | mmyc138 | CTAAAAACAAACTCTAT TTCTTAAA | |
| homopolymer run | 426516 | T16 | T15 | mmyc143 | GTAAAATAAAAGTAAG ATTTGGAT | |
| watermark | 564644-565713 | WM1 | 6000 bp | mmyc282-287 | AATTACCAAAAGGTGTA GTTTCAGTTC | |
| homopolymer run | 577948 | T18 | T17 | mmyc300 | GCTAAAAAGCCTATGTA AAGCCTTT | |
| watermark | 724794-725698 | WM2 | 1000 bp | mmyc447 | TATCAAGATACTTAGTA ATGCTAGTTTCTCC | |
| dinucleotide run | 727553 | (TC)12 | (TC)10 | mmyc449 | GGCTACTATCAAGTTCT TAAGTGCATCA | |
| homopolymer run | 900703 | T21 | T19 | mmyc622/623 | ACAAGCAATTTAATACA AACTTGTA | |
| watermark | 957779-958824 | WM4 | 1000 bp | mmyc680 | CAAATTCAATGCTAGAC AAAGCACTT | |
| homopolymer run | 1014079 | A16 | A17 | mmyc736 | TAAATCCAGCTTAGTAC TCATCAAA | |
| homopolymer run | 1064216 | T18 | T17 | mmyc786 | GCAGAGCTCGTATTATT CTTTTCTT | |

TABLE 18-continued

Differences between M. mycoides JCVI-syn1 and the natural genome YCpMmyc1.1.

| designed difference | Coordinate on JCVI-syn1 | JCVI-syn1 | YCp-Mmyc1.1 | Affected cassettes | Search string following difference | SEQ ID NO. |
|---|---|---|---|---|---|---|
| dinucleotide run | 1069129 | (AT)8 | (AT)10 | mmyc791 | TATAATGTGTCTTACAA AAGATAAA | |
| dinucleotide run | 1069967 | (TA)15 | (TA)12 | mmyc792 | ATGGTTATTGACAGGAA AAATATAT | |
| dinucleotide run | 1070891 | (TA)13 | (TA)14 | mmyc793 | ATGTGTCTTACCAAATT ATAAACAA | |
| dinucleotide run | 1071855 | (TA)12 | (TA)11 | mmyc793/794 | ATGATTATTGATATGAA AAATATAT | |
| undesigned | | sMm YCp235 | | | | |
| snp | 48020 | G | C | mmyc861 | CAAATAAAGTACCAAGT ACATAACCTA | |
| snp | 189893 | C | G | mmyc1006 | CAAATAAAGCGTTTGCT CATTATCGTT | |
| IS1 insertion | 308730 | IS1 (778 bp) | "—" | mmyc24 | ACTCTAATGTTGGGTTA AAATCATATGATT | |
| Snp | 347965 | A | T | mmyc65 | AAAAATGTTGCTAATGA GTAATAAAAAGT | |
| Snp | 678748 | G | A | mmyc400f/401 | GTTGAGTTGATTTTTTA GTATTTTCAGC | |
| Snp | 735321 | A | G | mmyc457 | AGATAAAGAACAAATGC CACCAACTAAT | |
| Snp | 858167 | A | G | mmyc580 | AAAAACAGCAACAAGTA GTGATGCTGA | |
| Snp | 858175 | T | G | mmyc580 | CAACAAGTAGTGATGCT GAAGAAGTATG | |
| snp | 1036988 | G | C | mmyc759f | TTATTCATTCATTTTTT CTTTAACAGAT | |

The differences are divided into two groups: 1) "designed differences"—25 differences between the synthetic genome design and the natural YCpMmyc1.1 genome, and 2) "undesigned"—9 observed differences between the sequenced genome arising from one transplanted clone of sMmYCp235 and YCpMmyc1.1. The differences are classified by type (column 1). The coordinate of each difference on the designed *M. mycoides* JCVI-syn1 sequence is indicated (column 2). The actual sequence differences on the synthetic and the natural genomes are listed for snps, and for homopolymer and dinucleotide runs; for watermarks the name of the watermark is given and the length of the substituted *M. mycoides* sequence is indicated; the size is of deletions and insertions given (columns 3 and 4). The cassettes affected by the difference and a search string to locate each difference is also shown (columns 5 and 6).

All designed 1 kb cassettes were ordered to be synthesized by Blue Heron; Bothell, Wash. All cassettes were individually synthesized and sequence-verified by the manufacturer.

Example 6B

Synthetic Donor Genome Assembly and Transplantation

A hierarchical strategy was designed to assemble the genome in 3 stages by transformation and homologous recombination in yeast (illustrated in FIG. 20). In the first stage, cassettes are taken 10-at-a-time to produce 10 kb assembly intermediates. In the second stage, these 10 kb intermediates are taken 10-at-a-time to produce eleven ~100 kb assembly intermediates. In the final stage, all 11 DNA fragments are assembled into a complete synthetic genome.

i. Host Vector Preparation

Polymerase chain reaction (PCR) amplification was used to produce a unique vector for the cloning of each assembly. The amplified vectors contain terminal overlaps to the ends of the assembly. The strategy for assembly vector preparation has previously been described (Gibson et al., *Science* 319, 1215 (2008)). Each PCR primer includes a 20 bp overlap with one end of the vector, a NotI restriction site, and a 40 bp overlap with one end of the cassette assembly. For the first stage of assembly, a yeast/*E. coli* shuttle vector, termed pCC1BAC-LCYEAST was produced for template DNA in PCR. This vector was constructed by in vitro assembly (Gibson et al., *Nat. Methods.,* 6: 343 (2009)) of AfeI-digested pCC1BAC with a PCR product consisting of 40 bp overlaps to the AfeI restriction fragment, a histidine selectable marker, a centromere, and an origin of replication (derived from pRS313 (Sikorski and Hieter, *Genetics* 122, 19 (1989))).

For the second stage of assembly, pRS314 (Sikorski and Hieter, *Genetics* 122, 19 (1989)) was used as template DNA in PCR (with the exception of the assembly of 831-840, which used pCC1BAC as template DNA). Unique assembly vectors were generated by PCR using the Phusion® Hot Start High-Fidelity DNA polymerase with HF buffer (NEB) according to the manufacturer's instructions except reactions were supplemented with 1 mM additional MgCl$_2$ and products were annealed at 60° C. and extended for 1 min per kilobase. PCR products were extracted from agarose gels after electrophoresis and purified using the QIAquick Gel Extraction kit (Qiagen) according to the manufacturer's instructions. Although we could have used the same second-stage vectors for cloning natural and synthetic fragments, an additional vector sequence was constructed for cloning natural 100-kb fragments. This vector sequence is named pCC1BAC-URA and was constructed in the same way that pCC1BACLCYEAST was constructed except pRS316 was used instead of pRS313. The primers used to produce the PCR-amplified assembly vectors are listed in Tables 19-21.

TABLE 19

Primers used to produce unique first-stage assembly vectors.
Overlaps to the ends of the cassette sequences are shown in upper case.

| Assembly | Forward Primer Sequence | SEQ ID NO. | Reverse Primer Sequence | SEQ ID NO. |
|---|---|---|---|---|
| 2-10 | GTTTTTAATTTAACTAATATTTATTACA AATAAAAAACTTgcggccgcgatcctct agagtcgacctg | | TTTTCCAGATATAAATGCCGGAAA TATTGGTTATAAGATTgcggccgc cgggtaccgagctcgaattc | |
| 11-20 | ACAAAGATATCTGGAGTTTGTTTAGTTA ATAAACAGTTTTgcggccgcgatcctct agagtcgacctg | | CCATATTCAGAAACTTTAACTTTA GCTCTTTCTTTACCATgcggccgc cgggtaccgagctcgaattc | |
| 21-30 | TCAACAATTACAAGAAAAACAAAAAGTT AAATTTATGTATgcggccgcgatcctct agagtcgacctg | | ATGAAGCTAGTAAAAAAGATAAAC AAAAAATAACATCATTgcggccgc cgggtaccgagctcgaattc | |
| 31-40 | CAATAGTAGCAATTTGAGAATTTAAATT ATCAATTTCGTTgcggccgcgatcctct agagtcgacctg | | TCTAAAGACTTAAAACTCATATAGT CACATTAATCCTTGGTgcggccgc cgggtaccgagctcgaattc | |
| 41-50 | TTTTAGTTCTCTTAGTCTATAAATTTCA ATCATTTCTTATgcggccgcgatcctct agagtcgacctg | | AATATCACTTGATTCTTCATATTT GTTTGTTATAAAACTAgcggccgc cgggtaccgagctcgaattc | |
| 51-60 | GTAGATGAATTATTAAACATATTAAAAA ACACTGATTTTAgcggccgcgatcctct agagtcgacctg | | GTCAATAATTTAGAACAAACTTAT AAAATAGCAAAAAAAgcggccgc cgggtaccgagctcgaattc | |
| 61-70 | TTTAACTTTCATATATAACCTCATTTAC TTTAATTATAAAgcggccgcgatcctct agagtcgacctg | | AAAAAATACGGAAAAGAATTTATT GATCTTTTAACATCTTgcggccgc cgggtaccgagctcgaattc | |
| 71-80 | AATTAAATCAAAATTCATTTTGTTATTT TTTACTAATTCTgcggccgcgatcctct agagtcgacctg | | ATAAAATTGATTTACCTAGTGCTG ATGTTGATAAAGTTAAgcggccgc cgggtaccgagctcgaattc | |
| 81-90 | TAATTACTGGAATTATTTCTAAATTACT ATCAATTGCTAAgcggccgcgatcctct agagtcgacctg | | ATTATTTTCTTTAACTAATAGATC TTCATCTCTAGTTTTTgcggccgc cgggtaccgagctcgaattc | |
| 91-100 | AGAACTGATAGAGTTGGTAACTTTAGAA AATATGAAAGAGgcggccgcgatcctct agagtcgacctg | | TAACATTTATCTTTTAATTTTTCA TTAACATTAGCAATTTgcggccgc cgggtaccgagctcgaattc | |
| 101-110W M3 | TCAAACAGCAAAGCAAATGTATGGAGAA ATGCTTCCAGAAgcggccgcgatcctct agagtcgacctg | | CATTAGAGTTTTTATATTTATATT GAGTTTGICAAATTCCgcggccgc cgggtaccgagctcgaattc | |
| 111-120 | TAATAGTTGATGCTATTATTAAAACACA AATTAATGATAAgcggccgcgatcctct agagtcgacctg | | ATCTTTATTAAAAGTACTAAAGAG TTTAATAAATTAAAATgcggccgc cgggtaccgagctcgaattc | |
| 121-130 | TTCTGTATTATAAATTTGACGTTTTTGT ATTGAGTCTCACgcggccgcgatcctct agagtcgacctg | | GTTCTACTTTAACTATTTTACTTT TTTTAAGTAGTTATTTgcggccgc cgggtaccgagctcgaattc | |
| 131-140 | TTGAAAACGATTTTAAAATTGGTGAATC AATATAATTTGTgcggccgcgatcctct agagtcgacctg | | GCTTTATTTGCTTTTATAGGTAGT TTATTACAAAAAAAGAgcggccgc cgggtaccgagctcgaattc | |
| 141-150 | TACTAATATAGCCGGTGTTGAAATAAAT TCTGTAAAGAAgcggccgcgatcctct agagtcgacctg | | TAGTTTATATAGTTTAGATTTTAG TGTTGATGCTAAAAAGgcggccgc cgggtaccgagctcgaattc | |

TABLE 19-continued

Primers used to produce unique first-stage assembly vectors.
Overlaps to the ends of the cassette sequences are shown in upper case.

| Assembly | Forward Primer Sequence | SEQ ID NO. | Reverse Primer Sequence | SEQ ID NO. |
|---|---|---|---|---|
| 151-160 | GTTGGATCTGTTATTTTGTTACTGTTAT TTAGGTATTTTTgcggccgcgatcctct agagtcgacctg | | CTACAGTATAAAACCAGGTATGAT GCCATCTACAACTCCAgcggccgc cgggtaccgagctcgaattc | |
| 161-170 | TAGAAGAATTTGAATCTTTAAATTTAGG TAATTTTGAAGAgcggccgcgatcctct agagtcgacctg | | ATTTGATGATCAAATTAAATTAGA TCATAATATTACTTATgcggccgc cgggtaccgagctcgaattc | |
| 171-180 | AATTTTCTATCTATCATAATGAACTAAT ATCATTACCTTGgcggccgcgatcctct agagtcgacctg | | TAATCAAGAACTAGAAATAAGTTA TATTCCAACTGATTTTgcggccgc cgggtaccgagctcgaattc | |
| 181-190 | ATTAGTTTTAACGCTTTGTCAAATTTAT TATTATCAATTAgcggccgcgatcctct agagtcgacctg | | TTATTTATATTCAACAAGTTGTTT TGTAAATGATATTAATgcggccgc cgggtaccgagctcgaattc | |
| 191-200 | CTTTGATCAGATGTACTACATACATATA AAATCTTTTTTTgcggccgcgatcctct agagtcgacctg | | CTGCTGTTAAACTTGGTATAGGAA TTGATTATAAATACCCgcggccgc cgggtaccgagctcgaattc | |
| 201-210 | ATTTATAATGATTATCCTTTAGATGTTT TGGTACATTATAgcggccgcgatcctct agagtcgacctg | | GTTTCAAATTCTCCTTTAACAAAA CCAACGATTAATTATTgcggccgc cgggtaccgagctcgaattc | |
| 211-220 | ACCTTTTGAATAATTATATTCATTTGCA TATTTAATACTTgcggccgcgatcctct agagtcgacctg | | ACTACTATTAATAAACTTGTTGAA CTAACTAAAATTTCAGgcggccgc cgggtaccgagctcgaattc | |
| 221-230 | TTCAACTAAAATTTCATTATTAAGATCA AAAATAAAATTTgcggccgcgatcctct agagtcgacctg | | AGTAATAGTTTTAGTAAGTTCACT AGTAGTTATTTTTAGAgcggccgc cgggtaccgagctcgaattc | |
| 231-240 | AAAATTAATGTTAAAGCTAAAGCAACAA AATAAGTTCATTgcggccgcgatcctct agagtcgacctg | | ATTTAGATAGATATGAGTAATTTT TTGAAGCTGTTAAAGAgcggccgc cgggtaccgagctcgaattc | |
| 241-250 | CATTTAGAAATGTAGTTTCATTTAATAT TACTAAAGCTGAgcggccgcgatcctct agagtcgacctg | | GTGGTAGCAACCTATTAGATTAGG TGCTTAAATAAGGGCTgcggccgc cgggtaccgagctcgaattc | |
| 251-260 | TTCATTAAGTTTTATCTCTCCATGGTTC TTAATAAGATATgcggccgcgatcctct agagtcgacctg | | TTATCTTAGCATCTTGACCTCTAA AAATAGTATCAAATCTgcggccgc cgggtaccgagctcgaattc | |
| 261-270 | AAGCAAATACTAGTATAAATAATAAAGC AGAATTCAAGGAgcggccgcgatcctct agagtcgacctg | | TTTAGAACAAAAAATAGGAGATAT AGTTCTTATAAAGGAAgcggccgc cgggtaccgagctcgaattc | |
| 271-280 | TTTAATACACTGAACTCCAAGCTCTTTA GTTAACCTTAAAgcggccgcgatcctct agagtcgacctg | | TTGTAACATGTAAACTCCTAAAAC TAAAATAGCTAATAAGgcggccgc cgggtaccgagctcgaattc | |
| 281-290W M1 | ATGGGGTTATCTTCATATGTAAACTATT TAAAAAACGTGTgcggccgcgatcctct agagtcgacctg | | AGATGATTGATTCTTATACCCAGT AATAACTCCACACAATgcggccgc cgggtaccgagctcgaattc | |
| 291-300 | TCATTATTAAATGTTGATCGTTCTGCTG CATTATTTGGTTgcggccgcgatcctct agagtcgacctg | | CAAATGAAGATTGAGAAGATTTTA TTGCTTTAGATGCTCTgcggccgc cgggtaccgagctcgaattc | |
| 301-310 | CTTTTCTACTAATTTCATCAAATTTATG ATTATGTCTTTCgcggccgcgatcctct agagtcgacctg | | TGGTTTTGTTTTCTAAAGATTTTA ATTTAGCTTAATCCgcgcggccgcg gtaccgagctcgaattc | |
| 311-320 | ACTAAATTTAATCTATCTCTTCTAACTA AAAACAAAGGCTgcggccgcgatcctct agagtcgacctg | | AAATATGTTTATATAAATAAAAAC GGAGAAGAACAAGATTgcggccgc cgggtaccgagctcgaattc | |
| 321-330 | TAAAAACTTTAAATTATTATTTGTAGGT GCTTCTAAATACgcggccgcgatcctct agagtcgacctg | | CTAAATTAATTTCTTTCATAATAA TACCTCCTATTAAGGTgcggccgc cgggtaccgagctcgaattc | |

TABLE 19-continued

Primers used to produce unique first-stage assembly vectors.
Overlaps to the ends of the cassette sequences are shown in upper case.

| Assembly | Forward Primer Sequence | SEQ ID NO. | Reverse Primer Sequence | SEQ ID NO. |
|---|---|---|---|---|
| 331-340 | AAAATACAAAAGAAATTATTGGCGGAGC TGGAGTTAGTGGgcggccgcgatcctct agagtcgacctg | | AGATTTTGATAAACTTCTTCAATT GTATGAACTAAAATTGgcggccgc cgggtaccgagctcgaattc | |
| 341-350 | AAATGATAATAATAAAGTTGAATCAGTT CATTTATTAGATgcggccgcgatcctct agagtcgacctg | | TATAATCTAGCAACTTCTTCACAT AAATCATTTTTACTAGgcggccgc cgggtaccgagctcgaattc | |
| 351-360 | TTCATATGATAAAATTGATGAAGTTCCA CTAAGCTTTACTgcggccgcgatcctct agagtcgacctg | | ATTAGGTTTTACCCTAACTTCAAC CTGCTCATGGCTAGATgcggccgc cgggtaccgagctcgaattc | |
| 361-370 | GGAGGACCGAACCAGTATTCGTTGAAAA GACTTTGGATGAgcggccgcgatcctct agagtcgacctg | | AAAGTAACTTCATTTGTGGAATA CCTCTAGGAGCTGGTTgcggccgc cgggtaccgagctcgaattc | |
| 371-380 | TGAAATTGATGCTAATGGTATTGTAAGT GTTTCAGCAAAAgcggccgcgatcctct agagtcgacctg | | GTTTGATTATTCTAGAAATCAAAA AGATGCTAAGTTTAAAgcggccgc cgggtaccgagctcgaattc | |
| 381-390 | ATATATTTAGTTGTAATCTTATCTTTAT TATTTATAAATTgcggccgcgatcctct agagtcgacctg | | TATGTTTTTTGAAGCAACTTCATT TAACCAAGATATATCAgcggccgc cgggtaccgagctcgaattc | |
| 391-400 | TATGACATATCAGTTACATTTGAAACAT TTCATTTACCAAgcggccgcgatcctct agagtcgacctg | | GTTGATTTTTAGTATTTTCAGCA ACTATCATCTTATCAAgcggccgc cgggtaccgagctcgaattc | |
| 401-410 | TCAACTAAAATCTTTTCAAAAAGATTT TGTGTTTTTTTgcggccgcgatcctct agagtcgacctg | | TTATAAATAAAAATTCGATTCTC AAAATGTTCAAATTGAgcggccgc cgggtaccgagctcgaattc | |
| 411-420 | AACTCTTTGCTAAATCTTCTTTTTCTTT AGCTTTTTGTTTgcggccgcgatcctct agagtcgacctg | | AGTGGTTTTTTGTTTAAATCTGGT TGATTTGGTGGTGTTGgcggccgc cgggtaccgagctcgaattc | |
| 421-430 | AGATCCAACTGAAAGAAGAGATCAAAC TCAGTTGAATATgcggccgcgatcctct agagtcgacctg | | TCCAATTTGATATGATAAGAAATT TCCTTTTTCTAATTCCgcggccgc cgggtaccgagctcgaattc | |
| 431-440 | TATAGATCATTTATTGATAAACCTGGAT TAACTGATGGATgcggccgcgatcctct agagtcgacctg | | CCGATTCTATGAACTGCTAAAAAT GCATCAGTTAGTCCTGgcggccgc cgggtaccgagctcgaattc | |
| 441-450W M2 | TAATGATTTATACACACTTTATGATAAA AATAAAAAAGAAgcggccgcgatcctct agagtcgacctg | | TGAATTAATTGTTCTGATTTCAT TTCACACATTACACTTgcggccgc cgggtaccgagctcgaattc | |
| 451-460 | CATAATAAAAGAAAAATAGTGATCATT ATAAAAAATTAGgcggccgcgatcctct agagtcgacctg | | AATTCAAAAGACAAAAATTTAGGT AATTTTGATAATATATTGgcggccgc cgggtaccgagctcgaattc | |
| 461-470 | AAGAACTTGATCAACATTAGTTTTTCTG AAGCTAATTTCTgcggccgcgatcctct agagtcgacctg | | CCTTTTAAATGAGGTAATACTAAG CTAACTGCTTTAGCAGgcggccgc cgggtaccgagctcgaattc | |
| 471-480 | TAAATTAGATGGATATGCATTACGTGTG CCAACTATTACTgcggccgcgatcctct agagtcgacctg | | TAGTATCTTTATTAATTTGAGTAT TTGGTAAAGAGTTTAAgcggccgc cgggtaccgagctcgaattc | |
| 481-490 | AAGTAATTGATGCTTTAATTGAAGTAAA AGCTGCTAGTTCgcggccgcgatcctct agagtcgacctg | | GTTTTTACATCTAATATTACATTA ACTGCAATAGTTCCAgcggccgc cgggtaccgagctcgaattc | |
| 491-500 | TTTAGATGTTTCTAATGGTATTATTCAA ACAATTGAAAAAgcggccgcgatcctct agagtcgacctg | | AAAATCAGATAGTTTTATAGTAAA TAAATTCTTAAGATTTgcggccgc cgggtaccgagctcgaattc | |
| 501-510 | ATTAAATTAGAAAATAAACCAAATTTTG GTTCTGATTATTgcggccgcgatcctct agagtcgacctg | | AAATAATTAATCCATTTGTTAATT GGATCATTGTTGATTTgcggccgc cgggtaccgagctcgaattc | |

TABLE 19-continued

Primers used to produce unique first-stage assembly vectors.
Overlaps to the ends of the cassette sequences are shown in upper case.

| Assembly | Forward Primer Sequence | SEQ ID NO. | Reverse Primer Sequence | SEQ ID NO. |
|---|---|---|---|---|
| 511-520 | CTGAAACTGGTCAAATTATAGTTGGTGA TTATGCTATTCCgcggccgcgatcctct agagtcgacctg | | TGGGAAAATAAATTTGTTCTTTAAT TCCAGTTGTAAAATTTgcggccgc cgggtaccgagctcgaattc | |
| 521-530 | GAAGTAGATTATGATAAAGTTATTAGAT TACGTGGTATGGgcggccgcgatcctct agagtcgacctg | | TGAATCATTACAGCATTATACATT GTATGTAATCCAGTAAgcggccgc cgggtaccgagctcgaattc | |
| 531-540 | AAACACAGCAACAATTGGTGGTTCATTT ATTTTCCCAATTgcggccgcgatcctct agagtcgacctg | | TCTAAACTAGTTAAAATAATATTA GCATCTTCACTAGTTAgcggccgc cgggtaccgagctcgaattc | |
| 541-550 | AATGACTAATTTTTTTGAAAAAACTATT AAATCAACTACTgcggccgcgatcctct agagtcgacctg | | AAAAATGCCATAGCATCTTTAATT ACTTTTCTTICTCTAAgcggccgc cgggtaccgagctcgaattc | |
| 551-560 | AAAAATGATTTCAATTAAAGATGACTTG TCATCTCAAAGAgcggccgcgatcctct agagtcgacctg | | TTAACAAATTGTACTAGTTGTTCA TTAAAATCGTGTTTTTgcggccgc cgggtaccgagctcgaattc | |
| 561-570 | TAAAGATTCACATAACTATATAACTTTA GATAGTTTAATGgcggccgcgatcctct agagtcgacctg | | ATATTAAACAATTTTATTTATTAG ATGATTATGATAATTTgcggccgc cgggtaccgagctcgaattc | |
| 571-580 | TATCTTTACATCATCTTCTTTCATGAGT TTTTGATCTATTgcggccgcgatcctct agagtcgacctg | | AGGATATGTTGATGATTTAAAAAC TGTAATAACTAATAAAgcggccgc cgggtaccgagctcgaattc | |
| 581-590 | CAAATTTTAATATCACTATTTTTATATT TATCACTAGTTAgcggccgcgatcctct agagtcgacctg | | GTATTCAATCCAATGTTTAAAACC TGCTTAAAATTTTCAAgcggccgc cgggtaccgagctcgaattc | |
| 591-600 | TAATGAATTTGAAAATATAGATGATCTT GATTTTTTAACTgcggccgcgatcctct agagtcgacctg | | AAAATATCTCTAATTACTAAATCT TTATCTAATTCATTTAgcggccgc cgggtaccgagctcgaattc | |
| 601-610 | AAAATTTATGTAATTTATTAATTTTTAT CTTTATAATATAgcggccgcgatcctct agagtcgacctg | | TAAACGCATCATAATGTCCAGTAG TATGAGCTATTTTATCgcggccgc cgggtaccgagctcgaattc | |
| 611-620 | TTAAAAAACAAATTCCAGCTAAAAAAAT AAAACTTTTATTgcggccgcgatcctct agagtcgacctg | | ACCAAATACTAATGCAGTTTTATT AAATGGCCCTCCTAAAgcggccgc cgggtaccgagctcgaattc | |
| 621-630 | ACTGTTGTGTTTTATCAATCATTAGCTC AAGTGTTATCAAgcggccgcgatcctct agagtcgacctg | | GGTTCAATATAGTTTTTTAAATAT AATTCAGCTGCTTTAAgcggccgc cgggtaccgagctcgaattc | |
| 631-640 | TAGAATGAAAAAATTTTCTAGTCTAAAA GAAAGATTAGATgcggccgcg atcctctagagtcgacctg | | TTTCTTCCTTCAACTAATTGATAT TATGGATTAAGTTTAGgcggccgc cgggtaccgagctcgaattc | |
| 641-650 | TAATAAATCAACCTTACTTAACTCATCA CATAATTGCTCTgcggccgcgatcctct agagtcgacctg | | TTAAAGGAGTAGGTAGCTCTCTAT CTTGTTTATCTACTAAgcggccgc cgggtaccgagctcgaattc | |
| 651-660 | AACTAGCATAATAAAATAAAAACCTATA CTAGTTCTAAATgcggccgcgatcctct agagtcgacctg | | ATCCAGATGAACCTCCATCTAAAG CTTTATGATCTTCATTgcggccgc cgggtaccgagctcgaattc | |
| 661-670 | CAATGGCTATTGATTCTTCATTTAATTT AATTGGTATTAAgcggccgcgatcctct agagtcgacctg | | TCTTTTTTAACTCATTTATAAATA CAGCTTGCATGATTGTgcggccgc cgggtaccgagctcgaattc | |
| 671-680W M4 | TAAAAAAAGGTTGTTTATATTTGAAGAT GATCTTAGTTTTgcggccgcgatcctct agagtcgacctg | | TACAAATGGTTTGTTAATTCACTC TGATCAGGGATTTCATgcggccgc cgggtaccgagctcgaattc | |
| 681-690 | TTTTTAACCTTTTTAAGTGCTTTGTCTA GCATTGAATTTGgcggccgcgatcctct agagtcgacctg | | AATATAGTAATAATCACATAAAAT TCTAAATTTTTGTCATgcggccgc cgggtaccgagctcgaattc | |

TABLE 19-continued

Primers used to produce unique first-stage assembly vectors.
Overlaps to the ends of the cassette sequences are shown in upper case.

| Assembly | Forward Primer Sequence | SEQ ID NO. | Reverse Primer Sequence | SEQ ID NO. |
|---|---|---|---|---|
| 691-700 | GATCTAAACACTCCTTTAAAAGATTTGA CTCAAAAACAAAgcggccgcgatcctct agagtcgacctg | | ATGCTTTAGCTGACATTGTTTCAG TTTTAAAAGTTGATGAgcggccgc cgggtaccgagctcgaattc | |
| 701-710 | TAGAAAAACTCATAGCTACACCTAAAAC AAAACGTTCAGCgcggccgcgatcctct agagtcgacctg | | ATTTTGCTAAAAAGATAAAAACG GTTCTATAAGTTTTGAgcggccgc cgggtaccgagctcgaattc | |
| 711-720 | TAAAAGTAGCATATTCTCCATAATCTTT AATTGCACCAAAgcggccgcgatcctct agagtcgacctg | | ATTTATGATGGAGAGGTTCTAGGT TTAGTTGGTGAGTCAGgcggccgc cgggtaccgagctcgaattc | |
| 721-730 | ATTTAAATTTAGATCTTTAATAGCAGTA AACTCTTTTGCAgcggccgcgatcctct agagtcgacctg | | AAATTCATCTTGGAGTCACTGATG ATGGTCATATTGACAAgcggccgc cgggtaccgagctcgaattc | |
| 731-740 | CTCCACCTTTAGTATTTAAAAAGCTAC AATTTCTCTTTTgcggccgcgatcctct agagtcgacctg | | CGTTTTTCTAGCATAAATAATAT CTCTAGATCTAGAGTTgcggccgc cgggtaccgagctcgaattc | |
| 741-750 | CTAATGACATTAACACTAATTTTGTTGA AGATGAAAACGAgcggccgcgatcctct agagtcgacctg | | TCTTCATAGTTCATATTATTTACT CTCTTTTAAAATTTGTgcggccgc cgggtaccgagctcgaattc | |
| 751-760 | ACTTGAAATTGGAGATATTATTGAATTA AAAAAACCTCATgcggccgcgatcctct agagtcgacctg | | GAAATTCATGGAAATAATAATAAG CTTAATGATGTTGGAAgcggccgc cgggtaccgagctcgaattc | |
| 761-770 | TGGTTTAGAATCTAATACTTTAGCTAAT GAGATAAGAATAgcggccgcgatcctct agagtcgacctg | | ATAGTTTCTAAGTTATAACCATAA ACATAAAAACTGTTGTgcggccgc cgggtaccgagctcgaattc | |
| 771-780 | GTTGGCTGAAAAAATTCATGCAATCAAA GAATTAAGCTTGgcggccgcgatcctct agagtcgacctg | | AATTTCACCATTAAAAAAAGTATG ATTTGCATCATTTTTAgcggccgc cgggtaccgagctcgaattc | |
| 781-790 | AGAAAACTTCAAGATAAGTTAGTTTTAT CAAATACTAAACgcggccgcgatcctct agagtcgacctg | | TAATAACCTCTAAATTAACGTCAC ATTCTAATTTAATTTTgcggccgc cgggtaccgagctcgaattc | |
| 791-795 | TGAAAAAATTAGTGGCATTACTTGCTGC TATTAGTGTGTTgcggccgcgatcctct agagtcgacctg | | TACTCTTCCCATTTCTCTTAGATC ATTACTATTAGTTCTAgcggccgc cgggtaccgagctcgaattc | |
| 796-799 | ATTTCAACAGTTTTACAATGCCTAGATA ATTTAAATAAAAgcggccgcgatcctct agagtcgacctg | | TTTTAACAAGTGTTTAACTATAAT ATTTTTGGAGACAAATgcggccgc cgggtaccgagctcgaattc | |
| 811-820 | ATGTGGAAAACGTGGAAAAAATCCTTAT AACATAGATATAgcggccgcgatcctct agagtcgacctg | | CTCTTGATGTCTTACTAAATGCAA CCATAGCTAGTATTGTgcggccgc cgggtaccgagctcgaattc | |
| 821-830 | CACCAGCTGCAGTTGGTGTACCTTTTGA TAAAGCAAAAGgcggccgcgatcctct agagtcgacctg | | TTACAGTAATAAGAGTGAAGAAAA TAATACAATTATAGCGgcggccgc cgggtaccgagctcgaattc | |
| 831-840 | TCTAATTTTAGTGACTGTGTATCTCTAT ATATATGATTCTgcggccgcgatcctct agagtcgacctg | | TGATTACGAATAAATTTTATTCAT CAACACATCGAGGTCCgcggccgc cgggtaccgagctcgaattc | |
| 841-850 | CTTCTATAAGGTTATCAATCCCTATATT GTTTTTTGCACTgcggccgcgatcctct agagtcgacctg | | TTCATCAGTGATTTTGAATCCTTG GTTTGATTCAGATTGTgcggccgc cgggtaccgagctcgaattc | |
| 853-860 | TATTAAAAAAATTGTTGTTTGTTGTGAA GCAGGAGTAGGAgcggccgcgatcctct agagtcgacctg | | AATTGATAATTCATAGTTTGGATC ACTTGATGATAATCCAgcggccgc cgggtaccgagctcgaattc | |
| 861-870 | GAAAATAAAAAAGATGCAGTTTCTATTT TAAATGTCTTTAgcggccgcgatcctct agagtcgacctg | | ACTAAATGAGAAGATCAACCAATT CAAATTATTAATAATAgcggccgc cgggtaccgagctcgaattc | |

TABLE 19-continued

Primers used to produce unique first-stage assembly vectors.
Overlaps to the ends of the cassette sequences are shown in upper case.

| Assembly | Forward Primer Sequence | SEQ ID NO. | Reverse Primer Sequence | SEQ ID NO. |
|---|---|---|---|---|
| 871-880 | ATGTTTATTTACATATTCAGTTTTTAAA TAATCTGAATCAgcggccgcgatcctct agagtcgacctg | | AAATACATAAAAAAGTGCCTTGTA TTTGTAGTCAAACTATgcggccgc cgggtaccgagctcgaattc | |
| 881-890 | GTTCAAAAACAACATCTGCTTGTTGGTA TCAAGATTTATTgcggccgcgatcctct agagtcgacctg | | AGTATTTAGAATTCCAATTACATT AAATGATGAATCAATAgcggccgc cgggtaccgagctcgaattc | |
| 891-900 | GAAGTTCAAGATGTTCCTGGAAGTAAAT ATATTTCAATTCgcggccgcgatcctct agagtcgacctg | | TATGCCAATTATTAAATTTAGTGG ACTAGATAAAGAACAAgcggccgc cgggtaccgagctcgaattc | |
| 901-910 | ATATTATTCTTCCTTTTTTCTATGTAAT TTTATTACAAAAgcggccgcgatcctct agagtcgacctg | | TTTATTAGACCAAACAATAGAAAT ATCTGGTGTGTTTAACgcggccgc cgggtaccgagctcgaattc | |
| 911-920 | AACTTATTGTTAAAGTCATTAACATAAA ACTTAATATTTTgcggccgcgatcctct agagtcgacctg | | AATTGGAATCAAATTATCATTGAT TTTAAATTCTAGTTCTgcggccgc cgggtaccgagctcgaattc | |
| 921-930 | AAATTTAAAACTAGTGACAATATAACAA TTTCAGCACTTAgcggccgcgatcctct agagtcgacctg | | ATCTCTTTTCTTCTTTTTCAATTT GTTCTTTAGTTGGATTgcggccgc cgggtaccgagctcgaattc | |
| 931-940 (94D) | TAGAAGATTGAGTTAAGGAATACCTAGA TAAAAATAAAAGgcggccgcgatcctct agagtcgacctg | | AGATTTTGTTATTTCTGATATTTC AGCTTGTATTTTTGTAgcggccgc cgggtaccgagctcgaattc | |
| 941-950 | TTAGAACCACTTAATGCAGAAAAAAACA AAATTGACAAACgcggccgcgatcctct agagtcgacctg | | TGTTGGAAATGTTGATTTTAATAA AAATGTATATCAAGCAgcggccgc cgggtaccgagctcgaattc | |
| 951-960 | GGAAGATTAAATTTTCCTTGTTGATTAA ATCTAATCATATgcggccgcgatcctct agagtcgacctg | | TAACACTTCCGACTAAATAATTAT TTTGTTTATTCATACTgcggccgc cgggtaccgagctcgaattc | |
| 961-970 | ATGAAGCTATTAGTTATAAAGCAAATAC TTTTATGATCTTgcggccgcgatcctct agagtcgacctg | | AAAATCTGAGCTTATGTTAAATCC GATGAGTGATTTATCTgcggccgc cgggtaccgagctcgaattc | |
| 971-980 | ATTCCAAATCTTGAAAGTGTTGCTCTAA TTTCAGGATCTAgcggccgcgatcctct agagtcgacctg | | TTTTAGTGATATAGATTTGTTGTA ATTTAAAAAAAAACTTgcggccgc cgggtaccgagctcgaattc | |
| 981-990 | ACAAAATAAAAGTTCAGATTTAATCTGA ACTTTATAATTAgcggccgcgatcctct agagtcgacctg | | CAACTAAAGAAAATAAATTTCCCT TTATTGCAAAACTTACgcggccgc cgggtaccgagctcgaattc | |
| 991-1000 | GAACTGGTAAGTTGAAATTATATGTATA ATAAGCTTTTGTgcggccgcgatcctct agagtcgacctg | | ATTTCTTTACAAAATATTACTTTT TTTGAATATGAAAAAAgcggccgc cgggtaccgagctcgaattc | |
| 1001-1010 | ACTTGTAACAAACATTAAAAAGATTTGT ACAAAAATAATTgcggccgcgatcctct agagtcgacctg | | TTATAATAAATATTACAATTTTAA TAAATTACCACAAGCAgcggccgc cgggtaccgagctcgaattc | |
| 1011-1020 | ATTGTTGCACCAACAAATCCCATTATAA TTCCACCAATGGgcggccgcgatcctct agagtcgacctg | | GAAAACTTTGAAATGCCAGCATTT ATGATCAACAATGCATgcggccgc cgggtaccgagctcgaattc | |
| 1021-1030 | TTCGTTTTTTTCTGCGTTTTTTCAAACC TAGTAGTATTTAgcggccgcgatcctct agagtcgacctg | | GTACATATCTTTAGAAATGCTGGA GTAAGAATTATAAGAgcggccgc cgggtaccgagctcgaattc | |
| 1031-1040 | ATAATAAGTTTATTTGAACTAGTTCCT TTAGCTAAAGCAgcggccgcgatcctct agagtcgacctg | | ATATCTTTTATGACCTAAATTAGC AACAAAATCAACTTCAgcggccgc cgggtaccgagctcgaattc | |
| 1041-1050 | TACATTCAATATGCAGATAATATTAATA CTAAAGAAAAAgcggccgcgatcctct agagtcgacctg | | CGAAATTTCAGGATTCCCATTAGC AAATCTTTCTGGAAAAgcggccgc cgggtaccgagctcgaattc | |

TABLE 19-continued

Primers used to produce unique first-stage assembly vectors.
Overlaps to the ends of the cassette sequences are shown in upper case.

| Assembly | Forward Primer Sequence | SEQ ID NO. | Reverse Primer Sequence | SEQ ID NO. |
|---|---|---|---|---|
| 1051-1060 | CCAAAAAATUITTTAGCTTGAAATTCAG AAGCTCCAGCTGgcggccgcgatcctct agagtcgacctg | | AATTACTATTAGATAATCAAAGAG ACTGAACAATGGCTACgcggccgc cgggtaccgagctcgaattc | |
| 1061-1070 | GTGGTAATAAAACATCACCAAATGGTCC TATAAATGATCAgcggccgcgatcctct agagtcgacctg | | TCAATATTAAAAAGCTTTTTAATT ATTTAAAATAGATTCAgcggccgc cgggtaccgagctcgaattc | |
| 1071-1080 | TTTTAACAATAATATTAAACTTTATAAT ACTGATTAAATTgcggccgcgatcctct agagtcgacctg | | AGCACGTGCTTCTTTCTTAAACGT TAATATTATATATATTgcggccgc cgggtaccgagctcgaattc | |
| 1081-1090 | CACCATTAGCTATTAGTGAAATGGTAAT AACTTTTTTTATgcggccgcgatcctct agagtcgacctg | | CAACAGTTAACCAATTAGTAGTTG GATTTGTTATATTAATgcggccgc cgggtaccgagctcgaattc | |
| 1091-1100 | GTTTTAGACCAATTATTAAAAACGGTGA AATAATTTTTTCgcggccgcgatcctct agagtcgacctg | | GTTTTAGGACATATTCAACGTGGT GGTAGACCAACTGCTAgcggccgc cgggtaccgagctcgaattc | |
| 1101-1104 | AGTTGCTTTAGTTTCATAACCACTAATT TTTTGAATTTTTgcggccgcgatcctct agagtcgacctg | | CAAATCTGTAATTGTATTTAAAAA CTCTTAAAAAACTAGAgcggccgc cgggtaccgagctcgaattc | |

Table 20. Primers used to produce unique synthetic second-stage assembly vectors. Overlaps to the ends of the 10-kb assembly sequences are shown in upper case.

TABLE 20

Primers used to produce unique synthetic second-stage assembly vectors.
Overlasp to the ends of the 10-kb assembly sequences are shown in upper case.

| Assembly | Primer Name | Primer Sequence | SEQ ID NO. |
|---|---|---|---|
| 2-100 | pRS-2AF | GTTTTTAATTTAACTAATATTTATTACAAATAAAAAACTTgcg gccgcgcaaggcgattaagttggg | |
| | pRS-100R | TAACATTTATCTTTTAATTTTTCATTAACATTAGCAATTTgcg gccgcacatccccccttcgccagc | |
| 101-200WM3 | pRS-101F | TCAAACAGCAAAGCAAATGTATGGAGAAATGCTTCCAGAAgcg gccgcgcaaggcgattaagttggg | |
| | pRS-101R | CTGCTGTTAAACTTGGTATAGGAATTGATTATAAATACCCgcg gccgcacatccccccttcgccagc | |
| 201-300WM1 | pRS-201F | CTGCTGTTAAACTTGGTATAGGAATTGATTATAAATACCCgcg gccgcacatccccccttcgccagc | |
| | pRS-300R | CAAATGAAGATTGAGAAGATTTTATTGCTTTAGATGCTCTgcg gccgcacatccccccttcgccagc | |
| 301-400 | pRS-301F | CTTTTCTACTAATTTCATCAAATTTATGATTATGTCTTTCgcg gccgcgcaaggcgattaagttggg | |
| | pRS-400R | GTTGATTTTTAGTATTTTCAGCAACTATCATCTTATCAAgcg gccgcacatccccccttcgccagc | |
| 401-500WM2 | pRS-401F | TCAACTAAAATCTTTTCAAAAAAGATTTTGTGTTTTTTTTgcg gccgcgcaaggcgattaagttggg | |
| | pRS-500R | AAAATCAGATAGTTTTATAGTAAATAAATTCTTAAGATTTgcg gccgcacatccccccttcgccagc | |
| 501-600 | pRS-501F | ATTAAATTAGAAAATAAACCAAATTTTGGTTCTGATTATTgcg gccgcgcaaggcgattaagttggg | |
| | pRS-600R | AAAATATCTCTAATTACTAAATCTTTATCTAATTCATTTAgcg gccgcacatccccccttcgccagc | |
| 601-700WM4 | pRS-601F | AAAATTTATGTAATTTATTAATTTTTATCTTTATAATATAgcg gccgcgcaaggcgattaagttggg | |
| | pRS-700R | ATGCTTTAGCTGACATTGTTTCAGTTTTAAAAGTTGATGAgcg gccgcacatccccccttcgccagc | |

TABLE 20-continued

Primers used to produce unique synthetic second-stage assembly vectors.
Overlasp to the ends of the 10-kb assembly sequences are shown in upper case.

| Assembly | Primer Name | Primer Sequence | SEQ ID NO. |
|---|---|---|---|
| 701-799 | pRS-701F | TAGAAAAACTCATAGCTACACCTAAAACAAAACGTTCAGCggc cgcacatcccccttcgccagc | |
| | pRS-799aR | TTTTAACAAGTGTTTAACTATAATATTTTTGGAGACAAATgcg gccgcacatcccccttcgccagc | |
| 811-900 | Mmyc811aF | ATGTGGAAAACGTGGAAAAAATCCTTATAACATAGATATAgcg gccgcgatcctctagagtcgacctg | |
| | Mmyc900R | TATGCCAATTATTAAATTTAGTGGACTAGATAAAGAACAAgcg gccgccgggtaccgagctcgaattc | |
| 901-1000(94D) | pRS-901F | ATATTATTCTTCCTTTTTTCTATGTAATTTTATTACAAAAgcg gccgcgcaaggcgattaagttggg | |
| | pRS-1000R | ATTTCTTTACAAAATATTACTTTTTTTGAATATGAAAAAAgcg gccgcacatcccccttcgccagc | |
| 1001-1104 | pRS-1001F | ACTTGTAACAAACATTAAAAAGATTTGTACAAAAATAATTgcg gccgcgcaaggcgattaagttggg | |
| | pRS-1104R | CAAATCTGTAATTGTATTTAAAAACTCTTAAAAAACTAGAgcg gccgcacatcccccttcgccagc | |

Table 21. Primers used to produce unique vectors for cloning 100-kb natural *M. mycoides* fragments. Overlaps to the ends of the 100 kb natural sequences are shown in upper case.

TABLE 21

Primers used to produce unique vectors for cloning 100-kb natural
*M. mycoides* fragments. Overlaps to the ends of the 100 kb
natural sequences are shown in upper case.

| Assembly | Primer Name | Primer Sequence | SEQ ID NO. |
|---|---|---|---|
| 2-100 | Mmyc2aF | GTTTTTAATTTAACTAATATTTATTACAAATAAAAAACTTgcg gccgcgatcctctagagtcgacctg | |
| 2-100 | Mmyc100R | TAACATTTATCTTTTAATTTTTCATTAACATTAGCAATTTgcg gccgccgggtaccgagctcgaattc | |
| 101-200WM3 | Mmyc101F | TCAAACAGCAAAGCAAATGTATGGAGAAATGCTTCCAGAAgcg gccgcgatcctctagagtcgacctg | |
| 101-200WM3 | Mmyc200R | CTGCTGTTAAACTTGGTATAGGAATTGATTATAAATACCCgcg gccgccgggtaccgagctcgaattc | |
| 201-300WM1 | Mmyc201F | ATTTATAATGATTATCCTTTAGATGTTTTGGTACATTATAgcg gccgcgatcctctagagtcgacctg | |
| 201-300WM1 | Mmyc300R | CAAATGAAGATTGAGAAGATTTTATTGCTTTAGATGCTCTgcg gccgccgggtaccgagctcgaattc | |
| 301-400 | Mmyc301F | CTTTTCTACTAATTTCATCAAATTTATGATTATGTCTTTCgcg gccgcgatcctctagagtcgacctg | |
| 301-400 | Mmyc400R | GTTGATTTTTTAGTATTTTCAGCAACTATCATCTTATCAAgcg gccgccgggtaccgagctcgaattc | |
| 401-500WM2 | Mmyc401F | TCAACTAAAATCTTTTCAAAAAAGATTTTGTGTTTTTTTTgcg gccgcgatcctctagagtcgacctg | |
| 401-500WM2 | Mmyc500R | AAAATCAGATAGTTTTATAGTAAATAAATTCTTAAGATTTgcg gccgccgggtaccgagctcgaattc | |
| 501-600 | Mmyc501F | ATTAAATTAGAAAATAAACCAAATTTTGGTTCTGATTATTgcg gccgcgatcctctagagtcgacctg | |
| 501-600 | Mmyc600R | AAAATATCTCTAATTACTAAATCTTTATCTAATTCATTTAgcg gccgccgggtaccgagctcgaattc | |
| 601-700WM4 | Mmyc601F | AAAATTTATGTAATTTATTAATTTTTATCTTTATAATATAgcg gccgcgatcctctagagtcgacctg | |

TABLE 21-continued Primers used to produce unique vectors for cloning 100-kb natural M. mycoides f at 37° C. for 30-60 min prior to the addition of buffer P2. Samples (up to 3 µl) of the yeast-extracted DNA were transformed into 30 µl EPI300™ (Epicentre) electrocompetent *E. coli* cells in a 1-mm cuvette (BioRad) at 1,200 V, 25 µF and 200Ω using a Gene Pulser Xcell Electroporation system (BioRad). Cells were allowed to recover at 37° C. for 1.5 h in 1 ml SOC medium then plated onto LB medium containing 12.5 µg/ml chloramphenicol. After incubation at 37° C. for 16-24 h, individual colonies were selected and grown in 3 ml LB medium with 12.5 µg/ml chloramphenicol overnight at 37° C.

DNA was prepared from these cells by alkaline lysis using the P1, P2 and P3 buffers (Qiagen), followed by isopropanol precipitation. DNA pellets were dissolved in TE buffer (pH 8.0) containing RNase A and RNase T1 (Ambion). Alternatively, DNA was prepared from the QIAprep Spin Miniprep Kit (Qiagen) according to the instruction provided.

Following purification, DNA was digested with NotI (and occasionally SbfI) to release the insert from the vector and sized by gel electrophoresis on 0.8% E-gels (Invitrogen) for 30-60 min. Bands were visualized using an Amersham Typhoon 9410 Fluorescence Imager.

Positive clones were propagated in 10 ml LB medium containing 12.5 µg/ml chloramphenicol and 1:1000 induction solution (Epicentre) and incubated overnight at 37° C. The cultures were collected and the DNA molecules were purified using the QIAprep Spin Miniprep Kit (Qiagen) according to the manufacturer's instructions. Assembly 211-220 was unstable in the Epi300™ strain, so it was transferred to the Stbl4 strain (Invitrogen), where it could be stably maintained. This assembly cannot be induced to higher copy levels in this strain and was not column-purified as above. Instead, this clone was propagated in 50 ml LB medium containing 12.5 µg/ml chloramphenicol. After neutralization of the lysed cells, these DNA molecules were centrifuged then precipitated with isopropanol. DNA pellets were dissolved in TE buffer (pH 8.0) then RNase treated, phenolchloroform extracted and ethanol precipitated. DNA pellets were dissolved in TE buffer. For each 10 kb assembly, NotI-digested DNA was quantified by gel electrophoresis alongside known DNA standards.

In general, at least one 10 kb assembled fragment could be obtained by screening 10 yeast clones. However, the rate of success varied from 10-100%. One assembly, 791-799, could not be produced by homologous recombination in yeast. This fragment was divided into two parts, 791-795 and 796-799, which were individually assembled by in vitro recombination (Gibson et al., *Nat Methods* 6, 343 (May, 2009)). With the exception of 211-220, all first stage assemblies were propagated in Epi300 *E. coli* cells (Epicentre). This cell line allows for induction of the cloning vector from single-copy to high-copy numbers. Assembly 211-220 was unstable in Epi300 cells and so was transferred to Stbl4 cells, where it could be stably maintained.

All of the first-stage intermediates were sequenced. Nineteen out of 111 assemblies contained errors. Our sequencing analysis revealed that assemblies 81-90 and 811-820 each contained a single error originating from cassettes 82 and 812, respectively. Cassette 82 was corrected at the 1-kb level and reassembled to produce an error-free clone of 81-90. The mutation in cassette 812 occurred in the 811 overlap, which does not contain an error. Therefore, when additional 811-820 clones were sequenced, some of these did not contain errors. One sequence-verified 811-820 clone was used in subsequent assembly reactions. We opted not to correct an error that was present in 121-130 since it was a synonymous mutation in a non-essential gene. This mutation served as an additional variation to further distinguish the synthetic genome from a natural one (Table 18). One mutation could be avoided by maintaining the assembled fragments at single-copy number during propagation in *E. coli*. One error was produced by incomplete removal of the NotI restriction site at one of the cassette junctions. Four errors likely originated from the primers used to PCR-amplify the cloning vectors. The remaining errors were produced during propagation in yeast. Alternate clones of 15 assemblies were selected and sequence-verified.

iii. Assembly of 100 kb Synthetic Intermediates
 a. Preparation of DNA

Equal amounts of the 10 kb assembly intermediates were pooled in sets of 10, digested with NotI to release the inserts, and then gel-purified. Approximately 125 ng uncut DNA was pooled in sets of 10, digested with NotI (and usually also with SbfI to provide better separation between the vector bands and insert) and electrophoresed on a 1% low-melting point agarose gel for 90 min at 96 V. Ten kb DNA fragments were cut from the gels and extracted following β-agarase treatment as described above. DNA was resuspended in 20 µl TE (pH 8.0). Ten microliters was used in transformation experiments with 40 ng vector.

b. Host Vector

These gel-purified assemblies were mixed with a unique second-stage host vector, which were prepared as above except pRS414 (Sikorski and Hieter, *Genetics* 122, 19 (May, 1989)) was used as PCR template. Since the selectable marker in yeast would be changed from histidine to tryptophan, we reasoned that the background of undesired clones would be reduced. Yeast propagation elements would already be present in assembly 811-900. Therefore, as with assembly 831-840, the cloning vector for assembly 811-900 only consisted of BAC elements.

c. Yeast Transformation

The pooled 10-kb assemblies and their respective cloning vectors were transformed into yeast as above to produce 100 kb assembly intermediates. This resulted in several hundred yeast clones.

d. Screening and Preparation for Final Donor Genome Assembly

To demonstrate the expected PCR patterns for each of the 100-kb assemblies, the multiplex PCR primers listed in Table 22 were used to screen YCpMmyc1.1, which was extracted from yeast. PCR amplicons are spaced 100 bp apart.

TABLE 22

| Amplicon # | Name | Primer sequence | Amplicon Size (bp) | SEQ ID NO. |
|---|---|---|---|---|
| 1 | 100F | GTAATTGAACCTAATTCTTTTTCTAATCGGAC | 337 | |
|  | 101R | TTGGTGGAATTAGACATC | | |
| 2 | 200F | TCAGCTTATTTAGCTACAAATTCTGGAAGAAG | 429 | |
|  | 201R | ATACTTCATGAACAAATG | | |

TABLE 22-continued

| Amplicon # | Name | Primer sequence | Amplicon Size (bp) | SEQ ID NO. |
|---|---|---|---|---|
| 3 | 300F<br>301R | AGAAGATATTGCAGATGCAGAAGAGTTGCATT<br>GCTTGAACTAGTTG | 514 | |
| 4 | 400F<br>401R | AAACTAGACAAAATGAAGATGGAAGCTTCATC<br>ATCTTCATATCAAGGAC | 589 | |
| 6 | 500F<br>501R | AACCATCTGCACCAGATAGTTCAGTGGTATAT<br>TTAGTTTAGCAAAACC | 726 | |
| 8 | 600F<br>601R | TAGCTGTTTGCTTGCTAAGGTCTGGGTTTGTA<br>TTTAGTAGTAGTGC | 846 | |
| 9 | 700F<br>701R | GAAGTTAGTGACGGATATGCAAGATTATATCC<br>AGTTGGAACTCCTG | 952 | |
| 5 | 799aF-2<br>811aR | GTCAAGTTCTTTTCATACCACTACTTGTTCAT<br>TACTTGCACCGATTAC | 685 | |
| 7 | 900E-2<br>901R-2 | GAAGTATGATTTCCAGAACAAAACAACTAGCT<br>CCGTGTTGCTTTG | 784 | |
| 10 | 1000E-2<br>1001R-2 | TGTAGATCTGCCAAGTAAGTCTCCCTGTAATT<br>TGTTTGATTGCTTG | 1010 | |
| 11 | 1104F-2<br>2aR-2 | AGGTGTGTTATCTTTGTGATTAGCATGGTCAA<br>GTTCCTGTAGCTAC | 1149 | |

With the exception of amplicon 10d (underlined; the region corresponding to 931-940), and assembly 796-799, all first-stage assemblies can be accounted for by this PCR analysis. Downstream analyses were used to further confirm the 701-799 and 901-100 intermediates.

The results indicated that *M. mycoides* 100 kb assembly intermediates cannot be stably maintained in *E. coli*, so the method used to screen the 10 kb assemblies could not be employed. Instead, one hundred ten primer pairs, producing amplicons ranging in size from 100 bp to 1150 bp, were designed such that they can produce 9-11 amplicons in each of 11 individual multiplex PCR reactions; one for each 100 kb assembly intermediate (Table 23 and Table 24).

TABLE 23

| | Amplicons | | | | | | | | | | |
|---|---|---|---|---|---|---|---|---|---|---|---|
| Amplicon | a | b | c | d | e | f | g | h | i | j | k |
| Set 1 sizes (bp) | 100 | 200 | 300 | 400 | 500 | 600 | 700 | 800 | 900 | 1000 | None |
| Set 2 sizes (bp) | 125 | 225 | 325 | 425 | 525 | 625 | 725 | 825 | 925 | 1025 | None |
| Set 3 sizes (bp) | 150 | 250 | 350 | 450 | 550 | 650 | 750 | 850 | 950 | 1050 | None |
| Set 4 sizes (bp) | 175 | 275 | 375 | 475 | 575 | 675 | 775 | 875 | 975 | 1075 | None |
| Set 5 sizes (bp) | 100 | 200 | 300 | 400 | 500 | 600 | 700 | 800 | 900 | 1000 | None |
| Set 6 sizes (bp) | 125 | 225 | 325 | 425 | 525 | 625 | 725 | 825 | 925 | 1025 | None |
| Set 7 sizes (bp) | 150 | 250 | 350 | 450 | 550 | 650 | 750 | 850 | 950 | 1050 | None |
| Set 8 sizes (bp) | 175 | 275 | 375 | 475 | 575 | 675 | 775 | 875 | 975 | 1075 | None |
| Set 9 sizes (bp) | None | 200 | 300 | 400 | 500 | 600 | 700 | 800 | 900 | 1000 | None |
| Set 10 sizes (bp) | 125 | 225 | 325 | <u>425</u> | 525 | 625 | 725 | 825 | 925 | 1025 | None |
| Set 11 sizes (bp) | 150 | 250 | 350 | 450 | 550 | 650 | 750 | 850 | 950 | 1050 | 1150 |

TABLE 24

| Multiplex PCR primers used to identify 100-kb intermidiates containing all first-stage assemblies. | | | |
|---|---|---|---|
| Primer name | Primer sequence | Amplicon size (bp) | SEQ ID NO. |
| C5a F Set 1(1)<br>C5a R Set 1(1) | ACTTATCTCGTAGACAAGATATTTATCAAAAC<br>GCAACCTCACAAGCTTCTTGT | 100 | |
| C16 F Set 1(2)<br>C16 R Set 1(2) | ATCAATATAATGTTAATTTTTCTTCATTATATTATG<br>ATAAGCATAAATAACATTATCTCCAACTTTTATA | 200 | |
| C25 F Set 1(3)<br>C25 R Set 1(3) | AAAACTATTACAGTATCTGATAATGACTTTTTTAC<br>TAATAATTCAACTTTTCCAAGTGTTTTACT | 300 | |

TABLE 24-continued

Multiplex PCR primers used to identify 100-kb intermidiates
containing all first-stage assemblies.

| Primer name | Primer sequence | Amplicon size (bp) | SEQ ID NO. |
|---|---|---|---|
| C35 F Set 1(4) | TAAGGTTAAACAAACTATTAGAGTAAAAACAATAAT | 400 | |
| C35 R Set 1(4) | ATTTTGTTTTTGAGTCTTTTTGAAATC | | |
| C45 F Set 1(5) | TAAAATTAGTTTGCTCTAGTTTTAAAAAAAGC | 500 | |
| C45 R Set 1(5) | AAATGATATTTTATTACAAGTTATTAAATTTTATGATTATC | | |
| C55 F Set 1(6) | ACATCAACATTAATATCAATATTTTTTTTAATATC | 600 | |
| C55 R Set 1(6) | TTTACAGGACAAACTGGAGCTG | | |
| C65 F Set 1(7) | CCAATCAGTTAATCTTGGTCTTG | 700 | |
| C65 R Set 1(7) | AACAATTGATCAAATTATTGGTGATC | | |
| C75 F Set 1(8) | TGCTTCAAGATATTTTAAAAATCCTTTAG | 800 | |
| C75 R Set 1(8) | TTAAAAAACCAGCTGTATTTGTTTTAAA | | |
| C85 F Set 1 9 | AAGTATGTGTTCTTTTCATATATCTCCTTATTT | 900 | |
| C85 R Set 1(9) | CACCCAATTAGGGATCGAAGTT | | |
| C95 F Set 1(10) | TTACATTAGCACCCCTACTTCTCAT | 1000 | |
| C95 R Set 1(10) | ATTTAAATAGTTTAAATATAGCAAGACAAAAAATT | | |
| C105 F Set 2(1) | TATTTTCTTTTAAAACTTCACTACCAGTTG | 125 | |
| C105 R Set 2(1) | TGATTTTATAGATAAAAAGGGTATGGAA | | |
| C115 F Set 2(2) | TAAACACTAGTGTTGGTACTTTAAAAAAAG | 225 | |
| C115 R Set 2(2) | CAATTGCTATAATTGTTGGAATATTTAAATC | | |
| C125 F Set 2(3) | TGAATATACAAAAAAAATCGTGTGAATAAAC | 325 | |
| C125 R Set 2(3) | TTTTGATTTTGAATCATCCATTAATAAAA | | |
| C135 F Set 2(4) | AATTTTATAATGCATCCAAAATATGAGTTT | 425 | |
| C135 R Set 2(4) | ACAGTACCAAAAATTGCAATTTTCAT | | |
| C145 F Set 2(5) | ATATTGATATGATAAAAAAAGCTTTAGAAGATAAAAAC | 525 | |
| CI45 R Set 2(5) | TCATATTTTTTGATTGTATAAAAAGTGTTTGTT | | |
| C155 F Set 2(6) | AGATTATATGGTTAAAGCTCAACAACAACTAG | 625 | |
| C155 R Set 2(6) | AACAAAAATAATAACATCAGCTTGTTCAATA | | |
| C165 F Set 2(7) | AGATGTATCAGGTTTAACAAAATATCAGG | 725 | |
| C165 R Set 2(7) | CGCCTAATACTACATGACTTCCTT | | |
| C175 F Set 2(8) | ACTTGACTATATTAATATTAAAGCTTGGTCAAA | 825 | |
| C175 R Set 2(8) | ATAATAATGAATATCAGTTGTGATTAGCTTTC | | |
| C185 F Set 2(9) | ACGTTTAGAAACTCAAATGGATCA | 925 | |
| C185 R Set 2(9) | CATATTTTATAATCTAAACTTAGATTTAAAAAATTATTAGC | | |
| C195 F Set 2(10) | CAAGGAATAGTTGTTAAAACTTTAGATAAAGC | 1025 | |
| C195 R Set 2(10) | TAAAAATTTTATCTTCATTAATATTTAAATCTTGTAAT | | |
| C205 F Set 3(1) | GAATATAAATAGCCTTTATAACTTGCTCATAATC | 150 | |
| C205 R Set 3(1) | TGATTCAAAAGAATCACAAGAAAATG | | |
| C215 F Set 3(2) | AAGTTTTTATTAAATAAGTATTATCAAAAAAATAAAAGTAAAAAAC | 250 | |
| C215 R Set 3(2) | AAAGATCAAAAACAAATAAAACTAAAAAATAGT | | |
| C225 F Set 3(3) | AGAPAAAAAACAACCACATATTGTAATT | 350 | |
| C225 R Set 3(3) | GTATTAAACTTTGCTCTAGTTCTTTGTTTTTAG | | |
| C235 F Set 3(4) | AGGCAACTAAAGACTTTTCTCCTC | 450 | |
| C235 R Set 3(4) | AAATTACTGAAGAAACCGCATTAAC | | |
| C245 F Set 3(5) | ATATATGTTATTTAAAAAAATAACAAATAATGTTCAG | 550 | |
| C245 R Set 3(5) | TTTAATAGCATCATAACTTAAACTAATCATAATTG | | |
| C255 F Set 3(6) | GATATAAATGATCACATTATTCATAATGCTAAT | 650 | |
| C255 R Set 3(6) | GTTTATGAGCAATTACAGTTCAACAAG | | |
| C265 F Set 3(7) | TTGATTAGAAAAAACTGAAATTCCAA | 750 | |
| C265 R Set 3(7) | AAGTTTTTATTATTATAAATTTGATCTAAATTAGTTGC | | |
| C275 F Set 3(8) | ATAAAATTACTTTTAATGATAAAAGTTTTATTTATTTATGAG | 850 | |
| C275 R Set 3(8) | CAGCAATTCCAGTAGCTCCAT | | |

TABLE 24-continued

Multiplex PCR primers used to identify 100-kb intermidiates containing all first-stage assemblies.

| Primer name | Primer sequence | Amplicon size (bp) | SEQ ID NO. |
|---|---|---|---|
| C288 F Set 3(9) | AATTACCAAAAGGTGTAGTTTCAGTTC- | 950 | |
| C288 R Set 3(9) | GTCTTTAAACTTTTGAGCACTATTTAATTTATC | | |
| C295 F Set 3(10) | TCAACTTCTGGGTTTTGAAAATATC | 1050 | |
| C295 R Set 3(10) | GTGATATTGATCAAAACAAATTTATGAGT | | |
| C305 F Set 4(1) | TGATCAACTCCACTCATTGC | 175 | |
| C305 R Set 4(1) | TAGTGACTTATGCTAGTGAATTAGATGATG | | |
| C315 F Set 4(2) | TAATTTAAAAATTTTATTTTTAATAATTTCAGCC | 275 | |
| C315 R Set 4(2) | ACAAGATATTTTATTGCTATTTGATAGTATAAAATC | | |
| C325 F Set 4(3) | TTTAGTATAACCTCTTAAAGTTGTACTTATTAAATCA | 375 | |
| C325 R Set 4(3) | ATGTGTTATGCACTAGTTTTAGGTGG | | |
| C335 F Set 4(4) | TTTTTTCAGCAAATACTTGATATGAATTA | 475 | |
| C335 R Set 4(4) | TATAATTGAGTTAAAAAAGCTGTTAGCA | | |
| C345 F Set 4(5) | TTGCTAGGTTTGGATATTTTTCATTC | 575 | |
| C345 R Set 4(5) | AAGAACAAGAAGAAGTAGACGAATTTG | | |
| C355 F Set 4(6) | ACATTTAAAACAAATTTTTTAACAAAAGTAGT | 675 | |
| C355 R Set 4(6) | TTATAGTTTATTTCAAGTAGTTAATCATTATAAACAATT | | |
| C365 F Set 4(7) | AAAACAGAACCAATAACAGCATTTC | 775 | |
| C365 R Set 4(7) | ACCATATGATAGAAATGTAATTACTGAAGC | | |
| C375 F Set 4(8) | GAAATTAATCTATCAACTAAAATTCCTGTTG | 875 | |
| C375 R Set 4(8) | GTTGTTAATGAAATTCAAAAATCTAATGG | | |
| C385 F Set 4(9) | TTTAAAAATCCTGTTATTTATAAAATCTGATAAAC | 975 | |
| C385 R Set 4(9) | TGTTATTACCATTTTTATAAAACTCTTTAATCAC | | |
| C395 F Set 4(10) | GCCAAAAAGAGATTATTGAAAAAATT | 1075 | |
| C395 R Set 4(10) | AGCTTGTGTTTAACTAATTGCTGTTTAG | | |
| C405 F Set 5(1) | AGAAAATCCAATTGGATTAAAGAGTT | 100 | |
| C405 R Set 5(1) | ATCTTCATATTCTTCAATTAATTTTAATTCC | | |
| C415 F Set 5(2) | TATGTAATGCTATAGGTTTAAGCACAGTT | 200 | |
| C415 R Set 5(2) | TTTAATTTGTAAGAATTGTAAAGCCTCTA | | |
| C425 F Set 5(3) | GTGAATAAGTAAAAAATAATATAAATGCAGAAATACTAG | 300 | |
| C425 R Set 5(3) | TTTCATTCTTTTTTGTATCAATGTCAT | | |
| C435 F Set 5(4) | CAACACCACTAATATAAATTTTTCTTGTT | 400 | |
| C435 R Set 5(4) | TTAAAGAAGAAGAAAAATAAAATTTTAACATTAGTATTAG | | |
| C445 F Set 5(5) | TGTTATTTTTCTAGTTCTATCTTGATCGT | 500 | |
| C445 R Set 5(5) | ATTCAAGGAGTAAAATAGTGTATTTTTAAAAAAGAAG | | |
| C455 F Set 5(6) | AACAATTCTTTTTATAAAACTAAAATTTATACTCAAT | 600 | |
| C455 R Set 5(6) | TATTTTAGTATCAATATTTTGTTCATTAATAGTTG | | |
| C465 F Set 5(7) | CCAGTAATTTTAAATAAAAAATCTTAATAAGTAATTAAA | 700 | |
| C465 R Set 5(7) | CGTTCTTTTGAATTTTTATTAAAAAATAGAATAAAC | | |
| C475 F Set 5(8) | CTTTTATATTTAGATCTAAAAATAGTTTTTCTAAAGC | 800 | |
| C475 R Set 5(8) | TAGTAAAGTTCATACTATTTTTAATCATACTTTAACAAATAC | | |
| C485 F Set 5(9) | AACAGTTTATCAAAATAATGATCTTGC | 900 | |
| C485 R Set 5(9) | GTGTGAAAAAAATGGTATTAAGCTAAGTC | | |
| C495 F Set 5(10) | AGTATTGTATTAAGTAGATTTTTTATTTTTATTTAGTATTACAG | 1000 | |
| C495 R Set 5(10) | TGATGGTTCTTATATGAAAAATTATTAAGTGTTTTAG | | |
| C505 F Set 6(1) | TCTTATGATTTTATTATTAATAAATTCATTAACAAATTG | 125 | |
| C505 R Set 6(1) | AACTTTTTCATCAATTCAAGCAAAAC | | |
| C515 F Set 6(2) | TCCAGGTAAAATGCGGATG | 225 | |
| C515 R Set 6(2) | TTTTGAACATACATATTTTAATTACAAAAGATGG | | |
| C525 F Set 6 3) | TTTCCTAAAAGTTGAACTGATGAACC | 325 | |
| C525 R Set 6(3) | AACAAAAATACCGTATTATTGACTTTAAAAGAAAT | | |

TABLE 24-continued

Multiplex PCR primers used to identify 100-kb intermidiates containing all first-stage assemblies.

| Primer name | Primer sequence | Amplicon size (bp) | SEQ ID NO. |
| --- | --- | --- | --- |
| C535 F Set 6(4) | GAACCCGTGTGTCCACGGAT | 425 | |
| C535 R Set 6(4) | CAATGAATGGTATGTTTTCTGGTGC | | |
| C545 F Set 6(5) | ATTTTTACATAGCATTGTTTCTTTATTAGTTTTAA | 525 | |
| C545 R Set 6(5) | TTAGGTAATGTTTTTAGTTTTGATGAGTTTTTAGAT | | |
| C555 F Set 6(6) | TTTAAATGTTCTAAATGTTTAATTTTATTATCATTTAAATAAAC | 625 | |
| C555 R Set 6(6) | TTATTCTCACAATATGCATAGAGTTGAAGTTAG | | |
| C565 F Set 6(7) | TTAGGTTTAAAAGTTTGAATTATATGAATAGTAGC | 725 | |
| C565 R Set 6(7) | TGTTAAAAAATATTAAGTTTTAAAATATTAAAAATCTAAATTATTAAC | | |
| C575 F Set 6(8) | AACTGTATGGGTATTTCTTTTATTCTTAC | 825 | |
| C575 R Set 6(8) | CCAAATAATGAAAATGAATCTTCAATAATT | | |
| C585 F Set 6(9) | TAACTCCACCAGCAGCTTTAACC | 925 | |
| C585 R Set 6(9) | ATATGAAAAATATGGATATTATTACACAACTACTTATAATTTAAAC | | |
| C595 F Set 6(10) | GGTAATTTTAAATGCACCAACTAATAACC | 1025 | |
| C595 R Set 6(10) | TTAAAGCTGATGATTCAAATATTGGAG | | |
| C605 F Set 7(1) | ATAGAAGTTATATTGTCATAAACTACGTATGATACAC | 150 | |
| C605 R Set 7(1) | AGAACAAATTAAAAGAGAAATAGAAATTTTAAATTAAAG | | |
| C615 F Set 7(2) | GCTCAGCTTCAATTATCAATTAATG | 250 | |
| C615 R Set 7(2) | ACCCACAAACACTATATGATATAGCTATAGATAT | | |
| C625 F Set 7(3) | GTTTGTTTACGATCTGGTCCTACTG | 350 | |
| C625 R Set 7(3) | AGAAGAATTGGATGATTAGATTTAGTTG | | |
| C635 F Set 7(4) | ATTTAAAACAATATCTAATTACAAAAGATCTAGAAAA | 450 | |
| C635 R Set 7(4) | TATTTTTAACAATTAAATGTTCAGACATAAAAAC | | |
| C645 F Set 7(5) | AATAGTTTGAGAAAAACCTTCTAACGC | 550 | |
| C645 R Set 7(5) | TGCTAAACCTGATGTAATCTTTATGC | | |
| C655 F Set 7(6) | CATTCCATAAACGTTATTTGGAAAC | 650 | |
| C655 R Set 7(6) | GTTGATGCTTTAATAAAAAGTTTAAAAGATAAAG | | |
| C665 F Set 7(7) | AATTTGATTAAAGTAAAGTTTTCCAACAG | 750 | |
| C665 R Set 7(7) | AAACAAGGTTGTTTTAGACAAAACTTATTAG | | |
| C675 F Set 7(8) | CATTTTGATGATATTTATCATAAACATCTATTAAT | 850 | |
| C675 R Set 7(8) | AAGACAAGCATATTTAAATTTATAACTTTTAATATG | | |
| C685 F Set 7(9) | CAACCAGTAGCTACACCACTTCTAATTAC | 950 | |
| C685 R Set 7(9) | CAAGTGATTGGAAGATGAGGTAAT | | |
| C695 F Set 7(10) | TATTTTATTAAATGATGATATTATTGGTCTTATAAGTTTATTAG | 1050 | |
| C695 R Set 7(10) | ATCAATTGTTGTATATGATAAATATAATAAACTTG | | |
| C705 F Set 8(1) | TGCATATTTAGAAGATTTGAAATCTTTAAATAT | 175 | |
| C705 R Set 8(1) | ATACTCATTTTCATATTTTTTAATATCAAAATAAAC | | |
| C715 F Set 8(2) | ACGCTCAAACTGTTGTTGATTTAC | 275 | |
| C715 R Set 8(2) | AATTGCATTTTGTAGTTTATCTAAAACTTG | | |
| C725 F Set 8(3) | GTTTGTTTAAACATCCCTCTCATG | 375 | |
| C725 R Set 8(3) | ATATAAAGATAATGAATGTGTTTAAATTGGATATT | | |
| C735 F Set 8(4) | AGAAATTTATAATGCTTTAAATATTAAAGTTAAAAAAG | 475 | |
| C735 R Set 8(4) | AGCTTCTGATTGAGTAACTAGAAATTCAG | | |
| C745 F Set 8(5) | ATTAATATAAGAATCTCTTAATTTAGAATCACTTAAATATAAATTC | 575 | |
| C745 R Set 8(5) | TTTTAAATTATATTTATTTTAATTATCCTGATAGTTTAATTTATC | | |
| C755 F Set 8(6) | CACCTAGTGGGACTATAAAAGTAAATAATC | 675 | |
| C755 R Set 8(6) | AAAAAAGAGCAAAACATCAAGATGTAG | | |
| C765 F Set 8(7) | ATTGCTTTTTTAAATAAAATAATAGCATTTG | 775 | |
| C765 R Set 8(7) | AATCTATTTACTGCTGGACAAATTAATG | | |

TABLE 24-continued

Multiplex PCR primers used to identify 100-kb intermidiates containing all first-stage assemblies.

| Primer name | Primer sequence | Amplicon size (bp) | SEQ ID NO. |
|---|---|---|---|
| C775 F Set 8(8) | TTTTTGCAGATCTACTAAATAAAATGTCTAAAAC | 875 | |
| C775 R Set 8(8) | CAGTATTTAACTATTTCAAATTTTAAACCTTTTTC | | |
| C785 F Set 8(9) | TAATTTGACTATTTTGATCAATTCTTAAAGC | 975 | |
| C785 R Set 8(9) | AACAAAAAAATAAATTAGAGGTTGAATTTAATAAAC | | |
| C795 F Set 8(10) | ATTAGGCTCTGTTGGGCTAGTT | 1075 | |
| C795 R Set 8(10) | CTAATAGTAATGATCTAAGAGAAATGGGAAGAG | | |
| C815 F Set 9(2) | TAGTAATTTTTAAATTTATATAATCTAAATATAAAGATTTTAGATATTAA | 200 | |
| C815 R Set 9(2) | GTAGAAATGTTTGAAAAACTAAAGAAAATC | | |
| C825 F Set 9(3) | ATCCAAATTGTGAAAACGGTTTTTTATC | 300 | |
| C825 R Set 9(3) | ATGGACTAGAAACTTTTAATATAAAAGTTAGACCAG | | |
| C835a F Set 9(4) | CTTAAATTCACTGATAAAAAGTTGGG | 400 | |
| C835a R Set 9(4) | CTAGAATACCATTGTAATCATCATATCTAACTG | | |
| C845a F Set 9(5) | AGGCCGAAGCAGCGTTGTTG | 500 | |
| C845a R Set 9(5) | CCATGTGCCTTCTTCCGCG | | |
| C856 F Set 9(6) | TCTCTATTATATCTTTAATATATCTTTATTGTATCATCTATATCAC | 600 | |
| C856 R Set 9(6) | TGAGAATAAGTAGAAAGGTATAGTTTTCATG | | |
| C865 F Set 9(7) | TCAAATTTTTCATCTTTAAAAATAGTTCTTAAAATAG | 700 | |
| C865 R Set 9(7) | AAATATCTCTTAGTTTTTTAGGAATCAGAACTC | | |
| C875 F Set 9(8 | AGTAAAATGAAAGATGGAGCTATTTTAATTAATAC | 800 | |
| C875 R Set 9(8) | ATAGCTTGGATAATTGGAAATCC | | |
| C885 F Set 9(9) | ATATTTCTAGCACTTCCTTGATAAGCAC | 900 | |
| C885 R Set 9(9) | TTGATGAAATTNTTGAATCAATTAGAACA | | |
| C895 F Set 9(10) | TTATCAAAAGTTTGCCTCAAGC | 1000 | |
| C895 R Set 9(10) | ACTAAACATTTATTTGAACTCAAGAAAATC | | |
| C905 F Set 10(1) | CTTCGATAGTTTTTGGTGAAAAAATG | 125 | |
| C905 R Set 10(1) | TAGGTATAATTATTTTAAAAACAAAGGGAGA | | |
| C915 F Set 10(2) | ACCAATTACAGATGACCCATACC | 225 | |
| C915 R Set 10(2) | TATAATTTATGACAAACTATTAAACTTTCATTTATTG | | |
| C925 F Set 10(3) | TTTTTTCAAGATTTTTATTATCTTTTATTGTTTTTAC | 325 | |
| C925 R Set 10(3) | CGGTCATGGTTCTTGCC | | |
| C935 F Set 10(4) | TTGTTTCAAAATCTTTTGTAGTTTTTCTAATATTAG | 425 | |
| C935 R Set 10(4) | TTCAAATAGATCAACTACTCCAGTTGATC | | |
| C945 F Set 10(5) | ATGTTTTAGTTTTTCAGGATCATTGAT | 525 | |
| C945 R Set 10(5) | GGAATTTATCTACAACAATATGCACAAAAC | | |
| C955 F Set 10(6) | ATTTTATAAATTGATCTAAAATATTTTATTAGATTTAGAAGC | 625 | |
| C955 R Set 10(6) | AAGATATTAGTATTAGAAGCTGAAATATAAATTTCATTAC | | |
| C965 F Set 10(7) | GATAAATACGATTGTTTTTGTTCTTTTG | 725 | |
| C965 R Set 10(7) | ATAATTCCAAATATAACTATTGGTGTGGTTGTAC | | |
| C975 F Set 10(8) | AGCTGTTGCTTTAGGATATGAGTTTATTTC | 825 | |
| C975 R Set 10(8) | ATAAACAGTTCCTCCACCCATAG | | |
| C985 F Set 10(9) | TATTAAAGAAAAATTTCTCTATTCTGTAATGTTCC | 925 | |
| C985 R Set 10(9) | AACAATTGCTTTAATAAATCCTCTAAATAAAG | | |
| C995 F Set 10(10) | AACTTTTCGTTCTAAAAATCCTAGTTTAAATAAAG | 1025 | |
| C995 R Set 10(10) | TTTTTCTAATTGGTTCTATGTGAAGTTCTATTTG | | |
| C1005 F Set 11(1) | AAAAATTAAGTTATTAGAATATGGGTGTCAA | 150 | |
| C1005 R Set 11(1) | CCAATATTAATTCCACCAATATAACCA | | |
| C1015 F Set 11(2) | TAATAAATTTAATATAAATGTTGATGTAGATTCTTTTTTAGTAT | 250 | |
| C1015 R Set 11(2) | TTGTAACATTCTTGCAAAGTTTACAAAC | | |
| C1025 F Set 11(3) | CTTGTAATAAGACCGTCTCTTTTTTTGG | 350 | |
| C1025 R Set 11(3) | AAAGATTTTAATAAAGGAATTCAAAGTATTTTAGG | | |

TABLE 24-continued

Multiplex PCR primers used to identify 100-kb intermidiates containing all first-stage assemblies.

| Primer name | Primer sequence | Amplicon size (bp) | SEQ ID NO. |
|---|---|---|---|
| C1035 F Set 11(4) | ATAATAAAACTAAACTAGCTCAAGAATATGAATCAG | 450 | |
| C1035 R Set 11(4) | CTCTAGCAATACCAATTCTTTGACG | | |
| C1045 F Set 11(5) | ATCCTTATTTATATTGCAACTTAATAATATAACATAATAGC | 550 | |
| C1045 R Set 11(5) | TAAAAATATTTTAGTAACTATTAAAGATAAAAAATTTACTTTGG | | |
| C1055 F Set 11(6) | GAACAACAGTTATGTCGCTTGTTG | 650 | |
| C1055 R Set 11(6) | TTTTTCAGATTCGTAAGTTGTTCTAAATATTTC | | |
| C1065 F Set 11(7) | ATTGGTATAATTATGGATCTAGTTTTAAATCATAC | 750 | |
| C1065 R Set 11(7) | AGTACCTTGCATTAAAAAGAAAGTTGTTAG | | |
| C1075 F Set 11(8) | GATAATGAAGAGTTATCAATTTCTACTTTATTTTC | 850 | |
| C1075 R Set 11(8) | ATTTAAATCATAAAAGAGAAGTAATTATTGACAAATTTAC | | |
| C1085 F Set 11(9) | TTTTATCTCTAATACCATCAGAATCCATATCTAAC | 950 | |
| C1085 R Set 11(9) | TTAATAAAATAGATAAAAAAGATCAAAGAAGTTTAGAAGTAG | | |
| C1095 F Set 11(10) | TACTAATTACTATTATAGGTTTATTGATTTTAGTAAATATTTTAAAATTA | 1050 | |
| C1095 R Set 11(10) | GATAAGATGACACAACCATAAAATCC | | |
| C1102 F Set 11(11) | ACAGCTGAAAATGTAAGACAAATTAAAGAAAT | 1150 | |
| C1102 R Set 11(11) | TAATATCTTTAATTGAAATCTCTTGATTATATTCT | | |

Because every 10 kb assembly intermediate was represented by a primer pair, the presence of all amplicons would suggest an assembled 100-kb intermediate. DNA was extracted from 10 or more yeast clones and analyzed by multiplex PCR with the respective sets of primer pairs. DNA was extracted from patches as above.

Multiplex PCR was performed using a Qiagen Multiplex PCR Kit using primers identified in Table 24. A 1/50 volume (1 µl) of the DNA extract and 1 µl of a 10× primer stock containing 20 oligos at 2.5-5.0 µM each were included in each 10 µl reaction. Cycling parameters were 94° C. for 15 min, then 35 cycles of 94° C. for 30 s, 57-60° C. for 90 s, and 72° C. for 90 s, followed by a single, 3-min incubation at 72° C. Then, 2 µl of each reaction was loaded onto a 2% E-gel® (Invitrogen), and 72 V was applied for 30 min. Bands were visualized using a Typhoon 9410 Fluorescence Imager.

For a small-scale isolation of 100 kb supercoiled circular assemblies from yeast, a 5 ml saturated yeast culture was grown in selective medium. The procedure is based on a previously described method (Leem et al. (2008) Genome, 51: 155) but scaled down and without emphasis on removing yeast chromosomal DNA.

Briefly, harvested yeast cells were transferred to a microfuge tube with 1 ml water, and resuspended in 1 ml Pretreatment Buffer (1.2 M sorbitol, 200 mM Tris-Cl, 100 mM EDTA, pH to 9.1) with 8 µl 14 M β-mercaptoethanol. Following a 10 min incubation at room temperature, cells were harvested, washed twice with 1 ml SCE (1M sorbitol, 60 mM EDTA, 100 mM sodium citrate, pH 5.75), and resuspended in 1 ml SCE plus 10 µl Zymolyase-100T solution (20 mg/ml Zymolyase-100T [USB], 50% glycerol, 2.5% glucose, 50 mM Tris-Cl, pH 8.0). Following a 1 hour incubation at 37° C., spheroplasts were harvested and then resuspended in 25 µl Tris/sucrose buffer (50 mM Tris-Cl pH 8.0, 25% Sucrose) and 20 µl proteinase K solution (10 mg/ml proteinase K [Sigma], 1 mM calcium chloride, 50 mM Tris-Cl pH 8.0). Next, 475 µl Lysis Buffer (20 mM EDTA, 50 mM Tris-Cl, 1% SDS, pH 12.45) was added and mixed by pipetting up and down. Following a 30-mM incubation at 37° C., 100 µl 2M Tris-Cl pH 7.0 was added and mixed. Next, 100 µl 4M NaCl was added and mixed. Following a 30-min incubation at room temperature, 70 µl 3M sodium acetate was added and mixed. A standard phenolchloroform extraction, isopropanol precipitation, and 70% ethanol wash was carried out and DNA pellets were resuspended in 100 µl TE pH 8.0 containing RNase A. Following a one-hour incubation at 37° C., 10 µl DNA was loaded onto a 1% Agarose gel in 1×TAE buffer and electrophoresis was carried out for 3 hours at 4.5V/cm. After electrophoresis, the gel was stained with SYBR® Gold and scanned with a GE Typhoon 9410 imager.

In general, 25% or more of the clones screened contained all of the amplicons expected for a complete assembly. One of these clones was selected for further screening. Circular plasmid DNA was extracted and sized on an agarose gel alongside a supercoil marker. Successful second-stage assemblies with the vector sequence are approximately 105 kb in length (data not shown). When all amplicons were produced following multiplex PCR, a second-stage assembly intermediate of the correct size was usually produced. In some cases, however, small deletions occurred. In other instances, multiple 10 kb fragments were assembled, which produced a larger second-stage assembly intermediate. Fortunately, these differences could easily be detected on an agarose gel prior to complete genome assembly.

iv. Final Assembly of Synthetic Donor Genome
  a. Preparation of DNA

In preparation for the final stage of assembly, microgram quantities of each of the 11 second-stage assemblies were isolated; this was not trivial since these assemblies had to be purified out of yeast. As previously reported (Devenish and Newlon, Gene 18, 277 (June, 1982)), we found that circular plasmids the size of our second-stage assemblies could be isolated from yeast spheroplasts following an alkaline-lysis procedure. To further purify the 11 assembly intermediates, they were exonuclease-treated and passed through an anion-exchange column. A small fraction of the total plasmid DNA ($1/100^{th}$) was digested with NotI and analyzed by field-inversion gel electrophoresis (FIGE) (data not shown). This method produced ~1 μg of each assembly per 400 ml yeast culture (~$10^{11}$ cells).

For a large-scale isolation of 100 kb assemblies from yeast, a pre-culture (5 to 10 ml) of each VL6-48N strain harboring one of the eleven 100 kb assemblies was grown overnight to saturation in selective medium and then inoculated into 400 ml of selective medium. Once the culture reached an OD600 of 1.5, cells were harvested (2,205 rcf, 3 min). Pellets were resuspended in 100 ml water and transferred to two 50 ml conical tubes and harvested as above. Cell pellets were resuspended in 40 ml SPE (1 M Sorbitol, 10 mM Na2EDTA, 0.01 M Na phosphate, pH 7.5) containing 0.4 ml Zymolyase-20T (10 mg/ml) and 40 μl 14 M β-mercaptoethanol. The cell suspension was incubated at 37° C. for 60 min. Spheroplasts were harvested (1,125 rcf for 5 min) and resuspended in 1 ml 1 M Sorbitol, and then 20 ml of Lysis Buffer (0.05 M Tris-HCl, 0.02 M EDTA, 1% SDS, pH 12.8) was added and the tubes were inverted 10 times. Cell lysates were incubated at 37° C. for 30 min and then extracted with 20 ml phenol/chloroform/isoamyl-alcohol (Invitrogen) following 20 gentle inversions and centrifugation at 3,645 rcf for 20 min.

The aqueous phase was transferred to a new 50 ml conical tube. DNA precipitation was carried out by adding 2 ml 3M NaAc (pH 5.2) and 20 ml of isopropanol, followed by centrifugation at 3,645 rcf for 30 min at 4° C. The pellets were resuspended in 1 ml TE (pH 8.0) containing RNase A (30 μg/ml) and incubated at 37° C. for 30 min. At this point, the two DNA samples were combined. The circular DNA was further purified by the Qiagen Large-Construct Kit. The purification was performed according to the manufacturer's instructions with some minor modifications. Ten ml of EX Buffer was mixed with the DNA solution, followed by the addition of 200 μl Exonuclease and 300 μl 100 mM ATP. After a 45-min incubation at 37° C., the reaction was stopped by adding 12 ml of QS buffer. This solution was then applied to the Qiagen-tip 500 column. The column was washed with 30 ml of QF buffer, and DNA was eluted with 12 ml QF buffer, pre-warmed at 55° C. DNA was then precipitated overnight at −20° C. by the addition of 2 volumes of ethanol, in the presence of 1.2 ml 3M NaAc (pH 5.2), 15 μl of GlycoBlue (Ambion), and 15 μl of yeast total tRNA (Sigma).

Alternatively, DNA was precipitated by the addition of 1 volume isopropanol. The precipitated DNA was recovered by centrifugation at 3,645 rcf for 1 hr at 4° C. DNA pellets were washed with 70% ethanol and resuspended in 150 μl TE (pH 8.0). A sample (0.75 μl) of each was digested with NotI and analyzed by U-2 FIGE. The FIGE analysis was performed on a 1% agarose gel (BioRad, catalog #161-3016) in 1×TAE buffer without circulation and the parameters are forward 90 V, initial switch 5.0 sec, final switch 30 sec, with linear ramp, and reverse 60 V, initial switch 5.0 sec, final switch 30 sec, with linear ramp. After electrophoresis, the gel was stained with SYBR® Gold and scanned with a GE Typhoon 9410 imager.

b. Yeast Transformation

The method above does not completely remove all of the linear yeast chromosomal DNA, which we found could significantly decrease the yeast transformation and assembly efficiency. In order to further enrich for the eleven circular assembly intermediates, ~200 ng samples of each assembly were pooled and mixed with molten agarose. As the agarose solidifies, the fibers thread through and topologically "trap" circular DNA (Dean et al., *Anal Biochem* 56, 417 (December, 1973)).

Untrapped linear DNA can then be electrophoresed out of the agarose plug, thus enriching for the trapped circular molecules. The eleven circular assembly intermediates were digested with NotI so that the inserts could be released. Subsequently, the fragments were extracted from the agarose plug, analyzed by FIGE (data not shown), and transformed into yeast spheroplasts. In this third and final stage of assembly, an additional vector sequence was not required since the yeast propagation elements were already present in assembly 811-900. Following incubation on selective plates, approximately 100 colonies appeared.

Topological Trapping and Analysis

Twenty microliters of each uncut 100 kb assembly were pooled and equilibrated to 50° C. One volume (2200) of 2% low melting point agarose, also equilibrated to 50° C., was mixed with the pooled DNA. Approximately 85 μl of this mixture was added to agarose plug molds (Bio-Rad), which were kept cold on ice. Following a 30 min incubation on ice, agarose plugs were added to the wells of a 1% agarose gel (1×TAE buffer) and electrophoresis was carried out at 4.5 V/cm for 2 hours. Plugs were removed from the agarose gel and washed by inverting in 5 ml 0.1× Wash Buffer (Bio-Rad CHEF Genomic DNA Plug Kit) for 1 hour at room temperature. This buffer was removed and 5 ml 1× Buffer 3 (NEB) was added. Following a 1 hour incubation/inversion at room temperature, the buffer was removed and fresh 1× Buffer 3 (2.5 ml) with 250 units NotI was added. NotI digestion was carried out by incubating the agarose plugs overnight at 37° C.

Agarose plugs were inverted in 5 ml 1×TAE/0.3M sodium acetate solution for 1 hour. Agarose plugs were then moved to a microfuge tube. A solution of 10×TAE buffer containing 3M sodium acetate was added 1:10 (~40 μl) to the gel slice, and the agarose gel was melted at 68° C. for 7 min after an initial incubation at 50° C. for 15 min. Following melting of the gel slices, they were incubated for 15 minutes at 42° C., β-agarase (New England Biolabs) was added 1:50 (~8 μl) and the incubation was continued for 1 h longer. Following a gentle phenol extraction (by slowly inverting the tube for 10 min), and a standard ethanol precipitation (in the presence of 1 μl glycoblue), DNA was resuspended in 20 μl TE (pH 8.0). All but 0.5 μl was used to transform yeast. This 0.5 μl sample was analyzed U-2 FIGE as above.

Yeast Agarose Plugs

Yeast cultures (50 ml) were grown in CSM-His plus adenine medium (Teknova) to an OD600 of 1.0. Cultures were harvested and then washed with 50 ml water. Next, the cultures were harvested and then washed with 10 ml EDTA pH 8.0. The cultures were harvested and then transferred to microfuge tubes with 750 μl cell resuspension buffer. Cell pellets were then resuspended in 150 μl cell resuspension buffer. This mixture was equilibrated to 50° C. and then mixed with 85 μl Zymolyase-100T solution (20 mg/ml Zymolyase-100T [USB], 50% glycerol, 2.5% glucose, 50 mM Tris-Cl, pH 8.0) and 225 μl 2% low melting point agarose. Approximately 85 μl of this mixture was added to agarose plug molds (Bio-Rad), which were kept cold on ice. Following a 30 mM incubation on ice, plugs were added to 5 ml Lyticase buffer (10 mM Tris-Cl pH 7.5, 50 mM EDTA pH 8.0) containing 500 μl Zymolyase-100T solution. Following incubation at 37° C. for 2 hours, plugs were washed with 25 ml water. The Bio-Rad CHEF Genomic DNA Plug Kit was used to carry out the Proteinase K incubation and wash steps and is described in the manual that is provided with the kit.

c. Screening and Analysis of Synthetic Donor Genome

In order to screen for a complete genome, multiplex PCR was carried out with 11 primer pairs that produce 11 amplicons ranging in size from 337 bp to 1149 bp, in one reaction (Table 25).

TABLE 25

Multiplex PCR primers used to identify complete assembled genomes. This primer set is referred to as TSS2; each primer set crosses one of the eleven 100-kb junctions.

| Amplicon # | Name | Primer sequence | Amplicon size (bp) | SEQ ID NO. |
|---|---|---|---|---|
| 1 | 100F | GTAATTGAACCTAATTCTTTTTCTAATCGGA | 337 | |
|   | 101R | CTTGGTGGAATTAGACATC | | |
| 2 | 200F | TCAGCTTATTTAGCTACAAATTCTGGAAGAA | 429 | |
|   | 201R | GATACTTCATGAACAAATG | | |
| 3 | 300F | AGAAGATATTGCAGATGCAGAAGAGTTGCAT | 514 | |
|   | 301R | TGCTTGAACTAGTTG | | |
| 4 | 400F | AAACTAGACAAAATGAAGATGGAAGCTTCAT | 589 | |
|   | 401R | CATCTTCATATCAAGGAC | | |
| 6 | 500F | AACCATCTGCACCAGATAGTTCAGTGGTATA | 726 | |
|   | 501R | TTTAGTTTAGCAAAACC | | |
| 8 | 600F | TAGCTGTTTGCTTGCTAAGGTCTGGGTTTGT | 846 | |
|   | 601R | ATTTAGTAGTAGTGC | | |
| 9 | 700F | GAAGTTAGTGACGGATATGCAAGATTATATC | 952 | |
|   | 701R | CAGTTGGAACTCCTG | | |
| 5 | 799aF-2 | GTCAAGTTCTTTTCATACCACTACTTGTTCA | 685 | |
|   | 811aR | TTACTTGCACCGATTAC | | |
| 7 | 900E-2 | GAAGTATGATTTCCAGAACAAAACAACTAGC | 784 | |
|   | 901R-2 | TCCGTGTTGCTTTG | | |
| 10 | 1000E-2 | TGTAGATCTGCCAAGTAAGTCTCCCTGTAAT | 1010 | |
|    | 1001R-2 | TTGTTTGATTGCTTG | | |
| 11 | 1104F-2 | AGGTGTGTTATCTTTGTGATTAGCATGGTCA | 1149 | |
|    | 2aR-2 | AGTTCCTGTAGCTAC | | |

35

Yeast clones containing a completely assembled synthetic genome were screened by multiplex PCR with a primer set that produces 11 amplicons; one at each of the 11 assembly junctions. Primer pairs were designed to span each of the eleven 100-kb assembly junctions. Of 48 colonies screened, DNA extracted from one clone (sMmYCp235) produced all 11 amplicons. PCR of the WT positive control (YCpM-myc1.1) produced an indistinguishable set of 11 amplicons (data not shown).

Figure 20:
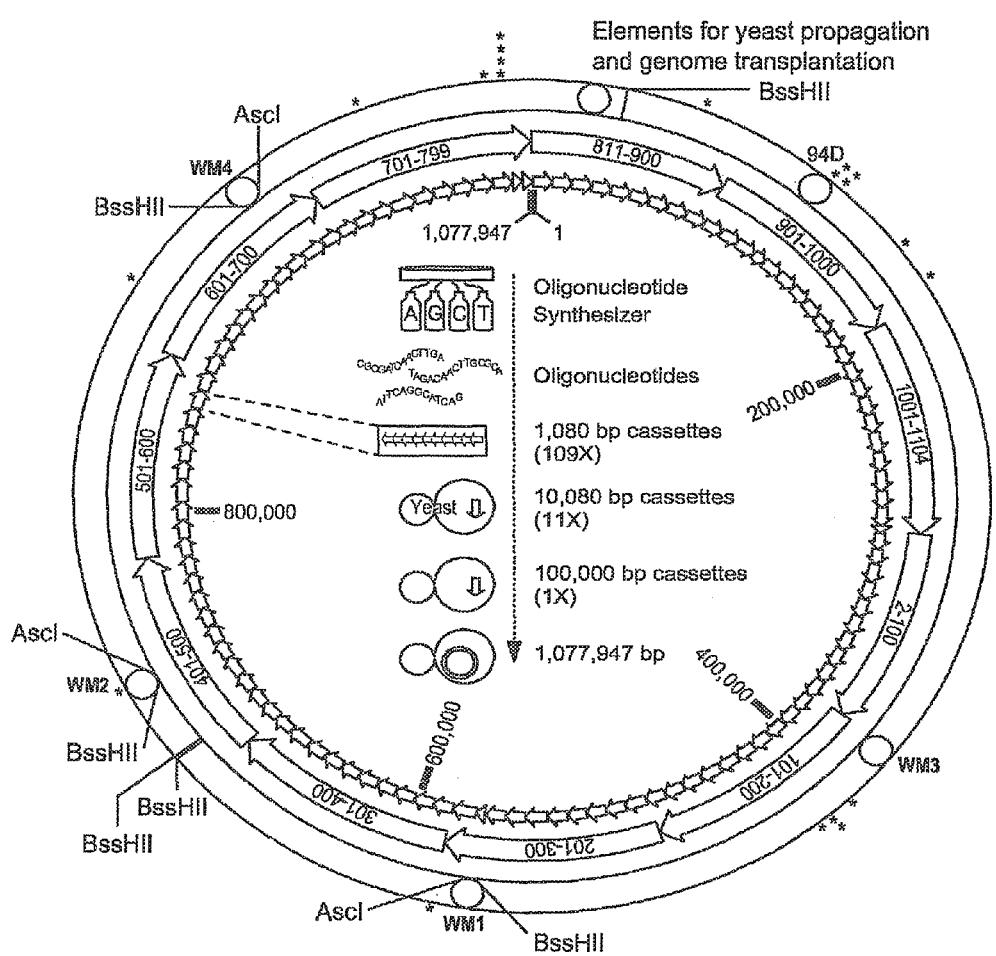
Figure 21:
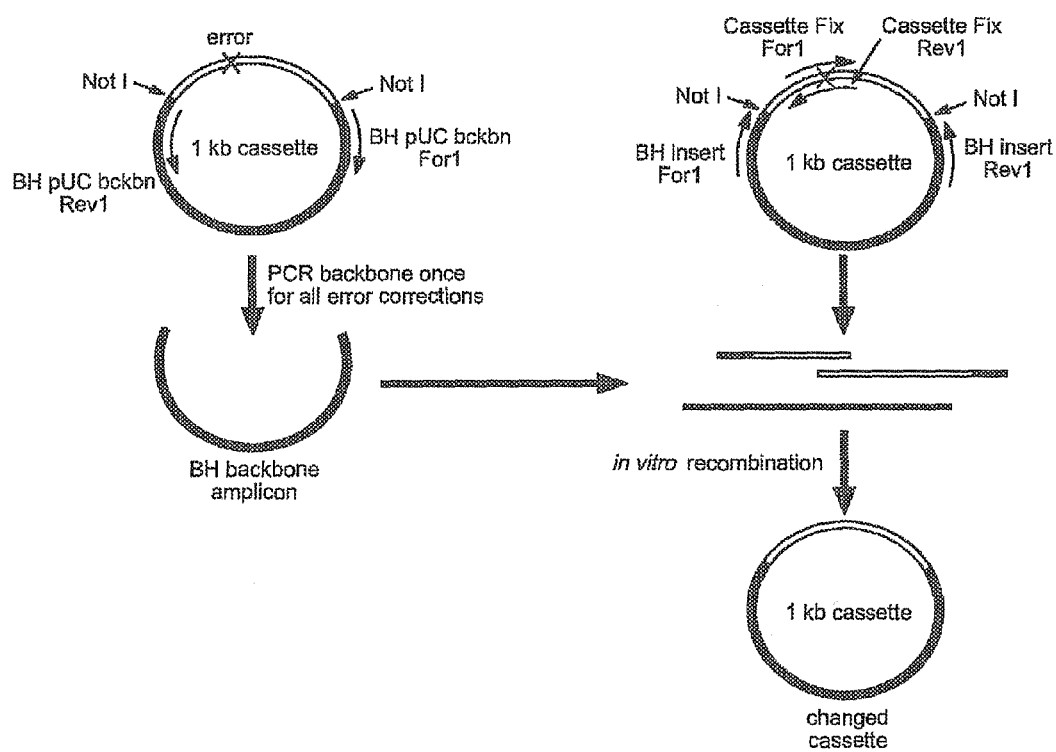

To further demonstrate the complete assembly of a synthetic M. mycoides genome, intact DNA was isolated from yeast in agarose plugs and subjected to two restriction analyses; AscI and BssHII. Since these restriction sites are present in three of the four watermark sequences, this choice of digestion produces restriction patterns that are distinct from the natural M. mycoides genome (FIG. 20 and Table 26). Natural (WT) and synthetic (235) M. mycoides genomes were isolated from yeast in agarose plugs. In addition, DNA was purified from the host strain alone. Agarose plugs were digested with AscI or BssHII and fragments were separated by clamped homogeneous electrical field (CHEF) gel electrophoresis.

Restriction Analysis of M. mycoides Genomes Propagated in Yeast

Yeast agarose plugs were washed two times for 1 hr in 1 ml of 0.1× Wash Buffer (Bio-Rad) and equilibrated for 1 hr in 1 ml of 1× Buffer 2 supplemented with BSA (NEB). The yeast chromosomal DNA was digested overnight with 50 units each of the restriction enzymes AsiSI and RsrII (these enzymes do not digest the M. mycoides genome). Plugs were then loaded onto a 1% TAE agarose gel to run digested yeast genomic DNA fragments out of the plugs (the circular M. mycoides genomes remain in the plug). The agarose gel was electrophoresed for 3 hours at 6V/cm. After electrophoresis, the agarose plugs were removed from the wells and were washed two times for 1 hr in 1 ml of 0.1× Wash Buffer and equilibrated for 1 hr in 1 ml of 1× Buffer 3 (NEB; for BssHII digests) or 1× Buffer 4 (NEB; for AscI digests). The M. mycoides genomic DNA was digested overnight with 50 units of the restriction enzyme BssHII or 50 units of AscI. Following incubation, all plugs were washed for 1 hour with 1 ml 0.1× Wash Buffer at room temperature and loaded on an agarose gel and subjected to pulsed-field gel electrophoresis. All restriction enzymes were purchased from NEB.

Pulsed-Field Gel Electrophoresis

Yeast agarose plugs (FIG. 4c) and M. mycoides agarose plugs (FIG. 5b) were subjected to pulsed-field electrophoresis in a 1% agarose gel in 1×TAE with 0.5 µg/ml ethidium bromide with circulation at 14° C., with a contour-clamped homogeneous electric field (CHEF DR III; Bio-Rad). Pulse times were ramped from 60 to 120 s for 20-24 hr at 4.0 V/cm.

Sequence Analysis of M. mycoides JCVI-syn1 Genome Isolated from M. mycoides JCVI-syn1 Cells.

Cells were grown in SP4 medium containing 10 mg/l tetracycline and genomic DNA was extracted using a Promega Genomic DNA Extraction Kit. DNA was sequenced using a combination of 454 and Sanger technologies. Gaps were closed using a combination of sequencing PCR amplicons covering the gap and direct genomic walks. The genome was assembled using the Celera Assembler. The sMmYCp235 clone produced the restriction pattern expected for a completely assembled synthetic genome (data not shown).

TABLE 26

| Strain | Digest | Strain Digest Fragment # and size (kb) |
| --- | --- | --- |
| WT | AscI | No sites |
| WT | BssHII | (4) 668 (5) 419 |
| Syn235 | AscI | (1) 685 (2) 233 (3) 160 |
| Syn235 | BssHII | (6) 533 (7) 233 (8) 152 |
| | | (9) 126 (10) 34 |

The sizes of the expected Asc I and BssH II restriction fragments for natural (WT) and synthetic (Syn235) *M. mycoides* are shown.

v. Transplantation of Synthetic Donor Genome into Recipient Cells

Additional agarose plugs used in the gel analysis above were also used in genome transplantation experiments. Intact synthetic *M. mycoides* genomes from the sMmYCp235 yeast clone were transplanted into restriction-minus *M. capricolum* recipient cells, as previously described (Lartigue et al., *Science* 325, 1693 (Sep. 25, 2009)). Results were scored by selecting for growth of blue colonies on SP4 medium containing tetracycline and X-gal at 37° C. Genomes isolated from this yeast clone produced 5-15 tetracycline-resistant blue colonies per agarose plug. This was comparable to the YCpMmyc1.1 control. Recovery of colonies in all transplantation experiments was observed when both *M. capricolum* recipient cells and an *M. mycoides* genome were present.

To rapidly distinguish the synthetic transplants from *M. capricolum* or natural *M. mycoides*, two analyses were performed. First, four primer pairs that are specific to each of the four watermarks were designed such that they produce four amplicons in a single multiplex PCR reaction (Table 27).

TABLE 27

| Amplicon name | Primer name | Primer sequence | Amplicon size (bp) | SEQ ID NO. |
|---|---|---|---|---|
| WM1 | MLC WM1 for | GCTCATTGCTGATCATAATGACTGTTTATATAC | 100 | |
| | MLC WM1 rev | ATGTATGTCAAAAACGAATCTCCCG | | |
| WM2 | MLC WM2 for | GATATTTTCATCCTTTGCAATACAATAACTACTACATC | 300 | |
| | MLC WM2 rev | CGAGCCAGGCATTAAATTATCTACAG | | |
| WM3 | MLC WM3 for | GCTGTAGATACAACGTCGTATTCTGTAAGTG | 500 | |
| | MLC WM3 rev | GTGCAGCACGGCATATTAGCAG | | |
| WM4 | MLC WM4 for | TCTGATACTATAGCAACGTTGCGTGATATTT | 700 | |
| | MLC WM4 rev | AATGTTCAGGGAACTTATTCAACGG | | |

Transplants containing a synthetic genome were screened by multiplex PCR with a primer set that produces 4 amplicons; one internal to each of the four watermarks. One transplant (syn1) originating from yeast clone sMmYCp235 was analyzed alongside a natural, non-synthetic genome (WT) transplanted out of yeast.

All four amplicons were produced by transplants generated from sMmYCp235, but not YCpMmyc1.1 (data not shown).

Second, the gel analysis with AscI and BssHII, described above, was performed. Briefly, natural (WT) and synthetic (syn1) *M. mycoides* genomes were isolated from *M. mycoides* transplants in agarose plugs. Agarose plugs were digested with AscI or BssHII and fragments were separated by CHEF gel electrophoresis. Restriction fragments corresponding to the correct sizes are indicated by the fragment numbers shown in Table 25. The restriction pattern obtained was consistent with a transplant produced from a synthetic *M. mycoides* genome (data not shown).

A single transplant originating from the sMmYCp235 synthetic genome was sequenced. With the exception of the known polymorphisms that occurred during the synthesis process, and 8 new polymorphisms and an unexpected *E. coli* transposon insertion, the sequence matched the intended design. This strain is referred to as *M. mycoides* JCVI-syn1. Colonies were grown on SP4 agar containing Xgal to make the cells expressing beta-galactosidase blue. Both the JCVI-syn1 and wild type colonies were 0.5 mm in diameter. In a test of the hemolytic capacity of both the JCVI-syn1 and wild type organisms, colonies were overlaid with agar containing 5% sheep red blood cells. The wild type *M. mycoides* lysed the cells directly beneath the colonies. This pattern and slight green tint of the agar is characteristic of alpha hemolysis. The *M. mycoides* JCVI-syn1 colonies did not lyse the red blood cells.

The transplants are outwardly no different from wild type *M. mycoides* subspecies *capri*. Colony morphology and growth rates were indistinguishable (data not shown); however we did program the synthetic genome to be phenotypically distinct from wild type *M. mycoides capri*. This mycoplasma species is an opportunistic pathogen of goats (DaMassa et al., *Am J Vet Res* 44, 322 (February, 1983)), but not humans. The virulence mechanism is thought to be bacterial production of hydrogen peroxide, which damages the tissues of infected animals. In *M. mycoides*, hydrogen peroxide is a byproduct of glycerol metabolism. To ameliorate the pathogenic potential of our synthetic genome, we omitted the genes encoding the *M. mycoides* ABC glycerol transporter (gtsA, gtsB, gtsC, and gtsD) (P. Pilo et al., *J Bacteriol* 187, 6824 (October, 2005); E. M. Vilei, J. Frey, *Clin Diagn Lab Immunol* 8, 85 (January, 2001)). As a result of this omission, *M. mycoides* JCVI-syn1 did not lyse sheep red blood cells, while wild type organisms demonstrated alpha hemolysis characteristic of hydrogen peroxide damage of red blood cells (data not shown). Hemolysis is a standard assay for mycoplasma virulence.

Example 6C

Semi-Synthetic Donor Genome Assembly and Transplantation

A method was developed to independently validate the viability of individual 100-kb synthetic assemblies, since any errors in the genome may not produce transplants. To aid in testing the functionality of each 100-kb synthetic segment, semi-synthetic genomes were constructed and transplanted. By mixing natural pieces with synthetic ones, the successful construction of each synthetic 100-kb assembly could be verified without having to sequence these intermediates. We cloned 11 overlapping natural 100-kb assemblies in yeast by using a previously described method (Leem et al., Nucleic Acids Res 31, e29 (Mar. 15, 2003)). In 11 parallel reactions, yeast cells were co-transformed with fragmented M. mycoides genomic DNA (YCpMmyc 1.1) that averaged ~100 kb in length, and a PCR-amplified vector designed to overlap the ends of the 100 kb inserts. To maintain the appropriate overlaps so that natural and synthetic fragments could be recombined, the PCR-amplified vectors were produced using primers with the same 40-bp overlaps used to clone the 100-kb synthetic assemblies. The semi-synthetic genomes that were constructed contained between two and ten of the eleven 100-kb synthetic subassemblies. Once viable colonies were produced following transplantation, the synthetic fraction of each genome was determined to contain no lethal mutations. It became apparent that only one of the 100-kb sub-assemblies, 811-900, was not viable.

Initially, the error-containing 811-820 clone, described above, was used to produce a synthetic genome that did not transplant. This was expected since the single base pair deletion created a frameshift in dnaA, an essential gene for chromosomal replication. We were previously unaware of this mutation. By using a semi-synthetic genome construction strategy, we were able to rapidly identify 811-900 as the source for failed synthetic transplantation experiments. Thus, we began to reassemble an error-free 811-900 assembly, which was used to produce the sMmYCp235 yeast strain. The dnaA-mutated genome only differs by one nucleotide from the synthetic genome in sMmYCp235. This genome served as a negative control in our transplantation experiments. The dnaA mutation was also repaired at the 811-900 level by genome engineering in yeast (Noskov, Segall-Shapiro, and Chuang, *Nucleic Acids Res*, (Mar. 12, 2010)). A repaired 811-900 assembly was used in a final stage assembly to produce a yeast clone with a repaired genome. This yeast clone is named sMmYCP142 and could be transplanted. A complete list of genomes that have been assembled from 11 pieces and successfully transplanted is provided in Table 28.

TABLE 28

Genomes that have been assembled from 11 pieces and successfully transplanted

| Genome Assembly | Synthetic Fragments | Natural Fragments |
|---|---|---|
| Reconstituted natural genome | None | 1-11 |
| 2/11 semi-synthetic genome with 1 watermark | 5WM, 10 | 1-4, 6-9, 11 |
| 8/11 semi-synthetic genome without watermarks | 1-4, 6-8, 11 | 5, 9, 10 |
| 9/11 semi-synthetic genome without watermarks | 1-4, 6-8, 10-11 | 5, 9 |
| 9/11 semi-synthetic genome with 3 watermarks | 1, 2WM, 3WM, 4, 6, 7WM, 8, 10-11 | 5, 9 |
| 10/11 semi-synthetic genome with 3 watermarks | 1, 2WM, 3WM, 4, 5WM, 6, 7WM, 8, 10-11 | 9 |
| 11/11 synthetic genome, 811-820 correction of dnaA | 1, 2WM, 3WM, 4, 5WM, 6, 7WM, 8, 9-11 | None |
| 11/11 synthetic genome, 811-900 correction of dnaA | 1, 2WM, 3WM, 4, 5WM, 6, 7WM, 8, 9-11 | None |

Example 6D

Verification of Cassettes, Assembly Intermediates and *M. mycoides* JCVI-syn1

Just as the construction scheme for the synthetic cell genome followed a tiered hierarchy (1-kb cassettes, 10-kb subassemblies, 100-kb subassemblies, and the completed synthetic genome), so did the quality-control efforts to ensure that the DNA being assembled had the sequence that it was designed to have. Because of variable cost constraints, variable time constraints, and the intrinsic differences in sequencing, many small regions of DNA with overlapping sequence from sequencing one large region of largely non-repetitious DNA, different strategies of sequencing were applied to each tier. The easiest, most economical, and fastest methods of sequence validation were substantially different at each of the different tiers of the construction effort. Also, the variable limitations of these methods caused a minority of mutations introduced at the cassette level to persist all the way to the 100-kb tier. Also, every tier of assembly was associated with the creation of some mutations in a minority of cases. This demonstrates the need for a quality control effort at all levels of synthetic biology efforts that endeavor to construct large regions of DNA.

1-kb Cassette Verification.

Cassettes were purchased from Blue Heron. Blue Heron also provided sequence trace files confirming the sequences of the delivered DNA; these trace files were processed in a semi-automated manner. In-house base-calling software was used to extract sequence from the trace files into fasta format. The resulting sequence files were aligned to the target reference sequence using ClustalW (Larkin et al., Bioinformatics 23: 2947 (2007)) with default settings. The resulting pairwise alignments were parsed with PERL scripts written for the purpose and sequence positions which did not match the target reference sequence were identified. Because each 1-kb cassette was covered by two or more Blue Heron provided trace files, which in turn gave rise to as many pairwise alignments, the list of mismatched positions from all pair-wise alignments covering a particular 1-kb cassette were reconciled with each other. This was done by another custom PERL script, and cassette-positions that differed from the target sequence when all reads were taken into account were then manually analyzed.

Of 1031 cassettes, 578 passed wholly automated screening. Of the remaining 453 cassettes, 370 had discrepancies that fit into categories that were judged not to require direct manual analysis of the trace files. There were two such categories: 1) The apparent sequence deviation was in the NotI site flanking the cassette. This was common due to the poor performance of Sanger sequencing immediately following the sequencing primer, but was not of any concern because the intactness of the NotI site was immediately testable in the normal course of the processing of the cassette which involved cutting the cassette out of the cloning vector with NotI, and gel purifying it. 2) Some of the Blue Heron trace files contained unusually broad C peaks as is sometimes associated with the oxidation of the C-big-dye terminator reagent. As a result, some of the trace files gave rise to incorrect base calls of C. Eighty-three (83) of the 453 cassettes that did not pass automated verification had their trace files inspected by eye; 62 were deemed to not require in-house re-sequencing, and 21 were re-sequenced. Three of the 1-kb cassettes were, in the final analysis, determined to have mutations (two single nucleotide deletions and one single nucleotide substitution), but only one of those was found during the screening of Blue Heron provided trace files. The failure to detect the other two errors at the 1-kb tier was largely due to the poor quality of a minority of reads (those with unusually broad C peaks) and in one case, the incorrect clone having been delivered. All 1-kb cassettes that passed this screen were used to create 10-kb subassemblies.

10-kb Assembly Intermediate Verification.

The 10-kb subassemblies were pooled and verified via 454 sequencing using non-paired-end reads. Initially, 116 10-kb assemblies were screened. These 116 assemblies include some 10-kb subassemblies that were duplicates or near-duplicates. This was the case because alternate clones of certain 10-kb subassemblies were tested in parallel. Also, alternate versions of certain 10-kb subassemblies that were identical except for certain designed changes such as the presence of the watermarks were tested in parallel. Because of the presence of duplicate or near-duplicate sequences that needed to be read independently, as well as the existence of duplicate regions in contiguous 10-kb subassemblies due to the 80 base pair overlaps, the 116 10-kb subassemblies were pooled into 4 separate pools that prevented any 10-kb subassembly from being in the same pool as either of the two 10-kb sub assemblies that shared 80 base pairs with its two ends. All alternate clones and alternate versions of specific 10-kb segments were separated from each other. Also, certain 10-kb subassemblies which had highly similar sequence to one another such as those that contained IS1296 insertion sequences were separated as much as possible from one another between the four pools. The four pools were bar-coded and then pooled into one pool which was sequenced by 454. The reads from the four bar-coded pools were then separated and analyzed with the use of the CLC Workbench software package using the high-throughput reference assembly tool set at default settings. The reads from each pool were assembled against an artificially constructed "reference sequence" which consisted of the 29 10-kb target sequences for that pool separated by runs of 500 N's. After assembly to this reference sequence, mutations were detected with a mixture of manual observation, the CLC SNP detection tool, and the CLC DIP detection tool. CLC does not have an automated way of detecting differences between the reference and consensus sequences. To bypass this defect, the following non-default settings on the SNP and DIP tools were used: Minimum Coverage=1, Maximum Coverage=999999, Minimum Variant Frequency=50% or count=999999. All other settings were at their defaults. Initially 18 of the 116 10-kb subassemblies were found to contain variations from their target sequences. Eventually, three of these variations were determined to be caused by sequence similarity between the markers in the synthetic genome and the markers in the plasmid backbone of the 10-kb subassembly clones with backbone sequence contaminating the 10-kb sequences. Several of the remaining variations were found to be associated with the plasmid induction of the 10-kb clones in $E.\ coli$ after targeted PCR and sequencing of mutation regions of selected clones isolated directly from yeast, from $E.\ coli$ before induction, and $E.\ coli$ after induction. One class of mutation that was observed 3 times was the introduction of a "GC" at the sight of an overlap. It is postulated that this might be a remnant of the NotI site flanking the cassette overlap sequences. Alternate assemblies of the 10-kb segments that were mutated in the first attempt to make them were then sequenced as before, except this time, in only two bar-coded pools. One of the three mutations in the 1-kb cassettes was detected at the 10-kb level. All the other mutations that were not caused by the induction $E.\ coli$, originated in construction.

100-kb Assembly Intermediate Verification.

Rather than sequence each of the 100-kb subassemblies, semi-synthetic genomes were constructed. These semi-synthetic genomes contained between two and ten of the eleven 100-kb subassemblies, and the rest of the genome was derived from natural $M.\ mycoides$ genome sequences. These semi-synthetic genomes were successfully transplanted, validating that no lethal mutations were in the synthetic fraction of the genome. It rapidly became apparent that only one of the 100-kb subassemblies was not viable: the one corresponding to cassettes 811a-900. Because this 89-kb segment was not available conveniently from yeast in quantities that would make direct genomic walking or 454 sequencing easy or cost effective, overlapping PCR amplicons were generated and sequenced with a sequencing primer every 200 base pairs along each amplicon alternating between strands.

This process was done for both the synthetic 811a-900 and the corresponding region of the natural *M. mycoides* genome that had been shown to be viable in the semi-synthetic experiments. Re-sequencing of the natural fragment was to guard against the possibility that the 811a-900 region had been designed with a deviation that would prevent viability upon transplantation. Whereas the sequencing of the synthetic 811a-900 was to guard against mutations away from the designed sequence, one such mutation away from the design was detected in the 811a-900 sequence. It was a one base pair deletion that was eventually determined to have existed in the 812a 1-kb cassette. This mutation was not captured at the 1-kb level. It was not detected at the 10 KB level because, coincidentally, many of the 454 reads happened to end or start in its immediate vicinity causing mutation to seem to be poorly supported across the population of read, and thus ignored by the automated SNP and DIP detection tools.

Discussion

In this current study, we constructed the 1.08 million base pair *M. mycoides* genome. However, obtaining an error-free genome that could be activated in a recipient cell to create a new cell controlled only by the synthetic genome was complicated and required many quality control steps. Success was thwarted for many weeks by a single base pair deletion in the essential gene dnaA. One wrong base in an essential gene in over one million bases rendered the genome inactive, while major genome insertions and deletions in non-essential parts of the genome had no impact on viability.

During this study we developed a number of methods to facilitate testing and error correction of synthetic genome segments. These methods include the combination of synthetic and non-synthetic genome segments followed by genome transplantation and DNA sequencing to find sequence errors and to test the viability of synthetic designs.

Our first successful genome transplants used native genomes isolated from intact cells. These studies proved that genomes could be successfully transplanted into related species replacing the existing genetic material and in the process converting the cell into the phenotype dictated by the new genome. These experiments proved that naked DNA could be transplanted. What we did not know at the time was that the DNA in *M. mycoides* cells was methylated and, therefore, protected from restriction when inserted into *M. capricolum* cells.

Because the final synthetic genome assembly was accomplished by yeast recombination, we developed new methods for cloning native bacterial chromosomes in yeast (Benders et al., *Nucleic Acids Res*, (Mar. 7, 2010)) and to isolate intact native and synthetic bacterial genomes from yeast (Lartigue et al., *Science* 325, 1693 (Sep. 25, 2009)). Initial transplants involving native *M. mycoides* genomes cloned as yeast centromeric plasmids failed. Subsequent extensive studies demonstrated that site specific DNA methylation was needed for genome transplantation unless restriction system genes were removed from the genome of the recipient *M. capricolum* cells (Lartigue et al., *Science* 325, 1693 (Sep. 25, 2009)).

These studies resulted in powerful new methods that allow bacterial genomes from species lacking genetic systems to be grown in yeast by the addition of a yeast centromeric sequence. Furthermore, a bacterial genome cloned in yeast could be readily modified with yeast genetic tools including homologous recombination. The modified bacterial chromosome could then be isolated from yeast, optionally methylated, and transplanted back into a recipient cell to create a modified version of the donor cell (Lartigue et al., *Science* 325, 1693 (Sep. 25, 2009)).

Though below-average size for a bacterial genome, the 1,077,947-bp double-stranded DNA molecule that we synthesized is the largest synthetic molecule of defined structure reported, and is almost twice the size of the *M. genitalium* genome that we synthesized previously (Gibson et al., *Science* 319, 1215 (Feb. 29, 2008)). Synthesis of a synthetic or semi-synthetic molecule, and the demonstration that it has the same properties as a naturally-occurring compound, has long been used as evidence to support a proposed molecular structure. The demonstration that our synthetic genome and semi-synthetic genome confers the phenotypic properties of *M. mycoides* implies that the DNA sequence upon which it is based is accurate enough to specify a living cell.

A cell controlled by an introduced genome (a natural genome, a synthetic genome, or a semi-synthetic genome" is referred to as a "synthetic cell", even though the cytoplasm of the recipient cell is not synthetic. Phenotypic effects of the recipient cytoplasm are diluted with protein turnover and as cells carrying only the transplanted genome replicate. Following transplantation and replication on a plate to form a colony (>30 divisions or >109 fold dilution), progeny will not contain any protein molecules that were present in the original recipient cell. The properties of the cells controlled by the assembled genome are expected to be the same as if the whole cell had been produced synthetically (the DNA software builds its own hardware).

From the foregoing description, one skilled in the art can ascertain the essential characteristics of the disclosed embodiments, and without departing from the spirit and scope thereof, can make changes and modifications to adapt it to various usage and conditions and to utilize the present systems and methods to their fullest extent. The preceding specific embodiments are to be construed as merely illustrative, and not limiting of the scope of the application in any way whatsoever. The entire disclosure of all applications, patents, publications (including reference manuals) cited above and in the figures, are hereby incorporated in their entirety by reference.

What is claimed:

1. A method for creating a self-replicating synthetic cell, said method comprising:
   (i) assembling a synthetic bacterial, cyanobacterial, or microalgal donor genome as one or more fragments and introducing the donor genome as one or more fragments and a host vector into a yeast host cell, wherein the donor genome and the host vector are joined prior to or after introduction into the yeast host cell;
   (ii) recovering the assembled donor genome from the yeast host cell;
   (iii) performing step a) or b) or c) wherein a), b) and c) comprise
      a) preparing the donor genome for transplantation into a bacterial, cyanobacterial, or microalgal recipient cell by methylating the donor genome;
      b) preparing a bacterial or cyanobacterial or microalgal recipient cell by removing or inactivating a restriction endonuclease function present in the recipient cell that cuts the donor genome;
      c) providing a bacterial, cyanobacterial, or microalgal recipient cell lacking a restriction endonuclease function that cuts the donor genome; and
   (iv) introducing the recovered donor genome into the recipient cell,
   thereby generating a self-replicating synthetic cell comprising the donor genome and controlled only by the donor genome, wherein the donor genome is sufficient to sustain viability and continuous self-replication of the recipient cell; and
   wherein the synthetic cell supports gene expression from the donor genome and has a phenotype of the donor genome,
   wherein the donor genome is an essentially intact genome that is at least a minimal genome, and is greater than about 300 kb in length.

2. The method of claim 1, wherein the donor genome and the host vector are introduced into the host cell simultaneously.

3. The method of claim 1, wherein the donor genome and host vector are joined prior to introduction into the yeast host cell by transforming the yeast host vector into a donor cell containing the donor genome.

4. The method of claim 3, wherein the host vector is a centromeric plasmid.

5. The method of claim 1, wherein the donor genome is modified within the yeast host cell.

6. The method of claim 1, further comprising degrading or removing the endogenous genome of the recipient cell.

7. The method of claim 1, wherein the recovered donor genome is methylated prior to introduction into the recipient cell.

8. The method of claim 1, wherein the recipient cell's restriction endonuclease function is absent, removed or inactivated.

9. The method of claim 1, further comprising introducing a second donor genome into the host cell, wherein the second donor genome is different from the first donor genome, thereby producing a host cell containing two different donor genomes.

10. The method of claim 9, wherein introducing the second donor genome comprises mating the host cell containing the first donor genome with a second host cell containing the second donor genome.

11. The method of claim 1, wherein the synthetic cell exhibits a phenotype corresponding to the donor genome incorporating any modifications thereto.

12. The method of claim 1 wherein the synthetic donor genome is assembled in vitro prior to introducing the donor genome into the host cell.

13. The method of claim 5 wherein the modification of the donor genome is selected from the group consisting of a substitution, a deletion, an insertion, a rearrangement, and a recombination.

14. The method of claim 13 wherein the modification is selected from the group consisting of: an insertion, a deletion, and a substitution.

15. The method of claim 5 wherein the modification is a homologous recombination.

16. The method of claim 1 wherein the donor genome is a bacterial genome and the recipient cell is a bacterial cell.

17. The method of claim 1 wherein the donor genome is a cyanobacterial genome and the recipient cell is a cyanobacterial cell.

18. The method of claim 1 wherein the donor genome is a microalgal genome and the recipient cell is a microalgal cell.

19. The method of claim 1 wherein the yeast host cell is *Saccharomyces cerevisiae* or *Saccharomyces pombe*.

20. The method of claim 16, wherein the donor genome is a *Mycoplasma* genome and the recipient cell is a *Mycoplasma* cell.

21. The method of claim 19, wherein the recipient cell is a *Mycoplasma capricolum*.

22. The method of claim 20, wherein the recipient cell is a *Mycoplasma capricolum*.

\* \* \* \* \*